US011801296B2

(12) United States Patent
Gladue et al.

(10) Patent No.: US 11,801,296 B2
(45) Date of Patent: Oct. 31, 2023

(54) DEVELOPMENT OF A NOVEL LIVE ATTENUATED AFRICAN SWINE FEVER VACCINE BASED IN THE DELETION OF GENE A137R

(71) Applicant: The United States of America, as represented by the Secretary of Agriculture, Washington, DC (US)

(72) Inventors: Douglas P. Gladue, Guilford, CT (US); Manuel V. Borca, Westbrook, CT (US)

(73) Assignee: The United States of America, as represented by The Secretary of Agriculture, Washington, DC (US)

( * ) Notice: Subject to any disclaimer, the term of this patent is extended or adjusted under 35 U.S.C. 154(b) by 216 days.

(21) Appl. No.: 17/363,875

(22) Filed: Jun. 30, 2021

(65) Prior Publication Data

US 2023/0000967 A1 Jan. 5, 2023

(51) Int. Cl.

| | |
|---|---|
| ***A61K 39/12*** | (2006.01) |
| ***A61P 31/20*** | (2006.01) |
| ***C12N 7/00*** | (2006.01) |
| *A61K 39/00* | (2006.01) |

(52) U.S. Cl.

CPC .............. *A61K 39/12* (2013.01); *A61P 31/20* (2018.01); *C12N 7/00* (2013.01); *A61K 2039/5254* (2013.01); *C12N 2710/12021* (2013.01); *C12N 2710/12022* (2013.01); *C12N 2710/12034* (2013.01); *C12N 2710/12071* (2013.01)

(58) Field of Classification Search

None

See application file for complete search history.

(56) References Cited

U.S. PATENT DOCUMENTS

| | | | |
|---|---|---|---|
| 9,808,520 | B1 | 11/2017 | Borca et al. |
| 2016/0130562 | A1 | 5/2016 | Borca et al. |

FOREIGN PATENT DOCUMENTS

| | | | |
|---|---|---|---|
| CN | 112063592 | A | 12/2020 |
| WO | 2015091322 | A1 | 6/2015 |
| WO | 2020193688 | A2 | 10/2020 |

OTHER PUBLICATIONS

GenBank Accession NC_044959.2. (Dec. 20, 2020).*

Borca MV, Ramirez-Medina E, Silva E, Vuono E, Rai A, Pruitt S, Holinka LG, Velazquez-Salinas L, Zhu J, Gladue DP. Development of a Highly Effective African Swine Fever Virus Vaccine by Deletion of the I177L Gene Results in Sterile Immunity against the Current Epidemic Eurasia Strain. J Virol. Mar. 17, 2020;94(7):e02.*

Gladue DP, Ramirez-Medina E, Vuono E, Silva E, Rai A, Pruitt S, Espinoza N, Velazquez-Salinas L, Borca MV. Deletion of the A137R Gene from the Pandemic Strain of African Swine Fever Virus Attenuates the Strain and Offers Protection against the Virulent Pandemic Virus. J Virol. Oct. 13, 2021;95(21):e0113921. doi: 10.*

Alcamí A, Angulo A, Viñuela E. Mapping and sequence of the gene encoding the African swine fever virion protein of M(r) 11500. J Gen Virol. Nov. 1993;74 ( Pt 11):2317-24. doi: 10.1099/0022-1317-74-11-2317. PMID: 8245848.*

Gladue, Douglas P. et al., 'Deletion of the AI 37R Gene from the pandemic strain of african swine fever virus attenuates the strain and offers protection against the virulent pandemic virus', Journal of Virology, Aug. 18, 2021 (published online), vol. 95, issue 21, e01 139-21, pp. 1-12.

International Search Report, dated Oct. 27, 2022.

* cited by examiner

*Primary Examiner* — Benjamin P Blumel
*Assistant Examiner* — Jeffrey Mark Sifford
(74) *Attorney, Agent, or Firm* — John D. Fado; Mark D. McNemar

(57) ABSTRACT

Provided herein are details on the construction of a recombinant African Swine Fever Virus (ASFV) live attenuated vaccine for prevention of ASF caused by various strains of ASFV, such as the highly virulent Georgia 2007 isolate ("ASFV-G"). An exemplary vaccine comprises the ASFV-GΔA137R modified virus, a recombinant ASFV-G modified by deleting a portion of the A137R ORF rendering the A137R gene nonfunctional.

18 Claims, 3 Drawing Sheets

Specification includes a Sequence Listing.

SEQUENCE LISTING

<160> NUMBER OF SEQ ID NOS: 6

<210> SEQ ID NO 1
<211> LENGTH: 190584
<212> TYPE: DNA
<213> ORGANISM: African swine fever virus

<400> SEQUENCE: 1
actgctgtag gcgtcaaaga ttaaaattat tactactgct gtaggcgtta aacattaaaa 60
ttattactac tgctgtaggc gttaaagatt aaaaatatta gtactgctgc aggcgttaaa 120
gattaaaaat attagtactg ctgcaggcgt taaacattaa aattattgta ctgctgtagg 180
cgttaaacat taaaattatt actactgctg taggcgtcaa agattaaaat tattactact 240
gctgtaggcg ttaaacatta aaattattac tactgctgta ggcgttaaag attaaaaata 300
ttagtactgc tgcaggcgtt aaagattaaa attattacta ctgctgtagg tgtcaaagat 360
taaaattatt actgtaggcg ttcatttcac aagatgcgga attatttcgc aaagattatt 420
ttttgaaacg ccgcggccgg aaatattttt ttttgcggtt gtaattgatt tttttttgcg 480
gctgggcggc gggccagaca aaattgacca taactggtgt tacgccgccg gtaataaacc 540
ctaccgtaaa tacttttttt tggggcggcc agagagacat tatcgccgta ggtatcaatt 600
actgctgtag gtatcaatta ttatactaca ggcgttaaac attattagta cacaggcgtc 660
aaagaagcta aaacttaatg ttttttcgtc aaaaatcgcc atgaatatct atcttgtgtg 720
gtttctctac atactattgg ggaacctgat attagcagta atatattgcg tcatagatga 780
ggtggtgtgt gacaatatcc atataaaaaa aaatgttgcc gcccctgaga tgccgcggcg 840
gttctaaatt ttaatgtttt tttcggcgaa catttttcac atatgcgata ttggcgctaa 900
agcgagcgta ttaccgcttg taacaacatt ttttttcgat cggcaataga taagtagaat 960
ataccatatt attgctattg ccatcaatga gaatgccacg taggcatagg tcatcctatg 1020
gccggaccaa tccatggctg cacttaaaaa tatcaaaaaa agtttaagtt ttgggccggc 1080
gttaaaattt aaaccttttc tggttgatct ttagccatgt atagctgcga tgtttggtgc 1140
cttatctaca tgctattggc attcctgata ttcgcactaa agtgctatgt tacaaccgtc 1200
ttatgcgtga tttttatcca ccttattggc cgaagggccg ccttgtattt cctgttaggt 1260
ggtttggccg tattctactg gtggcaagca gctatcaata aaatttaatg gctctcactt 1320
aagatccttg ctgtaagcgg gcgtttacat actttgatca agaaaaaaaa ttatttttgg 1380
accccccccc atgttttata caaaaatcat ataataaagt ggcgacaatc aacatattaa 1440
tcaaccacag cattttatga tgtgttaatc aacatatacc atattaatca accacagcat 1500
tttatgatgc gtcaatcaac atattattac ggagagcgtc aatcaatata atattgagaa 1560
cagcgacttg ataccgtgta tggtggtggc ggcggcatgt tgtttgtaac agcatttttc 1620
atcattcgaa gcttacaaaa gatatgtata agatagcata ttaatgttat taacagtaat 1680
atcaataagg cgtagctata gatcttcact ttggtagacc aataatccat ggttgcgctt 1740
aaaaatacca aaaaaaacat taagttttgg agggtaagat tggtttttca ccattggtaa 1800
agattattat tctaaatgtt taccccatag atgtgaaaca atgattcttc atatattaac 1860
atattttttg acttatactt ttcttcatct agtaaggcgt taattttttc cggatctgtc 1920

-continued

```
gtttttattg ataaaagaga agagtctgga ctgtaatttt taaataataa gatatttatt   1980
aatatccaat tattcgtttg gctcgctatt tccatgctct cttcgaaagc atcagctcct   2040
aaatctatac aaaggaataa gttaccttca caaaaattca ttaccgaggt aatcattgcc   2100
cgattaatgt cagcccccaa cataaaacaa taatatatag ttgtataatt acaatcatac   2160
atacaggcca actgcatcat ttcatcaatg tctatatttg tcttctcttt gttataaatt   2220
tcatgaaggt caaagacgtt gttataagca accccacata ttaaccgcca atctttaaaa   2280
tgactatatc gttgataaaa atattggatg gcttcagtaa gcttatatag tatcgccata   2340
ctataccaat acctagttag catttcgttg aatgaaatat tatccaatgt aaagttaatt   2400
gataatgtat ctagttcacc aaaaattctt aatttcagtt gagcattatt taggaaaagg   2460
ggattatcag ataataattc atggcataga ataatattac tgctagtttt aacatactgt   2520
acattataaa atatttctaa aattttattt tcactcaaag ctttcctcgc acctaacttt   2580
tggcataggt cctggtgcac tccatattga cagtaaccaa cccaaagctg atgtctgcac   2640
cccattcggt aaacagctct attaaaccat gattgttttc ctgtacagcc ttcattaatg   2700
caacatttaa tgttaaacca tgtttaaaac ttgctgtttt tattaatatt tgttcatcta   2760
tacaagtatg ataaatcgta attggggctt catgccacca caaaccacaa cgctctaaaa   2820
tacaataatc atcttttaac acaggctgtg tagctagtac tttttagta agtgcttgta    2880
aagtagatgg catcttctat ctgcaaaata attatttccg aaaaaaaaat caaattaaaa   2940
tactaaattc tatttttttt tttaataaag cctgtaaatt atataataaa tctcgcccac   3000
cgtattattt ccggacacaa ctttttatac ctcattatat ttttagatct atagtttttt   3060
aacaaggcat taatttttc tggatctgtc gtttttaaag ataaaagaga gacgtttgaa    3120
ctataataat ctttaaatga taatatttct actaatatat catgattctt ttgttttgct   3180
aattctaagc tctcttcgaa agcattagct cctaaatcta tacaaaagaa caagttattc   3240
atataaaagt tttttaccga ggtaaccatt gcccgattga tgtcagcccc caatacaaaa   3300
caatagtaaa tggttaaaaa attgctatct ctcatacagg ccagatatat catttcatca   3360
atattcatat caaccttttt tatatgatac atttcatgaa gatcagacac gttattaaaa   3420
gaaagcccac atattagccg ccaatcttta aaatgactat atcgttgata aaaatattgg   3480
atggcttcag taagcttaca tagtatcgct atactatacc aatatctagt tagcatttcg   3540
ttgaatgtta tttcattcaa tataaagttg atcgatatct tctctagaaa acaacaaatt   3600
attactttta attcctctat attctggaaa aggggattat tagataacaa tttatggcat   3660
aaaataatat tactactagt tttaatacga tgtattttat aaaatatttg tacaatatcc   3720
atttcattca aaatttttgc gcctaactcc cggcagaaat tccaagtatg ctccgtattg   3780
acagtgacta agctagagtt gatgtctgca ccccattcag taaacaactc tattagatca   3840
tagttgtttt cctgcacagt tttcattaat gcgagattta actctaaacc atctttaaaa   3900
attgctgatt ttatcatcaa ttgattatcc tcattagtag aaagcataat tggagctcca   3960
tgccaccaca aaccacaata tttcaaaata aagtagtgtt ctttagatat gtgctgtgtg   4020
gccagtattt ttttagcaag agcctgcaga gaaattggag tagacatatt tttttttgca   4080
aaatggttta agtttttcaa gaatacagat tggataaatt aggttgttga cttagttaca   4140
ggaggtatta aatattatgt agacataaaa atgagatcct ccaaaaaaat aaacaacaaa   4200
aaaaaatatg tttaatatta aaatgacaat ttctacattg cttattgctc ttattatact   4260
acttattatt attttagtag tgtttttata ctataagaaa caacaaccac cgaaaaaggt   4320
```

-continued ctgtaaagta gataaagatt gtggtagtgg agagcattgt gttcgtggat catgtagctc 4380
attgagctgc ttagatgccg taaaaatgga caaacgaaat attaagatag attctaagat 4440
ttcctcatgc gaattcactc ccaattttta ccgttttacg gatactgctg ctgatgagca 4500
gcaagaattt ggaaaaacac ggcatcctat aaaaataact ccatctccaa gtgaatccca 4560
tagcccccaa gaggtgtgtg aaaaatattg ttcatgggga accgatgact gtacaggttg 4620
ggaatatgtt ggtgatgaaa aggagggaac atgttatgta tataataatc cacatcaccc 4680
ggttcttaaa tatggtaagg atcacatcat agccttacct agaaatcata aacatgcata 4740
aataaataca ttaggctcat cgtatctttt taaaatccat aaatattcgt ttgatatatg 4800
ctgaaatttt tataaaaaaa aataactatt tcctataaat catctagaaa tagtcctcgt 4860
tttgatcggt ttatatctta taatattgtg catcgatgca caactgcttt ttttggtcct 4920
tctggaacat cattatattt tctttcatta atataccatt cagatgtaaa cgttgaataa 4980
tttttatggc aacaatctac cattgaatta tatttagtaa catctaatac atcgtttgtt 5040
ttatcaggct cagctctata atcttgataa tttttgttat cagcttctaa agctccatca 5100
ttatttttca aagaagtatc cataattatg tttggtaaaa atactttaag ttttaatgtg 5160
atatttaaaa tggttgttat ataaatttac cgcttacagg taatctttat tcagtgtcat 5220
aaactatact tttgatgatt cagtattttg tgaatcagta catttattat cattaatatt 5280
tttaggctgt ttttccaatg ttttattgtt gcaatgagcc tgctcctcct ttgacgagga 5340
agtgtctgtt ggagtcatct gtttaggaag agtatcatcc atatctatta tgaagaaaat 5400
atataaatat tgatatacaa tcaaaaatat ttttgatcac gtctttgtta tctatcgata 5460
ttgttgataa cgtcttgaat aacctacatc atttttttac ataaaaaaat agatataatt 5520
tttattatat ctcaattatt ttaaagataa ttatcaatac agcaaatatc ataagctaac 5580
atatttttcg aataatagtt ttttagtaaa gtattaatct tttcaggatt ggtttctttt 5640
gataataaga taggattcgc tttataaatt tttaaagata atatattcac aatgatagaa 5700
taaccgtata tatctgctaa tgtcttactg tgttcaataa cattagcccc taaatccata 5760
caaaagaaca tattttcaat acaaaagttt tttaccgaga ttaacattgc tcgattagcg 5820
ttggctccca atgcaaaaca gtagtaaatg gtcaaaaaat tattatcgcg catacaggcc 5880
agctccatca ttttattaat actcatatga attttcgttg tgttacatat ttcatgaagg 5940
tcaaacacat tgttgaaaga aagtgcacaa attaatcgcc attcatcaaa atgcctgtat 6000
tcttgacaaa aatattgaat agcttcttta agattatatt ttaccgctat gccataccaa 6060
tatttggtta gcatctcact aaatgagatc tcatttaaca tagaatttgt tgttaaatcc 6120
ttcaactccc aataaatgat catccttaaa tccaccatgt ttacattttg taaaaaaggg 6180
ttattagaaa ataattcatg acacaaaatg acattactac ttgttatttt acactttgtt 6240
tcaaagaaaa atcgtaaaat ttcacttgtc tcaagctctt ctttagctcc caattttcgg 6300
cataggtttc gagtatgctc gttattaata aaaagtaacc cataattaat atttgcaccc 6360
cattcagtaa acaacatgat tagatcatca ttgttttcct taactgccaa taccaatgca 6420
gtattaagcc ttataccctc tttaaagcat aatgtcctta tcattatttg attatcatca 6480
tctatataca ttgagatagg agcttcatgc caccataaac cataacgctc taaaatataa 6540
taatcatctt tagatacgtg ttgcgtggcc aatgcccttt tagcaagtgc ttgtaaagtc 6600
gatggctgca tgtttattct gttaaaaaaa aatcaaatta tcgggtaaac ataaggatca 6660

-continued

```
acccgtagtt aatatttgca gtagtatttt ttaacaatga attataataa aaaaataatt   6720
cattactatc tattataaaa cccatcttta actttaaaga agaactagat catctttttt   6780
tttgttgtgt cagaacttct tcaatttatt acccacattt tatctaaaaa aaataaaaac   6840
tacatcatat cttgtttctt catcaaatta tcataccatt tatagggtgt aggttgggaa   6900
cattccatca tgtggtaatc agggtattta tatatttttt gatagtaaca tctatttggc   6960
agatgtattg tccaacaatc atgtctaata aaatcatttt cacctatggg ggaatcatct   7020
taaaaacctt attcctacag attccatttt gacagtccca gcaaaagtca caatattttc   7080
catgagtaca ccaatgttca agctctcttt cgggaggaat gctgccaatt ttatgttttt   7140
tagcttctaa ctctctgtac aacatcagtt gggaaagcag aaagaagatt accaggagaa   7200
ccattaaata tataatagtc tgcaaactac gtttgcgaat gtaatttgca actaaaacac   7260
aacccacaag gtaaaatcca taagttaata acttttgcca ttttcgtatg acagcctcgt   7320
gccattcatg gttgtgttgt gggcattctg ttcggtaaac ttcatgaggc tttatagaag   7380
ttacatagta ggtacagaat tcattgtgac gaaaaacact gcagttagct atgtagtcat   7440
tttcaagaat gggagaatgg ttttcaaaga ccttattctt acagatgcca tcttgacagt   7500
cccaacagaa cctacaatga tttgcatagg tgcaccagta ttcaagctcc ttttcaggag   7560
gggttcttgt tagatccagg agctctagct catatgtata aagaagagtt ggaatggata   7620
gtaaagtaaa tatttgcaga ccaagcatgg ctacttgtga acaagtggct gctcgtcaac   7680
aaatagctgt ttatcagcaa atagctgttt atcagcaaca actaattatc agcaaatgct   7740
gcttgtgggt aagccaataa ataggccata cccttgaaag gagaattcag tttgataaaa   7800
aaaataacga gttttctaat aacccggtca agcatttaat aaatgaatag catcacacgt   7860
ctgcatcgtg cattctgcct ggaaaatggg cccatctcta atatatttac actgacggtg   7920
aatcatacag tgttccatgg gatagctatg ctcctgtaca ggaggcatat cttttagaac   7980
tttattctta caaagaccat cttgacaagc ccagcaaaac cgacaatttt tcacatattg   8040
acaccagtat ctaagctcct cttccagggg attgtcggtc gaaaacccct gtagactagc   8100
taggccagct agcagcaagc cgaggtaact aaagaacctc attgtagtgt tatattacga   8160
aaaaacatgt taaaatttgg aaaaaaaagc ccttttttata gatctggaaa aaaattttca   8220
caaatctaat taaaagcctt acagatcatc cttttcataa attttcatta acaattggtg   8280
ggggcggttg tgaggtactg gatcagaaca atccataaca tggtaatgtc catttccttc   8340
accatatgta cactggttat accagcgaga aacctcacaa gatgtcaaat aactgttctc   8400
aacaatcaat ggcatgctct tattcacctt gttcttgcaa attccatgtg cacattccca   8460
gcaaaacttg cagttttcca tgtaagtaca ccagtatcca agttcttctt gtggaggatt   8520
atccgttgaa cgaagatgcc ctcctgcctg agtaggtagt cctaagacct gattggccag   8580
caggccaaga atttccaaga agatcaccaa cattgctacg gctggctgaa cagctggcag   8640
atagctagct aattagcaaa ccaagtgact cgccctctct actcttaata tgagaattta   8700
agattcggtc cggctttttt cccatgtttt acagggaaaa ggtattttta gcctatgaat   8760
gtacatggtt ccgcacatta aaaaaaaata aaagaaatta tttaatattg gctgttattt   8820
tctttcaact agcaacaagc caggtaacta aagaacttca ttgtagtttt atattacgga   8880
aaaggttaaa ttttggacaa aaaaaatcat atctaattaa aaatcctcac agatctttct   8940
tttcataaat tttcattaac aattggtagg ggcggttgtg aggtactgga tcagaacaat   9000
ccataacatg gtaatgccca tttccttcac catatgtaca ctggttatac cagcgagaaa   9060
```

-continued

```
cctcacatgt tgtcaagtag ctgttttcaa taatcaatgg catgctatta ttcaccttgt   9120
tcttgcaaat tccatgtgca cattcccagc aaaacttgca cctttccatg taagtgcacc   9180
agtatccaag ttcttcttgt ggaggattat ccgttgaacg aagatgccct cctgcctgag   9240
taggtagtcc tacgacctga ttggccagca ggccaagaat tcccaagaag actaccaaca   9300
ttgctacggc tggctgaaca gctggcagat agctagctaa ttagcaaacc aagtgactca   9360
ccctctctac tcttaatatg agaatttaag atccggtccg acatttttcc gatattttac   9420
aagaaaaaga tatttttagc tacaaataca cttcatatat ccctaaaaaa aacaaaaatt   9480
tatttaattt taactattat tttctttcca ctctctcttt aagattttgt aaggattcca   9540
gggctttggt tcagaacagg ccattacatg gtgaatcccc tgtcctagat catacataca   9600
tttatttagc cagcgggaaa ctatacatga ttgcacatac tcattttcaa gaattgttgt   9660
attctccaat ttgccctcac aaaggccatt ttgacaattc cagcaaaact tgcagttttc   9720
tgtataagtg caccagtatt caagttcttc ttgtggagga ttatccgttg gatgaagttg   9780
tccagctggt tgattaggta gccctaagac ctggttgcaa ttcatggtat ggtagatacc   9840
cttatctaaa tcatacatac atttatccag ccaacgggaa accagacatg atttcacata   9900
ctcattcttg taaattactg acccatctat tttgtttata caagtgccgt cttggcagtc   9960
ccagcaaaat tggcaacttt ccatgtaggc acaccagtat tcgagttctt cctctggagg  10020
ctcctctgtt ggacgaagtt gtccaacgag ctgacttgaa acctggctgg ccagaaggcc  10080
aagaattccc aagaagatca ccaacattgc tacggctggc tgaacagctg actgaatagc  10140
tagccaatta gcaatccact gtacttttca taagatcatt taagattcgg tcggcatttt  10200
ttcaatagtt tgctaggaaa aaatttttaa ttttatagat tcacactact tcattctcat  10260
gcttaggaaa aaaacaaact aaatcttaca atgtatctgg atctaatgag aagctagaat  10320
tcatcttttt tcaaatcctt tctgggatgt tcattctttt tccactcctt ccttgcaatt  10380
ttataaggat tccagggctt tgggtcagaa cagttcatgc tatggtaaat gtgctcctcc  10440
acatcatatc tacataggtc accccagcgg gaaacctcac aatattttac atagtcattc  10500
tcaataatac ttgtggagtt gtttccccaa accctgctgg tacaaatccc atcttcacaa  10560
tcccagcaga accgacagct ttccacataa gtgcaccagt atccaagttc attctctggg  10620
ggttcaaatg ttagaggaag atgtccacct acccgagtag aagtggagga tgaaaccagg  10680
ttgctactgg ccagcaggcc aataattccc aggataatca ccagcattgt gctcaaccag  10740
caacggctag caacgactag caactgacta gcaatagcta gaaatggcta gcaatcagta  10800
gtagctaacg ctctactctt tataagaaaa tttaaaattc gatcagattt ttttagaatt  10860
gagaatgagt aaaacgctta tattcttttt ctagctagaa aaaataagct agtttaagat  10920
aggatttccc ttactaacgg tttaattttt agcaaaggta taggtaaaat acacttgtac  10980
ttagctgcaa aaaaataagc ttatggcgta taagccgcca taagtttatt taattaaaat  11040
gttaaactct gtgataagac tggaatctta ggcaggtttg atgtggagaa cagcatgaaa  11100
tacaagagtg cctgttacac gaataagttc tctcaaaccg gggatggtca tactcacatc  11160
tatgaaatcc tggtctagga gattcatttg atgcatgatg gccgcaccca cacttatgag  11220
acactgaaga actaaagggt ttaattttga tctgaatggt actatatagg atgatggcaa  11280
tccatatcaa gattagagca atcaaaatca cctcctcaag aagcatgatg tagccttaaa  11340
tcttagactg ctttaaacct taggccctca ctatctttaa tgaaggagtt taaattttga  11400
```

-continued tcccttttc aagacccatt tagaagaaaa aaataaagtt tatatcaatc taattcataa 11460
gtcatctctt tcataaatct tcatgtattc tctatgtgga taagtatggg atgttggatt 11520
tgcgcagtcc atttgatgat ctgtatggtt tttgggtcct tcataataac tacatatacc 11580
attccagcgg gaaaccgtgc aatttataat ccagtcattt tgatgaataa ctggccaatc 11640
tgtttgaatc ctgtttcggc agataccgtg gacgcattcc cagcaaaagt cacattggtt 11700
tgcgtaagtg caccaataaa ctagctcatg ttcaggagga taacgggttg gtagtaaatc 11760
ttctaattta cgtataggag cggcttgaag gacaaccacc cccagtagta ctagaatcag 11820
tacctttata gtggccaccc tacactagac ctctaagttg aagacaaaga actaaaattt 11880
agagccgttt aattactact aataattata ttttttattg tctacaatag gattctatta 11940
aaaaataatg atttttacca agaaatattt ttataaaaaa ttaatatatt ttgtaataaa 12000
ctttatttcc aatgactgtt aaaataagga aactatcctt agttagtcga ggaagatggt 12060
taggttattt cgcaatccga taaaatgttt attttatcgt aggtctcgta aaatccagga 12120
aaaaaaatta cggaagagtt taaaaaagct aaatttttac caccctccag aagattgttg 12180
tcaaatatat cgtttgctag aaaatgttcc tggaggaact tactttatta cagaaaatat 12240
gacgaatgat ttaattatgg tcgtaaagga ttcggtggat aaaaaaatta aaagcattaa 12300
attatatctt catggaagtt atattaagat tcatcagcac tattatatta atatttatat 12360
gtatcttatg agatataccc aaatttataa atatccctta atttgtttta acaaatatta 12420
taacatctaa gtaaatattc ttggaatgga ttttcttata gaatggttac aggatatgtc 12480
agcgacaggc ttaataacaa atttgttaat atttttttgt taaataaatg aacaggccac 12540
catttaatat tacccgttgc aaaataagaa aaaaaaaaca aacttatagt tacaaatcat 12600
cttgattaat cacatgtcgt tttaactcaa tgaaccattc taaatctttg ggttgtgaac 12660
aattcatgtt atgttgatag tgtatcctaa agtgagcttc atacatacac cggtcatgcc 12720
accgggaaac tgtacaatta acaatataat cattttgcgt aataataggg tggtcactaa 12780
acactttatt tttacacatt ccatctttac aggtccagca gaagtcacag tgttttgcat 12840
aggtgcacca gaacttgaga tccctttcag gaggcctacg catttgcatc ggattatctg 12900
tggaaagagg taggttcatt attatgttcg tcatcaaaat tcctaaaaga acatagaagc 12960
caagaaagat aagcagtctt gtagcggctt gcattcgcat tcgtgagtat tgtttgcgaa 13020
catagcttat gagagcaatg gtagctatca tacaaagaca agtatgtttg atattctcag 13080
tgtcaatgac cctatcctcc tttatttgca ttaactcatc aaaccaatca taatatgtgg 13140
gatttgtaca gctcatgatg tgaaagcggc gtatcctaga gtctgtaaag tagctacatc 13200
tttcattata gcgagaaacc ctacatattt gtatgtaatc atttttttttg atgagagggt 13260 gtttttcaaa aaccttattt ttacaaaccc cgtgtcgaca attccagcag aagtcacacg 13320
attttgcata ggtgcaccaa tactcaagct ctctctttgg aggtctccgg gtcattggta 13380
actctcctgt tcctggaaaa gattggcttt gaatgaccgg ctgcatgacc gccagtacca 13440
aaaggaacac aatcaccttc atggctgcaa cttataagtt gcaacttatg ggttgcaata 13500
ctgcaacgta taggttgcac cttatagatc gcgactcaaa aggtatgaaa accttaccct 13560
caatacagaa tttaagtttt aatcctgata atgtatctgt ttatgaaaaa aaattttttt 13620
tactcatgta tgaattctta tacgaatcat aatatgtagg ctgagaataa taattcatat 13680
acggtgttgc gggctcaata aaaattttgt taccacaaaa aataaatgct ggatttttaa 13740
gatatatatc tattaatgac taaacccttt atacgctgta ggctgaaaac aatccatata 13800

```
atgaatatac ggtgatttgg gtttaataaa atacatacaa cggtcaaaat agcgggcaat  13860
actacattga ctaatataat cattttgttt aataagaggc atatcatccc acactttatt  13920
tttacaaata ccgttcctac attcccagca gaaatcacag tgttttccat acgtgcacca  13980
gtattcaagc tctcttatag gaggcgtata agtccttggt aaattttgtt tcatataaaa  14040
gatggaaagg ggtcgattta aacccggctg agatagccaa atcaaaatac ataaaagagc  14100
aagtagtttc atagtggtat ttagatgtaa atttttatag tatgcaaata caatgtaacc  14160
tacaaataca atactaaata caaggtaaaa acaacaatgt cttataatga ttggccaata  14220
atcacccccc cccccccatt tttccatgaa tatttcattt cctgtatagg gtctaggatg  14280
tgaacactcc atgttatgat gattaggcat tttaactgat atttcataaa aacaccccca  14340
ggaattgcga ttaactatac agtttacaat cgaattcatc gaattagact catttgttat  14400
cttattttta caaatgccat tttgacaatc ccagcagaag tcacaattct ttacatacgt  14460
acaccaatat ggaagctcct ccttaggagg atgctgggtt cttggtaatt ctggtaattc  14520
atgtgcaaga atgaggactg agtagcccaa caaaagtcct agaaccttca tgttgtgtcc  14580
aaatggcacc tgtcatttta aaaaagattt aaattttgct accgcaaaaa aaaatccagt  14640
atgtattttt ttaatacata taattattga agtcttataa gataaagccg agaacactat  14700
attttgtata gatgatgtat ccggtattca aactctctta taagtacatg taggaaatgg  14760
tcaattattc aagattggct gagataacaa caaaaccaaa atactcaaaa gcataagtaa  14820
tttcatggtt gtactcagtc gtagattttt gcagatcgca aatgcaacgc aaccagcaaa  14880
tacaaagcta aatacaaggt aaaaacaata ataccttata atgattggcc aattcttatc  14940
cctccatttt tccatgaaca tttcatgttc ataaagtcta ggatacgaac aacatttcat  15000
gctatgatga ttaggtattt taagtgatat ttcataaaaa caccacgggg ttgttggtga  15060
ttgataggta agaataagga tggttgaata acctagtaaa agtcctagaa aaaccttcat  15120
attgcgttca taccacagat gttatttaaa aaaaatataa attttacagt atgtgatata  15180
cacataccac aaaaatgttc ttatattaac taaaatatgt gggcagagag caattcatat  15240
aatgaatata tggtatttta ggctcaataa agtacataca acgatcaata aaacgggtaa  15300
tactacattt actgatgtaa tcattttgaa caataagagg catatcatcc aaaaccttat  15360
ttttacaaat accattctta caatcccagc agaaatcaca gtgttttcca tacgtacacc  15420
aatattcaag ttctctcata ggaggcgtat aggtccttgg taaaatttgt ttcgtataaa  15480
agatggaaag gggtcgattt aaaactggct gtgctaacca aaccaaaata ctcaaaagaa  15540
cgaaaagttt catggttgta ctcagacgca gattcttaca aagcgcacat acaaagcagc  15600
ctgtatatgc aataccaatg atgaaataga gacagtattg ctttatagat aattgttgat  15660
ggtcaccccc cccccccccc ccatgtttgc atgaatattt catttcctgt atagggtcta  15720
ggatgtaaac attccatgct aaagtgatta ggcattttag atgaaatttc atataaacag  15780
gattgagtct tggaatcacg gaaaactcta cagtttacaa tagaatgatt ggagtcaatg  15840
aaacgagatt ccgttatctt atttttgcaa atgccatctt gacagtccca acagaaatcg  15900
cattgtggta catacgtaca ccaatatgaa agctcactct tgggaggatg ctgggttctt  15960
ggtaagtctg gtaattcatg tgcgagaatg aggactgagt agcccaacaa aagtcccaga  16020
agaaccttca tgttgcgtct aaatgacacc tgcacttaca aaaaaaaatt taaattttga  16080
atataacaca aaaaaaccac cttaaaattt cttatattat ttcttggatc tgccccgacg  16140
```

-continued

```
tcatacaatg tattaaaatt atagaccaat catctttttg tatataggct aatcatcttt  16200
atatatagat tttagatgtt tgcttgttgt atcaacttaa ctgctagcga agaaaatgga  16260
taaaaacttt ctgtattttt ataggttgaa atcattttat gcacatcgct aggatctaat  16320
attttatttt gaagaaccga atgtgggctt aaaatttttt tcttagaaaa aagtagaatc  16380
ataatattgc tatgtttttg tttaatgatt tcttgtatct tttttgtata cgggttggca  16440
cccaaaccta tacaaaaata tacattactc aaataactac cttctataca taatcttttt  16500
tccccacgta ttttcctatt tatttcccta tttatggaat taaaggatat caatctctct  16560
aaggcacggt caaggtctgc gcctaaggca aaacaataat atatacctaa tttattccca  16620
gggcgtgcac aggcaagaaa catcatgacg tttagcccta aacgtatatt ttcctgaaaa  16680
tacgcatgat gaacttcatc aatattacct aagtatatgg ccgtttgtaa acgccaaaga  16740
tctaaatgag gaaatttttt actaagataa tgaataggtt ttgtgagatt aaaatctatg  16800
gcgaacttat accaaaattt taatacaagt gtatttctcg tcatttcttc ttctttttca  16860
tctaaatata agataaaacg attgtaaaca aagtctatca ataggtgaaa atcattgcta  16920
ttaaagctgt cgagaatcaa aatattgtca taataaattt cgatcgccag taaaaccttt  16980
tttcgtttga cgagataaac aaacatatta tacaacccta catctaaaaa ttctggattg  17040
gctcctagtt ggatacacag gtctttagtc tgcttcgttt tggcacacat gatgccaaaa  17100
ttaatatcag caccccataa aacaaataac ttgattagat cagtctggtt ttccttcaca  17160
gcttttacta aggctctgtc aagctcatag ctgtcgacat cagagcatga catagagcca  17220
ccggttacca ttttacattg cttacaaaaa cctatgggtc cgttttccca ccatagtcca  17280
agctgttgta gaataaaaat atcatcctca tgataatttg aaaaagcctt ggtttctatc  17340
aagacttttt ttgtaagaac ctgtaaagag ttcatcgtat tattatgaat aacaggagta  17400
aacgtaatca attataaaag tgattttttc gaaaaaaact ttagatggtt gaaaatgata  17460
atgtacatgt tcatacaaaa aatagatgca gtgatgtcta aaatcaaaat ttaattttct  17520
atgtaaaaag tacagactta cttatttggg ttaaattgtt tattttaaac tttaattaac  17580
cgtttgagtt agcgatgttt gatttatctt ccatactcat ccgggggggg ggtccttata  17640
gctctgacat tattgtggat tattgaatat aatgaatact tcatagatgc taaacatttt  17700
aatagtagtt ctgaggctta attgtactct ataaatttat aaaaactttt tgatcaaaat  17760
ttaatttctt ataaaaagag tacagacgtc gcttgtttaa gcttcatcat gtttcattca  17820
ttactttcta caattacggg ggggggagtc ccctcatagc tttagtattg ctatggttta  17880
ctaattatta tgtagaattt atagaagcat atgtacctga aagtatacct actctataaa  17940
attaaataat ttcagtatat tttttttatg aatagaacgg aaatgatata aaaataattt  18000
aatattgcaa aaaaaattca taatgttggt atgtattata aacataatag catgtgtaat  18060
ttataaactg actcctctat ataattatta gatgaggtac caacctactt atgatatgcc  18120
gatgatagat attgtatact ataaaacaaa attattttaa atgtattcat ggatacatta  18180
taacattttt accgcaaatt gtctctcagc gaagaaaatg aatgaaacgt ttctgtatat  18240
tcataggttg aaattatttt acgcacttca ctaggttcta atattttctt atgaagtatt  18300
gaatgggggc ttaaaagtcc tttcttaaaa agaagtttca tcataacatt cttttcttgt  18360
ctaagaagag tttcttgtat tttttttgta taaggattgg cacccaaact tatacaaaaa  18420
tgtacattac tccaaatacc ataatttgaa aagaaagtta tttccctatt tacttcatga  18480
ttaatgaaac ctatcaacgt ctctaaggcc gtattgatat ttgcgcctaa ggcaaaacaa  18540
```

-continued

```
tagtatatac ccaatttatt ttgagggtac atacaagcaa gcgacatcat gtcatttgga  18600
tctaaacgta tattttcctg aaaatatgca tgatggattt catcaacatt acctaagtat  18660
acagccgttt ttaaacgcca ataatctagg tgaggaaatt tcttactaag aaaacgaata  18720
ggttttataa gattaaactc tatggcgatc ttaaaccaaa attttaatac atatgtattt  18780
tttatcattt tttctttttc atctaaattt aagataaaac gattgtaaat aaagtctatc  18840
aacacgtaaa aatcatggct atcaaaactg tcgagaatcg aaatattgtc ataataaata  18900
tctatagcta ataagacctt ttgttgttta attagatcaa caaacatatt atacaaccct  18960
acatctaaaa attttggatc agctcctagt tgaatacaca gaactttcgt cctttccgtc  19020
ttggcacata tgatgccata attaatgttg gcaccccata aaacaaataa cttgattaga  19080
tcagtctggt ttttcttcac agccctcacc aaggctctgt caagctcata gctgtcaaca  19140
tcagaacatg acatagagcc actggttacc attttacatt gtttacaaaa acctatgggt  19200
ccgttttccc accataatcc aagctgctgt aaaataaaaa tatcatcctc atgataattt  19260
gaaaaagcct tgttttctat caagactttt tttgtaagaa cctgtaaaga attcatcgta  19320
ttatcatgaa tgaaagcagt aaatgtaatc aattataaaa ttgacttatt gaagagaaat  19380
gttaaatgag tgaaatcggt gtttatgatg atgtacatga tcatacgaag aaacacgttc  19440
actggtgtcc atgatcaaaa tttaatgttt tacgtaaaaa gtacagatgt taactgttta  19500
gtttaaacat aaatttaacc tttagtttaa accctagtta atgatgttta atatttcttc  19560
tatactcatt cagggaagtg taatgattct aatactgttg ttatggatta ttaatgaaaa  19620
ctttacagat gctggaggga ataattttaa tcatactgtt ttaatgtagc tatataagct  19680
ttcatcaaaa tttaattttt ttttataaaa atacacgaat taaactaaag tctaaacttt  19740
agtttgacta tttgagttaa tgatgcttaa cttatcttcc atgcttatca aggggggggt  19800
cctaatagtt ttgatactat tgttgtggat tgttgaatat aataaatact ttatagatgc  19860
tgaaatgttt gaaaataata gtacatcaat gttgtaagtt tgatcaaaat ttaatttctc  19920
ataaaaaagg tacacatcaa cattgctcat ttaagtttca tgatgtttga ttcattactt  19980
cctacaatta ctgggggggg gggggggtc tttaatagct ttagcattgt tatggtttgc  20040
tgactattat gtagaattca tagaagcacg tttagatagt aatatcactg cagtgtagat  20100
tatgaaatac atactaaact aatttcagta tatttttttt gttcatataa gttaaggtac  20160
aaaaatgatt aaacattgca aaaaaagaaa atcacaatgc tattatacat agtgatcata  20220
gtggcttgta tcatttctaa actagttcca aatgaatatt gggcaataca tctatttttt  20280
atcattatga tttttatggt atatatgtat gaaaagttag atatacatca aaaatctcag  20340
ttctggaatt ataccatgtc aggcttatct ggacataacg tacaggtaac atgtaagtgt  20400
tactaaatac tatgaagtat ctattttttt ttgttgtaaa aaaaagaact tgatagtatt  20460
ttttaaaaaa taaaataatt aattgtacgt caacttcctt attttattct ttaaaaataa  20520
ctcgtaagta ttatttatct attttttgaa aaaatagatg taatcggttt catcatttag  20580
gtgtgtattt ctttttagca tctatcaaga attcattgtt tagtgatatg aaaacaatga  20640
atgatcatta tcttctattt aacaaccacc taaataaatg aacgtctttt tcatcttaac  20700
tgattaccaa aagttatttt gcgaaaaggc atacatatga tcaatatcag acctacaatg  20760
aatatttcca taatatccct ttattgtaat aattctattt ttgcattccg atatctcatc  20820
atctgtgcta ttatatgttt ccataactgt ttcatcatca aacataaatc ctgttaaata  20880
```

```
ggcaaaagac tttaatcccg gatagatttt taccattttc ctgagagccg tgtatagctt  20940
gtaataaatg gccaaaaata tgcaataaag cgtagaaaga gagtaatttt tggcataaaa  21000
gattttgaag gtttgatgaa tggctaaatc gcatataata taagatacga ttttaaagcg  21060
cacctgttca cgcagatttg ttgaaaaatt cgtggaaaga tttaacaaat aaaaggttat  21120
taatagttgc tcatcattcc ccttatacga catcgtcaga cgctctaata ttttactact  21180
aggcacatct gccacatgtt gaacatttaa agcctgttct tcttctgtgt tacggcaaaa  21240
gagccgtgcg tattcaggtg aagctcccca ggataacaac gtccttgcta cggctaaatt  21300
ttttttgacg atgactttta tcagaaataa gtctttattt ttgcattgat cactatgcga  21360
atttgtatag ttgacgccgt tgcattgagt acattgatat aatgttttac aattccagcg  21420
tagccctaaa tggtataaaa gaactgtatt ttcgacataa gcatgctgat taacgatgtt  21480
tttgagacaa cacgtcgtta aggacaccat attgtctcca atttgttaga taaaagtctt  21540
tactaaaaaa atagattttt agttttaaca atcgagattt tattatttgg atgcatcatc  21600
aaaaagattt ataagtataa gaggttgtat aagaaaaaaa atgatgttat actatttatg  21660
ttaaaattta atttatcata taaaaagtac agatttaatc agttggttaa actatttagt  21720
taattaaact aaatagttta accatttagt cagactactt ggttagcaat gtttgagctt  21780
tcttccattc ttatccgggg gggggtccta atcgttctaa tactattgtg gatagttgaa  21840
tataatgaag actttataga tgctataatg atgaattcta gtatgcctgt ataaaataat  21900
taaccttttt gatcaaaatt taattttttt ataaaaagct acagagtagt gttttattaa  21960
acgtggctta tttaaaagtt acacaatgtt aaaatctcta cttactttaa ttctttgtgg  22020
ggttttatta actttatcca tattatggct tactacttac catgtagaac ttatagaggc  22080
aatagatgat ttctacgact gaaatataga atagtccatt ttctatttgt aaaataatga  22140
tttatattct ttcctaaaaa tgatacttta tatggtttga aaacaaatat taacaacttg  22200
attttttttt ctataaataa actataaatg aaaatagtaa aactcataga gtcttataag  22260
tgaacatctt cataatgtta ctcaaacgtt ggactattaa aaaatattcc gtgtgcatta  22320
ttgcttttaa tcagtatgat tactttatac gaagccgcta ttaaaacgct tatcacacac  22380
cgaaaacaaa ttttaaaaca ccccgatagc cgtgaaattt tactagcttt ggggttgtac  22440
tgggataaaa ctcatattct tgttaaatgt cgtgaatgtg ggaatatgag tcttaccgga  22500
aaacacagta caaaatgtat taacattaat tgtctactta ttcttgccat aaaaaaaaag  22560
aataagcgta ttgttgatac cttgatagga atgggcgcgg atgtaacata tatacatctt  22620
ttaaagaata agataaaact gtcatacaac cagctgtcta tgcttaaaag caactcgcag  22680
atttcattga aggagcttca tgctatatgc tatcttttat atggtcggct tcccaaaaaa  22740
attaaacaag ggatgcgact gtgtaaaaca atggcgggac tatgtggtga acttttatgt  22800
gcatttttag ctccgtaaat gataatatgt atttaaaaca aacagatatt accaaaatat  22860
attctatgta cataaatatct gggaaattat ttttttttct catacccctta aatataaaaa  22920
tattgggttt cttcactaaa ctttagaggt aaaaattttt ctttgttttg caccatcatg  22980
tatgggttta ggctgtccca gggattgttt atttgaatat ttcctaaata ggaacacaac  23040
gccatgatca tatatctttc attctggtaa gctttttgat acatcttcaa agatgccgta  23100
cctccgagtg tgtaacagca aacaaacgtc cgtacttttc catgggtcgc agcccattcc  23160
attccgtagc tcagcatctt ttgctgtatt tttttattcg ctttataaaa aaagtttttc  23220
atccattcca cgttctcata aaaacaggca cttaaaaaga gcactagggg tagtgtagtc  23280
```

-continued

```
ttattataga atgtaggaat gtatgtttta gttatttttt tcaacgcgtg ttccatacta  23340
tgttttaccg ccataaaaat acaaaaccaa taccaacttt ttctataaaa ggttttgctg  23400
tacacatata aacgagcaaa atatatttca aactctatat tctttttata aaaaaactcg  23460
agacagtcgt ttatgttacg actttttcta aatacctcaa aaacagtaat taattcactg  23520
tcgctgtgga aatgttcgta agctaactgt ttaatgtctt taggggtcaa ttcttttttt  23580
gggagcagtg gtttgagatt cggcaaaggt cgtctaaagt agtgagcgaa cttttcattc  23640
gctccccaac acaaaagccg ataagccagc atgtagttat cacgttttac cgcgtaaata  23700
agcaaatagt ttatattgat acatgtacca tgttgctgcc cgtttggaca tatgttgccg  23760
cattctgaac acttatgaat gagatcatag ttcttacaac ataaccccaa acgggttagt  23820
acttctttgt cacgttttaa aaactcgaca tgattcttta atgttaatgc tttgagcgca  23880
atgttaaata aactctgcat tttattaaaa tgaggttagt atcatgtttt agtataaaat  23940
ttagcggctg tttacataat gctaaataaa cttaacgttc ctactaaacc aaaaaaaaat  24000
caaattgact aagtcataga gaatttgacg atgttggtag gtaatttttt aacatggtat  24060
atattttttt agggtcggtt atattaggta ataaaagagg acgtgccgtt aaagtatttt  24120
gcttaagatc ctttagatcc ttacaaaaat atagattgtt cgtctgatga tgccactgtg  24180
ttgcagtgat ggcttgatca atatcacctc ccaagacaaa acagtagtat atcgttaaaa  24240
agttgtaatc tttcatacaa gccaactgca tcattttatc gatgtccata tgaacgatct  24300
tttgctcgta tatttcatga aggtcaaata cattgttgaa gtaaatggcg cacatgagtc  24360
gccacatact aaggtgccca tatgtttgat agaaaaagga gatagctctt ttaagcttat  24420
attttactgc tatggcatag cagtatttaa cgaatacgtt catgggtaca ttatctaaga  24480
tataaaatat gaaaaacttt aactctcgat gaatctcttc ccccatttcc tgtacattta  24540
gagcttccaa cataggattt ttatcaaata tttcatgaca taaaataatg ttattgctcg  24600
ttttatgacg cattaaaccg gtgaaaattt ccttattatt taaactatct ttagctccta  24660
actttcgaca cagctcctga gtttgttccg tcctagcaca ggtcagccca taataaatgt  24720
ttgctcccca ctcggtgaac agccttatta cgtcatagtt attttctttt atggccatga  24780
ttaatgccac atcaagatga agaagttccc ccttaaaggg ggttgagctt aaaataacgt  24840
aattacagta gtgacataag ctaatgggct tgttttgcca ccataagcca caatatttta  24900
aaatataatg atactcctca ggcacgctct gtttggccac agccttttttg gccagggttt  24960
gcaaggagag catgataact tcttgaaaaa aaaactcaaa ttaagttcct actttttttaa  25020
aatattagta tggacagatc taccatcata tgaaggaatt ctttcatcgt taaacactga  25080
agagataata ctttcatcgt atagagaata tcatgtcaat ccatatattg aatgttatat  25140
atcattaaac ccatcattaa tatagtgttt atgtgctatg gacaggtttt ttgaatgata  25200
atcttttaac atacgtttta taacttcggg atcagtttct tttaaagata aagaatcatt  25260
catgttataa caatttaatg ataacatgct ggcaatgaac gagttgtctt tttgatgcgc  25320
tagagtcttt ccctcctcaa aggcattggc gcctaagtct atacaaaaga atatgtttcc  25380
gatattatag aactgaatag aatgaaacat ggcctgattg atatcagccc ctaagacgac  25440
gcaacagtaa taaatcgtta aatagttata gttcttgcga caggcccact ttagcatttc  25500
attcatgtct atgcgaatcc tctccttttc gtacacttcg tgaagttcaa acacattatt  25560
gtaaaaaagg gcgcacataa gccgccaccg atgtagatga gcatatctct gataaaaata  25620
```

-continued gcaaatcgcc tccttaaggt tacattctat tgccatcgcg taccaatatt tagtaaacat 25680
ctcgcttaat atatcggttt ctaccattaa tccctccagt tgttcataaa tcattccctt 25740
tacttcaaaa cgatttatgg tatctaaaat gggattatta gaaaatacct catggcagaa 25800
aatgatgtta ctgctagtta gatcacgttt caatgtgtaa aaaaatcgta aaatttcctg 25860
gtcatttaac tgttctttgg cacctagctg cctgcacagg tctcgggtgt gctccgtgtt 25920
gacagaaagc aaaccgtagt tgatgtttgc accccactcg gtgaacaatt ctattagatc 25980
gtgattgttt tcctccacag ctttcaccaa ggccgcgtta agatttgtgc cgttcttaaa 26040
atacggcgtc catatttttct tttgatgata catgataggg ccattatgcc accatagacc 26100
gcagcacttc aaaaaatgag gatggcattt ggccggatac tggctggcca gcaccttttt 26160
ggtgagagtc tgcagagaga ggaccatatt tcttttttttt gaaaaaatca aattaaaaaa 26220
atcatgcttg tttagcatac atgtaatatt gttataatta cgttataatt acgttataat 26280
tacgttataa ctatattata acaatggtat aacaatggta taacaatgtt ataacaatgt 26340
tataacgatg tatcattgat gtcatcattc aactaggcca acatactttt taatttatag 26400
tttttaata gatgatatat tttgttagga tctgcttctt ttaacgttaa tagcgaggag 26460
tctgcactat aaatgtctaa tgataaatga tgagatatca aatagtaatt ccgttgctct 26520
gctagggcct ttgcctcttc aaaggcgtcg gctcccagat ctatacaaaa gaacaagtta 26580
tccatattat aaaatcgtac gcaggcaagc atagctgaat taatattagc tcctaagaga 26640
aaacaataat atatggttaa aaaattgtta tcttttgtgc aggccatccg catcatttca 26700
tccacgtcca tgcggatctt ttcctttca tacaaattat gtaggtcaaa cagcttatta 26760
aaacaaagag cacagattaa ccaccacgta tttagatact taaaatgttg gtaaacataa 26820
gaaatggcct ccctaagatt atcctgcaat gccactataa aacagtatat cgttaacata 26880
tcaccatccg acatattact taatatgtcg gtgtcttcta ctaacctttt caacttccaa 26940
tatatggatg accttatttc ccttataatg acataggctg gaaagggatt atcattaaaa 27000
agtttaagac ataagataat attactgcta gtagtgccag ggtgtattaa tttaaagaac 27060
atgtgcataa tcttcttttt atccacgcgg tacttggctc ctaattccca gcaaaattct 27120
cgaacaggcg gcgtattggc gcaaattaac ccatagttga tgtctgcgcc ccattctgta 27180
aacagtttta ttaactgata gttgttttcc tttgtagcca acattagtgc cgtattaagg 27240
tccaagccgt ctgcaaagct tggcagcttt atcagcatat gtttgcaatc aagggaaatt 27300
ggggccttat accaccatag tccgcagcgt tctaagataa catggtactc aatagatact 27360
tgctgtctgg ctagtacctt tttggcgaag gattgtaagg aaggaaacat cctgtttctt 27420
ttttttttaa aaatcaatta tctttgttca taatcaagaa aaatccccat atttattgag 27480
tgataatttt ttaacatgca atttattttt tcagggtccg taacgatcga caacagagaa 27540
ataaccggat tgtaatgctt taatgataag gcatgggcta tcagataatt ttccttttgt 27600
tctgccaaag ctttgccctc ctcaaaggca tcggcaccca ggtctataca aaagaacagg 27660
tttccaagat tatagttttg tatggaaaca agcatggctt gattgatgtt ggctcccatg 27720
ataaaacagt agtaaatggc cgaatagcta taatcttgga tgcaggctat gtgcatcatt 27780
tcatcaatat ccatgcggac cctttctatt tcgtacagct cgtgaaggtc gaacacgttg 27840
ttgtaaaaaa gggcgcacat gagccgccac ctatgtagac gcgggtattt ctggtaaaag 27900
tagcggatag catctttgag gtcatagtcc accgctatcg cgtaccagta tttggttaaa 27960
acagtgctaa agctatcatc atggtccagc atgaaggtta tctccatgag ccctcttaac 28020

-continued

```
tcccacatga tttccccct cagatccaga ttatctataa tccttaaatt ggggttattg  28080
gaaaacacct cgtggcaaaa gataatattg ctactggttt tatcgcgcgt tgtatcaaag  28140
aaaattttta aaatatactc tctttctaaa tattctttgg ctcccagctc tttgcacaga  28200
tcacgggtat tttccgtgag agcacaaatc attccatagt taatatctgc accccattca  28260
gtaaacagct ttatcaagtc atgattattc tccttcacgg ctttcatcag tcctatgttt  28320
aactcgatac cttgactaaa acaggttgac cttataaata atttattgcg tcgaatatga  28380
agcataatgg ggccattatg ccaccacagg ccacaacact tcaggacatg atattgatct  28440
accggtatac actgcccggc cagtactttc ttcgtgaggg attgcaggga aggcaacatg  28500
cctttccatc ctttgacgga aatcaaatta tctactaata actatcagtg tttatattaa  28560
gtatttagat attatcccgg gctggatacg tagtatcgct attcacatgt acttccaact  28620
ctagccggag cctgcagggt catttatttt taatattgat tctttttgt atttaatcat  28680
ttagagaagg tcatcatagg agccagatgt tctctctcca gaacttatgt cgaaaaacat  28740
tacctaaccg taaacttcct gaattttttg acgaatatat attacaactg ctgggattat  28800
actgggaaaa ccatggaact attcaacgag caggaaacaa ctgtgtgctt atacagcaac  28860
ataccctcat tcccgtaaat gaagccctga gaacagcagc atctgaagaa aattatgaga  28920
tcgtgagcct tttattagcg tgggagggga acctttacta tgctattata ggggctctag  28980
agggcaaccg ccacgactta attcgtaaat atgatgacca aatcaaggac catcatgaaa  29040
ttctgccatt cattgacgat ccagtcatat ttcacaaatg ccatatcatg cggcaatgct  29100
tttttgattg tattttatat caagctgtaa aatatagtaa gtttcgcgtt cttctttact  29160
ttaaacatag attagaggat gatttgccct tcactcattt acttattgaa aaggcatgta  29220
aagatcataa ttatgaagtt attaaatgga tatatgaaaa cctacatatc tacaatatga  29280
tagatacctt tgaatgtgct attgcccata aggatctaca tctatattgt ttggggtata  29340
gatttatata taacagaatc gtacccgata agtatcatca tttagatatt cgcatgcttt  29400
caagcctaca actcctacat aaggtggcag ccaaaggata cttagatttt atcctagaaa  29460
ccttaaagta tgatcataat aaagataata taaatattat tctaacacaa gctgcaacct  29520
ataaccatag aaaaatttta atctatttca ttcctcaatc aacccacgca cagatagaac  29580
aatgtttact agtggcgata aaagcaaaat cttccaggaa aaccttgaac ttactactgt  29640
ctcacctaaa cctttccatc aacctcatca aaaaaataag ccattatgtt gccacttaca  29700
attcaacaaa tataataggc attctgagta tgcggcggaa aaagaagata tatttagata  29760
tcatattgac aaaatttgta aaaaaagcta tttttaataa gtttgtcgtt cgatgtatgg  29820
atacattttc tataaacccg gaaagaatcc ttaaaatagc cgcgcgaata aataggatga  29880
tgttagtgaa aaaaatatct gaacatgttt ggaaaaatca tgcggttaga cttaaatacc  29940
ttaaacatgc ggtacacacg atgaagcata aagatgggaa aaatagactc atgaacttta  30000
tctatgatcg ctgttattac catatgcaag gggaagaaat ctttagcctc gcaagatttt  30060
atgcaatcca tcatgcacca aagttgtttg acgtttttta tgattgttgt atcctagata  30120
cgatacgatt caaaagcctt cttttagatt gttcacatat cataggtaaa aacgctcatg  30180
atgctaccaa tatcaacatc gtgaacaagt atatcggcaa cctgtttgtt atgggagttc  30240
ttagcaaaaa agaaatctta caggactatc catccattta ttctaaacaa tacatgcctt  30300
agtttatttt ttttgcggcc gaaacattat tcttacccta gaaaacgctt atagtcatct  30360
```

-continued

```
taaatcatag gtaaggaaga tcatcatatt ttttgaaacg taattttttta acgcatgatc 30420
tatgatttca gggtccgtgc ttttaggcaa cggggtggtg gccggactat aaatctttag 30480
ggataaaatg ttctttataa gctcataccc ttcccctaaa gctgtagtac cctcttcgaa 30540
aacatcagcc cccagatcta tacaaaagaa catgttttct atattatagt actgtattga 30600
gctaagcatg gcttgattga tgttggcgcc caggacatag cagtagtaca tggttgaaag 30660
gttgtggtct ttgatgcagg cgatccgcat catctcttct atgtccatat ggatcttgtc 30720
cttttcatac gcctcatgaa ggtcaaacac attattaaaa caaagagcac atgttaaccg 30780
ccacgtattc aggtgtgtat atttttggta aaaatactgt atggcctctt tcaggttata 30840
gcgtatggct atagcgtacc agtatttgag tagtaatgta ctgagcgaaa actcattatt 30900
tagcagatcg gtttttacta ttaactccct taactcccag aaaatttcta tcctcatttt 30960
tatattattt actttttgta atatcggatt gttggaaaac acctcatggc ataaaataat 31020
gttactacta gttttatgaa actttagatc tataaaaatt tgtaaaattt cttcttcatt 31080
caaggtttcc ttggcaccta gctctcgaca gaggtcccag gtgtgctccg tgttgacaga 31140
taccagcccg tagttgatgt ccgcccccca ctctgcaaac agttttataa ggttgtagtt 31200
gttttccctt acagccttca ctaacgccgt atttaggttt aagccctctt taatacctgc 31260
tgattttatg agccttaggt tatgatcaaa cgtgatcgga gcatcatgcc accataggtc 31320
ataacacttt aaaagataat gttggttcgt gggcacgcat tgtccagcca acaccttttt 31380
ggtcagagat tgcagggaag gcaacatgtc tcttcatctt ttaaaaaaaa atcaaattaa 31440
ttagccgaat aaatttttct ttcgagggct ttttaaaaga gctctttaag agctctttaa 31500
gagcttttta agagattaaa aaattattct tgctggcatt ctgccaagta tgcggcattc 31560
ctatcatcta tagtatatta tgagaatatt cccaaatgat ggataagttt tttgatttat 31620
aatcttttaa taaactgctt atttcttcgg ggtcctttaa gtttagtggc aaggaagcat 31680
ctgagctgta aatatccaaa gccaaactat ggctcagaaa attataacct ttttgttccg 31740
ctatggcacg accctcttca aaggcattac cacccaaatc tatacagaaa aatatattac 31800
cgatgttata atattgtact gaagtaagca tagcttggtt gatgttgccc cccagcgcgt 31860
aacagtaata tattgttaat ggattgttat ccttggtaga agccagacat atcatgtcat 31920
ggacgtctat ttggatgttt tccttgtggt acatctcatg aagctcatat attttgttat 31980
aatacaggag acattttaat cgccattcat taagatccgt atatttctca tctagaaaac 32040
aaatggcgtc cttacaatcg tattgtactg ctttggcgta ccaatacttc actagtaaac 32100
catttaactc gtccgtttct tttatttcta tgagccccca tagtctttta taaattaagc 32160
cccttaattg tataacaaat ttgttttcta aaataggatt attcataaaa atttcatggc 32220
acaaaataat actgccgctg gttttattgt gcattatcct ggtaaaaata cggaaaatat 32280
cgttgtcctc tagagtttct ttggcgccta gctgtctaca caactctcgg atgtgcttcg 32340
tattgataga aagcaaacca tagttgatat ttgcgcccca ctctgtaaag agctttatca 32400
gactatagtt gttttcctta acagctatta ttaatgccac acgaaggtct atatcttctc 32460
ctaaaaatcc tgattttatt tgtattcggc cacgatccat acaaagcttg agaggagcat 32520
catgccacca taggccacaa tatttcaaaa tgcagtgttc atctattgac aaacactggc 32580
tggctatcgt ctttttgacg agggtctgca gagagagcgg caacgacatg tttctttttc 32640
accaaaaaaa aatcaaatgt tctcgtcttt aaaggttaat tcatgttctt aaaatgttca 32700
tttcatgata gtgattaata atatggttta ataacgctag aaggcttgtt tataagacag 32760
```

-continued

```
tcataagcag tctataagac agtctataag cagtctataa gacagtctat gacttagtct  32820
ataactataa tttctggatg ggctgtaaga tactcttcgg ctcgtttcag attttttgaa  32880
gtatatgtct ttagcatatc atatatttcc tggggttcgg ttacatctaa taccaaggtc  32940
acatcacggc tgaaaagctg ctttactaag aaaatgttgc tcaagttata catataagct  33000
ttgtgcgcaa tgagttgtgc cctatcaaaa tcggcagccc ccaaatcaat acagaaaaac  33060
atgtttaaag tattattgtt atagatagaa agattcatgc cataatcgag actagccccc  33120
aacctatgac agtaataaat ggccgcgtaa tttttttccc gcaagcaagc aaatttcatc  33180
atcagattag ggctgatgca aatctctttt tcacgacaca actcgtgtat gtcaaaaatg  33240
ttattaaaat aaaggctaca agctacccgc caatagaggt gatttttatg ccttttatag  33300
aaatagtgaa tagcctttgt aaaattatgt cgtaatgcca gggcaaacca aaactttgtt  33360
aataggtggt gcgccgtatc cccgtcaac ggaatgtttg aacaggtgta cgtaactgtg  33420
tctaaagtgg ttctagttac ggtttccaag agtggattat gacaaaacat gtcataaccc  33480
agcagaactc ctgcacagga ttttagcctg gccacttctt ttaaaatttc cagaagacgg  33540
ggttcggata caggcgttaa gcctcccagt tccgcacaca gccgctttag atacacggca  33600
ggaacacgta taagcccata ttcaggattt gcgccccaat ccacaaataa acgtataagt  33660
tcaagattat cgctcttcac ggcctttact agcgccgctt cgagacaaag atcatcctca  33720
gaaaaacact gtaaatgttt atacgaaaaa acttgcttac aattgttaca taggtgaata  33780
ggacctaaat cccaccacaa accaaaacgc tgcaacgtat aatcatagtc acttgaaaga  33840
taattgcatg ccacaacttt tttggccaac gtttgtaaag acaacatact aagtttaaaa  33900
catcttaaat ctaagctagc taactttcaa gaaaaccctc tatccctaag aatatatctt  33960
ataactagac ttatagcagt aaaaatcaac tttggttatt ctttttaata taaaacgtct  34020
aattacttgc aaaggactat aaagcccatt ttcctcagct agaattttta ttttttaatg  34080
aagtaggggg atatgttttc ccttcaagac ctttgccgaa agcatctttt tattcttccc  34140
gatgtttttg gcgagcatgt actacaacga ttaggactgt attggagatg tcacggctcc  34200
cttcaacgca taggagacga ccacatactc atacgacggg atctcatcct ttccaccaac  34260
gaggccttaa gaatggcggg agaggaagga aacaatgaag tagtaaagct cttgttactg  34320
tggaagggaa atcttcatta cgccgtcata ggagccttgc agggtgatca atatgacctg  34380
atccataagt atgaaaacca aatcggcgac tttcatttta tcttaccatt gattcaagac  34440
gcgaatacgt ttgaaaaatg ccacgcttta gaacgttttt gtggtgtttc atgtctgcta  34500
aaacatgcta caaaatacaa catgctccct attctccaaa aataccaaga agagctgtct  34560
atgagagcgt atcttcacga aaccctattt gaactagcat gcctatggca gaggtatgat  34620
gtccttaaat ggatagagca aaccatacat gtttacgacc taaagattat gtttaatatt  34680
gccatctcca agagggatct gactatgtac tccttaggat atattttcct ttttgataga  34740
gggaacaccg aagctacgtt gctaacgcaa catctcaaga agacagcggc caaagggctc  34800
ctccactttg tgctagaaac gttaaaatac ggcggcaaca tagataccgt cctgacccaa  34860
gccgtaaagt acaatcatag aaaactttta gattattttc tgcgtcaact acctcgtaaa  34920
catattgaaa aacttttgtt gctggccgtg caggaaaagg cttctaaaaa aacattgaac  34980
ttactgttgt cacatttaaa ctactccgtg aaacgcatca aaaaactacc gcgctatgtg  35040
atagagtacg agtccacctt ggtgataaag attttattaa aaaaaagagt gaacctgata  35100
```

-continued

```
gatgccatgt tggaaaagat ggtaagatat ttttctgcga cgaaagtgag gacgatcatg  35160
gatgagcttt cgattagtcc ggaaagagtc attaagatgg ctatacagaa aatgagaacg  35220
gatatcgtaa tccatacttc ttatgtttgg gaggatgatc tagaacgtct tactcgtctt  35280
aaaaatatgg tatacaccat aaagtacgaa catgggaaaa aaatgttaat taaagtcatg  35340
cacggcatat acaaaaactt attatacggc gaaagggaaa aagtcatgtt ttatttagcc  35400
aagctctatg ttgctcaaaa cgcggccacc caattcagag acatttgtaa ggactgttac  35460
aaactggatg tggcacggtt taaaccgcgg tttaagcaac taatattaga ctgtttagaa  35520
attattacta aaaaatcttg ctatagtatc ctggaaatct tagaaaaaca tattatttcc  35580
ctgtttacta tgaaagttat gactgaagaa gaaaaaaacc tatgtttaga aatattatat  35640
aaagtaattc attataaaac aatacaatgt taaaattcaa tagatatcca tcattaatat  35700
tgattatatt ttcgaatatt atcttctatg gtgcaagata atcatctagc gcgtgaaaca  35760
tgtcctcttc tcttcaggaa ctttgtcgaa aaaagctgcc tgactgcata cttccagagt  35820
tttttgacga ctatgtattg caactgttag gactgcactg gcaagatcat ggttcccttc  35880
agcgtatcga gaagaaccag atacttgttc aacaggaacc catccatatc aatgaagcac  35940
tcaaagtagc agcatcggaa gggaactatg aaatcgtaga gctgttgttg tcatgggagg  36000
cagatccccg ctacgccgtc gtaggagccc tagaaagcaa atactatgac ctggtttaca  36060
aatactatga ccaagttaaa gactgccatg atatcttgcc gctgattcaa aatccggaaa  36120
cattcgaaag atgtcatgag ttaaacagca cctgttcact gaaatgctta ttcaagcatg  36180
ctgtgataaa tgacatgctg ccgattcttc aaaaatatac agactatctg gataggtggg  36240
agtattgcag ccagatgctg ttcgaactgg catgtagtaa aaaaaaatat gagatggttg  36300
tgtggataga gggagttcta ggcgtcggca aagttacatc tcttttcacc attgcgatta  36360
gcaacagaga cctacagctg tattctctgg gctactcaat tatccttgag aatttgtact  36420
cctgtggaca ggaccccaag tttttactaa atcatttcct gcgagacgtt tcaataaaag  36480
ggcttctacc ctttgtaatc aaaaccatag aatatggtgg aagcaaggag atagccataa  36540
ctctggctaa aaaatatcag cataaacata ttttgaaata cttcgaaacc tgggaaagct  36600
aggttcagta tggtgtactc actattgtag tgaatcgtat cctgtaaatt ttgtaaaaaa  36660
gcttaaactt ttgaccacat catattgttt tagaaatctc aaaccagtga acaacagtct  36720
tatcatacat taaaattcca gtaaaattta tatttttttt ggtaaacaaa tgttttctct  36780
tcaagacatc tgtcggaaac atctttttca acttcctgac gcttttgatg aatatatatt  36840
acaagcgcta ggactatact gggaaaaaca cggatctctt caacgaataa gaaaggacgc  36900
tgtgtttgta cagcgaaaca tcgtcctttc taccaatgag gccctgagaa tcgcagcctc  36960
agagggaaac gaaagggtaa taaaacttct gttatcatgg gagggaaatt ttcattatgt  37020
gatcatagga gctctagagg gtgaccaata tgacctaatt cataagtatg atagtcaaat  37080
taaagactac cacatgattt tatcattgat ccaaaatgca aatacctttg aaaagtgtca  37140
tcagttatcc aatagtaata tgtggtgtct tatacagaat gctataaaat ataatatgct  37200
ccctattctc caaaaacaca gaaatattct gacacatgag ggagagaatc aggaattgtt  37260
tgagatggca tgtgaggaac agaaatatga catagtttta tggataggac aaaccctaat  37320
gttaaatgag ccggagttta tttttgatat cgccttcgaa cggatagatt tttctttatt  37380
aacaatgggt tatagccttc tttttgataa caagatgagt agtatagaca ttcatgatga  37440
agaagatctt acttcattac caacagaaca cctcgaaaaa gcagccacta agggatgttt  37500
```

cttctttatg ctagaaactt taaaacatgg tggaaatgta aatatggcag tcttatctaa 37560
agctgttgag tataatcata gaaaaatttt agaccatttt attcggcggc aaaaatgttt 37620
atcacgtgaa gagattgaaa acctattatt aaccgccata accaattgtg catccataaa 37680
aacgttaaac ttactcttgt cttacctaaa ctattccgta aaaaatatca ttggaaaaat 37740
agtacaacat gtcataaaag atggtgatta taccatcata ttacttttaa aaaaaaagaa 37800
aataaaccta gtggaacctg ttttaacagg ttttatagat tattactata gctattgttt 37860
tataaaacat tttatccaag agtttgctat tcgtccggaa aaactgatta aaatggccgc 37920
gcgaaaaggt aaactaaata tgattatcga attccttaac gaaaaatatg ttcataaaga 37980
tgatcttgga actatattta aatatctcaa aaccctagta tgtaccatga aacataaaaa 38040
aggaaaagag acattaattg ttcttattca taaaatatat caagatattc atctggagac 38100
taaagaaaaa tttaaattat taagatttta tgtcatgcat gatgcaacta tccaatttct 38160
atctatgtgc aaagactgtt ttaatttagc cggttttaaa ccatttgttt tagaatgttt 38220
ggatattgct attaaaaaaa attaccctga tatgatacaa tatatagaaa ttctatcgaa 38280
atctgagtaa aatttatttt tttgatcaga gtaagaaaat gttctccctc caggagatct 38340
gtcgaaagaa catctacttt ctacctgact ggctcggtga gcatgtgatt cagcgactag 38400
gtctgtactg ggaaaaacat ggttctcttc agcgaatcgg agacaactat gtacttatac 38460
aacaggacct catcatcccc atcaatgaag ccctaagaat ggcaggggag gaggggaatg 38520
atgaggtggt acaactccta ttactatggg agggaaacat tcattatgcc atcataggag 38580
ctttggagag tgaccattat agcctaatac gtaagctcta tgaccaaatc gaagactgtc 38640
acgacatcct tcccttgatt caagacccaa aactctttga aaaatgccat gaattagata 38700
aatcttgtaa cattttatgt ctcgtattac acgccgtaaa aaacgatatg ctttgcattc 38760
ttcaagagta taaaatgcat ctaagtggag aggatattca agtggtgttt gaaacagcat 38820
gccgttcaca aaaaaacgat attgtgtcat ggatgggaca aaatattgca atatacaacc 38880
ccgaagttat ttttgatatt gcctttgata agatgaatgt gtccttatta tctataggt 38940
atacgcttct tttcaatcat catataaata atacgaacga aaatattaat tctttattga 39000
cacaacatct tgaatgggct gccggcatgg gccttcttca ttttatgctg gaaactttaa 39060
agtatggcgg ggatgtaacg ataatagtct tgtctgaggc cgtaaaatat gaccacagaa 39120
agattttaga ttattttctc cgtcgaaaaa acttgtacca agaagatctt gaagaactat 39180
tattgttggc gatacgtgca gattgttcta aaaagacctt aaacttgtta ttatcttact 39240
taaactattc cataaacaat atccgtaaaa aaatattaca atgtgtaaaa gaatatgaaa 39300
cgaccgttat tataaaaatt ttacggaaaa gaaagataaa tctgatagag cccattttgg 39360
cagactttat aggatatcat agctatacct atatggtaga ttttatgcgt gagttttcca 39420
tccatccgga aaaaatgatc aaaatggctg cacgagaatc gagggaggac ttgatcataa 39480
aattttccaa aaaagtttgc aaagagccta aagatagact tcactatctc aaaagcttag 39540
tgtatactat gcgacataaa gaaggcaaac aactgttaat ttatacaatc cataacttat 39600
acaaagcttg tcatctagag agtaaagaaa tgtttaattt ggcacgattt tatgcacggc 39660
ataatgcagt gatccagttc aaatcgattt gccacgatct ctccaagctc aatattaata 39720
tcaaaaactt gttgttagaa tgtttaggta ttgctattaa aaaaaattac tttcaactta 39780
tcaaaacaat agaaacggat atgcgttatg agtaacattt ttagatgagg gaagattcta 39840

-continued

```
ccaaactaac taagaccttt cgctagaatg tatcttattg ttaatataga tgagatatgt  39900
cattgtgaaa aaatagatta ggtaggttgt gaaaaacaga ttaaacttaa aattatgtgt  39960
attatgtaaa attttagaaa taaaaattta ttttttttta ttgagggtac ggaaaatgtt  40020
ctccctacag gacctctgtc ggaagaacat tttcttcctt ccaaatgatt ttagcaagca  40080
taccctacaa tggctgggat tatattggaa agagcatgga tccgtccatc gagcagaaaa  40140
agacagcata atgatacaga atgaattggt tctttctatc aatgatgctt tacagcttgc  40200
aggagaggag ggggacacag atgtagtaca gctcttgtta ttatgggagg gaaatctgca  40260
ttatgccatc ataggagcct tgaagactga aaaatataac ctaatatgtg agtatcatag  40320
ccaaattcag gactggcata ttctcctacc catgattcaa gatccagaaa cattcgaaaa  40380
atgtcatgat ttaagccttg gatgtgactt tatttgcctt ctccaacatg ctgtaaaata  40440
caacatgctt tctattcttg tcaaatataa ggaggatcta ctaaatgcaa ggattaggca  40500
tcgtatccaa tccctgtttg ttttggcatg cgaaaatcgg agaattgaaa ttattgattg  40560
gataggccaa aatctgccaa ttcctgaacc tgatgccatt tttagcattg ctgttgctac  40620
aagagattta gaactgtttt ccttagggta caagattatt tttgattaca tgcaaagaca  40680
gggaatcatt caattaacca atggagttcg catggttgtg ctaaatcgtc acattagcat  40740
ggcaatagat aatggtcttt taccttttgt tctggaaact ttaaaacatg gtgggaatat  40800
acatagagcc ttatcttatg cagtaacaca caatagaaga aaaattctgg attatcttat  40860
tcgccagaaa aatatagccc ctaatacaat tgaaagactt ttatatctgg ccgtgaaaaa  40920
tcaatcttcc aggaaaactt tgaacttgtt gctatcttac ataaattaca aggtgaaaaa  40980
tgttaaaaag ctggtagagc atgtagtaaa tgagaaatcc actcttgtgt taaaaatttt  41040
attagaaaaa aaggaaaatc tagtggatgc tgttttaaca agacttgtaa aacattctac  41100
atatttccag gtgagagaat ttatccagga gttttccatc agcccagaaa aattcattaa  41160
aatagctgtg cgggaaaaga aaaatgtgtt aatcgaggct atttctgaag atatttggga  41220
aaatcccaca gaaagaatta cttatctcaa acagatagtg cacaccataa aatatgaaag  41280
tggaaggcga tttttggtag acatcattca cagcatttac caaagttact cactaaaaca  41340
cgaagatatt cttaaactgg caacatttta tgtcaaacac aatgcaatca cccattttaa  41400
agacctctgc aaatatcttt ggctgaacag aggaacagaa agtaagaaac tgtttttaga  41460
gtgtttagaa attgctgatg agaaggagtt tcctgatatt aaaagtattg tgagtgaata  41520
tattaactac ttgtttactg caggagctat taccaaggaa gaaatcatgc aagcctatga  41580
tgctttagag tagccatgta ttaacattct gaaagtagaa taaaatatac tatatactaa  41640
aaaccaaatt agccattttt aactatcttc ttcttaaaaa ctctggataa aaatttattt  41700
ttttttaatt tgggtaggga aaatgttctc ccttcaggac ctctgtcgga agaacacctt  41760
cttccttcca agtgatttta gcaagcatac cctgcatttg ctggggttat actggaaggg  41820
gcatggatct atccaaagga taaagaatga tggtgtgctt atagagcatg atcttactct  41880
ttccatcaat gaagccttaa ttcttgcagg agaagaggga aacaatgaag tagtaaagct  41940
cttgttacta tgggaaggaa atcttcatta tgccatcata ggagctttga ggactgagaa  42000
ctataaccta gtatgtgagt accatagtca aattcaggac tggcatgttc tcctcccttt  42060
gattcaagat ccagaaacat tcgaaaaatg tcatgattta agccttgaat gtgatctttc  42120
atgccttctc caacatgctg taaaatataa catgctttcg attcttgtta aatataaaga  42180
ggatctacta aatgtactat ttaggcaaca aattcaagga ctatttattt tagcatgtga  42240
```

-continued

```
aaatcggaag cttgagattc ttacgtggat gggtcaaaat ctgccaattc ctgatcctga  42300
gcctattttt agcattgctg ttgtcacaaa agatttagaa atgttttcct tagggtacaa  42360
gattgttttt gaatacatgg aaaaccaagg acttcattta acccaggtag ttcgtatggt  42420
tatgctaaat catcactttg gcatggtaat aaataaagga cttttaccct ttgtgctgga  42480
aattttaaat tatggtggga atgtaaatag agccttatct tatgctgtca cacaaaataa  42540
aagaaagatt ttagaccatg ttgttcgcca aaagaatata ccccataaaa ccattgaaag  42600
aatgttgcat ctggctgtaa aaaagcatgc tcccaggaaa actctgaact tgttactatc  42660
ttacataaat tacaaggtga aaaatgttaa aaagttgtta gaacatgtag tgaaatacaa  42720
ctctactctt gtgataagac tcttgttaga aaaaaagaaa aacctgctgg atgctacttt  42780
gacaagatat gtcaaagatt ctacatactt tcaggtgaaa gaatttatgc aagacttctc  42840
catcagccca gaaaaattca ttaaaatagc tgtgcgggaa aagagaaatg tgttgatcaa  42900
gggtatttct gaagatattt gggaaaatcc cgcggaaaga atcaggaatc ttaagcagat  42960
agtgtgtacc ataaaatatg aaagtggaag acaattcctg ataaatatca ttcacaccat  43020
ttaccagagt tattctttga aacctgaaga aattcttaaa ttggcaacat tttatgtcaa  43080
acacaatgca accacccatt ttaaagatct ctgcaaatat ctttggctga acagaagaac  43140
agaaagtaag aaactgtttt tagagtgctt ggaaattgct gataagaagg agtttcctga  43200
tattaaaagt attgtgagtg aatacattaa ctatttgttt actgcaggag ctattaccaa  43260
ggaagaaatc atgcaagcct atgctttgga gtatgccatg tattaaattt ctgaatcagt  43320
aagcaataga tagattttag aatatgctgt attaagttag tttctgaata agtaattaat  43380
agatagattt tagtttatgt aaaaatgtta acatttgttc ataagtttta gataccattt  43440
tagagttact tttttagata ttactatttt agccattatt atcttaaata atcactattt  43500
tagataggtc cccgtattaa aaaccaaatt aaccattatc tatgttttta ataatacttt  43560
ttaaaaaccc tccataaaaa tttatttttt tttcataaaa gtagagaaaa tgttctccct  43620
acaggatctc tgtcggaaga acctttttct tccacttgag cccttaggca agcatgtggt  43680
tcaacggctg ggattatact gggaaggcca tggttcagtt aaacgagtgg gtgattgctt  43740
tatatgtgta gaccagattt ggatgctatc aatccataag gctatacaaa ttgcagcctc  43800
ggaaggaaat gagaacattg tcaagctttt cttactatgg aaggggagtc tacaatatgc  43860
catcatagga gccttagagg gcaggcaata tgatctgatt caaaaatatt acaaccaaat  43920
tggggactgc catcagattc taccactgat tcaagatcca gaaatttacg aaagatgtca  43980
tgaattaaat gttacatgta cctttcaatg cttatttcaa catgctataa gagataacat  44040
gctgcccatt ttccaaaaat atggagaaga tctgaatgga aacaggagaa tggttcaact  44100
tctgtatgag atggcatgcc gattacaaaa ttatgatatc atcaaatgga taggatctaa  44160
cctgcatgtt tataacttgg aagccatttt tagcattgct tttgttagaa aggatttaac  44220
tttgtattct ttaggctaca tgcttcttct gggtagaatg agtactgaag atagaaactt  44280
tatctcaatc ataacacgcc atcttgaata cgcatcaaaa aagggacttt ttgactttgt  44340
actagaatct ttgaaatatg gaggtcaagt ggatacagtg ttgtttcagg ctgtaaaata  44400
caaccatagg aaaattttgg cccattttat tcatgaaatt ccccgtgaaa cggttgaaaa  44460
gctgatactc catgctgtgg agtcacgggc ctccagaaaa acattcaacc tgcttttatc  44520
ttccataaac tactgtgtga accctttgt caaaaaacta ctgcacgctg tggtgaaaca  44580
```

-continued caagtacatg cttatcataa agcttttgct cgagcggccc aaaaagaaga taaacctggt 44640
agatgctgct ctattcaaac ttgtaaaata ctctacttat acagaaatag taaaatacat 44700
gggtgagttt tctgtggacc caaaaagggt ggtcaaaatg gcagcacgac tcatgagagt 44760
ggacctgatt aaaaagattt ctaatgatgc atgggaagat aaactagaga gaatcaagca 44820
ccttaaacag atggtaaata ccatgaacca cagaaatgga aaaaatctat tgatgtacaa 44880
tattcacaat attactggat atacctatct gaacaccaaa gaagcattta acttaacaag 44940
attttatgct gtccacaatg caacatgttt gtttaaagaa atgtgtaaaa gctgttttgt 45000
acatgataaa atacagctca gagaattgct tgaagattgt ttacatattg ctaataggca 45060
tgattatatc cagattgcag aaaccgcaga tgaatgtatc aaatatatag atcttattac 45120
atttaagtaa accatgtata tatcaagtaa atccagatta aatcaggcta attgtaaata 45180
gttgtagata ccatataatg aatgttttat taggatagta gttcagttaa gatagtagtt 45240
tagttaagat agtagtttag ttaagatagt agttatgtta agatagtagt tctgttaaga 45300
taatagttta gttaaaacta gttcatgtta agttaatagt tttgttaaga caatagttca 45360
tttaagtcaa tagttcagtt aagtcaatag ttttgttaag tcaatagttt agttaagtca 45420
atagtttagt taagtcaata gtttagttaa gtcaatagtt atattaagac attagttctg 45480
ctaatacatt agttttgtta agataataaa aatttatttt tttttcatca gggtagagaa 45540
aatgttctcc ctacaggagc tctgccggaa gaacatttac attcttcctt acccccttggc 45600 taagcatgta cttcaacaac tagggctgta ctggaaggga catggatctc ttcaacgaat 45660
cggagatgac catgtactct tacagcagga cctgatcttt tccatcaacg aggccttaag 45720
aatggcagga gaggaaggaa acaatgaagt agtaaagctc ttgttactat gggagggaaa 45780
ccttcattat gccatcatag gagctttaga gggcgaccga tatgacctta tccataaata 45840
ttatgatcaa attggggact gccacaagat tcttccttta atccaagacc cgcaaatctt 45900
tgaaaaatgc catgaattga gtaactcctg taatattcga tgccttttag aacatgcagt 45960
aaaacacgac atgctttcta ttcttcaaaa acacaaggag caaataagat tacacatggc 46020
attaacccaa atactatttg aattggcgtg tcatgaacgt aaaaatgaca tcattagatg 46080
gatcggttat tccctgcaca tacaccatct agagactatt tttgatgttg cattcgccca 46140
taaaaattta tccttatacg ttttagggta tgaacttctc atgcacaaag taaatacaga 46200
ggctgcatat atagaattac ccaatttgct atcatatcac cttcgaactg cggcggcagg 46260
aggtcttctt aactttatgt tagaaacaat aaagcatggt ggatatctgg ataaaacggt 46320
tttatccgcg gctatcaggt acaagcatag gaaaattgtg gctcatttta ttcatcaggt 46380
tccccgtaaa accgttaaaa aactgttact ctatgctgtg caggctcggg cccccaaaaa 46440
aacactgaac ctacttttat cttccttaaa ctactccgtg cacaccatca ccaaacaact 46500
cgtacacaat gtcgtcatct acagttccac gcttatcgta aagcttttac tcatgcggcg 46560
aaaaaacaag ttaaacctag tagatgccgt tttagccaga cttgtaaaat attccaccta 46620
tacagacatt gtacaattca tgggtgagtt ttctgtgagc ccagaaaggg tgatcaaaat 46680
ggctgcacgg gaatccagga cctttctgat tgaaatgatc tccaaagctg cttggggaaa 46740
tcacccacag acgttgattc atcatctcaa acaactaacc aataccatga agcctcaatc 46800
tggaaaagac cacatcatat ataccatcca ctatatttat ctaaactcta atatgctggt 46860
agcggaggag gaaaaaaata tttttaaatt agcaaaattt tatgcgaatc ataatgcggt 46920
aaacaggttt aaacaaattt gtgaagacta ttatatatta gatgcacgat ttaaaacact 46980
tattttagaa tgttttgaaa ttgccgtcca gaaaaactat cctagaattg caaatattgt 47040
ggatgactat attcgattcc ttttttacag gggaaatata accgaggaag aaattcgtga 47100
agcctattct ttaaaagatg ctgaggttta tgtagattta aaatggttac aacaaggaga 47160
aatggtttaa accaaatccg gtttaaacta aatccaattt aaactacatt tggtttatca 47220
ttagtcattg aaaccatcga aaaaaaagct atttgtttat ccccataaac tcatcttttt 47280
tttgtctcaa agtttgacac taaaattcag tgttttatag tgtttataat taagtgtttt 47340
gcatgcattg cagaaatttt catctttttt aattggttca ataccacatg tcatacaata 47400
tgttgtttga ttatcaagat taactttatg aaaggaaagt aagtgagccg caaatttaaa 47460
agtaaaatat ctttcattta aaatgatctt atgaatgtat tttcgataag gaggaatgaa 47520
agcatttgcc aaaataaatc gcataaaagg cttggaaaaa cccatatctt ctaatctttt 47580
gtgggtataa accctatttt ggtgttttac aaaaacttca ttgttataat agtcgttata 47640
gctatcaatc atttttttaa gtcctataat gcccaaggtt gcacgcataa agccacagtt 47700
tctgctccaa aaagcatgca cctgtaaagg gtgcttttca tataaccaat tacaaaattt 47760
cattccgcaa cagtagcatg ttatttcagt gggggatgta tagaataatc cggcattcga 47820
aaatttttca taatttttta tgtcatggat tgcgaagctt tgatttcgtg catctatgga 47880
gctatagcct acatatttag gttttacttc aaataatcgc aaagagatgt atggatctat 47940
cgtatttatt ttaggaaaca tttcataatt ttaaattctt atatataata taaaaaaaat 48000
tacaaacatt tgtaatgatc atcctcaatt gaaggctgag ttgtaggctt tatttttcta 48060
attatacgaa gaaggtaggt tctcataaag ccttcaagat gactattgat gtttccaata 48120
cattttctca atgagttcat aaacccagac attttgctaa tggcttggca aagtgccaac 48180
aagttgtcca caaagtactg gtagattgcc actagctata gctagctata gtgagccaac 48240
ctctctgtat gtattttata tatttcattt tttaatagat ttaatatttt tataaaaaaa 48300
tatttagttt tttatacaag aatgtcgaca aaaaaaaagc ccacaattac caagcaagag 48360
ctttactcct tagtagcggc agatacccag ttaaataaag cattgattga aagaatcttt 48420
acaagtcagc aaaaaataat acaaaatgct ttaaagcaca atcaagaagt tattatacca 48480
cccggaatca agttcaccgt cgttacggtg aaagctaaac ctgctcgcca gggccataat 48540
cccgccacag gagagcctat tcaaattaaa gctaaacctg aacataaagc cgtaaagata 48600
cgagcattga aacctgtcca tgatatgtta aactaaacta taaagtcata ttcttcttta 48660
tcgttattat cttcaatata tttttgccaa tcgaaatcga ataaattcag atcctggaca 48720
tttaaatact tatcatcgta cattttaata taatttaaac atgagttgtt gtcaaaaact 48780
tttagcgttt ttgttaaaat tatcatatga ataatttcct tattaagagt tgccggaata 48840
atacaaaacc tatttttagg tacatcatcc atgataatag taaaattagt aaaaattgtt 48900
tcttgttttt cttttgtttc aaataaacgt tgtaaggtta aaggtttctc gttcaatggt 48960
ttctttgaag ataaaaagaa tgtataatct ggtttaaagg tatttttggt ttcaatcgtg 49020
attccatctg cttgagcata tactaaacca gaccaaatat aacggtccac tattacaata 49080
taatttagct taagtagcac tgcaatttct gcgataaatt cactacgatg ttttgtaaat 49140
aatttatgta attgttccga tgacatttct atggttttat ttaacacctg caatataaga 49200
tcaccggtgg tcgtgtctgg attaggaaaa tgtatacata tagcattata atccatgcat 49260
tccaatgttt cttttaattt cattgcctgt gtgcttttc ccacaccatt gattccctcg 49320

-continued

```
atggcaatga gtattccacg catgattaat aaaaggaaaa aaagaattca gtttttaaca  49380
tttcttacaa atcttttttt atacaacatt gtacaacact gcattagcgg tatatgatgt  49440
tatagcttca ttaaatattt gcttttatat aatctttacc aacctatatt tggtagatca  49500
ctgcagatgg tcataaatag gccataacta agataaaaat tatttcagac gctactacgg  49560
tagtattatt aaaatcatgt gtggcaatgt atgacgtctt aatagataaa acatttaagg  49620
aaaacaaatt tgaataaaaa aaataattgt tatgatggcg ttgttacaca aagaaaagct  49680
tatagagtgc atctatcatg agctagaaaa tggcgggaca atattgcttc taacaaaaaa  49740
tattgttgtg tcagaaattt catacattgg caatacttat aaatatttta cctttaatga  49800
caatcatgat ctgataagca aagaagatct taaaggagca acatccaaaa acattgctaa  49860
aatgatttat aattggatta taaaaaatcc tcaaaataat aagatttgga gtggtgagcc  49920
gcgtactcaa atttattttg aaaatgattt atatcataca aattacaatc ataaatgtat  49980
aaaagatttt tggaatgttt caacttcagt cggtcctcat atctttaatg atcgtagcat  50040
ttggtgtact aaatgcacat ccttttaccc atttaccaac attatgtcgc ccaatatatt  50100
ccaataaatt agatatcttt gctattaaaa tagttaaaaa ccttatagga taattaggta  50160
ctttattacg ataaattatg atattttata attagttact ttattataat taatctcttt  50220
attaatgaat tatcataaga taactaatta tttttttcca tatatcagat aataaatctg  50280
atatgggcta aaagtatgtt tcaaactatt tacaatagaa tttctgttaa gaaaacatac  50340
ataatttgaa taaaattttt ttaaatatca ccgaaacaat caacatggtg ttaatagagt  50400
ttttaacagg tttcttctat ttatatggaa agagactgtt ttccattagt aaagtcatgg  50460
acatgatatg tctagactat tataccatta ttcctgctcc tctggcgatg atgttagcgg  50520
caagactaaa aaactatgac ctcatgaaac gactgcacga atgggaaatc tctattgact  50580
acgctctact tgtagtagat gatgtgccgt ctattgacta ttgcttaagt cttggcgcta  50640
gatccccgac tagagcacaa aaaagagaac tgctgaggga caacacgttt aatcccgtgt  50700
ataagtatct tatgaactgt tccggcttcc caacaaagag agaaaaaaac attccttgtg  50760
atgttcaatg cgaaagactg caaaaaaaca ttataaaaga actggtattt aactgctctg  50820
tactgcttga aatggtactg cacacagaaa gagaatatgc atacgcccta cactgtgctg  50880
caaaacataa ccaattgccc atcctcatgt attgttggca acaatccaca gacgcggaat  50940
ctattttgtt gaaaacctgc tgttctgata agaacatcaa ttgttttaac tattgtattc  51000
tatatggcgg cgcccaaaat ttggatgctg caatggtgga agcggcaaag cacgatgccc  51060
ggatgctgat aaactactgt gtcatgcttg gtggaagatc cttaaacgaa gcaaaagaaa  51120
cggctgccat gtttggacac attgaatgcg cacaacactg ttttaaactg cagtcttacg  51180
tcgtggacac atcgaataca gacgacactg attaaagcga caatcttacg tcatgaacga  51240
ctgtcttttg agtatctata cttacattat atttttttat gaaaaaaata taaaggttgt  51300
atacaaacct ttgtatacaa gaaatttgga tcattaaaca ataattaatt tggacacagg  51360
aaacgatcta gatcgatcaa aaagctattt tttttgcaca cagaacattt agataattga  51420
gagattactt tccatacttg ttaagctttt ttacacacag gaactttgga ttctgttcag  51480
gaagttttc atagacatta tgtttacagc cagtaataat aattttgggc tttttcttaa  51540
accaccggtg gaaaacatcc agcttgtaaa gagggaaatg catgtagaga ggttttggta  51600
gtcatggtta agagatttga ctaactccat gtttcctgta aagactgccc agtcccaagc  51660
agtaaaacct ctatgatagt ctttttgagt cggatctgct ccaaatttta tgagagaaag  51720
```

-continued

```
catatttaaa gaacggcccc gtattgcggc cttcatcaca ggagtcatcc cattaaaatt  51780
cggtaaacaa attctggtcc catttttttcc gaaatagccc aacacccctt ccaggattaa  51840
atgatttttt ttctcagcta aataatgtaa agcagagttt ccatctttat ccctcctatg  51900
agggttaatt atttctccag gataagattc ttgttcaaaa agaaatttta aaaagtctat  51960
acgtccgtag atgcatatcc acatgaatac cgaggatcca tttttatcgc atctattgac  52020
aatccacgga tctgttttaa aaaattcctc aaatagtgta agattcccat ttctaatatg  52080
tttttaatc catttaacaa acaagttttc tatctccctt tctggaaaca tgtgttccat  52140
tttgaatgtc gcccctactc cactatatga ttttactcct ttaattttta atgtcctttt  52200
ttttcggact tctttggata agctgtttat taccatcttt aaatgcctta tagcggggag  52260
gagccaggcc cttttcccat atgtgcggta attcttggtg tttatgcttg cctttggcat  52320
aaccaggcca gtatttttcg atatattcag ggtttgtttt tacgtattct ttaaaggtcc  52380
gataggcttc ttgaatacag gtaggctcac cggtataatt tccatgttca tcttccttta  52440
aaaagccatt aaccctgtcc tttctccact taagattgtg ctttccaaaa atgcgatcaa  52500
gatcttgcgc ctgctggggt ggaatcataa atcccttttt aggtcgaagc tttttatttt  52560
ttccatagct tcggccatcg cgttgcgaaa cagtggttag gacgcctgat agtctttcca  52620
tgggcgtcgc atctaatcct atccatccac cctgatgaat atcaatggca acaagctctc  52680
ctttattttg ggcaagccaa gtttccaaga atgccatgct ttcttcccag ggataaggcc  52740
cgccaacacc acgggttgtc caatcttgca aggactccag gtccgacacc tggtaaggct  52800
ctaaagaaga cggttccttg tttttgtact gcaaataaga tttaatgacc catttatacc  52860
atgtgtcgaa ccgcagcgtg gcgcctccaa agtgaaagcc gtcgttgatt ttaggatatc  52920
tgcaacatat ttcaaccgta cgtttgagtt ctgcaaaagc ggccttccaa ggaagtcttt  52980
cgctgcgggt aagacggtct attttgccct gcgtgccata gcgtatggca tgtcgtgcca  53040
attgcaacaa ttctgacacc gatccgtggg ccccgatcca gtttatcgga taggcaacct  53100
ccgaagggtt taaaagatgc tcgtaaaagc gtggatcttc agatgccaag gcgtctgcaa  53160
aggggataat gctagaaaac ctgtctagac atacgttttc tgtgtttact tctaaaggta  53220
gaaaaatggt tgcgtgaggc ttttgaacct gcttgttcag cggtctgcat atgctttgaa  53280
taatgtctct aggactatgt cgcggcgctg caaaaaaatac cgcgtttagt tctggaacct  53340
ctacgccctc ttgaaagagt cgacagttta ataaaataac gggttccttt gaggaacaaa  53400
attctgtaaa tgttttgagg ataacctgtc gcggcagggt tgagtgagct atcagggcat  53460
agacccttg gtctaccaac gccgcgtata gctccttggc ctgtttaata tcacgggtaa  53520
ataccagcat tttaggagcc ggtatattgg tttttaaata ggctaaggcc attataattt  53580
gctttactat gatctgtttc gtggtctcct ctttggtact cggttggtgg gccaatttag  53640
gcgcggctac catctgcaat tcaaaatcat ttacatagcc ggcctctatg ccttctcgca  53700
gatagtagcg aaaggcaacg ccgccaaaaa gttcacgatt tttcatggaa agcggggtgt  53760
cgtacctggg cgttgccgtt aaaaaaagtc ggtgcccttt tttaaagttg agcaacacgt  53820
gggtaaaggg ccgtgtctcc cattcgccgc aaatccggtg acattcatcg ctaataataa  53880
gatcgaaatc atccaccagt agcgtggagg attggtaggt ggcaatcaca agaagagaag  53940
gggcctcccg tatccgtttt gcaataaaga caggattggt ggtcatttct atattgtcgt  54000
gatttagcac aatgcgggtc tggtcagacc ccacaagcaa aacgttcttc aaagaaattc  54060
```

-continued

```
catactgata gagtttttcc agagtctgcc gtagtaggga caggcccggc accaggtaca  54120
aaacttttcc ttgaagataa ttggagagga taagataggc gacgcgagtt ttgccgcatc  54180
ggcaggccat ctgcagaatg gccctcccac ttcgccgcag ctcctgatag cccatattgg  54240
ccgcctcctt ctgataaagt cgatcctcga ttgcagtccg tgtctcatct gtagaaaaaa  54300
ataatacgtc atctgcgaaa tgttcatctt ccacaggagt tatcaccagg tgtctcagtt  54360
tctccttgct tatcagcgga tcagagggca aagatggctc aaccactatc gtggaatcat  54420
tcatctcata ggcgggagaa tcacacaaag tatagcttat gtccagacag tttgcaacat  54480
cctcagccaa ttgttttatt ttttcgggta aaagacatac gagttctttg tttttgacgc  54540
gaaaaaactg tgcacaatat aacacccctg cttcaatttt ttgcgcatcc ttctttgtag  54600
atgtttccaa tgtgaaacaa tacttccatt catccgtaaa acaggttgta taagatccat  54660
catgaagcct agcggccaag tttcctgtgt gcccaacttt atgtaaggat tgggcctcca  54720
gccagggatg aaccgccacg taaaatcctg cgcacatgct atatcaaatt gcagtttctt  54780
aataactgta cacaggatct gaaaaacatg tgattacaaa atttagataa gaaatattta  54840
atattaaaaa tcacagaata catgtcactg tgtagagaga aagccaaaaa ctcctcttga  54900
ccgccgtggg aaatcatcca gggtagtagg ttgtgtttca taaagttgta tgccgtagtg  54960
atcaccgtgg actccagatg gttattggca tctttgcaat actttgccat cttggcagaa  55020
aagacgataa atccacaaat tctaccccag ttgataagat ccttaaacag ctcagtcaca  55080
accccagtaa actgggtttt aatttcttga acactcgtaa gagaaaaggt aattgtaacc  55140
tgtttgttca aacactcatc ataataggtt aaaatttttt ttatttgttg ttgatatggg  55200
ctaagctcat gctctgaaat atcattaatg taatatttaa tatatcccac tagtatttca  55260
ttaatgatat tatgatatat taactcttct ccctccatag cggcacccta tatttttta  55320
tttaggtttc aatgttatca caattgcgat acaattgtga tacaattgtg acacaactgt  55380
gttgtataca acaaatgtta ggccacgtat agcaacctat atgttaagaa atatttttat  55440
cccaacatta gttggaaacg agcagccgca aagaagtcat ttaaaataag ccatttaaag  55500
atttagaatt tatatgtata caactgtaca atggaagcag ttcttaccaa actcgaccag  55560
gaggaaaaaa aggctctcca aaattttcat cgttgtgctt gggaagaaac taaaaatatt  55620
ataaacgatt ttcttgaaat ccctgaggaa cgatgcacct ataaattcaa ctcatacaca  55680
aaaaaaatgg agcttttatt taccccctgaa ttccacaccg cctggcatga agttcctgag  55740
tgcagagagt tcatattaaa ctttttgaga ctcatttcgg gacatcgagt ggtattaaaa  55800
ggccctacat ttgtttttac aaaagagatc aagaatctgg gcattcctag taccatcaat  55860
gttgactttc aggccaacat tgaaaatatg gatgatctac agaagggaaa tctcatcggc  55920
aagatgaata tcaaagaagg ctaaataaaa caactaacat caaaaaacat taaaggctat  55980
gttgtggacg atgcctttgt ctcaatagtt tcgaggtcat ccaataactc atgtaacgta  56040
aaaaagttgg tccatttttt tgaaaacatt aaaagacgtt cgtcttcata aataaaaaag  56100
tcattcgaag gaaaaatgat atactcaata ccatagtctt gtaatatttt ttttaggtct  56160
ctcagggtcc agggatttac caggcttcta cgcgaagtga gcatcataaa aatatctaat  56220
attttttgcg ccataagcca gcgcggattc tcattggccc acaaatcaac aataattctc  56280
ttatcaaccg tgagcattcc tacttgattc gaagaaatga ttagatgccc agcagtccac  56340
cccatgagta gataacgcag cgttgtagaa atgtcacata tggaaggcat tcctccacaa  56400
catgaaccca aattaggatg cgtgtgaaac acaaacatag caggcttgtt ggccaccctg  56460
```

```
ctataaatat cagcaggcat catagcctcg ctgccaaaat aaatgttctc tcctgcccta  56520
taggggcttg gaatgatttc cactatctcg ggtacaccgt ttatcatatt aatgcggccg  56580
caccattcac ggtcatcgtc caaaaatttt ttgatggcac cccgaacatt gtcccagtta  56640
agcaacagag tattcacaat ctcattacgc tccgcccagt attccttaaa acttctttta  56700
gacttgctga gctgttccca ggattcgaac tcagtccaat gttttttttc ttttggggaa  56760
gacttccctt ttgaaacatt ttttgcggct ccaccatcta cactatgatt ttccaaaata  56820
atctccttca tcgtttgagt tatatgggca ttgctaagca ccttagtggt aacctgttta  56880
cctatgtgat ttagcagaaa accaagtttg tccatttgtg tctcaaccat ttattcttaa  56940
caaaacaaaa aaaaattaaa aatcatcgtc gtttaaaaag agtttgaagg caaacgcatc  57000
atccttaaca cagttctgat actgcgtagg tcttaactcg aaaaagttgg tttttttctac  57060
ttcattaaga aagaatttag tcatctgagg aaaagggttt cccaccttat aaatgctttt  57120
gcactgcatc atgaagcaca aattatctgt aaagtagcgt atatattgaa atagcatttc  57180
ttttgaaaaa ccgggaactc ttcctcttgc cttgtcaaag gcatagttaa taaactcatc  57240
caccaactcc acagcctcct tcaaaatttt gtgaatgatc ttttcctcgg gaatgttata  57300
cacgtaattt gagataagaa aacacgcaaa actacagtgc atcccttcat cacgtgagat  57360
aaactcatta tagcttacaa gccccggcat aatattctgt tccttaagaa actggatcgc  57420
cacaaagtgg ttttgaaata aaatgccttc tacggcggcg aagcccacca gccgctcacc  57480
tagagtgttc ctgtcggggt ccatccactg ccgcacccac tgcgccattt tttttatgat  57540
agggtgtttt tcaatgccgc taaagatgcg ctgttgttcc ttctcatccg ggatcagcgt  57600
ttttacctgt attgagtagg cttcgctatg aacgcactct tgggcagcct gcattgtata  57660
aaagtataac acttccttta ctttaatttc gcgcataaaa ttggttaaaa ggttttcgat  57720
aacaatttcg tcggcaacaa caaagaaggc taaaatttgt ttataaaatt cgcgctgtgg  57780
ctttggcatg gcttcccaat catcaatgtc cttacacatg tccacctcct gcgccgtcca  57840
cgtcaaactt tctaattttt tataccagtt ccaacattcg gggtgctgaa taggaaaaat  57900
agtgaaacgt tgggaatttt caattagtaa ttcctccata tttgaaataa atattaacat  57960
cttcaaattt attggctgcc atggagacgt tttttattga gacgttggca tctgatgtgt  58020
atggaaaggc gttaaatgtt gatttagata gactatcgca ggcgcaggtt aaatataccc  58080
ttcaagagct tatttcctac tgcagcgctc taaccatttt acattatgac tattcaaccc  58140
ttgcggcgcg tctttcggtg taccagctgc accagtcaac ggcctcctcc ttctcaaagg  58200
cggtgaggct gcaggccgca caatcctgct cacgcctgtc cccccagttt gtggacgtcg  58260
tttacaagta caaagccatt tttgacagct acattgacta tagcagagat tacaagctgt  58320
ccctcctggg gatagaaacc atgaaaaatt cttatttgtt aaaaaataaa gatggggtca  58380
tcatggaacg cccgcaggat gcttatatgc gggttgccat catgatctat gggatgggaa  58440
gagtggtcaa tatgaaaatg attctgctaa cctatgacct gctttcccag cacgtcatca  58500
cacacgcgtc gcccaccatg ttcaatgcag gcaccaaaaa gccacaactc tccagctgtt  58560
tcctgctaaa tgtaaatgat aatttagaaa atttatatga tatggtcaaa acggccggca  58620
tcatttcagg cggcggcggt ggaatagggc tgtgcttgtc aggaatacgg gcaaagaata  58680
gttttatttc tggtagtggt cttaaaagta acggcataca gaattatatt gtgctgcaaa  58740
atgcttcaca atgctacgcg aaccagggag gcctacgtcc cggagcctac gccgtctact  58800
```

```
tagagctgtg gcaccaagac atctttacat ttttacaaat gcctcgccta aaaggacaaa  58860
tggctgaaca acggcttaat gcccctaatc tcaagtacgg cctatgggtc cccgacctat  58920
tcatggaaat acttgaagac caaatacaca acagaggcga cggcaaatgg tacctctttt  58980
cgccggatca ggcccccaat ctacataagg tctttgattt ggaacggtcg cagcacgaaa  59040
acgcacaccg cgaatttaaa aagctttact atcagtatgt tgctgaaaaa aggtacaccg  59100
gcgtcacaac ggccaaagag attatcaaag agtggttcaa aacagttgtt caagtaggga  59160
atccctatat cgggtttaaa gatgccataa atcgtaaaag taatctttca catgtaggca  59220
ctatcacgaa ctccaatctt tgtattgaag tcacaatccc ctgctgggag ggtgataagg  59280
ctgaacaagg tgtttgtaat ctggccgcag taaatctagc cgcctttata cgtgaaaatg  59340
gctacgacta ccgtgggctc atagaagcat caggcaatgt cacagaaaat ttagataata  59400
ttatagataa tggctactac cccacagaag ccacgcggag aagcaatatg cgtcaccgac  59460
ctattggcat cggggtcttt ggcctagccg acgtgtttgc gtctttaaaa atgaaatttg  59520
gttcacccga ggccattgcc atggatgagg ccatccatgc ggccctatac tacggggcca  59580
tgcgacgatc catagaactt gcaaaagaaa aaggaagtca tcccagcttt ccggggtctg  59640
cggcctcaaa gggtctactg cagcccgacc tatgggttcg ctgtggtgat ttagtttcct  59700
cctgggaaga acgcgtggca cagacgacgc agggtgtgtt gacgccgaaa aggtggtcgc  59760
agctacgcct ggcggctatg cagggacttc gaaatggata tgtcacagct cttatgccca  59820
ccgcaacctc ctcaaattct acaggaaaaa acgaatgttt tgagcccttt acatccaatc  59880
tatatacacg tagaacgtta agcggggagt ttattgtttt aaataagtat ttaatagacg  59940
atttaaaaga aattaatctt tggacagaag ccattcaaca gcagctacta aatgcgggag  60000
gtagcattca gcacattttg gatataccgg ccgagatccg cgatcggtat aaaacctcca  60060
gggaaatgaa tcaaaaaatt ttaacaaaac acgcggccgc acgaaacccc tttgtatccc  60120
aaagtatgtc cttgaactat tacttttatg aacctgaact aagccaggta cttacagtgc  60180
tcgtcctagg ctggaaaaaa ggtttaacta ccggttccta ttactgtcat tttagccctg  60240
gagcgggtac ccaaaaaaag attataagaa actctgagaa agcgtgtaat gcggactgcg  60300
aggcgtgtct tctgtaggtg tctcgcggta aaagagcagc ggggaccata tggtaaaccc  60360
caacaagagg ataatgaata aaaaaagtaa acaggcatcc attagttcca tattaaattt  60420
ttttttcttc tatataatgg aatattttgt tgcggtagac aatgaaacct ccttgggggt  60480
ttttacttct atagagcaat gtgaagaaac gatgaaacaa taccccggcc tccattatgt  60540
cgtttttaag tatatgtgtc cggcggatgc agaaaataca gatgttgtat atttaatacc  60600
ctcgttaacc ttgcataccc ccatgtttgt agaccactgt ccaaatcgta ccaaacaagc  60660
acgacacgta ttgaaaaaaa taaacttagt gttcgaggaa gagtctattg aaaattggaa  60720
ggtttcagta aatactgtgt tcccccatgt tcacaacaga ttatctgcgc cgaaactttc  60780
catcgacgag gctaatgaag ccgtagaaaa gtttttgata caagcaggac gactcatgtc  60840
tctgtaaatg tctcttcctt tatgggtgac gtctcttcct ttgccgagga agtctctgtt  60900
atgggcaaga ggtttgaaac aacgcaagga ctctgcttaa tctgctgtct cacaaaggga  60960
atcaaactac ctgctttcgt atttttaatg tagtaattac ccttgttgtg atgaatttta  61020
agaccatagc gtagtcccag tactttatta atgaatttta aaattgtttg agggtccgtt  61080
ttattgggct ttttaagctt aaactcaaag ctgatcgcgc ttaaatcata ctgaacaaat  61140
tcatcaacga gtttcgtcat taattgttca ttggtcaata tattagggtc ctgaacgcat  61200
```

ttaaagccgc acttagttaa tagcataata gcgtacatat gagattgaaa actataatta 61260
aattgtagat catgatgctc tgcgtgttgc atggcccatt gatgaaagtt taattcctga 61320
gtttgtaaca tagtgagcga ctcgtatact gtctttccgc ggcttatttg gacacggcca 61380
gtatagttct gttttgtcat aaaactattg tattgttcaa caaatttggg agtaatttta 61440
tgaccgtgcc atgcataaaa ttcgagtagt ttatactttt catacgcaaa taggtcttgc 61500
tggtctactg tgatgccttc ctttaagttt tgtttaattt gtaaagcttt attggcatca 61560
atggtttcag ccgaggcaat gtttacatag tcctggtgtt taatttccat tttaatgctt 61620
gtatattgtt tgactgtctc cagcttttca cccgtcagta taaacacctt agcgccggtg 61680
tcggcgatct ggttaataaa tcgggttata aagtgatttt ttgatagatg ttgtatccgc 61740
attgtttcga gccatagatg gtagtatgga gttttataat atatcggcct acctgtttcc 61800
ttactatacg tgaaggaaag ctggtgattg cttatggtct gaaaaagggt gtcacgtttt 61860
tgtaacgtaa acatttcaat gtcttcgatg gtttctggat agtaattttg tttcccctgt 61920
aagcagattt tataacactt actttttaat tcacgcacgc ggcccaacat ttggcaacat 61980
gtttctacgt cacacgacat attgttaaaa aagccgtata aaacatcaaa tctcttatct 62040
tcgtatgaaa cacccgctga aatcgtgggc gtatagataa ggatatcaac gagcccccaa 62100
taatacgata cattattaaa atgggattcc cgttcatgag cagtgctttt agaactataa 62160
aacccaattt ttttttccgg aaactttttt tggataaatg attgcaacag ccgggcctcc 62220
attaatgaat ttgtagggat aacaattttt ttgtcttcta gcaaatcctt taaaaggtta 62280
tttaaccaag tttctcgtga agaggtaaaa taatacgtgt catgctgggc ccttttatat 62340
tgattccagt gaaagaagat agggacatcc ccgcgaaaac gctgtagaat attatacgtt 62400
cgatttccta ggtttgcgtc caagcatata acataatttg ccgtttcgag catccacatg 62460
aaaatggcaa aagagggagc aaagtatttg tgcaggccgc tattgaattg attaaaaatc 62520
gattctacct catccaaaat aagtaggtct acaggctcgg ctgtggaggt tagccggaaa 62580
agtgattcta cctgaatgat gactctttcg tagctgtcca aatctccagt tacttcgctg 62640
tacaatgtga aattcggtag ccgggattgt atattttttg agaagatctg tcgaaacgtc 62700
acaaaccgta tggtttgttg ttttgaaata gaattattgc cgtagtattt ttgcaaatag 62760
ttgcgcagtt ggacggtttt acctattttc atttgagcct ttacaacaag cgtagggact 62820
cgttcatatt ctcgcatact actttcatca tagatgtgtt tttgagtatc aggcagttct 62880
tcaaagagaa tggactcatg aacctctatg ctctttgtca tcacttggtc cacatatgtt 62940
tccacaaaat tatttgtgcc ggaaaggctg cccatgagaa ggctatgttt attgtcatgg 63000
cgacagtgtt gatacacttt gtttcccgtg actcttaaaa ttagggtatt gtccttatca 63060
tgcatacgct tacatatttc gcagtaactt ggacttgtac gtttaaacaa tactaaattt 63120
ttatgaacac ggaggaagca atgattttta catagtgttc ctgcaaattt taatacctct 63180
tcaagttcac tttgttggat agtatcgcag gaactcggtg ttgtttcttt tacatttgtg 63240
aagatacaag gtaaacacgt cgtttcaaag gggg ttgcta taagggtatc actctttttc 63300
gtggttgtac tggtctcaaa cacctctgca agctcctcat taaacatttt aacacgcatg 63360
ctaccttttt tatgagaccc tatgatgcga aaattttgaa tacttttgtt gacctggggg 63420
tcaacaaaag gataaacgtg tttgggaaga ttttctaaca ctttggatgt aaagactttg 63480
gcctcattat tgtttaatac tgagtatgta taaagtatga tatgaaagga gtatttaagt 63540

-continued

```
tctcgctttt tatttaatcc gatagaatct gttagcaaaa tttgttcacg cgttagattg  63600
atgttataag gtaaagaata tgtctcgtaa aatacatcca tgatgacgtt aattatcatg  63660
tcaaggatgt catagacatt gtcttcgaca ttatcattgt catcaacatt gtcatcagag  63720
tatgacttat ttaccggaaa gtcgatgtca aattttaagc gctgaggcaa aaacccaaat  63780
accacttcgt ggaaacactt ctgctcaaag ggctgagccg cctcccactc ccaaaagtca  63840
tcacgacttg aaaaaactct aaaaagatta ttatattcat ctcgcaccac gaagtgattc  63900
tttaaggttt cgagagaata tttatcctct acggcttctc cttgggagtt acagcgaaga  63960
aacttgaatg tttcttgcat tttgatattt aaaattaaat caattatgat gcggccgcta  64020
atgcggcggt tgacgcggcc gcgccgctga cgcagccatc atacataaag cggcatggcc  64080
gttttataac gactagtcgg ccgttatatg acgaactata taaaaatgaa ttcttttaat  64140
tagagttaag tattgttgat tgtataatcc atcatggttg agccacgcga acagtttttt  64200
caagatctgc tttcagcagt ggatcaacaa atggacactg taaaaaatga cataaaagac  64260
attatgaaag aaaaaacgtc ttttatggta tcattcgaaa actttataga acgttacgat  64320
accatggaaa aaaatattca agaccttcag aataagtacg aagaaatggc ggccaacctt  64380
atgaccgtca tgacggatac aaaaattcag cttggagcca ttatcgccca acttgagatt  64440
ctaatgataa atggcactcc acttccggca aaaaagacaa caattaagga ggctatgccc  64500
ttaccttcat caaacacgaa taatgaacaa acgagtcctc ccgcctcagg caaaacaagt  64560
gaaacaccta aaaaaaatcc cacgaatgcg atgttcttca cgcgtagcga atgggcatcc  64620
tcgaatactt ttcgagaaaa gtttttaaca ccagaaattc aagccatatt ggatgagcag  64680
tttgcaaaca agaccgggat cgaaagattg catgccgagg gtctttacat gtggagaacc  64740
caattctctg acgaacagaa gaaaatggtc aaagagatga tgaagaagta atatttttgg  64800
taaaaatatt tttatcaaaa ttttttttacc aaataataaa aaatattttt tactttttt  64860
tcttcataat atacatagaa tgcctacaaa agctggcaca aaaagtaccg caaataaaaa  64920
aacaacgaag ggctcctcca aatctggttc ttccagaggc cacaccggca aaacccatgc  64980
ttcttcgtcc atgcattccg ggatgctcta taaagatatg gtaaatattg ctagatctag  65040
aggcattccg atttaccaga atggatcgcg tcttactaaa agtgaattgg agaaaaaaat  65100
taaacggtca aaatgaatat aatcaggaaa cttaagcctg gaacaattag ccttgtgctg  65160
ggacccatgt ttgccggcaa aactacgttt cttattcatt gcatttacat gctcgaacgt  65220
ttggaaaaaa aagtagtctt cataaaatct accaaaaaca cccgagacaa aactattaaa  65280
acacactccg gtatacagct acgacccaaa caatgtaaaa tcatagaaag cacacagtta  65340
tctgacgtgg gttctctcac cgatatccat gcagttgtcg tagatgaagc gcattttttt  65400
gacgatttaa tcacatgccg cacttgggca gaggaagaaa aaattattat tcttgcggga  65460
ctcaatgctt ccttcgagca gaaaatgttt ccgcccatcg ttcgtatttt tccttactgc  65520
agctgggtta agtatattgg ccgcacctgt atgaaatgta accaacataa tgcatgcttt  65580
aatgtgcgta agaacgcaga caagacgctt atccttgcgg gaggaagtga actgtacgta  65640
acatgttgta acaactgtct aaaaaataca tttattaagc agttgcaacc tattaaatat  65700
taaaaatctt atacaataat ggatcattat cttaaaaaat tacaagatat ttatacgaag  65760
ctcgagggtc atccctttct ttttagcccg tcgaaaacca atgaaaaaga gtttattact  65820
ctgctaaacc aggccttggc ctcaacgcag ctttaccgca gcatacaaca gctgttttta  65880
acgatgtata agctagatcc cattgggttt attaactata ttaaaacgag taaacaagag  65940
```

-continued

```
tatttatgcc tgttaattaa tcctaaactc gttactaagt ttttaaaaat aacgagcttt  66000
aaaatttaca ttaatttcag gctgaaaact ttttatataa gtcctaataa gtataataat  66060
ttttacaccg ctccctctga agaaaagact aaccatcttc taaaagaaga aaaaacttgg  66120
gcaaagattg ttgaagaagg aggagaagaa tcctaagtcg cttacatttt tttttgctat  66180
ttttatagaa tgtacacgca tgttgatgtt gtcggaatag ctgaagcctc agcggccctc  66240
tacgtgcaaa aagataggga tcgctactta gacgtgctaa caaccattga aaactttatt  66300
taccaacaca aatgcatcat aacaggggaa agcgcccacc tactcttttt aaaaaaaaat  66360
atttatcttt acgaatttta ctccaacaat gtggcggagc acagcaaggc tttggcgacc  66420
ctgctttata aacttgatcc ggaatacctc actcgttaca cagtactcat taccaaaatt  66480
cccaaccatt ggtatgtgat taacgtagat cagcgagaat ttgtgcgcct atatgccatc  66540
ccggcagtta aacaacactt accgattccc attttaccct tctattgcac cagcgcactc  66600
acccagcaag aattgttttg tttaggacct gaactgcagt taatacaaat atattccaag  66660
ctctgtaacc ccaactttgt cgaggaatgg cctacgttgc tcgactacga aaaaagcatg  66720
cggatgttat ttttagaaca gtttccgcaa agattggaaa tgacgggcgg gaagaaggag  66780
gagaaggaaa agcatgaaag tatcattaaa aaaataatac tagaaatggt ctctacccgt  66840
cagcgaatcg ttgttggggg ttacatacaa aaaaacctgt acaaccatgt actcaagaat  66900
agaaatcgtt tacagcttat tacgagctta aatatttatg aagaaaaaga tatcatccag  66960
caattttgtg attcaaatgg actgaagatc aaaatacgta tcaacaatcc gctcttgcct  67020
acaaatccgg aattacggcg tttgactatt tattttaatc ataataatga tgatgatcag  67080
tcatatctaa tagtagatat gtacaacacg ggaagctatg agctagtgcc tacaaatcag  67140
ataaacacgc ttgatggcag ctttttaata ggaacaccct tcgtgcaagc gcgatttttg  67200
ttggtagaga tctgggtgct tatgcttatt gcgcagcaaa ctaaaaagga caccaaaaaa  67260
ataatacaat tttttataaa tcaatatgaa atgcttatga atagtccttg gcccagtatg  67320
gaggcccttt ttccctcaag cagtaaaaga tatttaggca actatgtaga ccctaacgcg  67380
ctcataaagt gggcacaact caaattaaaa agaataccgc ctttttatcc tggaaagccg  67440
gatgaagaat catgttaagc cgattaaaaa atcatgttaa gctggttgaa aaatcatgtt  67500
aagctggttg aaaaactctt ggtgaaagca cggatgtaat attaacattg gccgctcgca  67560
tttcgtgttg aaatacgatg gaagagcgac ggctatctac catgccgata tcggcctgga  67620
catcacagtt catgcacttg tagatgggat gactcgcgtt atagatggca ggctcgccac  67680
agtttctaca gatgtaggag atgcagccat ccgagtcgtc gtgcgatttt tctatgatgg  67740
tttgcatggc gccctgcgcc gtaagcaccc aatgctccat ttctcccaga cgaagacctc  67800
cgtgcgatcg tttgccgtcc aacggctggc ctgtgagggc atccgtgggc ccatagcttg  67860
caacggcgta tcggtcatcc agcacaaatt tttgcaggcg ctggtgatag gtcggtccta  67920
tgaagatggc cgcatcaaag tactcgccgg tctggccgtt gaacattttt tggcatccat  67980
tgaagcgtag accttcttgc gccagtcttt ctgaaagaag ctgcacatta ataggcagga  68040
atgcggtgcc gtctgttacc accccctgta gggcatttgc tagaccaacc gtggtttcta  68100
tcatttgacc gttggtcatt cgggagggat gtgagtgggg gtttacaatg aggtcgggct  68160
gcaatccgtc ctctgtgaag ggcatgtctg aagtgggcag ggccagcgcc gcaatgccct  68220
tgttcccgct gcgagaactc attttgtcgc ctatattgag atttctttca tagcgcaggc  68280
```

gcatgaggcc aaagatctcg tcattaggcc catggggacg catcacagca tccacgacgg 68340
ccggctcatc gaagccgtac atgacagacc ggtcgatgta tttgttgagt tcgtcttttt 68400
cgccccgtat tttggccact tttcctataa tgatgtcgcc ctttttgacc accgttccta 68460
cgggcacgaa tccatctaca agcttttcgt aattagcacc aggcttaaga tttttggtga 68520
ttaaagggtc gggcttccca aacgactcta tatcgctttc taattctact ttttcttctc 68580
ggtagaaggt gccggcaaag ccgcccctgt caataaagga ctgcgacacg atcacagagt 68640
cctcctgatt gtagccgccg tagatcatat aagccacaat ggtattaagc ccgttgggta 68700
tgacatagtt atgtgctatg gtctttacaa gcggcatttc attgtaaaac tggaagaagc 68760
ggttcatgtc gacacgatat ggccagctaa agcaatacca gcccccgtt tgccggcctt 68820
ggtttgtttc ataggtaaca cgcgcaggtt gggtacagtt tgcgtagggg gacactaggg 68880
cggcaaggcc caaaatagct tggggcacgt ccacgtgtgt gaaacgacgc gttacatcat 68940
gtttatgttt gcgtagctcg atgatggaga aggcaacaag acagttttcc gcctcctcgg 69000
gggtaatgaa ctcacagatg ccctgtgcta cgagatcttc aagtgtaagc gttccggcta 69060
aaatgtcttt tgccatttga ggcgtaaatc gcgtattttg aatgaaaggg attttatgtt 69120
tttcccagtc tttatcgcct ttttttctgg cctctgcggc cttgtagcag gcttgattgt 69180
atttttcaat attattatct acaatgagta gggggcgggt cagcctaccg acgtccaacc 69240
aaaattctac ttcgtctacc atgctatccc agtagatggt ggtatgggga tgcacaacct 69300
tgccctcacg gcgaagcatt ctataccgct gagcaagctc aaaggcattg gtgcagcagc 69360
cgatccattc tccgttgata aatacgcgcg ctaggccctt tcgtacaatg tccttgttgg 69420
aaacatcggc taactgttga atggccggat ctgatagaag gcgttgtttt aacgaaagta 69480
cttctccggc ggtgcagaca ttggcagtga tggctaactg tttagacatg cctacttttt 69540
caccagtatc ggctgactgg gctacgcaga tgtatccagg ataggatgcg tgcacgcgac 69600
gcatcatgtc agccctttct gtttgtttgg atgcgttggt ggtgttatga gtatttaccg 69660
tacgcaatgc tgaaatggta tttaataaat tttttctttc caaactttga gtagatactc 69720
tgtttacaat ggggcgctgt cgcaccatga tggttttatt tcctgaaatg atagactgtt 69780
ccatactgcg attaagatcg gaggcggtat tttttgataa agcggcagaa aatgcctcga 69840
taatgtttcg ctgagtaagc tcctcaaagg ctgtttgttt aagaagttct ttgaacccat 69900
tgatgatggg tgctatcacg gaagtattaa aaatagcctt aaaggccttg gcgagtgaga 69960
cccctgagcc gtgcacccgc ttggtgcggt agctatcacg gtccgtgggt ggaaacacat 70020
tcataatgac aagaagtatt ttatgaataa gcaggcctaa aaagcgcagc tttcgtacac 70080
gtgtatctgc ggtttggccc atgtgtggca gcaatatttt gtctaaaata gtaagttgtc 70140
tttcatttaa gtattgtacc gcattttcat cgcttttgta agcagatggg tttgagacaa 70200
atttggaaac cttctcggat aaaaactgga taattttttc tcggttcagc tcgtgttgga 70260
ccggttgaaa tatggggtct aaaacatgaa tggatttttc cagaatttct atcatgaagg 70320
tattcacaag ggagttggat tctagatcaa ataccacttg ctcaatgatg ctgtcatcgc 70380
ctgtcattcc aaacatgcga aagatgagat accaaggtat gcgaagtttt gagaacttgg 70440
tgctattgat ttcaatggta atggcgccgg tggtcatgta gcgtataata atttgagagc 70500
tattttcgaa ggcacctccc ggttgggaga taaactcgcc gcgaatgatt tcattattcc 70560
cttgttgcat ggtatggtaa tggatgtgaa gcgtgttaaa gcggatgttt tctaagaggt 70620
ctacgaccca ttccccgcct cggctataa agtagccgcc gggttcatta gggtcttctc 70680

```
ctatttcttt ttttgcggtt tttgataggt gatgagtgtg gcagcggttg ctgccccgca  70740
tgatgggaaa tgtagatacc tgaaaaggag gaatacttgc tcgttttacc tcctgccgac  70800
cattgctgta gtgcgccgtt aaaataacct cggcggctag attaaccggg cccgaatagg  70860
aaaggccaca caggcgtgcc ttattgggta gtaaatttat cttgtttccc tgtgaatagt  70920
ttcgatgttg cgggcgttca atgttcacat ctgtaaagtt aaattggatc tgaactgatt  70980
cccgaagctt atctatttca gtatggtcgc gttggtcttt ataagtaata tccacgttaa  71040
acatttgttt tacaatttgc ggaattccat tgtccataag atcgtcgaag cttttgatgt  71100
tataccctat caatcctgta gagtttactg cagcggagat aaagctcagc atatcagcct  71160
ctgtaagctc ctcattatcc acggtttcaa tggggccgta ggttatttgc ggccgcaagg  71220
gttccatgat tatgaagtac tacattaata ttcagttatt ctttaaaata aatctttatt  71280
tataaatctt atttataata taagaatgcc ttatgcaaga gacatcacaa agtttattac  71340
ggcaacggaa ccagaggtgg gtcttcccct gttggcgctg cagcgctcca aatccatcat  71400
aggggttatt cttcttgtaa taagtttgtt atttattttc attggcatta ttatattatc  71460
agtgagtagt ggtcatacca cagcagcctc tatatttatc gtattgagtc ttatcctagg  71520
tggcggtggt ttttttctta tttataaaga taattcttaa cccacataaa atttgaaaaa  71580
atatagagta agaaaatgtc caattactat tattactatg gcggggggag atatgattgg  71640
ttaaaaacag tagaacccac taattttttta aaaatcgggt tgccttacca ggcacaccca  71700
ttacatcttc aacatcaggc aactactccc ccatctatct tagaaaaatt taaacgagca  71760
gacattcttc ttaatgaggt gaaggccgaa atggacccac tcatgttaca accagaaacc  71820
gaaaaaaaac tattccagat attgagtagt attgatatgt tcaaaggtct gcgaaaaaaa  71880
gtagaattca cgtacaatgc tcaaattgtt acgaatgctt ggcttaaaat gtatgagctg  71940
ctaaatacca tgaattttaa taatacatct caggcatttt gcaattgtga gcttccagga  72000
gggtttataa gtgcaattaa ccattttaat tatacaatga tgcattaccc tacttttaac  72060
tgggtagctt cctcccttta ccccagttcg gaaacagatg ccctggaaga tcactatggt  72120
ctttatcagt gcaatccgga taactggttg atgcaatctc ctttactgaa aaaaaatata  72180
gattataata acggggacgt aaccatcgct agcaatgtaa aaaacctagc gcttagagcc  72240
acacaaaggc tgacgcccat ccatctatat acggctgatg gggtattaa tgtaggacat  72300
gactacaata aacaggaaga attaaatctt aagcttcact ttggtcaagc ccttacgggt  72360
ttgttgagtc ttagcaaagg cggaaacatg atactcaaac actatacctt aaatcatgca  72420
tttactcttt ctttaatatg tgtattttct cactttttg aggaactata cattaccaaa  72480
cctacctcct ctcggcccac aaactctgaa acctatattg tgggtaaaaa cagattacgc  72540
ttatttaccc ccaaggaaga acaagtcctt ctaaaacggc tagaattttt taatgatacg  72600
cccctcgtag acctaagtct ttaccaaaat ttacttgaaa gcgtttactt tgccgtagaa  72660
acaatacatc taaaacaaca aatagaattt ctaaacttcg gaatgaaatg ttatcgacat  72720
ttttataaca agattaaact acttaacgat tatttagctc cgaaaaaaaa gatttttcag  72780
gataggtggc gtgtgcttaa taagctttat gttcttgaaa aaaagcataa acttaagctt  72840
tgtgcctcct agggatctgt tgcttaattt aacagatgca atcttaacag atgtaaacta  72900
aaaagtgtgt tcatacaagg attgtattta tgaatattta ttaacatata aggttgtgat  72960
gtaacactgt ataacctata taactacact atgaagcacg gcgtataata atttatattg  73020
```

-continued aacacgatgt tgactcattt atttgcaaac aaatatttgt ttgcaagacg tttgcatgca 73080
tttactaata tgttgttgac tagtttattt gcaaactaga tgtttgattg caaactagat 73140
gtttgcacgt atttatttga actaatatac actccttgtt ttatttgtta tatacacagc 73200
atacataagt gtatattgtt tacacttatg tttataactc gacgtaataa cattttacac 73260
gctttttttt tgcaaatctt aataatattg tatgataaat caaacaatgt cttatatatg 73320
tggtttatta ttttaggcgc cgcaagatgt actccattct cattgcatgc ttggtgttat 73380
tactctgtct agttatatat gtcggtcatc gtgccgatca tgcacgaaaa tatttagaag 73440
gaatgtggca tggagatccg gtttttctaa aacagtcggg gctacaatcc ttttatctct 73500
acatacaacc tgaccataca tgttttttta gcattgtgaa taaaaatggt gaaaagctga 73560
tggaaaccaa aataccttgt acgataacaa ataaaatata tatgtttttt aaacctattt 73620
ttgaatttca tgttgtgatg gaagacatac atagctactt ccctaagcag tttaactttc 73680
tgttagatag tacagaaggt aaacttattt tagaaaacaa tcacgttatt tatgctgtat 73740
tgtataagga taatttcgcc accgcactag gaaaaacggt tgaaaaatat ataacacaaa 73800
attaatcatg ttttctaaca aaaagtacat cggtcttatc aataagaagg agggtttgaa 73860
aaaaaaaata gatgattata gtatattaat aattggaata ttaattggaa ctaacatctt 73920
aagccttatt ataaatataa taggagagat taataaacca atatgttacc aaaatgatga 73980
taagatattt tattgcccta aagattgggt tggatataat aatgtttgtt attattttgg 74040
caatgaagaa aaaaattata ataatgcaag taattattgt aagcaattaa atagtacgct 74100
tactaataat aatactattt tagtaaatct tactaaaaca ttaaatctta ctaaaacata 74160
taatcacgaa tctaattatt gggttaatta ttctttaatt aaaaatgagt cagtactatt 74220
acgtgatagt ggatattaca aaaaacaaaa acatgtaagt ttattatata tttgtagtaa 74280
ataatatttt taattactta aaatttttat atataagttt ttgatactat attataaaac 74340
atatgttcat aaaatgataa tacttatttt tttaatattt tctaacatag ttttaagtat 74400
tgattattgg gttagtttta ataaaacaat aattttagat agtaatatta ctaatgataa 74460
taatgatata aatggagtat catggaattt ttttaataat tcttttaata cactagctac 74520
atgtggaaaa gcaggtaact tttgtgaatg ttctaattat agtacatcaa tatataatat 74580
aacaaataat tgtagcttaa ctatttttcc tcataatgat gtatttgata caacatatca 74640
agtagtatgg aatcaaataa ttaattatac aataaaatta ttaacacctg ctactccccc 74700
aaatatcaca tataattgta ctaatttttt aataacatgt aaaaaaaata atggaacaaa 74760
cactaatata tatttaaata taaatgatac ttttgttaaa tatactaatg aaagtatact 74820
tgaatataac tggaataata gtaacattaa caattttaca gctacatgta taattaataa 74880
tacaattagt acatctaatg aaacaacact tataaattgt acttatttaa cattgtcatc 74940
taactatttt tatacttttt ttaaattata ttatattcca ttaagcatca taattgggat 75000
aacaataagt attcttctta tatccatcat aacttttttta tctttacgaa aaagaaaaaa 75060
acatgttgaa gaaatagaaa gtccaccacc tgaatctaat gaagaagaac aatgtcagca 75120
tgatgacacc acttccatac atgaaccatc tcccagagaa ccattacttc ctaagcctta 75180
cagtcgttat cagtataata cacctattta ctacatgcgt ccctcaacac aaccactcaa 75240
cccatttccc ttacctaaac cgtgtcctcc acccaaacca tgtccgccac ccaaaccatg 75300
tcctccacct aaaccatgtc cttcagctga atcctattct ccacccaaac cactacctag 75360
tatcccgcta ctacccaata tcccgccatt atctacccaa aatatttcgc ttattcacgt 75420
agatagaatt atttaatatg tactatatat taattattta acctttcaag ctggtcttca 75480
tttaaattta aaatccacta ataaaatgta ttttctagta gcagatcatc gagaacatca 75540
tgtgattcct tttcttaaaa ccgatttcca tcacatgcat caaaatccta tacaaaaaaa 75600
tcaagctctc ctagaaatca aacagctttt tactggagat tatctcatct gcaaaagccc 75660
ttctaccatt ctggcctgta ttgaacgaaa aacctacaaa gactttgcgg cttctttgaa 75720
agatggacgt tataaaaatc gccaaaaaat gctgtcgctg cgagaacaaa ccaactgtca 75780
actttatttt tttgtagaag gcccggcatt tcctaaccct caaaaaaaaa ttaatcacgt 75840
tgcctatgca agcattatta ctgctatgac gcatcttatg gttagagatc atatttttgt 75900
cattcaaacg aaaaatgagg cccacagttc ccaaaagctt gtgcagcttt tttatgcctt 75960
ttctaaggaa atggtgtgcg tcgttcccac ctccctcacc cccacggatg aagagctatg 76020
catcaagcta tggtcttctc tttctggtat ttcaggcgtg ataggtaaaa tcttggcaaa 76080
cacttgttcc gtagctcatt tggttcatgg aaagctttca tcgcagaata ttgatcagtt 76140
aaaaactccc tccaaccgac cattccccaa aaaagtaaaa cgtatgctta taagcattag 76200
caaaggaaat aaggagttag aaataaaatt gctctcgggg gttcccaata tcgggaaaaa 76260
attagctgcc gaaattttaa aagatcatgc gcttcttttt tttctaaatc agcccgtaga 76320
atgcttggca aatatacaaa tcgttcaaaa aacccgtacg attaagttgg gaatgaagcg 76380
agccgaagcg attcattatt ttttaaactg gtgtggctct gcccatgtaa ccgatgatag 76440
ccaaaatatc acagaggcgt cgcggtccac aatgcaggtc gcgacgcagt ccgccgcaat 76500
acagcccgct gcaacgcagc cattgcacga agtatcagat gatgcatcat cagatgcttc 76560
atcacccgta gggtatcaaa cattatctaa agaaatgtta ttgaacacag cctgatgtta 76620
ataattcact acatctaaag aaatgttaac ctcgatacta aaaagtcatt gaacacaact 76680
actggggcgc taagttgtcc aacacatcta aagaaatgtc aacatcctcg atgctaaaag 76740
ggtcatcgag ccggtcaata atgtcttccc caaaaagtcc gggagaactg taggccgaga 76800
tgtcgtccat ggagctatct tccccagagc acacaaagtc ctctccaaaa atcataaagt 76860
taaatgcacc gggcttactt aacagctttt cgctttgaat aatagtgttg agttctgtca 76920
gcgcaaactc tctcacaata ttcacaaccc aggagggctc tttaatttca tacagcgtta 76980
agaaacttat acataaaaat tctatagagt aaagcaaggc gctggcagga tctgttaccc 77040
gtaggtgttt aaatgtagtg tgatattcat tcacaacgtt aggcagcacc ttttccaaat 77100
cctcctttc ctcgtacgac aggtgcttta caagcctttc aacatgtata ggaggcttgt 77160
taaatgtact aacgtgccgc aaacagttat aattatataa gaaaatacgt acggcagagt 77220
cgaccgccat gagccttgga tcatccattg aggtaggtgg tggcggggca ccctggcctt 77280
ccctgatgtc tgcgtaggag cgccccctcca tggcccctat ggcctctatc acagcaggac 77340
tgatatccaa aatcttggcc gtcttgatta tttttccgta atcgaaagtc catggctcct 77400
gtggaggctt gggttgtgtt tcggtggagg gcgtggtcat atctttcttt atttgaatag 77460
aacggatcga catcttttcc ttatcgtact ggtctttata attattataa tagtcatgaa 77520
ctaattcggg ttgagaaaga tgatcgtata taatataggt aaaaagtccg cacttgacac 77580
attttttatc ctggaagtcg tgtaatcctc ccttggggca gcgtgactcg tagaaggcat 77640
aaaaggtgtt aaattctaag ctcgccttta gggctgtttg gaccttttt atgtttaatt 77700
gccccacctc atgttgtagc acgtggcata cagaacagcg tagatcggca agtgcataat 77760

-continued

```
ggttgtcaat ttttttatg acgtctttgc gtgttacttc aatctcggcg ggtttctgcg  77820
aactgtctac ggccttgtaa acgtaaatgg tccacttatg aggaagcccc ctttcatcgt  77880
atagggttga aatgggaagc cttttatact caaacagccg agtccgttgg tcggctcttc  77940
ctgtgttagg atcaaatatg ttataaaatc cttgctgagc aagcagggcc ttttgctcgc  78000
cataagcatt ttcgtacgtt ttgaattctg caagttcgga gttaaaatta ggtgcatttt  78060
gtaaatactt aagaaataat tcataggctc taaggtaaat gagagttgag gtttttttcct  78120
catcccgtcc tccccaccac acccgcaggc tttcttcttg aaaatagatg tcattcagac  78180
gcgtcaactg cgtaaaatca ggccgatatt tagaggtata aattttatca taaaattctt  78240
tttgcgataa tagctcggcc ggggtacgtc ctatcacggt tttaaactca tattcagcct  78300
ccttgggagt ccgtggtttg tgcataggga tgctgccgtc aatacgggcc actgtggcag  78360
cataatcata catggggtcc agcagaatct ctgtcaaaag taccttggtg tcgtcctgca  78420
cgctaagccc ttgtagccca ttttggtgga taatttttt gaaagcctcc cgaaaattat  78480
tagcaatcca ctgatccgta atctcagata gctgatttat tataccgcta tattgctgca  78540
tcattttctc caaaagaaag gtcacgtatg cattcaaaga gctatccgcc ttcattccat  78600
gaatggtaat cgtaagaaat tctttatttt tttgcgagct ataaatgaga ttcaaaatat  78660
aggcatagat gtagatcaca gcatacagct gcgttaaagg atcgtaatcc tcttcctttt  78720
taatatttc gatgctatac acgagcggca ggcagacatt tacggctata ttggcaaact  78780
gtttcacgtc tacaagcttt ccaaagtgga taaacgtgca ggccttcatg gtttcctgcc  78840
aaataaaaac acggagctta ctattaagat cgccgatgat gcccacatct gccgtacgat  78900
cctcttgaat aaaatgggcc agctcttcgc cacaaatttt gcaaaagtag gagtaaataa  78960
gcccctggtt gttttctttc tccttgttta ttcctgaaaa tttcattagc ttggttcgca  79020
tggtgtcgta ggacgcttct gccgcttgaa gctgtataag catgtccaca tggggacaaa  79080
gcagcttaaa cccgcaggct ttgcatagat tccaattggt ggtattgttt ttttccttgt  79140
agagtacacg aatactttct aatactttta ataactccgc gtattgaaga cccgaacgca  79200
actgttttac cagcttgaga tgagcacatg catttttttc ttggagttcc cactgttttt  79260
taatgtttag gtattctgtt gtaataagtt ctgcctcctg tttcccacag gctttaatga  79320
cttcttgaag gatgctgtta gggtcatcca ctttaccctc cattgtaaga atttcacgta  79380
tagcatccga ctgcacccta cctatttttt cttccataat tttaaaatac tgtctcgcct  79440
gggtaatgac ctctgtgagc ttcatgtcca cctgctgcag aatcatttgc tccttttcac  79500
gctgttcagc atgttgtaaa aacttttgtt ctacagggtt ccaaagcacc tccaaatagc  79560
ctgctctata taggtcataa agcaagggca tgtatcccga tgtaaaaacc ggggacaccg  79620
agtacatcgt agacaactct tttaaaaaaa atatcacgcg cttaatgttc tcctccggtt  79680
caatctcctc ggtttcaacg atattagata tatgactgcc ctgatcctca cggtctagct  79740
ttcggtgtac catctcctct gctagccgat taatgagcca gctatgcccg ccgctccgca  79800
aaaacttata aagttcgata tactggtgcg taaactggat gatgttttcc ttggtggtta  79860
cgacaacccc ttctccgttt tttttccagg tttcttgatc cacgcatttc ataaatactc  79920
gaataaaatt ggtcaaattg gctcctgagg cgacgtagcc caaggtttca ggcgagaagg  79980
agcctatctc agccatacgc ataaaacact gcggggaaaa agtttttagc cgcaacttaa  80040
gtccatagat ttcaatgggg gcttctgcgg gaacggccag gtgcgtccca ttaattaaaa  80100
aaatttcttt gcgtgtgcta gggcgaacac gtaattcctt tttttttca ctcacgatgg  80160
```

```
ggaccacatc ggggtctacc agcagttgac gtatgtaggc ctctatgggc atggatagat  80220
cgggcagctt tgactgctcg gcgcgaacat ggttcacaaa atcttttaga gtgaaaagaa  80280
agtctattaa acgtatgttt tttatatcat tagacccttt aagggtagag tagatttcat  80340
ccactagtgc ctcgatttcc tcattattga gcgataagat atctgtgcca cggtggacta  80400
tttgcgcgat cgtaattact tcctccatta gatagaaact gaatattata tttaaaataa  80460
atacaaaatg tcaaatgaaa gttttcccga aacgttggaa aacttacttt caatgttaca  80520
gaccaaacag caaaacgcaa ttcagtcaga ggtgattgaa tggctgcaca gcttttgtga  80580
aacctttcac ttaaaaatac actgccataa acagtttatt cctagcgggg aaaaaaaacg  80640
agctaaaata cccgctcaag aaacacaggg aaacacgcag ccctcccacc atgtgtaccg  80700
ggttgttctc tccagagcac agccagtcaa agcacaggaa tctctgctaa caaccatgtg  80760
caacggactg gtgctagatg caaacacatg gacatgccta gccattcctc cgcctgcgcc  80820
ctttcaacag gcgacccgcc aggtccaaca cttttaccgt aacaatttct acgaagtggt  80880
tcccatccag gatggcaccc ttctcacaat ctaccactgg gatgaccctg aatatggccc  80940
ctcctggtgc ctagcaagta cccacggata tgatgtgagt aactactgtt ggataggcga  81000
caaaaccttc gccgagcttg tatacgaatt gctgcagcag cactctacct gcgacgtcac  81060
cctggaaaaa aataaaacgc ggggaacgcg tcttttcttt gataacttaa atcccgatta  81120
ctgctatacg attggaatcc ggcaccataa tttacagccg ctcatctatg accctcaaaa  81180
tatttgggcg attcaatcta caaacctaaa aacgcttaaa acggtatatc cagaatacta  81240
cggctatata ggcattccag gaattcagag tcaagttcct gagcttcccc agtatgattt  81300
accttatcta atacgatctt ataaaactgc tatgaatcaa gccaaaaatg ctataaaaaa  81360
tggcaaaaaa gacaagggat actttaatta tggctattta ctcatttcgc gagcgcctgc  81420
cattactaaa agtacttcta atgttttgtt aaaatcgcct ctgctggtat ttttacaaaa  81480
aagtgtgtac cagaaaaaac acaatatctc taacagccag cgactagaat ttattatact  81540
gcaaaactac ttgatgcagc attttcgaga tcatttcatt gctctatttc cgcagtacat  81600
atcctattat acgaaatacc aaaacatgtt gaatatgatt atccatagta ttgcaactaa  81660
agataaagat catccctttg caggagccgt ggtaaaaaaa gtgttggaag atattgaaaa  81720
cgccgaaaac attattgatc atacaaccat tcaaaactat gcccatcaaa gcaagtacgc  81780
catgctttac ttgtcaatta tttcccattt ttaatctaat acggccaaag ccgcgggttt  81840
tttaataaac taacatttaa aaaaactgtt ttattaaaaa ttataatact tttattatat  81900
atggaacatc catctacaaa ctatactccc gaacagcaac acgaaaaatt aaaacattat  81960
gttttaatcc ctaaacacct ttggtcttat attaaatacg gaacgcatgt ccggtactac  82020
accacacaaa atgttttccg agtcggtggc tttgtgcttc aaaatcccta cgaagccgtt  82080
ataaaaaatg aggtaaaaac agcaataaga ctgcaaaata gttttaacac aaaagcgaaa  82140
gggcatgtaa cgtgggccgt cccatatgat aatattagca agctatatgc caaaccagat  82200
gcaattatgc ttaccataca agaaaatgtt gaaaaagctc ttcatgcttt aaaccaaaac  82260
gtactgacgc tcgcatcaaa aatacgttaa atataatttt tgtagaggat aaaaagctat  82320
tttagctaaa aaataattca tatacgttta tgcagaggaa gaacggtggc tttcaaattc  82380
agattgcatc cacgtagacc gtagcgtttt ttttgcttct ggtttatatc gtaaaccgta  82440
ataaacatca tcatttgtat ccgttggatc tttttcccac tccggataaa aaatcggttt  82500
```

tcttttttttt tggtcgtttt ttgcagtaag ctgtaaatta agggaatata gcttatcgaa 82560
aagttgttcc tgatccatat aaatagcagc atatattaaa aaaaaataaa aaaagacgct 82620
tcaacgagtc agtaccactg cttgccaacg atttacgttg gttggtgcat tatggtgata 82680
tagtaatgag tgcctgcaca agtgcttgca caagtgcctg cacaagtgct tgcacaagtg 82740
cttgcacaag tgcttacaca agtgcttgca caagtgcctg tacacattac tgcatcgcca 82800
aagcacctgc aatgcctact tcctcaacag agtacgataa ctaaatgctt ttaagcaccg 82860
cttgcgtcga tgtgtccttc ggggcaatcg ggttcaattg gatccaatat tattagtcat 82920
aattacctaa tacttattca attttatctt ttttaccttg taagatttaa acagcgtttt 82980
agcttgttta aagcaacgtt taaaacaagc taaaatgctg tttaaaacaa cgttttaaac 83040
aagttaaaac aaataagctt ataaatatac catgacaaaa ttagcccaat ggatgtttga 83100
gcagtatgtc aaagatttaa acctaaaaaa tcgagggtcc ccctcgttcc gcaaatggct 83160
cacattgcaa ccctcactgc tgcgctattc gggtgtgatg cgtgctaacg cctttgacat 83220
cctaaaatat ggctatccta tgcagcagtc aggttatacg gttgctacgc ttgaaatcca 83280
ctttaaaaat attaggtctt cctttgccaa catttactgg aaccgtgata gcgaggagcc 83340
tgagtacgtc tgctgttgtg ccacctatca atcgcacgat ggcgaatacc ggtatcgatt 83400
tgtttggtac caacccttca tagaggctta taatgccata gaggcggccc tggatcccct 83460
ggaaaccatt atcctgaacc tcattgcggc acgagatcta gacttcgttg ttcacatatt 83520
tccttataat aagggccatg aagactattt ggcctccacg caacttattc tcaaaatctt 83580
tattgcgacg cttttaatgg acattttaag aattaaagac aacacgttgg acgttcactt 83640
aaattccgac tatattattg tgatggagcg gctttggcct cacataaagg atgccataga 83700
acactttttt gaagcccata aggacttact agggtactta attgcctttc gcaatggggg 83760
gaactttgca ggaagtctta gaccctcctg tgggcaaaag attgttcccc taacgattcg 83820
agaggtccta caaatgaatg atattaattt agccgtatgg cgggaggtgt ttattatgca 83880
ggaatgttcc gacttagtca tcaatgggat agcgccctgt ttccccattt ttaacacgtg 83940
gacgtatttg caaggtatta accagatttt ttttgaaaac acgtctttgc aggagaaatt 84000
taaaaaagat tttattgccc gagagctttc caaagaaatt atcaagggcc aaaaaacgtt 84060
gaatgacaag gagtttaaaa agttaagcct acatcaaatc cagtacatgg aatcctttct 84120
acttatgtcg gatgttgcca ttatgattac cacagagtat gttggctata cccttcaatc 84180
cctgccgggt attatttcgc gatccagcta tttatccccc atcgtgaaaa acattttgat 84240
ggacgaagac tcttttatgt ccctactatt tgacctatgc tatggcgcct acgtgttgca 84300
taaaaaagaa aatgtgattc acgcggattt gcacctgaat aacatgacct actaccattt 84360
caacccaacc agttttacag atcgcaacaa accaggaaaa tacaccttaa aggtcaagaa 84420
tcctgtgatt gcctttataa ccgggcccaa agtcgaaacc gaaacgtacg tgttcaagca 84480
catagatggg ttcggctgca tcattgactt tagcagagcc attatggggc caaaccatgc 84540
aatcaagctt gagcggcagt acggcctcgc ttttgtaaac accttttacc gcaatcaaag 84600
tgagcatatt ttaaaggtat tacggtacta ttttcctgaa atgctaacca atcgcgaaaa 84660
cgaaatacag gggtgattt tatcaaactt taatttcttt ttcaatagca ttactgccat 84720
tgatttttac gccattgcta gaaacctacg tagtatgctt tctttggact atttacacac 84780
ctctgaggtg aaacgaaacg tagaaatttc gcaaacattt ttggatacat gtcaattttt 84840
ggaggaaaag gccgtggaat ttttgtttaa aaatcttcat actgtcttat ctggcaagcc 84900
ggtcgaaaaa acggccgggg atgtgctttt acccatcgta tttaaaaaat ttttataccc 84960
aaatattcct aaaaatatat tacggtcttt taccgtaata gatgtataca attataataa 85020
tataaagcgt tattctggga aagctataca aacgtttcca ccctgggctc aaaccaaaga 85080
aatcttgacg cacgccgagg gtcgtacatt tgaagatatt tttcctagag gagaattagt 85140
ttttaaaaag gcttacgcag aaaacaacca tttggacaaa attttacagc gtattcgtga 85200
gcagcttgct aatgaaaatt tgtaaggctt gcagttcttg tatggtcaga acctatgtcg 85260
atggaaacat tatttttcgc tgcagctgcg gcgaaagcgt tcaaggggat agtcagaact 85320
tgctcgtctc tagcaaggtg taccacaccg gggaaatgga agataagtac aagattttta 85380
ttaaaaatgc accctttgac cccacgaatt gccaaataaa aaaggattgc ccaaattgtc 85440
atttagacta tttgacacaa atctgtattg gaagccaaaa aatcattata ttggtgtgcc 85500
gctgtggcta tatgagcaac agaggataaa ccatatcatc ccaccgaatt atgacattcc 85560
tttaaaaccg tccgcctaaa tagttttcac acctttggtg gcagactatt ttataaaaag 85620
taatgttggt tcatgaagat aaagtgtgcc aaagaaactt ttataaacaa atgattaatg 85680
taggtgctag tcgtgtgtac ttaaacaggg tattctatag ccaagtattt tctatagcca 85740
agtattttct atagccagta ttagtcaagt atttagatgt cagggtattt ttatagccag 85800
tatttttcta tatgtacaaa ctattccagt aaacatatgt gtgttcttta ttgagcagca 85860
tcatggcatt aacaagttta ttaaactgct ctaatgggca ttaaatgaca actcggtgct 85920
tagcaaaagt gcctatacct tttaacaatt agggccggga ggcattccca gctttttct 85980
ataatcagcc atacagtacc cctgagcctc atacacggga ataaggtcct tccattcctt 86040
gttgggatcg gcgggccagc tctcaaatga ggtgtgaatg taagggtcct gttcttttc 86100
cttaatgaag cgtttaatct ccatttgatg ttgtttactt ttttgtttgc ggcggagcgt 86160
gttccgcacc aatacgtaaa aaataccaag aatcacacat aaaagaatta ttaaaaaaaa 86220
tatcatcatc gcggggttta aaaaacgatc ccatgcaaca ggaatcgttc ttaaaacctt 86280
gtctggcagg gctgtaaaca tgaagtctcc tcctataatc ggggtgggac tgtagcctaa 86340
cagttcaagg tcctgtcgtt ctagatactt attggcgaac tgcccaccct ttgcccccgt 86400
tttttatta atcaagcagc gctgcatttt ccaccattct aaatcttcag gagaaagctc 86460
aatgccatat atcaacttta acgttattgc atcttttca atatccttat caatttggct 86520
gagcttttga gctttaagcg ggtctagtgt gtacttccat ttaaacttag tgtcctgtag 86580
tttggctaca tgaaatacgg aacatttcgg cggggccttt gtgacgccct tacactgcgg 86640
aagtttatca ttaggacagg cgcatagatg agactgcgcc acagcatcgc gaactacatc 86700
gcagacggag tacattttcc tcctatgtta aacaataaat ttttttcata gctgaaattt 86760
gtgggcctat cttttccctt gcccggataa taattataag ggagtgttga aacatctggg 86820
agagaattgc ttaaaaaatg ggtttttggg aggggtaact gcgactgttg tacgtcgttg 86880
gccagggaga ttctatatgc cgggctaaag gtgcaacgtt cctgtgaaca acttagtacg 86940
cgcgttgtta atacaaatgg actggtatta gcaaacctcg taaactcttc cggacttgtt 87000
tgtttttgta tgatgtttag cagggagtct gccttttcga gaatccaaag cgtcgcattg 87060
tagtaaaata aaaatagcga cttatcggca ggcgttgcaa aagcgccgta tagaaaataa 87120
agcagtaagt actggggaga caccacaata aggttatctt gaatgataga tatcgctagc 87180
tctttaaaca tagtgctaaa aaaatgtatg tcgttcgtct tgaatatagg gggactatag 87240

-continued tccatgtagg gctcacatat ctcagtcagg tgaaggccca tttcttttat gacttcttcc 87300
gggttgtacg tcgctaacac cagcgcggga taggctttgg gcatatccac ggtaagtgtt 87360
atgtttttat cattcttatg gtaggagtaa gatggttgtg gaaattctgt tttccactcc 87420
gggactttgc aggtaattct cagctcattt agagtctggt acaggagggc gtatgccgca 87480
aagccgtgta tggccacttg tttaaaggga attgaaaacg ttttactttc gtatgtcgac 87540
ttcacaggaa caacgggaat ggggtaatat ttttctatga ggttataccg ctgcaaatcc 87600
tttttaaacc tgctaaaaac atcttccctt ggtgggttat caaaaggaaa gcaaaatgct 87660
aggtgtagcc cggcccgctg gtaatcgggg tgaatgattt taaggttttt atacgttaat 87720
gtgggtatgg tgttaaagat attgggggc atatatgaaa gatcagcaac ccacacaaag 87780
tccgtgcgca cccgcatggt ctgcacatgg atggcgcgca ccgtgcccac ctgcttgaag 87840
cccttttcat acaaaatgtc agcaagttcg taggcgtcct caacgtggtt gggggaaaac 87900
atatcaaagt cgggtctttc tccctcggga taaattgagc tgcctttaag atgcagggca 87960
taatcaatgg caatcccccc gtacaaaata agctttttct ttatgataaa ttcgcggacc 88020
acctccaaag ccgcctcaat ctccacggca tttgcctcac gtttttgagc aatgagccgg 88080
tacttagaaa cattaaaatc agtctttagt aaagacgtca taaatagtgt ttaatatata 88140
ttaaaggttt gaataaaata ctaaatagta aaaatggatg ccctattaaa ggaaatagaa 88200
aagttatcgc agccatcctt gcagaaagaa aacaatgatg tatgcgatct ctgttttatg 88260
caaatgaaaa aaatttctaa ctatcagctt ttatgcgaag agtgcggtca gctgaaggac 88320
tggtttgaac ctgaatataa tgaaaaattc acggtatatt ctcgtctaaa gatcgtgggt 88380
gccaatagtt cctatcacca gcgcgatttg gacaaggcca actcaagtga ctatagctcc 88440
ttgcaatttc atcacatttt agaggagctc aaatccctaa atgttaagta tatggatgcg 88500
gggcaaaagc cctttcctat tcaggtgtta aaagaaactg ctcacagtta taaccaagta 88560
caacaacatc gggtcatacg cagcattaca aagcttcaga tcttagccag tattctacgt 88620
agcatttgtt taaaattaaa cattgcttgt acggtggcag acgccgcgag gtttactcaa 88680
cttaatacca aagggatctc aaggggcatg gatcttctgc gctccctatt tgtagacaat 88740
aaaattactt taaacgttga tttaaaccct atagacagct ttattaatag tacctacagt 88800
gccttacaaa ttaaacaaat ccaccaagaa ctgcaggagg aaaatgttta taatttaaaa 88860
gaaattgtta agagctttat attatacgcg gatgagaaga acatcggcgt cgatcttaac 88920
aggagaaccg ttgtgattgc tacgatgtat aatgttttac gccgtgccta ctaccccata 88980
gaaattgata cggtggtgta tcaatgtaaa atacgaaaaa atacaattac acgtgctctt 89040
aaaatgtatg aggattacta ctcccacttt aagtctcttt atgagcagta tcatttaaac 89100
gcggcaaaaa aattaattta aactaaacgt ttaaactaaa tgtttaaact aaacgttaaa 89160
actaaacatt tcgactaaag tttaaaacct agtctaacag cgggatgccc atttccctgg 89220
ggttccatat ttcaacaatt ttttgacctt cgggtgttac cttgatgcag cgcatgacga 89280
gcagtggaat tttcctatta aagagttctt gcttagctat atcaatagga ctgctatatt 89340
ttttttaag cattgtagat ccattaattg ccaattgttg cgctctaacg gcgaccaacc 89400
ttgtggcctc aaaggtggtt aaaacgttgg aggtaatgcg ctcgttatcg ggtataatga 89460
ccaatgtttg cgacgaggcc tgcacaaagc cctcgcagat ggacggagac tccacgatct 89520
cgtccttgtc ctcggactcc tcctcactgt cgacgaggtt ctcctcttcc gtttccacat 89580
attcctccac gaggtcatcc atgataagat cctcgttgtc attatcagcc atattacact 89640
gttatcaaat gtactgttta atacgcaaat ggatttacta cgttttaatt gtatgtcttc 89700
atgtgcaggc tctagtggaa agtaattttc tcacaatttt tggcaccgtt acacttgtgc 89760
ccacaaaaac ccgcgatttt tttattttat attacttttg gaagtacgag tttaaccagt 89820
cgctttcaaa ccttatgcgt ctatctcgcc aaaaaacgct cacagcggtg ttggatatta 89880
cctttaaaaa aataacatta atttttacca cagagggcgt attgcgtatg gattctacga 89940
ataagccagg cgtgccactc gatatagacc cccagttcat tgaccttgat agtattttaa 90000
tggaactgga tcattaggac ctctcccgcc catttaaatt tttagtttct acaataataa 90060
aatgcgcgag gaatcatggg aagaccacga taccattcag ctcaccgctc agcgcaaata 90120
cctcgccgag gtgcaagctc tagagaccct tttgactcga gagctttcag tctttctcac 90180
agagccaggc agcaaaaaaa caaatattat taatagaatc acaggaaaaa cctacgcact 90240
tcccagcaca gagctactaa gactctacga gcatctcgag caatgtcgca agcaaggcgc 90300
cctcatgtat tttttggaaa gacaggggac ctactcgggt ctcatgttgg actatgacct 90360
taaactcaat acaaatgctg ttccccccgct ggaacccccc gcgctatcac ggctttgcca 90420
tcgaatattt gtgcatataa aaaacagcag tgtgctgcct gagggcagcc ataaaatcca 90480
cttctttttt acattaaaac ctgaagtggt tcagggcaaa tatgggttcc atgtgctcat 90540
tcctggtctc aagctggcgg cttctaccaa aaaaagcatt ataggatccc tacagcacga 90600
tgccaccgta caaaaaattc tacacgagca gggcgttaca aatcctgagt cctgtctgga 90660
cccccactcc gcctccgttc cctcgctcct ctacggctcc tccaaactaa accacaagcc 90720
ctaccaactg aaaaccggct ttgagttagt ctttgatagc tctgatcccg actacattcc 90780
cattcatcaa ataaaaaatt tagaatctta taatttagtt tctgagttga gccttacgaa 90840
tgaacaggga agccttgtaa gacctgtcta ttgcgcggca gacattgccg ctgagaagga 90900
ggaagagatc ccgaccgagg atcactcgct ctccatatta atgctacatg atcccgaagc 90960
ccggtattta cataaaattt taaatctgct tcctccggag tattatgtag agtacccccct 91020
atggagcaac gtcgtattcg ctttggccaa tacatccgct aactatcggc ccctcgccga 91080
atggttttcg caaaaatgcc ctgaaaaatg gaatacggga ggaaaagaga aactagaaaa 91140
actttggaat gatgcctcgc accacactga aaagaaaatc accaagcggt ccattatgta 91200
ctgggcccac aaacatgccc cccagcaata caaagaaatt gtagaacaag gctacttttc 91260
cattctcgct gaatatgtgt atagctataa cggcatgctt gagcactaca tgatcgccaa 91320
agtcatctat gctatgatgg gcaacaagtt tgtagtggac gtggattcaa acgggaagta 91380
cgtttggttc gaatttgtgc taccgggcca gccaatgaat cagggagaaa tatggaagtg 91440
gcgcaaggag gtaaacccgg atgagctgca catctatatt tccgaaaact tttcaagggt 91500
gatggaccga atcacggagc acatcaaata ccacctcagt caaccccatg aaagcaatat 91560
tttaaattat tataaaaaac tattaaaagc ctttgaacgc tctaaaagta aaatctttaa 91620
tgacagcttt aaaaagggag ttatcaggca agctgagttt ttatttcgcc aaagaagctt 91680
tattcaaact ctggatacca atccccacct actgggggtt ggcaacgggg ttctctccat 91740
tgagaccatc ccggctaagc tcattaatca ttttcacgag catcccattc atcagtacac 91800
acacatatgt tatgtgccct ttaatcccga aaacccctgg acaaaactat tattgaatgc 91860
actccaagac atcatcccag aacttgatgc taggctgtgg atcatgttct acctaagcac 91920
ggccatattt cgcggcctga aggaggctct gatgcttttg tggcttggag gcggctgcaa 91980

-continued

```
tggaaaaact tttctaatgc gacttgtggc catggtattg ggcgatcact atgcctccaa  92040
gctcaacatc agccttctta caagctgcag agaaaccgcg gaaaaaccca acagtgcctt  92100
tatgcggctt aaggggcggg gatatgggta ctttgaggaa accaacaaaa gcgaggttct  92160
aaatacgtcg cggctgaagg aaatggtaaa tccgggcgat gtcaccgctc gagagcttaa  92220
tcaaaaacag gaaagctttc agatgacggc caccatggtc gccgcgtcca actataactt  92280
catcattgac acgacggacc acggcacatg gagaagactg cggcattatc ggtcaaaggt  92340
gaaattctgc cataaccccg accccagtaa cccctacgag aaaaaggaag atcctcgctt  92400
tattcacgag tacatcatgg atccagactg ccaaaacgca ttcttcagca tactcgtcta  92460
tttttgggag aagctacaga aggaatacaa cgggcagatt aaaaaagtgt tttgtcccac  92520
cattgagagc gaaacggagg cgtacagaaa gtcacaagat acgctacata ggtttatcac  92580
agaaagagtc gtggagtcgc cctccgcaga aactgtgtac aacctatccg aggtcgtgac  92640
ggcctacgcg gaatggtaca acaccaacat taacgtaaag cgccatattg ccctcgagct  92700
atcccaggag ttagaaaact ctgtgctaga aaaatacctt cagtggtctc ccaacaaaac  92760
gcgaattcta aagggttgcc gtattttgca taaatttgaa acgctgcagc ccggcgaatc  92820
ctacattggg gtgtccacgg ccggcacact cctaaacaca cccatatgcg agccaaaaaa  92880
taaatggtgg gaatggtccc ctaatccctc tgcccctcct gagaaagaag cgtctgcacc  92940
aactccttag ggaatatcct tagaagcatg tctttcggca gagccattac cggtagcaaa  93000
aaagcaacat tgagtatatt atatgcctta gcctgctcat aagcgtcctt ttttttcatg  93060
gtattttatg tttttaaata tttttaatta ttttttaaat acgatgaaca gttcgtgctc  93120
cgaaggctgt ttactaaaaa tcggtgtgaa tccgcattct ttaaatatgg tttcccattc  93180
ggggatggta tggaaatcca tgtctctacg aatagtatgg tgcccaagtg cgtcctgcag  93240
gctgtgaagc cagaaggcct cctgaccttg atgaaggtcg tacatgataa gaaaaccatc  93300
aggtttcaac agatggtaaa gcttgttaaa atcgtttatc gtaagatgat gcgccgccat  93360
aggtaaccct atgagctcca cagagttttc atgctggaca tcgtccatat cggtataaaa  93420
cgtttcacag taaatgagac gcttaaacga gtatcgatga caaacattta tttccaagta  93480
ggtttgcact acgtttttag gtatatcggg aatcatgttg attaaggttg tttcgggaaa  93540
cttaatcatc tgactaggct tcattttcaa ctctttaaag gatttcccgg agaagtgaaa  93600
atgggtcttt acgtatttat gtaaaaatac ctgaatgggc agagggggct cctcctcttc  93660
gttctcgacg cctcccaaaa tatttggaat ttcctgacgt ggcaaaagaa agtttatgtc  93720
cacgtttacg aatccatcga ggacggacac aaagcttggc tctaatctcc attccatata  93780
ctgtttagaa acgggagata gcataatcct aggcgtcaca atgcacgaag ggtttttaat  93840
caccgcatcg tggtaagaaa agtgtattcc atttcttcca gtataaagaa gcctatgttc  93900
gtcgtagcag aaacaattaa ggcggtatgc ctcatacata cactgtttca aagtacaaac  93960
acgttttaaa aaggtttctg cattggcgga ggccaagcgg ttttgccatt ggtggaaggg  94020
gttcaatcct acaatggcca gctcgtttaa aatatcttcg cggcgcgcta aaatctgcac  94080
catagaagaa tactttagca tttttttttc gcaccattcg cgaagatgtt tagctacatt  94140
attaacctta ttattgataa agtatacgat ggcatgttgg aagccttcaa aaataaagag  94200
cccctccaaa agatcatctg ccaatagaag atggatgttg gtgtaagcat tgtcaatatt  94260
ttgtagaaac ggcggaatgc ctgccaaaac cgcttcagca agcatagctc cgttccgttg  94320
tttactgtcc aatagattcg taagtttttt gtccgcaaca gacacgacgg ctaggatggt  94380
```

-continued

```
tgcaatgtca gaaatggcgg cttgccagaa ataacccgaa aagcacatgc gcgcttcttc  94440
tatagataaa aacgaaaagc gagaggcaat gtctccgagc tgcgtgagtt gaagaccttt  94500
ttctcctctg gttaaaaggc ctgccacaat ggcccgctca atggctgatg ccagcgcatc  94560
cgtgggggga ggatccagca tatcaatctc ctctgcctta aacacgcctt ccttattttt  94620
tttaatcgtt tctacgacaa tgctaagaaa aatggcccca gggccttccg taatgatttc  94680
aggatactgc tgcactggta tttgctcaaa gacgtgtttt gtgtaaagcg ggtaaaagtg  94740
cccaggaaat actctcccta cacgcccctt tctttgctcg atacggcttt gagccgcggg  94800
gcgcgtaata agccctcccg cccattcggg atagtaggtt tcaatgcttc tgttccaccc  94860
gggatctatg acgtacttca gcgtttcaat ggtaaggccc gtttccgcaa caaccgtgga  94920
aacaatgacc cttcttaaag gtttttccac tttagcggtt aagggatttt tcacccacag  94980
attcttaatt tccgctttca ggccaaggta ggcctcattt tcctgcgcaa tcgcctcact  95040
atcgatcggc aaaatcaaca ttaacggcag cttttctttg gcaaggtcca tatttgcatt  95100
attcagcaac atcgaaagga agcgtatttc agccataccg ggcatgaaaa ttaaaatatc  95160
tgcttccgtg ggacgatcat gaatgttttc tttatgaata gtgagagccg tttcgcaggc  95220
ggtcttaatg tagttgttgg tgttatacag cggccagtgg gtttccacac cgtactgtcg  95280
tccttccacc aaaataatgt tttcttttcc gataccaaaa taggttgagt atttatgggt  95340
atcaatggtg gcggaggtta aaattacaaa gggaatacgc agcgccccta tgcttcctct  95400
ttgcaacatg cgctgaagca tacttttaat atacatgagc ataaggtcga tgcctagggc  95460
tcgctcatgg gcctcatcta taatcataaa ggcatagcgg gaagctatct catcatccgt  95520
cattgtatgt agctgcgcca acagaacccc cgcggttgca taaataaggc cccgattggg  95580
tttttccgtc agaggcttcg tttggtagcc cactgtttgg cctaatatca tgtcggggta  95640
gtgggttgag gcgccgatgt ctttggcgag ggtcaccgcg gttaggactc ttggctgggt  95700
acaaataacc gagcgtccca agtatttttg gaaagaatgc gtgttttcat ttctcagaat  95760
tctgaacacg tgtacgggta aggccgtgga ttttccggaa ccagtgcgtg actttataat  95820
gagcacccgg tctgcgaggg aggttggaat ggcccctcca aactccggga gacgttgttt  95880
tatccaagtg atgatgtaat gaataggaac atcattcttg tgctcagcgg gcacgttata  95940
gagatgacca ggctccaata aagtcggttt tcccatattc tattgtttta aggattgatt  96000
gttcataaat atttttatac tctgaccaag aaattatttt tttattaagc cggttattta  96060
cgttgttatg gaacgcgaag gtccagtact gaaagtcctc cgagttgttt aatgtcaagg  96120
gattttttgt aagatacgaa aaggcgtggt gctggcacct ggtgcatggc agagactcga  96180
taaagttcag tatccattgg atggcttcat atttttcttt ccagctagga gcgtctgaaa  96240
aaaagatagc atatagatgc aaggatcgcc agtatttagg tccccaatgc aacatttata  96300
accttttgaa aaatctcatt ccatatagag gtaaatattt tttttccatg gagaattttt  96360
ttgcactctt gaagggattg cgccacatcg tcaaatgttt tttgttttcc atgtattttg  96420
gcgtaattcc agccagtatc tgtgtcatgg tccttaatgt catccgctaa ctgaaaggca  96480
tgtccaaaac aatgggcagc cctttcaatc atcccaatgt cttcaacgga tccagttcct  96540
aaaacccagc ccataataaa cgcgatctta aaaaagggaa tggtttttttc tggagtgtct  96600
actaactgac cggaacccgc gctgtttaga gagtggctta caaaggtaca cagcagcgct  96660
cccagttggt tgggatccgg aaaccttgga cagtgttcct taatccagtc gatttgccgg  96720
```

```
caaatatttt gaaatccttg catggttagc gccagagcgc tcatctgcgc cttggctacg  96780
ccaaagcggg cccacactgt atctttattt cgccgcttca catcgttgtc aaaggagggc  96840
atatcatcga taatcaaaga agctacgtga aagtactccg ctgctagggc ggcctctgcc  96900
ggataaatag gcgccccaaa ggaatgttgc aactgacagg cccgaacaat ttccatcagg  96960
ataatgggac ggatatactt cccacctctt agagcgtaag agcaaggctc tgttagttgt  97020
cccttaaagt ccccatcttc aatagcatta tttaagatgg tctcaaactc ttcactaaag  97080
gttttataat ttttaggatt cagtggatgt attccatgaa aaagcgcgac actacgcggt  97140
gctgtgattc taaaatactt aggtttgcgc gtataggata ttaaaataat aataagaact  97200
acaatgatgg agatatagat gagatgcaac atgctgagtt gtctccccgc agggaatggt  97260
ccttttccgc gcttgttaac ggtaccgagg aggcgttgaa atctttagga aaggtgctgt  97320
ctagtttgga atctccaatt cctcccgtat atttaggtat ataattattg tgtctagaaa  97380
ttgtttgctt tgaggtatca aaatattcag cctgaccgct atttctttta gaataattcg  97440
gtatagggct tgagtagttg gcaatactct taaaccgggg caccaaggta acaatatttt  97500
ccatataatg ggtttgatac gctttgttta aaaatgggct taccggcttt atgcttgtta  97560
gttgtgcatt gagtaccggt atgtcttcta ggatttgtgg ctttatagaa tgattagcaa  97620
acacagaatg tagtatatta gatacttgta gcatatgtct atttgcggaa aattcctggt  97680
attctctgcc gtgttgcgaa tctttgggcg gaaggggacc aagcatcggc acgtccgtgt  97740
aggtactggt ggattttatg agttcctgct ctatgttcgg tttgacatgt ggatttccta  97800
aaggaatacc tctacctgca atccctttttt ctaccgacgc aggtagattg tgcgctaaac  97860
acaaaatatt gtacacgtct ttgtgcggaa tatatccgtt atagtgctgg cccggcatct  97920
gatcgccaag gtgctgctca tgcttaatgg taccctttgt tctgagttta ggaagatcct  97980
cgtacgaaaa aaattttgtg tgctcgctga acctcgtaga aggaaccgaa ctattttttg  98040
ggtttttttaa ggaaggcaat gaggaaggct gggtcagaca atttttctgt gtgcccttta  98100
agctagccac ctgcggaaat gttttttttt ccgtacgaac aacattgcgc ctaattaggt  98160
tttccgtatg ggttgaaaaa gcaggacgat gatttttaaa atgattaaaa agtttatttt  98220
ttggaatgga gctgtacggc tccagatctt gcgcatcgcc gtaaccaatg tttttgtgct  98280
gagggttcag cataaaagaa aagttacgta gatcactgag ttgcaatccc ttttcagcct  98340
tttcaggact attagtgtat tcattgtata caggcgcagc tccatttttg ttgccgcagt  98400
accgggaatt tagtatatta tcagaatacc ggttatgacg cggcaaatcg ctttcccaaa  98460
gaggtggatc tgacctataa tcggctaaca gctttgaagc ataatcatga tacattgtat  98520
ataaaagtta attattatat tgagaaggca taattacttc ttgtaggggt acaagaggct  98580
ttgaatcagg caaactgacg ggttttgaat cggccggctt tggaccggca ggtatctttt  98640
taggttgatc ttcttctagc tcattagaca cggatggggg agaaatagga ggaataattt  98700
catctccgcc cttatatttg tcatggatag aagaaacaat tacatccatg tttgatttat  98760
tataaatgtc gtttaactgg tgatttaaaa cataataatg caaaaataat agggctacaa  98820
tgcatatata tacgtaaata gccgtcttcg tttttcgttt tttatccacc ggcggattac  98880
aaattgcaaa aaatacaact aataccaccg ctgtaatgat taaggccaca atgaaaggat  98940
tttgaaagga tgttttgaac ggttcgcacg tataaatttt ttctcctaaa ttattgatac  99000
ccgcaataaa atctacattc attttatata tttataaatt atgaaaaatt tagagttaca  99060
tctccgccgg accaatcatt gctaaaattt gaagattctt caaaaaggcc cgactggttg  99120
```

aatgtcttct gctcaggttt ccaaaaattt tccaagaatg gattttgaac aataggctca 99180
tcttgatttt cttcttcaag gatattttct ttgatatcaa gaacagcttc tttaaactca 99240
ggtgtatctt gattaaactc aggtttatcc tgatcaatcg caaaaatatt atcttcttca 99300
gatatatcct gtttaatcgc aagaatagtt tcttcctcag gtttatcctg atcaatcgca 99360
agaatatttt cttcttcagg tttatcctga ccaaactcaa caatatcttt ctcgctaaat 99420
ccgtttttag tgtgaagctc ttggttttga agagaattat caaaatctat tttagttgtt 99480
gtcctagacc gtggcacggg atagttatct aatggtttac ttactatagt cctcgaatgt 99540
ggcacgggat aattgtttgg tgacttgctg gttagctctt ggcttgttaa tagttcttgt 99600
tttctcaata attccatctc tactacttct ttttgatccg ctggtgtctc tttttggtat 99660
tcttcattag aaaaatgttc agagggtaat gtttcaataa actttgtgag tggatagctg 99720
ctctttgatg tagaagagcg ttgaatttgc tgataaagga gttgaacaag tcgccggtat 99780
tcactctgtc tttttttcata tttttttacgt agcgtggaga gatctgctaa gagcgacttg 99840
ttttcagatg ttaattcttc aatttgatga agaaggctgc gattgtatga actaagtctt 99900
gcatacgttt cttctaattc tgtctccggc tccacatagg cctgttttcg cagaaattta 99960
ttgtatagtt ccattctttt tttgagcaga aaggtaagac tataatcttg catttctttc 100020
gtaactttat ggtagttttc tttccggttt ttgataataa agggcagcat tttttctgtt 100080
gtgataaagg tgcccagatt gctaatgtag tcgcacagta gcaattccaa gatagattct 100140
ttcttttcaa ggcttataga ttggctgtat tctttaggta tgaaagaatc aacaatcgtt 100200
gttacgaagt ttgaaaagtt taatgttttg ctgttaattt gggtaatgtt acaaaaaatat 100260 ttgtaaaaac tatctagcat tttttcataa agttttttat tttgtttaac ccctaaaata 100320 tagccctttta cttgatactg atattccgta acaatggaat gtttttgta tagtgcattt 100380 ttgtataaaa agttataaaa aatgttgata aaatacgcac caagggtttc aaaaatactt 100440
ataacgtggg attcttcctg atccattata tcatatgtaa tattatttta ataaaaaatt 100500
actgacgaat aacatgcaaa aaaaatatgt ttaaacttat tttaagctag cacttattta 100560
aaagtgtttt aaacacgttt taaattgtat gttaatacac ttaaaaatta agccgaaatt 100620
tgctccaata aggattactt ttatcaatga ccacctcttt actataaacg gctttacata 100680
attttaataa tgctttagag ccaaagctga aggcagtggg aagcggcact gtactatggt 100740
aaaaatgttg ccgatgttca tcctcgcgga tgtacacaag tttcctatat cctttaaaca 100800
caatatggct aatttcttcc acatactcct tatcctgttt ggaatagcgg ttgctttgac 100860
gggaaaaatt cgacatacaa atagaggcat ttgtaaaaat ggaaacaaat gcgtttttac 100920
gaagattggc gggtaaatcg gtatcatctt ggcagcaaat aatcatcgaa ataaaacagt 100980
gacgattttg gtaaaaaaac tttttaaaaa tttcttttgt aaataatggg tgcagttcgg 101040
ccgcgcagtc gtctaatatt aaaagtaaac gaggattaag attgatatag tttaacgtaa 101100
acttttcatc ctctgtaagg cataagtttt tatacatatg aatgttctgt ataataattt 101160
tttttaaaag ttgctgataa agcgatgtaa tcttttcttc tttttttttgg tccgtttgtt 101220 cagcctttaa gcactccact tttgcaatat ttttgttttc cttttgctgt atatcgatcg 101280
gaagtttatg atacaatgtt tttagcatat cgatgttgtt tactcgactg tagatggagg 101340
acatcatagt ttgccgctgc cagatggcct ccaaaaagcg ttcagcgccc ttgttgtcat 101400 ttttttttttg cttatcggcg agccacaagc ggtagtgtat tagagttgga tgtacaaaac 101460

-continued cctcatatga acgatttgag ggttccgagg gggcaaccac taaaatttgt tcaatatggg 101520
gttgcaggat tttcataata tgtttaacgt acacggtttt gcctgttttt gaggggccat 101580
atagcacagt tgttttatct ataaaatgat gtgctttgaa ctgtagttca ggaattagct 101640
tccctgaatg ggtcgttagg gccatctcta tattattaca attctgcttt tgtatataaa 101700
atttcttttt cgagtttatt attattgttg acccacatat ctacccgtat cgtatcatca 101760
ggcacattga gcatttcaag cgcattatct aactgttttt ttgtttttat cagctcgctt 101820
tcttcatcgg gggttaaatt ttctttacta agcagttgct taatttttttc ttcgcagtcg 101880
tctataaaat catactctcg agcttttttg atatttccag atgcttttttc taggtttttt 101940
agctccttaa aggaaagcag tcccttaatc ccgctatccg tgtgaaaggt tgaattatag 102000
atggagagcc ccggagcatc cgggccagtt tcttgtatat tttttgcttt tttgtggtaa 102060
atagtatttc gtaaaatctc ttttcctatc tttaggtctt cctcatgacg gtccaaaatc 102120
cgttttatta tttcattatt ttgattaaaa taattgtagc gctctctgtt ggccttaaag 102180
cttcccagga gtgtccagtt gcctaattga atggatgaaa cctctgagaa aatctggtct 102240
ttatatttat aataaaattc atcaaccttt tgttggttgc tgctatccac cacatcataa 102300
ataatgaagg caaactctag gtcgggtttt tctgggtaga tgctttccgt agcggcccgc 102360
aactcttcgt aattatcctc aatgtaataa ttccacttat aaaaagtatc ctgaggtgga 102420
atatgctgcg aaagatatct agtaattttt gtgttaaaga gaatgggttt aaacgccctc 102480
ggattttcaa gcatatgttt aatgctttgg tgaagttcta tattttgtaa tatgtgggct 102540
gctgccctat agccctgtgg ggtttgggtg attgcatcaa tatcggcctg aagctcatta 102600
ggcacattta atgtttttttg catgatgtgt aaagggatgc gctcaggatc tgctaaatcg 102660
gtgtattctg tgcttgtaca agtgcttgca caggtatcta cattggtatc tgcacacatg 102720
cttgcacagg tgtctacatt ggtatctgca cacatgcttg cacaagtgtc tacattggta 102780
tctgcacaag tatacgcact ttgagcatga agattaggat caaacacaaa atgttctcgt 102840
aaaaagctat cgatcgttgt tttagcttcc ttgcttttct gcgtctgggt tttgcagcta 102900
tctgctatag ataaaattgt atttactacc gattcagagg gaacatcatt agtttcctgt 102960
ttcaaagtat caactaacgt tattagctca ctgagaagag ttttggtcgt gtgggtaggt 103020
tttgaatagg aaggcatcca ttcctgcaga gctttgaaga catatccaat aaagctagtc 103080
attataagac gtcgaatata ctgctcccgc aaatttgtaa aagagcaaaa ggccaccctg 103140
ctatcatttt tgaactgttt gtaagggttc gtcctttggt aaagctgttt aagcgtttct 103200
tcggatattt cagtagaggg atcctccaat acgtttttga gaagctcatc aatattaaat 103260
tctgccatat cttagagttt attatataca tattaaagct ttaatataag gggggtataa 103320
caatggacga aatcatcaat aaataccaag ctgttgaaaa actttttaag gaaattcagc 103380
aaggattggc cgcgtatgat caatacaaga ccttaattag tgaaatgatg cactataata 103440
atcatatcaa gcaggagtat tttaactttt taatgattat ttcaccttat cttattaggg 103500
cgcatagcgg agaaacgctg cgaaacaaag taaataatga aattaaacgt cttattttgg 103560
ttgaaaatat caataccaaa atatctaaaa cgctggtaag tgttaatttt ttactacaga 103620
aaaaactttc aacggacggg gtgaaaacga aaaacatgtg gtgcaccaat aatcccatgc 103680
tgcaggtaaa aacagcccac aaccttttta agcaactatg cgacacacag tccaaaactc 103740
aatgggtaca aactttaaaa tataaggaat gcaagtattg tcataccgac atggtgttta 103800
acaccacgca gtttgggctg caatgtccta actgcggttg tattcaagaa ttgatgggaa 103860
ccatttttga tgaaacacat ttttacaacc atgatgggca gaaagcaaag tcaggtatct 103920
ttaaccctaa ccgtcactat cggttttgga tagaacatat tcttggtaga aatccagaac 103980
aagagttggg gaccaaacaa gatccctgcg gaaccaaggt gttgcaacaa ctaaaaaaaa 104040
ttattaagcg cgataataaa tgcatcgcgc ttttgacggt cgaaaatatt cgaaaaatgt 104100
taaaagagat aaaccgcaca gacttaaata attgtgtttc tcttatattg cgtaaactta 104160
ccggagtagg gccgcctcaa atatcagagt cgattttact acgaggcgaa tacatattta 104220
cagaggcaat taagatacgg gaaaaagtgt gtaaaaaagg gcgtattaat aggaattatt 104280
atccgtatta tatatataaa atttttgacg ccattttgcc tccaaatgat accacgaatc 104340
gacgcatttt acaatatatt catttgcaag gaaatgatac gctagctaat aatgatagtg 104400
agtgggaatc tatctgtatg gagctccctg aaataaaatg gaagcccaca gatcgaaccc 104460
attgtgttca tttttttaa agatgaagat tttttagatg atttttttta gtttttaaa 104520
agacgaaaaa atttttaaa agatgaatat tcttaaaccc cgcaaattac ttttttttag 104580
gtactgtaac gcagcacagc tgaaccgttc tgaagaagaa gaaagttaat agcagatgcc 104640
gataccacaa gatcagccgt agtgatagac cccacgtaat ccgtgtccca actaatataa 104700
aattctcttg ctctggatac gttaatatga ccactgggtt ggtattcctc ccgtggcttc 104760
aaagcaaagg taatcatcat cgcacccgga tcatcggggg ttttaatcgc attgcctccg 104820
tagtggaagg gtatgtaaga gctgcagaac tttgatggaa atttatcgat aagattgata 104880
ccatgagcag ttacggaaat gtttttaata ataggtaatg tgatcggata cgtaacgggg 104940
ctaatatcag atatagatga acatgcgtct ggaagagctg tatctctatc ctgaaagctt 105000
atctctgcgt ggtgagtggg ctgcataatg gcgttaacaa catgtccgaa cttgtgccaa 105060
tctcggtgtt gatgaggatt ttgatcggag atgttccagg taggttttaa tcctataaac 105120
atatattcaa tgggccattt aagagcagac attagttttt catcgtggtg gttattgttg 105180
gtgtgggtca cctgcgtttt atggacacgt atcagcgaaa agcgaacgcg ttttacaaaa 105240
aggttgtgta tttcaggggt tacaaacagg ttattgatgt aaagttcatt attcgtgagc 105300
gagatttcat taatgactcc tgggataaac catggtttaa agcgtatatt gcgtctactg 105360
gggcgtccag ctataaaacg tgactggcgt acaaaaagtc caggaaattc attcaccaaa 105420
tccttttgcg atgcaagctt tatggtgata aagcgctcgc cgaagggaat ggatactgag 105480
ggaatagcaa ggttcacgtt ctcattaaac caaaagcgca acttaatcca gagcgcaaga 105540
gggggctgat agtatttagg ggtttgaggt ccattacagc tgtaatgaac attacgtctt 105600
atgtccagat acgttgcgtc cgtgatagga gtaatatctt gtttacctgc tgtttggata 105660
ttgtgagagt tctcgggaaa atgctgtgaa agaaatttcg ggttggtatg gctacacgtt 105720
cgctgcgtat cattttcatc ggtaagaata ggtttgcttt ggtgcggctt gtgcaaatca 105780
tgaatgttgc ataggagagg gccactggtt ccctccaccg atacctcctg gccaaccaag 105840
tgcttatatc cagtcatttt atcccctggg atgcaaaatt tgcgcacaag cgttgtgaca 105900
tccgaactat attcgtctag ggaatttcca tttacatcga atcttacgtt ttcataaagt 105960
cgttctccgg ggtattcgca gtagtaaacc aagtttcggt acgcattctt tgtgccgggt 106020
acaatgggtc ttccaaaagg atctacaagc gtgtaaacgg cgccctctaa gggtgtttgg 106080
ttgtcccagt catatccgtt gcgaggaaac gtttgaagct gcccatgggc ccccatctgg 106140
gacgtgccct gaatcggagc atcctgccag gatgaatgac atgcacccaa tatatgatgg 106200
cccaccatat catggaaaaa gtctccgtac tggggaatac caaaggtaag cttgtttccc 106260
aaggtggggg tacccgtatg cgggcgtact ttattgtatt caaaccctac tggaacataa 106320
ggcttaaaat gcgcattaaa atgcaccaaa tgtgtttctt cgatttgact caaagtgggt 106380
tcgggatcgg gtttcccata acttttgttc acatttttaa tgttagagat cctgctattc 106440
agcaagtctt gggccaatat aatcttgtcg gccttcccat cgttagcaat aagacaaaaa 106500
gctcctcctg atgccatata taatgttata aaaataattt attgttttta ttaaatatgg 106560
cggtttatgc gaaggatctt gataataaca aagagttaaa ccaaaaatta attaacgatc 106620
agcttaaaat tattgacacg ctcttgctgg cagaaaaaaa aaactttttg gtgtatgaac 106680
tacctgcccc ttttgacttt tcctccggcg accctttggc cagtcagcgc gacatatact 106740
atgccatcat aaaaagcctc gaggagcgcg ggtttactgt caaaatatgt atgaaagggg 106800
atcgtgccct ccttttcatc acctggaaaa aaatacaatc cattgagata aacaaaaaag 106860
aagaatatct gcgcatgcac ttcatacaag acgaagagaa agcattttat tgtaaatttt 106920
tagagtctag atgagctttt acgcaatgtt gtacagtgtt gtatatatgt cttgtaagca 106980
tttgttgtag agtaataagt aaaagataaa taaaaatgac tattaaaata aagcccaaac 107040
cattaaaaat atttttatct gttagattta atttaataaa tggctcatgg aatgtgtggt 107100
gcgccgctgc atgaggtgtg gccgcatggg atgtggtcgc ataagatgta gctacatggg 107160
atgtggcatt tgcttgcatg taaggatcat gatgtgttgg gtcttcatcc cagcaataat 107220
cgccatcttt atctagctga attgtatacc ccattatata tcacttatta ttttttttta 107280
atgtttcatg aatttcatta taggcggtga aagggtcctc aggccccttc tgtaaaagat 107340
tatagagatc ttcggacgct ttatgtttcg tgcgaattaa ggcgggatat aacaaaagag 107400
agggccccag ttccaaacaa attttactta gcgggctcat attttgcacc aagtttccca 107460
ctacttgcga tgtttcataa cgcattttaa agagctttat cataaaagtg ttatgcaggc 107520
cggtgtagtc tggcctatag ttaaggaagg ggatttctct ggtaccgtca aacacgatct 107580
caagtcctct agcaagcccg atcaaaattt cttcagcaat ggatgagtat ctaattccta 107640
cattacgaag cgtaagcatt tctataacat catctatttc ctgcatagag gaatctattg 107700
taggaatttt aatatcatct gtgctgattt gttcattccc aagataggta agcagcatat 107760
taatttttc tagctttact agcttagtct tacgctcata atcatgatct tttttataaa 107820
aagagttggg atcaccgttg gaccgtagat gattaataag gcggtctact tgctttgtac 107880
taggtttaat actttttca ctatactcgc tttcagcata gtggttttta cgatctcttt 107940
tagaaatagc tgttttttga gatgcctcag actctgcata ttttttcta tgcgtagaaa 108000
gagaataacc gcggtcatta cgtgaactac tgttgcatgc aaggcctcgg cgcgtcttac 108060
cgctgcgcac actgccattg cgtatactgc catcgcgcac actgccgctg cgtatactgc 108120
cattgcgtat actgccgctg cgtatgctgc cgctgcgtat gctgccgcta catacactat 108180
cactacatat gctgtcagta catacgctat cgcggcgtat gccgccgtgt accttatcgc 108240
cgcccctacc cgagggtttt ttagatataa tactgtgtgg ggagtcaagc gaaaattcag 108300
ggtcattaaa gttaatgccc aatgactttg ccaatccatt aagctcttca tcaaaatgat 108360
cggtaggaaa actttgttgc ttgcccatga cctgttttc aagttcctcc aaattggctt 108420
gctcatttat atggagatta ttcataagcg tcgtaattcc agcaagattt gctccttcta 108480
aaaatgtggt gtcctccatc ggatatacta tactatttaa aagcttttaa ataaaaatgt 108540
gtttggaaga aatgctctct tcaagcgtgt gtagctcaga tataaatgcc tcctcagaaa 108600
gctttccacc atactccttt ctcatcgtat aggagggcgc cggtttaatg taggaaatcc 108660
actgggaggt aaaaaaccgg tacaacatat ttagcagctc gcgggcctcc cacctttttgg 108720
gctccgtata gtgcacatca acataagagg cggcgcatga aaagctgcaa aagttgccga 108780
gaacgcccat ctcaatctct cctcgctcat tttcacgcat ataggtgggc acgaattttg 108840
ggacagtctt gaaatagaga tgacatgtcc agcatttaaa gctagaatgg gtaacccatt 108900
tggaaacagt ggtgaatacg gagggtagct ttttttcgac ctcggcttca tcgtcattcg 108960
tatttaacgt atcggtggca gtttttttgg attgcaagca ttcttcaatg gtaatcccgg 109020
ataagtataa aatattagga caattagttt ccataatttt gatagttatt tttatacaac 109080
atggatttaa ttaaagataa atggaggacg aaacggaact gtgttttcgg tcaaacaagg 109140
tgacgaggct tgaaatgttt gtctgcacat acgggggaaa aattaccagc cttgcatgtt 109200
cgcatatgga gttaattaaa atgttgcaaa ttgctgagcc ggtgaaggca ttgaactgca 109260
actttggcca ccagtgccta ccgggctacg aatctttaat aaagactccg aaaaaaacta 109320
aaaacatgtt gcgccgtccg cgcaaaacag aaggcgatgg gacttgcttc aatagtgcca 109380
ttgaagcctc cattttgttt aaggacaaga tgtataaatt aaaatgtttt cctagtaccg 109440
gggaaattca ggtcccgggc gtcatttttc cggattttga agacggaaaa aacattatac 109500
agcagtgggt agacttcttg caacatcaac ccattgaaaa aaaaatccag attattgaat 109560
ttaaaacgat tatgattaat tttaagtttc aaataaaccc agtgtctccc cgcgtcatca 109620
ttcatttaaa aaaatttgca gctttgttgg aacacatccc tactccatat cccatacgtg 109680
aaataaagcc tccattagaa gactcaaaag tatccgcaaa atttatggtc agtccgggaa 109740
aaaaagtacg cattaatgtt tttcttaaag gtaagataaa tattttaggc tgcaacacaa 109800
aggaatccgc ggagaccatt tatacgtttt tgaaagatct tatcagcgta cattggcaag 109860
aaattttgtg cgtgttaccg gtacccgatt aaagaatgtt ttcattaata aggtaatcga 109920
ctatgctaaa aagaataaca agaaaaatac cttgaagaac tataccaaag taggtaggtt 109980
ttctgcatgt cacggcatgg ttaaaattgc taataatgta gtccacaaaa gcattgctca 110040
atacgactaa aaatagtaaa aaaaggataa gtgctctttt tatatccata tactttaaaa 110100
cttatttttt acactaataa tttcctgcgg ccgcaatata aactgtaggt catctataac 110160
gcccagacct gttaaaagta gagtactatg ttttaaggga tttaaaatat ccgccgcaag 110220
aatgtgaata taattttcaa agtggtttac aggaatgcgt aagcgttttt ttttgcactg 110280
cggttggttt agggtcgaat actggcagga ggtatatata ttaataagac cgcggtcgat 110340
ggtttcaata tcttcataga attcaatgcg cggcgtcaaa agttttttaa gatgttgaca 110400
taactcatca tacgtgtagg actggagggg ggaaagaagg gtgtagtcaa agttaaaaat 110460
gttttttga agaaccttta aagcatgttc cgcgtccgtg gtttccaaaa tatgttttat 110520
ggtatgaatg tcatttaaat ctacaaagtc tgacagcttt gtgtagaact cggtgacgga 110580
ggttattttc tggaaatcgg ttttttgaaa aagattttca atgtgtttgc gggttgagtt 110640
gctttgcagt ccatacaaga catcaaaaaa ttcaatcagc aaaaacttat acaaatggtt 110700
aatataaaaa gctttgttgg ccttattctg ctgaggatat ggttcctcta ggggatatag 110760
aatggcttgg tctatatccc taggatcaat agtcaatgtt gcgatgggaa gcttttccag 110820
cgtagcggga agagtttggg ttggagcgta gtaaaagtat agcccggttt ttccctctga 110880
aagaaagccc acaaattctt tttttatatt ttgcagcacc gctgagggta cgatttcgta 110940
ctgtttatac tgtttgttga aaagggtaat aaatttccag gtttcttcaa agcttgcaat 111000
ctgggtgggc cgcagatcaa agtcgatggg aatgtcgtca tgaatgtagg atgatagtct 111060
tataggaaaa taaatagggc gatcggtgtc tgaatcgata agtaaagcat aacaaaagtt 111120
atgcctgttg ataagttttt taccaaccgt gtagccggga atgtttttca cgtcatggat 111180
atcccaccag ttatccttgc acataaactc gctcatagac tggatgacct ccatcacagg 111240
gtcatcttcg gtaaaaatat actgggcctc actgtttttc agaaatcttt tttgctgggt 111300
gatggccatt gggtagatcc cttcgtccgt gtcaaagata atggctatct tcttcgatgg 111360
gctaagaatt ttttgtattg tgctggggga cacctcaaac ccgatgtcgc cctgtttatc 111420
tttaaaaaag acacagtgaa ggtcgtagca tatggcaaca aggtccagaa agatgtcctg 111480
ccatgtggtg tcccattgaa gcagttggtt tttttgttca acaaaggttt gtaagataag 111540
gtttgccagc tccgcgccgc tggaaaacat gttgccggcc ccattcccca aaatatagta 111600
ctgcggtgtg ttggccgcct ttgcaatttc aatggcaagg gccttggggg caagatccaa 111660
aattcgagca agggaataaa aaagcccggc attgctaatt ccaagcatgg tttgctccac 111720
ccccacaatg caaaaaatgt cgggctcttt tatcgtattt aaaaacagtt catctgctat 111780
ctggtggggt agaaaggcaa tccggttcac cggtattttt tttccatagg acaaggtatg 111840
acgcgatgtt tgtgtattaa gatcctccag gtcttgttct acaaacgtgt gcttggtgag 111900
gcaggtattg ttaatataga accgctttgt gcccagcagg gccttcgtct tttggcagca 111960
cggcagacag taatttaggg ggtggcggcc ttctagtagg cttagatgag ggtagtcagg 112020
atgcgggcag ctatagtagg caggtacccc ctccgtgaaa ttccaatact ttactagctc 112080
cttgcgcttg gctggcggca tggacttcac ctcggcctct gagtaaatga cgggtggccg 112140
tgggtgctgg cataggacgg agtaaaccgt tgcctgcgtg tcgtacttgc gcaggtcata 112200
caggtcgggg tcctgttctt gaagcgcacg tagctgagag gctccctttc cttgttgttt 112260
atcgtgcagt tgagagagtt tattaaccaa aattttgtca ggcccggtga tcaagttatc 112320
taaaaacaca aataggtaaa cccaaagata gttaaactct tcctgggtaa tgttaaacat 112380
ttctattttg atatctgtaa ccctatggta gatgcgaatg ttgcggccgc cgtagattgt 112440
ttcccaccgg gccgcaacat ttgtgtcaaa gaggtacgca tacgtgtttt ggagcaacgc 112500
aacattgatg tccattttgc gccccggacc ggaggaaata atgatcatcc gttcgatttc 112560
gtggggatca tacgaataaa tccccttttt aaataaaaaa ttgtagaccc cggtttgctg 112620
gaggccccgc acggaaataa tccctgcttg ctcgtattcc cgccaacgac ttttgagctc 112680
ggtaaatccc ttgctagaaa gcgtataggg ccaaaaggtg gacaccgaca tggagctgat 112740
agaaatttgg atgtcctcgt tggagggaag ggcagactc cctccacgag gaaacgcggc 112800
aggccccata tcattaattg tatgaataat aggatttatg aaattattta gggtggacac 112860
cacggagtta aagtcgtggc gctcgttttc tgaccaattg ctttcgataa agtagtgccc 112920
attattttgt atggtaagaa taaaggcctt tttattgata aagcgtatta aaataatagt 112980
gggtacacgg aatgttttat tgctgaattt ttcaggctcc gtggaagtta tgtggtgttt 113040
ggaaaccacg gtgggacctg ttttactata aaagaacacc accagctgag gaatatcggg 113100
agtagctgga aataggtcga aaacattgcg cacattaatt tgaatattta cgaggggtga 113160
aattttaatc attgccgagg tgacggccaa cgtgccgcgt gttagtctat tcccctcgta 113220
cttggcaatg acttgttgtg ctctggcata cgtaaagttt attagttttt gctctaggag 113280
aagcctcttt ttaagactgg tcaaggatgg agaaagagca ggatactgtt tttccatttg 113340

-continued taagggagat tgtaccaata gtttaaaggc atcgggggaa agaagaggcc aatacttcat 113400
aataaggccg taatagagta agtcaaattg gtaattatcc tctatggcaa tggagatttg 113460
gcgccgcatg gggccacta gcgtgttgag gtctgctaca aagatgtgat gaatgttttt 113520
tatgagctgg aagctgtcga gcgcttccac atagagctca tctttttgac tttccataga 113580
tgcgtcgatg ttcaccccac ccacctgttg aaactccttt ttgtagtcgc gaatgtctaa 113640
cgccaccccg ctaccgctta acaataggcg atacgttacc tgaagcgcat tgttttgaaa 113700
aaagaaaatg tgttgtctat aaggggggat ccctgtggca acgtaaattt tttctcgaat 113760
gtctttaaaa gtgtcttcag ggaaaatact atactcgcta tacatcgtct caatttctgg 113820
catcatcacg tttgtctcct cgccacgatc ctccacaaaa agtttttcaa actcatctaa 113880
atcatcgcta tctccaccca ccacgtattg ggaaagcttt ttctcccaat cctcgccgta 113940
aaaattttgt aaaatttctt tgtccttagg ggttcgctgc aggtctttgc ggcaggcctg 114000
taacacgttt gcaggaacgg atcccaaaaa aataaacgtc ttcgtgtact cattttccac 114060
aggattataa agagtaactc gtagaggatt tgttaaaaag tcattttgga aatccattat 114120
acccggtata gaaaataaaa tttaaaataa aaaacggatg atatctatca tggaccgttc 114180
tgagattgtt gcacgggaga acccggtgat tacccaacga gttacaaatc tcctacaaac 114240
caatgctcct ctactattca tgcccattga tatccatgaa gtacgatatg gagcctacac 114300
acttttcatg tatggttccc tcgaaaacgg ttacaaagca gaagtaagga ttgaaaacat 114360
cccagttttc tttgacgtac agattgagtt caatgataca aaccagcttt ttttaaagtc 114420
gctactgacg gctgaaaata ttgtgtatga acggctggag acgctcaccc agcgtcctgt 114480
aatggggtac cgcgagaagg aaaaagagtt tgcaccatac attcgaatat tttttaaaag 114540
cctgtatgag cgacgaaaag ccattactta cttaaataat atgggctaca acacggccgc 114600
ggacgacaca acctgttatt accgaatggt ttcccgagaa ttaaaactac ctcttacaag 114660
ttggatacag cttcagcact attcctacga gcctcgcggc ttggtacaca ggttttccgt 114720
aacccccgag gatcttgttt cctatcagaa tgatggcccc acagaccaca gcatcgttat 114780
ggcctacgat atagagacct atagccctgt taagggaacc gttccggacc caaatcaggc 114840
aaacgacgtg gtgttcatga tatgcatgcg catttttttgg attcactcca cagagcctct 114900
agcgagcacg tgcatcacca tggcaccctg caaaaagtcc tcagagtgga ccaccattct 114960
atgctcctct gaaaaaaatt tgttgttaag ctttgctgaa cagtttagcc gctgggctcc 115020
tgatatatgc acagggttca atgattctcg gtacgactgg ccctttatcg ttgaaaaatc 115080
tatgcagcac ggtattctag aagaaatctt taacaaaatg agccttttct ggcaccaaaa 115140
gctggatacc attctaaaat gctattacgt aaaggaaaag agagtcaaaa tctcggccga 115200
aaaatcgatc atttcctcct ttttgcatac ccctggatgc ctacccattg atgtccgcaa 115260
catgtgtatg cagctttacc ctaaagccga aaaaacaagc ttgaaagcgt ttttagaaaa 115320
ttgtgggtta gattcgaagg tagacctgcc gtaccatctc atgtggaagt attatgaaac 115380
acgagacagc gaaaaaatag ccgacgtggc ctattactgc attatagatg cccagcgctg 115440
tcaggacctt ctggtgcgcc acaatgttat ccccgatcgc agagaggtag gaattctgtc 115500
atacacctcg ctgtatgact gtatctacta cgcgggagga cacaaggtat gcaatatgct 115560
cattgcctat gccatccatg atgaatacgg ccgtattgct tgcagtacca ttgcccgagg 115620
taagcgggaa cacggaaaat atcccggcgc ctttgtgata gaccccgtta aagggcttga 115680

-continued acaggataaa cccaccacag gtctcgactt tgcgtcgctg taccccctcac tcatcatggc 115740
ctacaacttt tcgccagaaa aatttgtagc ctctcgggat gaggcaaata gcctcatggc 115800
caagggtgaa tctcttcact acgtctcctt tcactttaac aatcgtctcg tggaaggatg 115860
gtttgtgcgg cataataacg ttcctgataa aatgggattg tacccaaaag tactcatcga 115920
tctacttaac aaacggaccg cccttaaaca agagcttaaa aaactaggtg agaaaaaaga 115980
atgtatccat gaatcccatc ctgggtttaa ggaactacag tttcgccatg ccatggtaga 116040
cgcgaagcaa aaggcgttga aaattttcat gaacacgttt tacggcgagg caggtaacaa 116100
tttgtcgccc ttctttctgc ttcctctagc cggaggagtc accagttcgg gtcaatataa 116160
tcttaaactt gtctataact ttgttatcaa taaaggttac ggcatcaagt acggtgacac 116220
cgactcatta tacattacat gcccagatag tctttataca gaggtaacag acgcatattt 116280
aaacagccaa aaaacgataa aacattatga gcaactctgc cacgaaaaag tgcttctgtc 116340
tatgaaagcc atgtctacac tatgcgccga ggtgaatgaa tacctgcgac aagataatgg 116400
caccagttac ctacgtatgg cctacgagga agtactcttt cctgtgtgct ttacaggcaa 116460
gaaaaagtat tatggtattg ctcatgtaaa cacacccaat tttaatacaa aagaattatt 116520
catccgcgga atagatatca ttaagcaggg tcaaacaaaa ctcaccaaaa cgataggaac 116580
gcgaattatg gaagaatcca tgaaactacg ccgccctgag gaccatcgcc cccctcttat 116640
tgaaatcgtt aaaacggttt tgaaggatgc tgtggttaac atgaagcagt ggaattttga 116700
agacttcatc caaacagatg cgtggagacc ggacaaagac aacaaagcag tccaaatctt 116760
tatgtctcgc atgcacgctc ggcgtgagca actaaaaaaa cacggcgctg cagcatcgca 116820
atttgctgag cccgagccgg gagaacgctt ctcctacgtt atcgtggaaa aacaggtaca 116880
gtttgatatc cagggccacc gcacagattc ctccagaaag ggggacaaga tggaatacgt 116940
ctctgaagca aaggctaaaa atcttcctat tgatatattg ttttatatca acaactatgt 117000
tctaggcttg tgcgcgagat tcattaatga aaatgaagaa tttcaacccc ctgacaacgt 117060
cagcaataag gatgaatacg ctcagcgccg agctaaatcc tacctacaaa aattcgtgca 117120
atccattcac cctaaagaca agtctgtcat taagcaaggc aatgttcatc gacagtgcta 117180
caaatacatt caccaagaaa ttaaaaaaaa aataggcatc tttgccgacc tttataagga 117240
attttttaac aacaccacaa accccatcga aagctttatt caaagcactc agtttatgat 117300
acaatacttt gatggagaac aaaaagtaaa ccattctatg aaaaaaatgg ttgaacagca 117360
tgctacggct agtaatcgag ctggtaagcc cgctggtaat ccagccggca atgcgctgat 117420
gcgggctata tttacgcagc tgattacgga agaaaaaaaa attgtacaag ccttatacaa 117480
taagggggat gcaatacacg atcttctcac ctatatcatt aacaatataa attacaaaat 117540
tgccacgttt cagacgaaac agatgttgac gttcgagttt tccagtactc atgtagaact 117600
gctattaaag ctgaataaaa cgtggcttat tttggctgga attcatgtgg caaaaaaaca 117660
tctgcaagct tttttggatt catataacaa tgaatcgccg tctagaacat tcattcagca 117720
ggctatagag gaagaatgtg gcagtattaa accatcttgc tacgacttta tttcctaata 117780
cttcttaaga aactctttaa acaaggactt cgcatggtca aaggttctaa acccatggcc 117840
cttatgattc gccaaaaaag cggtttcatc aagattttct aaccctttca cggatgaaga 117900
aataaggtgt tcggcctcgt ttgcccattt tctatgattt tttttcacct cgggttctag 117960
atctgttttc tccatatact cattgtggtc atattttttt ttgggaggag gcgtgggtgg 118020
aggaatgggt ggaggaagta cacccgactt tcccgcttca accgttttat aaaaaaatag 118080
aagcataata caaagaataa ggactatcgc aaatatgata accagtgtcc cagtcgaggg 118140
cattttgtta tataagtaac gttttttttt attttttata attcgaatga agaaccatgt 118200
tgaatagtct tctactcaaa gacattttgt tatacggtaa atgagaattt ataaaatccg 118260
aatatcacta tcatactgtt tatctgagaa ggtctcactg ggtcctgtga tggagaaccc 118320
atactctgta atgctggggt ttataatgtg gtcaggactg acaagcacat ttctgaactg 118380
cgagagttct aggtttagac gcagtcgtaa tagtcgctgt atatttgtaa taaatattag 118440
attgcgtatg aggcgagtgt caaagcgatc ctttccaatt tgtactaagg tgggcttttg 118500
tattccaact cccacttgtt taacgatgga ccagggtcct tcttcccgat tttgttccgt 118560
gatataggtc agcacactat tttctgtata tgaggtatga tgtcgcatat taatacctgg 118620
tgccattcca actggcggtt gtgcaattcg ggctgtaccg ggacccaacc atcgtggagt 118680
tttataaaca tatcgttcta gcgtatttaa aaattcctta aggttattta cgagtagcat 118740
gaagggtgct attaaaacag gtggatggtt tataaccatt gtcataaacc attgcattgc 118800
ttcaatatca ttttgtaatg cttgacgggg aggcggggca ggtaatccac gtatgttgaa 118860
taaagcggtt aattgtgcac cggctgtttg gggcgtaata ttttgtatta aatttatcat 118920
cgaattggct tgcccggcat ttcctataag atcgattaaa ttggttattt gacctcgata 118980
ttgttgtacc cagttttgaa tggcagcgat gatctcaggg gttggattgt tttgaatttc 119040
aggtgtttgt attagattat tcacttctct tcgtgtatct tcaagctgag tcctaaatgc 119100
atttaactcg cctataattt ggtttctatc aataacattt cttaaacctc gaactgtttc 119160
agccaatcgt atagtacgca caatttcatg taaggcctgg tttatgtata ttgacatggg 119220
atggccccac cgctcacgtc cacgttgaat acctgcggcc aaactaggac ctgcctcgtc 119280
ataatcaaat tgtgtaggat aaaggcttcc aaatagcact ttattgaaaa tttggtcaga 119340
aagaaattta gggcggccca tatttagcgc gttgtcccct ctaaagatgc gtgacatgta 119400
tccggcgttg cctttggata gtaactcatt cccatattga gtaatagaga ccgagacata 119460
ggggtttata agaagtttta gcataaattc tcgagtattt atggggggac gattcggaat 119520
gtttaatacc tctgcaacat ctggttgagg agccgtggtg tccagagatc gtactttttc 119580
agccgaaatg ccgtacataa gacaagcaat ttcttcaaaa ctatagtcat agttgtaaat 119640
attggcaagt ggtatagatc gcatcagcgc atttacattg ataggtataa tattcatatc 119700
aaacaagtta aatatgcgct cgcgctctct attagagcca agagtgcgtg tttgaccttt 119760
cggcgacact attttgtgaa tatgattgat ttgctcctct tggtaagagc tttccacgaa 119820
ggaaattacg tcttgcaatg ttttacgaag cgaatacact gcattcatcc ctattcccgc 119880
tgttataatg ggtttatcgt ctctgttctc gctaataaga ttaactccac caaaagtatt 119940
ttcattgtac atcatcactg ttttaaaact acggatattt atgataaatc ggagagcctg 120000
aatggcgtgg gtataaaagt gttcaaatcg cgtgggagta atttgttcgc gagcaactac 120060
cgtttcatta tagtttttca tgataagctg tactccgggc atatctgaga gctgtaccgg 120120
atcatttccc agtaattttc ttgtgccgta tagtagttta aactcggggg agccgctttc 120180
aaggttcggg taaagaagag gatcatatac ctcattattt tctattctta ggtcatgtaa 120240
ataatagagc gaaagtgaaa atggcataag aggctcctta ttgtaccggg acatatagtt 120300
ttgaatgaag tgttcttctg tttcaagata gatgggatga tcggtaagct cgtgcaggac 120360
ctccatggca gaatctgcca gagtgtgaga gcctctaatg atcccgtcga tcactgcgac 120420

-continued cagtcgcttt cgcacaacat cgctcgtatt attttgtgcg tctcctaggg gcataagcgt 120480
aacattggga cgaaatacgc cgccaattcc ccgcagggcc gcctgaccga cggatagtcc 120540
tgtcgcagga acattgttat tattataata aataacggaa tcattattgg ctcccaagag 120600
tgccgtcaga ttagggcgag ctagttggac atttgtgtat tgtataaatt gttttagaag 120660
ctctccctgg ctaataagaa tattaaacat tttgttaaat agtggaagat tggctctata 120720 atttcttta aggtaaatgg gaatttctgt taaagtagaa ataagatgct gactcaggcc 120780
ctggcgattg gtatccttaa taagccgctg aagtataagt cccaaagaca gaagaagcac 120840
cgactgctct gtggggtcgc ctctatgacc aaagacgttg ttattgcgtg ctaagtcagg 120900
gtgagcatat cccatctcca tcactgcttg gctaaagttc ccattagcga atgcattaat 120960
aagatttaga tatatttttc cgctgggagc atcataaaat cgggtaatat atgaagctat 121020
gagctggtta aacaccatca tcatactacg attattttga ataccatagt ctgatccgta 121080
taggcgataa cgtcgaaggt tgtttgcggc atcattgaca ttggcatagg ttctgagcgc 121140
tatgttgtcc cagtagctaa gagtattttc ctcctgggcg ttgttggtac gaataagatt 121200
ggagagtcta aagtctccta gtgccacctg ctctacacga agtccagagt tattctccaa 121260
agcatcgtaa aatacgagtc tactgaatac tcttccgtat tgttcaaagc gttcagagga 121320
ttggggattg ttatttattt gaatattagc cgcgtccctt ctttgcgccc cacctcgaag 121380
ttgcagtaca ttataaggct ttgtaagcaa ggtgtaggtt ttattaatga tttggttaac 121440
cccctccagg cccaattcac cgccaggaag cggccttcct ccggcatcgg taggtggttt 121500
aataagtttg tcaattaaat gttcttccaa ccagtaaaat gagccaggat tagatctatt 121560
ttcatagtat tgaataatgt ttttatcaat atgcgggcgt agaagatcaa gaaaatactt 121620
cgtgtcggcc atcaaagaat caattaagga aataagacct gtaaaatcta aatgcacttg 121680
agcggtgctg gtttcaggga agcgaacttg aaccattttg ttaaaactgg aggtcatttc 121740
gaagatattg gtcaacagga gctgcatgat tcgctgatta tctactaaat accttgcggc 121800
caactcttgc tccggacgaa ctcctccacc agcaggaata cccacatatg gtacaatcca 121860
agcaaaaaga gtttctgtgg ttaaatttcg gtcttgggct gctgcagccg cttcggtagt 121920
gggatcaggg tacaccatag aaagccgcat attgatttct ttaatgacta atcctggatt 121980
tctaatctca gagatggccc cgtgttttct tccgagccag tcaataagat tggcgcggtt 122040
cacgttggca gcttgtgtct ctcgtaacca ttcgataatg ctttttttgaa tcgtatctag 122100 gtctaaacct ttaatgttat tacgaaagtt attaagaagt acgtaaatag cactcaataa 122160
gttaagacct gtaataacgg tttcatgaaa cagaaatatt ttgttaacat ctgtatctgc 122220
cagtgactca gagccttgaa taagttttga aacgatttga attttatcgg tatgctcctt 122280
tttgagttca ttgatagcct ggcgaatgag ttcttggtag gaaattttgc ccaattcttg 122340
ttgcagactg ggatcttcaa acatctcact aagctgtttc ctaaattttt gtaccaaatc 122400
ccactgggag ttgggctgca gcattcctgt ttggacatcc acagagtcta tattgtatag 122460
tgccgggcgc cacttggggg taggctgggt tgaaggacta ataaacctat cggagggaag 122520
taattgtgag gattgtgtat agccatcctc atcaggaaga atggagtagt tggtttgatt 122580
catcattcca aaatcattca tagttcgcgc ttcctgaaca atgcgttgaa atttttccca 122640
ttcggtgcgt gtaatgacac cgaatctgcg gtttatttca tttacaaaat ggataagcgc 122700
ttttttggtt gcttcttgtt caccatactc taagttaaag tgttggtaaa tgacgtttat 122760
ttctttgata agctgacgaa tttcggtttc tgagtagtca ccaatgttaa taagctcaat 122820
aggacgcata aagataatgc gaataagtcc tgagaagatt ccttccagct caggaagcat 122880
cgagatctgt acattttcat ctctaaagga aaacaacttt tgataaaatt cggcgaggcg 122940
gggaaggcgg aagtaaagct ctgctgcctc gggaattacc tcgggctcta gctcatcggc 123000
acccccccaat atcatacgcg tgggtataag tttgtacacg ggctcaggcc gttcaaacat 123060
gtcgtaaatc cctaatacaa taaaaatctt ggcggccata cttttcagca tgaaggtgaa 123120
gaagacgtcc tcggtttccc agcgggttga tagggcgtcg ttaactctca cagtagagag 123180
gtagacccgc tgagccgctt cctcggcagt ctgtgcaagc gccatccttt gtcctccaat 123240
ttctgattga tttagatttt taagtcccac ggaaagcgca gaatgttgaa gatattcaag 123300
caaggtttta tagatttgca ggggcgacat gggcaccatt tgccgcagct cctctccccc 123360
aagcatgtcc ccaatccggg caaaggcatt gatgatattt ttaagcgcct gaaagttaga 123420
aagagagcgc ccgataaggt cgcgaatgtt tttagcctgg cttgctctga cgggacggag 123480
ggtaccaacg cttcggcctt gttggatttc agccgcaact ttttcgtagt agtggcccgc 123540
aggagcatta tccgtaaaga cgttggagtc gttgcctgtg gaggtgggaa aactttcaaa 123600
gacttgtgca agcgtgtccc ctgttgtctc ggtgaaccat cgtcctataa tgcgcacgcc 123660
atccagcatc tgttggactg tttgaataga atctatgttg tttacaaacg ttttggtaat 123720
gtttttaaga taaagatcta gcccttccag agctcgatag aatcggcgtt ttacatcata 123780
ctccagctcg atggcgctta cggttgcctt ccagtctact tcctgggcac ctccaggatt 123840
tgggcccacg tgtcctctgg caagatctac agccggagaa ttaatgcgcg catttttttc 123900
cgtatccaac tgcatgaggc gtcccgcaat agcatctccg agaatagtgg catagttttc 123960
ctcgtaggat tgaaactcct gtttgttatg cgttaaattg gagtaaatct gggccacata 124020
atagtaatac ataaaggtgt taattgcctg gttgaggtca acctgcgatc gcgcggcctt 124080
gctgagccca agctcttcaa ctgttagggc agcaccgcct acccttgtac actcgcagtc 124140
ctcctcgcct ccatactttt tttgcacaat atcggtataa aaatcaataa tctgtagcaa 124200
gcgagagcag gagtcataaa gatttttaaa attagggtcg gttttagata tctcctccaa 124260
aacattttta acaagcgtaa gctgtgttaa gaaggtttcg cgttcttctc gtgcggccgc 124320
attggtgtaa aagccgataa gacttagatc aagtgcgatg gtgcccatat cattaatgcg 124380
cgaaagagca tctcgaagcc tcgttatgtt cggcgtcaag gcaatttctt taacaagttt 124440
gatgcctatt tttttcacat tttccaaaaa gtcgttatag gcttgtgtgc ttttattcaa 124500
aaattccatg aggatgtgct ttctatccag tctttgcgct tcaatcctcc tatctagtgg 124560
cgttttctcc tcatcgcccc cctttttggc acaactgttc tcaaggattt tgtggcgttc 124620
attaaaggtc tgtcgcaaca ggttcacggc tttttcaaac tcagcaatgt tttctgcgga 124680
gacaagacca ctaaaccttt tgaggtcaag ctccttgtca aactccgccc agtttttgct 124740
ttgaaggtac tgttcaacct tgagtcctac tttctggaga gccttattaa ttttattcgc 124800
aacagacgca gcaataccta gattacaaag tgtgtacgaa agtacttttc caaaattttt 124860
ggttcccaag acactatttg tatcatttaa aagtttaata atatccacct catccgtctg 124920
cagtttatca agttcctttt gggtgggagt taaaatattg tcaataaaat tcgttaaaat 124980
gttgatttgc aggttttgtt catttaaaag tcgacgatat actgcttcaa tcatggtgac 125040
tgcattaatg acttcctcat tgggggctgc tttggttacc tccgtcacca tgcgctcgtg 125100
aagttgctta atggcgtcgt ttaacagctt gatattttca agtgtatttt ctatactgcc 125160
gtgtacatca agatactctg cgcgcagtcc atgagttagg gagttaatgt acagaactat 125220
ttgtcgacat atactggcgg ccccttcggt ggtatctata agcttatcct gacctaaatc 125280
aataaattcc tggttaatgg cgtctgcaat cattttacag acggtctcct gtttttccgc 125340
attttttaca aaggtggaac cggctcgagg atcgggcagt tgttttttga tatctttaag 125400
aatatcttcg atgggctgct ttgtgtctac tttgaaccct attttggcaa tcgccctgat 125460
aattccttct ataatccgca gctttgcttt actcgatacg gagtctatgt gataatcttt 125520
aatgtgttgt acaggatttt tgtccccccc gccattaaaa tatcctcccc ctgaaaaagg 125580
acgagtttgt ctttgtatat gatcctgtaa cttcgcatat atatttgctt ctgatgaagg 125640
cagtggtcta ctagaggttg aagatccacg gttacccatt ataataaaaa aaaataaaga 125700
tttaaaacta caaatatttt gctgtttata aacccaatca tataagacta actaaaacat 125760
taaatgtagg tgagataaaa gcttattttt tttttaaaag tttaataacc atgagtctta 125820
ccacctcttt ttcttcttcc tttagagggg ttccataaat ggtttgaata aaattatgtg 125880
ctctaataac cttgttaaaa tcaggtgcct ttccatattg ttcaatatgt tgcacagtct 125940
tttgtgcaag catatacagc ttggagtctt taggtacctc cgatgagggc tcttgctcaa 126000
acaacgtttc aaaggaggat gtgcattcat tggtttcatt atcatttttt tcatgaatgt 126060
tctccgaaga tgctgaggat tccgtctcct cttcaaacag cacatgcaga atcatattcc 126120
attcttcttg agcctgatgt tcagtatacc cttgccctgc atatatacga gcagatttca 126180
caatatcata cttaacagta ctaagcaatg tttttatagc ggtcgtaaca attctaccgc 126240
tattgataat ctcaacagaa aaccaattat acaggctacc cgcatgaaac acaacttgtg 126300
aagatgatct taaatccgtt ttgaagatga cctccatttt catggatata tttaaaataa 126360
aatccattca attttaaaat tataaaataa taagaagatg ccctctaata tgaaacagtt 126420
ttgcaagatt tctgtatggc tacagcagca cgatccagat ttattagaaa ttatcaacaa 126480
cttatgtatg cttggcaatt tatccgcggc aaagtacaaa cacggagtta ccttcattta 126540
ccccaaacag gcaaagatcc gcgatgaaat aaaaaaacat gcctactcca atgacccttc 126600
acaagccata aagaccttag aatcactcat ccttccattt tacattccca ctccagcgga 126660
gttcaccggg gaaatcggct cctacaccgg agtgaaatta gaggttgaaa aaacggaggc 126720
gaataaagtt attttaaaaa atggagaagc ggtcctagta ccggcggccg attttaagcc 126780
ctttcctgat cgccgactag cggtctggat catggagtca ggctctatgc ccctggaggg 126840
tccccccctat aagcggaaaa aggagggtgg ggggaatgac ccgccggttc ctaagcatat 126900
ctcgccgtat actccgcgca cgcgtattgc cattgaggtg gaaaaggcct ttgatgactg 126960
tatgcgtcaa aactggtgta gtgtcaataa tccctatctt gccaagtcgg tctccttgct 127020
gtctttcttg tcgctcaacc atcccaccga gtttattaag gtactgccgc ttatagactt 127080
tgacccccttg gtgacctttt atctacttct tgagccctat aaaacgcatg gggatgactt 127140
tttaattccg gaaaccattt tattcggccc taccggatgg aatggtacag atctgtatca 127200
aagtgccatg ctggagttta aaaagttttt tacccagatt actcgccaaa cctttatgga 127260
catagccgat tcggctacta aggaggtaga tgttcccata tgttactcgg atcccgaaac 127320
cgtacattcc tatgccaatc acgtgcgtac tgaaattttg catcacaatg ccgtcaataa 127380
ggttacaaca cctaacctcg tcgtgcaggc ctataatgag ctcgagcaaa ccaataccat 127440
acgacattac ggccctattt tcccggaaag taccatcaac gcactgcgtt tttggaaaaa 127500
gctgtggcag gatgaacagc gatttgttat ccacggcctg caccgcacgt tgatggatca 127560
acccacctat gaaacctctg agtttgcaga gatcgttaga aatttacggt tttcgcgtcc 127620
cggcaataac tatataaacg agcttaatat tacaagtccc gctatgtacg gcgacaagca 127680
taccaccgga gatattgcgc ccaatgatag atttgccatg ttggtggcct ttatcaacag 127740
tactgacttt ttatacaccg cgattcccga ggaaaaggta ggggggaatg aaacccaaac 127800
cagtagcctt acagacctag ttccaacacg gctacactct tttttaaatc ataatctaag 127860
caaacttaaa atcttaaacc gcgcgcagca aacggttaga aatattcttt caaatgattg 127920
tcttaatcaa ctgaaacatt atgttaaaca cacgggaaaa aatgaaatac taaagttact 127980
tcaagaataa gtatgttgat acctgtggtg tgttttacct gtgggtttcc tattggaacc 128040
tacgcggcaa tttttgacaa ggctcgtacc gagtatatta aaaccaaaat gggcggaaca 128100
ttgccgcaaa atatcccatt agatgcttct ctccagattg agttaaaaga cctcattaca 128160
gctctgggaa tcccaatgcg ggtgtgttgt cgcactcatt taattactac gttggattat 128220
cgtaaatatt attaatatct aaaattgaaa aaatattttt aatgttacta gtaaaaatga 128280
ctacacacat ctttcacgca gatgatctcc tacaagcatt gcaacaagca aaagcagaaa 128340
aaaatttttc atctgtattt tctttagatt gggataaatt acgcacagcg aagcgtaata 128400
caacggttaa atatgttacg gtcaatgtca tagtaaaagg caaaaaagct ccgctaatgt 128460
ttaactttca aaatgaaaaa catgtaggaa ccattcctcc cagtaccgat gaagaggtta 128520
tacggatgaa tgctgaaaat ccaaagtttt tggtgaaaaa acgtgacagg gatccctgtt 128580
tgcagttcaa caaatacaaa atctcgccgc cattggaaga tgatggtctc actgttaaaa 128640
agaatgagca gggtgaagaa atataccccg gcgacgaaga aaaatctaag ttgtttcaaa 128700
ttattgaact gttagaagaa gcctttgaag acgctgtgca aaaaggtcct gaagccatga 128760
aaacgaaaca tgttataaaa ttaattcaaa gaaaaatttc taatagcgcg gttaaaaacg 128820
cagacaaacc tttgccgaat cctatcgcac gcattcgtat taaaatcaat cccgctacaa 128880
gtatactaac accaatattg cttgataaaa ataagcccat tactttacag aatggtaaaa 128940
caagctttga agagttaaaa gatgaagacg gcgttaaggc caatccggat aatattcata 129000
agcttataga atcgcattct atacatgatg gcatcattaa tgctagatct atttgcatca 129060
gcaatatggg catttcattt ccgctttgct tggaaatggg agttgtaaaa gtttttgaaa 129120
aaaataatgg gattgatgtg aactccattt atggctcaga cgatatttca actcttgtta 129180
atcagattgc tattgcttaa acaatttgct caaaacaagc ttataaacgt ttcttaggta 129240
tgcgatacgt aaatcctaat tctttaataa gttctttttc agtagtgatt tttagaggta 129300
ctaaagtttg atttttaaat aatccatact gatttagctt ataattcttt ttttttaacg 129360
cagctcgaat tcttattaaa taagaaacgg gacccgtaaa atgaagtact gcgtatggct 129420
tttcctcggc taaggccgta aaaagatcaa gttgatatgt gttttttttc cattcaataa 129480
aaagtacaca ctttcgttct ccgcagactt ttacagaaaa agaaagatcc tttatgcgaa 129540
tgttgggcag gacgtgtttt aaaagttttt tttctggaac aataataaga agatccacgt 129600
cattaagcat tttctcttcg cgtcttaagc taccaacagc aacgatgttt tttgataaaa 129660
tttttataag ttgtccatta tattcaaacg caagtcggga gcgtaagtca tttacaattt 129720
tttttccttg aataagcgtt aacattttat atttaatatt aaaatctttt cattttatat 129780
attatatacg caaaatggca cttgatggtt caagtggtgg aggctctaat gtagaaacat 129840
tacttatagt agcaatcatt gtggttatta tggcaatcat gctttactat ttttggtgga 129900
tgccccgcca gcaaaaaaaa tgtagcaagg ctgaagaatg cacatgtaat aacggaagct 129960
gttccctaaa aacaagttaa aacatgcaat tatatgcatg catataaacg catgcatata 130020
aacgcataca tataaaatgc gtaaatacta tataaaaaac tataacatat caatcaagga 130080
atcaacactt ttataatttt ccgtaatata tttttcatcc ataatgatgt cagagtacat 130140
ggtccctatg cgaggaacag agcccataag ggtaggcgcg gcaataccgt aaatgggatt 130200
cacggcggag tcaaccgcag catctgtcaa gacctggact ggagacgaca aggccattcg 130260
caacaacacg ttggaaggct ctcttgcatt aagccctgcc ttttctagag aggtaacctg 130320
tcccgttctt gtcatgagat ctgcgtacat gagtaaatga cgatggttgg gacccttgtc 130380
ccccataacc gttctaattt cactaataat tttttgccgt gccgcttcta tgccgtaaag 130440
ctccatggtg tctcctatag aggacgatac gatggtgtat gggtcgatgt tatcatcaag 130500
cattgcgcca aaaatattag tcccgtttgt tttgatggcg tagatattgt ctagtcttac 130560
cagtttcccc tgggcatcca cacggtggcg cataagctta acaacattcg catttttgat 130620
gcctggtatt cctctaatcg tgctatttaa tagtttatcc accacattta cggcaatttt 130680
ttcatccgta gccattcggg tattggtact gcgtctaaag gcgctttccc gtaggtatat 130740
gcgaataatg atgggaatcc ctgaggccgt gttttccaca gaatgcatga tgtaggtgtt 130800
ggggtgttta gctcttagac tattaataat actttctaga ctaatgcttt ttaatatcat 130860
ggttgttttg tttaattcca agcggataca ccagtttgca atatcctctg gggctgtag 130920
tagaggatgg ttttccagaa aatccgtcat ccattccaca tcacttgcaa aatcggggta 130980
catcacattt ttttttgtgc ttgaatacgt ttcgtacaat aggtgccact gcaatatcaa 131040
ccgttcgaac gttataagct ctatgctgtt agcaatttct tgcgcatatg ttttatttgt 131100
ttccacttcc gggttcttta gacgtaaaag catttcagag gattgttcag cctctacggg 131160
cttcgcgcta aagatctcct ggggccgcac aattcccgac ttgttggttc ccccggccac 131220
ggaccggtgg tgggagtcca gcatatattg tgtcaagggc tctgatacgg actgcgccgc 131280
caggattccc actgcctcac cgtagttaat aagactttga gtatattgta gccttatgag 131340
gtccaggatg gcactcatct gctcgcaggt aatgtttaat gttttaacgg ttgccagttc 131400
gatgcgaata agcatgcgca tcagagaggc agcccgttta agataaacgg gtatgggcgt 131460
ttgtagtcgt tcctgaatgt tgttaataaa cacgtatgga agatttttgc aaaacgtttt 131520
gaccatcgcg tatttttgta gaatactttt ttcgtcgaag ggaagcacgc cactggtgga 131580
gctcagtaga atgtttttta cgatgctggc cacgtttacc ggcacctgtc taacatctgt 131640
aagcagctga ctgaaattaa aattttcgac gtttaggaag atctgtcgat atttatctct 131700
atccttttta aggcgtgaaa attcttcttc aaacaagggc gattgtatcc cggtgtactt 131760
gaatttgtct tcaagttcct ggtccgacag catgatggtt tcaaaccgta cggtttcaag 131820
ctggcgcgca tcaaggccgt cctctccgta caactgctgc acaagacgcg tatcgatgga 131880
aacccgtcgg taataatcca caatacagga ttgaaggcca aagatggctt tacggttggc 131940
atagcctgtg gatgatgtcg ataatgcttt gttgatcaag tcgaatcttc cattcatttc 132000
cccaaagata aattcagggg aggtaaggcc cgcaatatag ctgttgcaga tgaacccgta 132060
ggcctgcgcc tccagggcaa acctggggta gtacaccagg gtcctaccga aggaaaactg 132120
gggttgaatg cgttgtgtat taatttcaat ttggccgatg cccgccatga tgtgaatcat 132180
attggggttt gagcccttgg cgccagtggc caccatctga aaaagcccat tggtttccgg 132240
attaatggaa ttcataatcg gctttaaaat tctatcggga aatttaagcg cattcagctg 132300

-continued caattttttcg tagaagtcat gcgttgtcag gcctataggc ggcatgatgt ctccatgaag 132360
cagccggttg tttatttcct ccgactcaag cagcagttca ttgataattt cttggacctc 132420
ctgatgtgcc tccggggtta ggagcatgtc ggccgtggac actgtgaatc cggcgttgcg 132480
cacgtagttt agggcgagct gctgggtcgc aaatatcatt ttcaaggcct gctgcggccc 132540
atacctacgc gaaataaggt gatagattcc accggaggaa cccgctccga cggccttttt 132600
gtcaaggacg ccttcaatga gttcgccgtt gcgtatttgt gtagagatgt cctgcttgtt 132660
ataatgcatg tagggtgcat acacttctga gtaccatgtg gggggctcgtt gataattgat 132720 gggggtctgc ctcagtagca tagatacaac cgatttgcca tccagcaggt cagttgggga 132780
gtagttggca aaacaaggtg ggtcggtttg ggttgtttga aacaaccccca tggcgtgcag 132840 cttgttcatc acatttttcc ccatgggggt gttcgtgcgt gtaagcaaaa agcttcccac 132900
cgtggagtcc tgcacctgcc cattaacggg acccgagctc tttgtggaaa tgaaccagtt 132960
tcgcacagaa caaagtagtt cggcctcaac gcggctcatg acgctccagg gaacccagag 133020
attcatctga tccccgtcaa agtccgcatt ataccaggca catgcgctga cattcatttg 133080
aaacgtagaa atttttgggt tttcaagaac gacaatccgg tgaaccccta tgctgcttcg 133140
ttcgagagaa ggctggcgat taaaaaacgc gacgtcgcca gtgacgacgt cacggtaaag 133200
gatgtctcct acctccagcc taaagtcttg tttgagaccc tcaatgtcgt gaacggattg 133260
tgttatttgc ttatacactc ttgaacaacc agggtactgg cgctttccat ttaaaaaata 133320
gggcattaat ctattaatat tataatgttg cactgtttcc gcaacttgca gcgttcgtgc 133380
aaaggaaatg ggatagccaa cctcgtccag gtgaaggtct gagttcccgc agatggtgga 133440
ccggctgatc gaccatacct ggctgcccag tagggattta cgaattcttc cctccttgcg 133500
aggaagtctt cgcatgatgg agggagcagg gcgtgccccc atgacgatcc cacgctttcc 133560
cgtgcctccc tgggttgcgg tggtggaaac ggaatccaac aaaaagttat agtaaagttg 133620
ctgtatggtt tgcaaattgc ggtcaatatt taaaggtatt ttttggccgc gcacgatttg 133680
taggtccttc gggatcagca gattctttcg aaccagatac tgaatcacgt tgttaatgtc 133740
gtgaaagctt tgggggcctg acccgattcc caatctgatg ccaggtcgta tgctgatggg 133800
ggggatctga atggccttaa gcacaagttt ttcgggatgg gagtttttac ttcgccccag 133860
ttttacaacg gtgtcgtagg ttacgcgcga aaaaatctct ctgatgatct gcgggtacag 133920
tttgtcaatc ttgccctgct gatccgccca aaaggtaaaa taatcttccg agtccttaac 133980
aattttgggg tgtactgcct tacagacgta gcactgcttt ccttcggttt ggcttgaagc 134040
cgcttcaata agacgcttag gcctaataag gtgctcgtac ctctttaggt caacgatggg 134100
agccccgcag ttgagacata taacccttaa ccatcgtcgt atttcggcga tgaagagcgg 134160
ctgaagcacc ggagcatgca tctgcagtat cccagggtgt cccatacatt gcttgcgctg 134220
gtgtgagcaa gtgatgcatt tataatggtg atcggtggtt cccattcgcg catcatagat 134280
acccccttcg gcgggaaggg tgccctcaaa taaattagaa atggtaacct ccataacgcc 134340
ttgcctctta tgatcattgt caccggcaat attgaactga acggcggcta tttcggcata 134400
tccagcctcc atatttttgc taaatacata ataaaacttc aaatgttaaa aaaaaataac 134460
atcggttggc atattttttt gttaaaacca agtgttaaat gatttctaaa acatttatcg 134520
gttcacgaaa acctaccgca cgggcctgaa gaggaatgcc agttttgggg gaaagctcgg 134580
catattccac ggtaagctct tttccataaa gatgtttttt aaataaggcg ggcgtgagtt 134640
tttgaaaaag agcataacga tccgcgtacg tcaaatgctt aggagtgact acaaaccgct 134700
ttttgtttgg caattcgcaa acccataaaa tggcgcctaa gtcctttccc ttttttccct 134760
gagtatagtc cactaaaata aattcagcgt ctagcagcgg tttcagcttg gcaagatgcg 134820
ctgagtggta gttgttgtat cccggctcat agggcccatt ggcattgcgt acgatggctc 134880
cctcgtagcc ctccttaata aactgcgcct taagcctaag ggcctcatcc acattcttca 134940
cgctaaaatt ttcaacttgg tggataaagg taagatcttc cttctgttta aaaatatttg 135000
ttaatagctg ttgtctcttg ttggaaggca tttgaagctg atcactccaa aaacagtcaa 135060
acacgtaaaa gtgcagctcg gaggaatctg tcttcgcatt cgcctgcccc gcgatccatt 135120
gcagaggttt gcggtgtaaa taaagctcac catccaaata tactctcacg tctataaata 135180
aataaagctg tttgagctct tttttaatat tgtcaagacc taaaaattcc tttttcgtgc 135240
gcgaatacaa gagaatgcta ccatcgccct gctggcaggc cacagctcga acgccattac 135300
gcttgcgctg cacgatggga tctgtttctt cttcaaaaaa tgtcttagga attatattaa 135360
aatattttac cagcataggg gggataattc ctctatttgt gtgggctccc cgcttttgtc 135420
tggcatggcg attatattta ctaagggcgt ccttgaatgc ctgatggact accgttgtgg 135480
catttttttt acccaagttt tttccctcgg taacacgtgt catttttgat atccgcaccg 135540
ccccttcttc cacaaaaaat tttgtgaaaa tttcagcaac ggcgtctttt acatctgtgg 135600
aaaacatctc atctgtgatg ggaatgatcg tgttgtgctg caccacttgc acacaaataa 135660
tccatgaggc ctttttttccg cttttcgttt cagactcaat cggaggaaaa caaaaaatgt 135720
tgtttgaata ttgcccagga aattgattta gcatggtttt aacaataaaa taagcctatc 135780
aattttttta taatttgaat agttattcca aattcaatat ggcttcttta gataatttag 135840
tggcacgata tcagaggtgc tttaatgacc agtctcttaa aaatagtact attgaacttg 135900
aaatacgttt tcaacagata aattttttat tattcaaaac cgtatatgag gcacttgtgg 135960
cacaagagat ccctagcacc atctcccaca gcatccgctg catcaaaaaa gttcaccatg 136020
aaaaccactg ccgggaaaaa attttgccgt cggaaaatct ttacttcaaa aaacagcctc 136080
tcatgttttt taagttttca gagcctgcat ctctgggctg taaggtctcg ctggccatcg 136140
agcagcccat tcgtaaattt atcttggact cctccattct cgttcggctc aaaaatcgta 136200
cgacctttcg ggtatctgaa ctttggaaaa tagagcttac cattgtaaag cagctgatgg 136260
gaagcgaggt ctctgcaaaa cttgccgctt tcaaaacgct tctgtttgac accccagagc 136320
aacaaacgac aaaaaatatg atgacgttaa taaacccaga tgacgaatat ctttacgaaa 136380
tagaaataga gtatacagga aagcccgaat ccctaacggc ggcagatgtt ataaaaatta 136440
aaaacacggt gttgacactt atttctccaa accatttaat gctaacagcc taccaccagg 136500
ccattgaatt cattgcctcc catatactgt cctcagaaat ccttcttgct cgtattaaga 136560
gcgggaagtg gggcttaaa cgcctcctcc cccaggtgaa atccatgacc aaagcggatt 136620
acatgaaatt ttatccgccc gttggctact atgtaacgga caaagcagat ggaattagag 136680
gcatcgccgt cattcaggac acgcaaattt atgtggttgc agaccagtta tacagcctag 136740
gtaccaccgg cattgaaccc cttaaaccaa ccattttgga cggtgaattt atgcctgaaa 136800
aaaaagaatt ttatgggttt gacgtcatca tgtatgaggg caatctattg acgcaacagg 136860
ggtttgaaac aagaattgag tctttaagca agggcattaa agtcttacaa gcgtttaaca 136920
taaaagcaga aatgaagccc tttatttcgc taacaagtgc agatcccaac gtgctcctca 136980
aaaactttga aagcattttt aagaaaaaaa ctcgcccata ttctattgat ggcatcattt 137040
tagtagaacc tggcaattct tatctaaata caaacacctt taagtggaag cccacctggg 137100
ataacacatt agactttttg gtgcgaaaat gtccggagag tttaaacgta ccagagtacg 137160
cgcccaaaaa agggttttcc ctgcatctac tatttgtagg catctccgga gagcttttta 137220
aaaaattagc gctaaattgg tgtccaggat atacgaaact attccccgtt acacagcgca 137280
accaaaacta ctttccagta cagttccagc catcggattt tccattggca tttctttatt 137340
accacccaga tacctcgtca ttttctaata tagatggaaa ggtccttgaa atgcgttgtc 137400
ttaagagaga aatcaatcac gtcagctggg aaattgtaaa aatccgggag gataggcagc 137460
aggatcttaa aaccggcggg tattttggca atgatttcaa aacagccgaa ctcacatggc 137520
ttaactatat ggatcccttt tcctttgagg agctggcaaa gggcccttct ggaatgtact 137580
tcgccggtgc caaaaccggc atataccgcg ctcaaacagc acttatttcc tttattaaac 137640
aagaaatcat ccaaaaaata agtcaccaat cctgggttat cgatcttgga ataggaaaag 137700
ggcaggacct aggacgttac ctggacgcag ggataaggca tcttgttggg atcgataagg 137760
atcaaaccgc gcttgcggag cttgtttatc gaaaattttc gcatgctacg acccgacagc 137820
acaagcacgc taccaacatt tacgtgttgc atcaagacct cgcagagcct gcgaaagaaa 137880
tcagcgaaaa ggtacaccaa atttacgggt ttcccaagga gggagcttct tccattgtta 137940
gcaacctgtt tattcactat cttatgaaaa acacgcagca ggtggaaaac ctggccgttc 138000
tgtgccataa gcttcttcag ccgggggaa tggtgtggtt taccaccatg ttgggagaac 138060
aggtcttaga attacttcat gaaaatagaa tagagctcaa tgaagtatgg gaggctcgtg 138120
aaaacgaagt ggtcaaattt gctattaaac gtctctttaa agaggatata ttacaggaaa 138180
ctgggcaaga aattggagtc ctgttaccct tcagcaatgg cgacttctac aatgaatatc 138240
ttgtgaacac agcgttttta attaaaatat ttaaacatca cggcttttcc ctagttcaaa 138300
agcagtcctt taaggactgg attccagaat ttcaaaactt tagtaaaagt ttgtataaaa 138360
ttcttacaga agccgataaa acttggacaa gcctttttgg gtttatttgt ctgcgcaaaa 138420
attaaatatt ttttcataag aagtactacc caggttttaa agaaatagct aaaaatatca 138480
tatggatact gccatgcagc ttaaaacgtc tattggttta attacatgtc gtatgaacac 138540
ccaaaataac caaatagaaa ctattctggt tcaaaaacgt tacagccttg ctttttcaga 138600
atttattcat tgtcattact ctataaatgc taatcaaggt catctgatta aaatgtttaa 138660
taacatgaca attaatgaac gactgcttgt caaaacactg gattttgacc gcatgtggta 138720
tcatatttgg attgaaactc cagtctacga actataccac aaaaaatacc aaaaatttag 138780
gaaaaattgg cttctcccgg ataatgggaa aaagcttatt tcattaatca accaagcaaa 138840
gggctcagga acacttctat gggaaatccc taagggtaag ccgaaggaag acgagtcgga 138900
ccttacctgt gccatacggg agtttgaaga agaaaccggg attacccgcg aatattacca 138960
gattctccca gagtttaaaa aatctatgtc atactttgac ggtaaaacag aatataagca 139020
tatctacttc cttgcaatgt tatgtaagtc gttggaggaa cccaatatga atctttcttt 139080
acaatacgaa aaccgaattg ccgaaatttc taaaatttct tggcaaaata tggaggctgt 139140
acgttttatt agcaaacgcc agtcattaaa cctggagcct atcatcgggc ctgcatttaa 139200
ttttattaaa aactatttac gatacaagca ctaggatgcc gcattaaaat gccacataag 139260
gtaatacact aggaatgtcg cacacgcaca agaatacaac gtcgccggag atttattatc 139320
tagtacacgt tttatgtatg tacaatccgc cttcatttaa tatattgagc ggatgtacta 139380

-continued tgtatttatt ttaacaaaaa acattatttt tttttaatct tcatcatctg tttttataaa 139440
ctcagtaata tcaaaagtag cttgtggggt ttcagagggt tcaccttggt tatcctccgt 139500
gaggataaca tgttcttcag gttcgtcgtc actggagaac ccatcattta attcctcttc 139560
actcaacatc tgtaaaaaat cttccaagct ttcgctatcg ttaaaatcct catcatccat 139620
aagaataatg gtaccttcct catcgtttcc tccttgtttc gtgtctaaat aggcctgcat 139680
ggcatttgca aaagtatcaa aataggctga gtcagattgc tgttccaaaa tatggccttg 139740
cgtattaaat gtggttgcat cgttgttaaa tgcttgcaaa tacagtaagg gatttatatc 139800
cattattatt aagcaaaaaa aatttaaatt atttttcgac cgatgttagg taaaattaaa 139860
caattgctat aggtgttaag caatgtttat tgattttaag tactcaacaa ccatgatgta 139920
aatactatac agcacttttg gatttttaat caaatccaga ttaatactaa cttcttttgt 139980
gatacagttc gtaataatag tatcctgctc atcgttttgt aagatttctt ttaatatatt 140040
tttttttacc gggatactaa gcaattgatt attttctttt aaaaactcct tttgatattc 140100
aatcgtctta ttcattgaat atttgtatat aactataatt acaaatgttc aatgaattgt 140160
tattcatgtc gggagatggc tatttaaaaa tcatgtccta tttttctttg ctcaataagc 140220
atccaaatat tttcatggcg ttttattaat tgttcattat tgaacgtatc acaaagatca 140280
tttataaatt gcagatagtt tattatttct ttcaagagag taacaaacat tacttcagca 140340
gaacatataa taggtaattc agtggcgtta aaagaatttt gatcttgttg atacgccaat 140400
ggcgaggact taaggagatt tgggggtctt gcccaaaacc ctaggctgct gttcttgttt 140460
tttagggcgt cataaagaaa tgaaagcaca ttgcaaggct taagccgcga catctccttc 140520
cccttgggcc ctttccatat ttttagatct aagatctcat ccgagcttat agagtaggta 140580
tagtaaagtt tttcaaaaaa gcatatctgc ttgaagtctt ttttagaacg actttcaaga 140640
agcatttcta taatgttaac aagttttgtt aggtttaagg cctgttcctg tgtaagctcc 140700
tcttgcacgt gatagactga aaaagtgtgc ttaggaatga aaatactccc cgtggcactg 140760
gcctgttgtc tgccaggtat atagtacacg ctgctgttag caagctgtac cggcacaatt 140820
tgccccactt ctgcaacatt attttgcgat tcggacgagg gtatgacaat agttacgggt 140880
tcagtcaata ggctttcgcc gagaataata ttactgtcat ttttaataat tttaacggcc 140940
gctattaaat caaaggcatt taagtaagaa acaacagcag aaaatcttac atgcatatat 141000
cctcttccgc tattattcgt acgcataata aaacaagggg agcgttgtat aacgccagta 141060
atattaagaa taaaactgtt tttgaaacac ttacccacat aaatgttttc aagctccttc 141120
aaaagatgag cctccacatt tgtacaaaaa ttggtaggat catcaatatt caacgttgtc 141180
tcaaaaattt tttggtcgat catatctata atatattctg tctatttcaa tttaaataat 141240
atacgaataa ataacgagat tattttatta aataagcaat ggtgtataca ctttgtattt 141300
actttgagat atactttgtg tatcacaacg tgccctaaga tgtgtgcaca agtgacggca 141360
ttttgtcgtt aaaaaggtaa aaccagcgga ttccatcctg cattccattt ggttgattac 141420
gagcctccat ttctttttgc aaaaggttat tgcgaatgag taagcagagc ttgatggcac 141480
taatctttgt aaggtttaaa cttatgccca attggtcagc aattttttgt tgctcctccc 141540
gtccgcgtgt ttcgcatacg gctccccggt ttagcatgcg aatatcagta atctcattct 141600
tttttaaaac ctggataggt gggcggattt taaatttaag ggcctttccc ttgctttcca 141660
tatagcctat gacgatgtcg ttttcttttc gtttaacatt aatattaagc atataaagcg 141720
gaatttcatg ccaggtttta tcttctcgcg aggtaataag tcgcacggag tcctccgtgg 141780
catagcccac tagagtgttg tcatccccag gcacgtggct tataatttta aaaatgtccg 141840
gaaatggctg aatatctttt tttgaaaaag cgatgaaaaa ctttttataa acctcgacaa 141900
gggcccccat acctgcaaga ttatctataa taagtgcttc tagcatcgta tagtgaaatg 141960
aagcggggta gtggatgagt acctgctcca ttggctcatc ctgaaaatcc ttctgaaact 142020
tttcatacaa tacttgaaag ggttctttgg tctgcgagtg ttcgaggtat ttggtaatac 142080
ggatgctgtg catcgcggga ggctgaaaat cccgaatata tgtttcaata tctaataccg 142140
gttccttttt atggttaagc accgcagcga cgtacaaatg ctcaggcttt gccggcacat 142200
gcataatggt gcaaagacga ttctgtatcc ataattcctt gcactggttt tttgagtagc 142260
atagagaaat gagcgccagc gcgaagttgt cctctgagaa gagtttatta tcgatggtaa 142320
ttccctgtat gagcttggga gtggaaacag ccttccatag ctcggagtac gtccacacgg 142380
ggcgtgccat aaacaaagat ataataatat tagaaattgt ttttacctct tgctccccgt 142440
atccataggc ctcaaaggta ttgaggacgg tggctccgac gtttgccggc gtgatggatg 142500
gactaagggg cagactttcc aacataggct tatcaatctt aatctggttg gtgaacccat 142560
caatggcgtg ctttcgcagc gccttatccc cctcctgtat taaaatgtat tcttttaatt 142620
tttgtgcgta cttagcgagc tctggccctc catcgggtgt tgtcgatacg tacaaataaa 142680
ttgtcacgtt gcgctcactg ggggggagct ccatgtgtga attttttcgc accaccctcc 142740
caaatacctg aataagccgg ggaatatcaa ggggcaatga cataatcatc tcgtaccgca 142800
cggcctgaaa gttcaaaccc tccacaatca ccttggaccc gatgagaata cgcagctggt 142860
ggccttccag gttggacgag gcgttaaaaa gagccaggct tcgttcgcgt acagcgggct 142920
ctatttcgct gtgcagaatg gtgaaccgta ctggaataaa ctgatggtcg ctatgtgtgt 142980
gctcatcgcg aatcgcggcg cagatggagc agcgggtcgt tcccacaggg gacgaaactt 143040
catttaaaat gccattactt tgtaaaattt cttgcaagat aagaaccccc gacatgcgga 143100
cccgattgtg gtaaattaaa attttccccc ggccttgccg aataatggaa agaatgtctt 143160
tcatcatttg agtgtatttt ccgctataaa aggccaatcc cgagatgtgc gttggtggct 143220
gcagcgacaa aaagctgcca ctcacattaa agggggctct acgcgaaggc tcaataatct 143280
gtaccccgtt ttccagaagc cagtctgtgc ttgccataga aagggcggtg ggggtttccg 143340
tcgagttaaa caggccgtaa gccttgggtt ccgtttgttt tgaaaatttt gggttgggaa 143400
acaccatgtc ataaatgctg tacgcattac tcgagatttt agggtcaggg cccagctgtt 143460
taagcgtttc aagctgatac tcagacatgg ggcattcgat gaaatgtaag tacggcaatg 143520
tttcgtcttt ataggacaac atctttccgg caaatattct ttcggggtaa aaattggtgt 143580
tggtatccaa caaaaaagat acccttccgg tgctcagtct ttccacaaga gctagggcgt 143640
ccttttttcca tttaacggaa tgcccactgc tgtcaaacag ttgctggcgc tggaggggct 143700
ggccgttggg cagctcatgc cgcggaacca aaaggtttaa caggtcgacg tattccatga 143760
cactcccggt tacgggcgtt gccgacatga agacggccct gggggcctgg tgaggtggaa 143820
aggcatccag gacatactgt aaagcgatgc cataattatt tcgttcctgg atattgtaca 143880
cgttgtgtat ttcatccgca atgagcagtc ctcccctaag ttgctccatg attttttgat 143940
tcacccggat gaggccgttt gtctcggcct cgctaatttt ttgcacgaac tgagatatat 144000
cgttctcatt caatgtatct tctgcttcgt cagaacgatg aaacagagaa agcacatcaa 144060
agtttttctc ttcaccctta ctcgtaatat tgaaaagctt ggatgcaaat tccttatagc 144120
cgtaaaactg aaaaaagcct ccgcggtttc tatcggttaa acggcgcttt aacgtactaa 144180
cgaacccatt tagatgccgt gattcgaccg acgtggtgct gccagactgc tttgcaatgt 144240
gaagaagccg gtgtagctca gcgacctcct tgtaagaaac aaatcccagc tcaggacgtc 144300
ttagcatttc tgtttgaatg atggcgcgtg taaagcctac cacaaaaatc cagggcgcat 144360
tttcaataaa attcatgtag tggttcataa attgacgcgc gatggcaatc gcggcaatgc 144420
tttttcccgt cccggtctgc cagtttaata aaagacgcga gtagggcgtg ttgggatttt 144480
gaaagttttg gacgaaaagc tgggcattat gcaattggag acccttgatg gaaggaaagg 144540
gcgacgcgta ggggtcacac ggaaaaaacg ctcgcccccc cttctcgcag ccaggcccac 144600
cgatctggac aaaatgagcc cgcagatcac gaatgagctc tttttggtcg acaggagggg 144660
aaatcaacga tttaaactcc tttcttcgcg ccaactgctg caaaaagtct gcggcatcca 144720
attcgggata cgccatatta tcataaaaaa aataaacctt tttatgaaaa cttttatgtg 144780
attctgtatt gcaattgttt tttatgaata ctgtaaataa gcgtatcaac ttgtttttct 144840
aacgaagagg cgttattctt tttttctgga tataaaataa taataagtat aataattaag 144900
actaaacagc aggcaatcac tatcaaactc atattatact tacttttta taaaaagtat 144960 tatatcttat gaatgcgcaa gttcagctaa ttgttcgtcg cttggaatgt gggactgcag 145020
ggaggtggag tttttccttt ttctaaagaa taccgggaaa tggtggtgag gctcaggttg 145080
ttgtacatag tagctaggag gaggtttagg tatgctcgac ttgcagtcaa tagtccggtt 145140
atagtaaacg atggcaacga tgataagaat aataatgagc aaaatcaaaa tgcccaggag 145200
aatcgcagtt gttccgggat atttggcgat tgtatgggct aaaaggcctt gggtgctttg 145260
tttaattccc tcgcgggttg acaggttatg agaaagcagt ggagacgttt cagtgtccat 145320
ttattacaat tgaacagtta tattaatctc aaataaaata taacacaaaa ttaattatgg 145380
ccatgcaaaa gttatttacg tatatttacg agtttattga atatcgtaag atggtgctgt 145440
tggaagaaaa ggtaccatat gataagtttg ttcaaatggt acttaataca ggattttttc 145500
gtattaacgc ggagacgctg aatcacggaa tcgtatccgt gtttatcttt ggagcaaatg 145560
gcaagtacgt tcaccacgga ggcgacatga gaacgctttt aacgaatacg cttaatgaaa 145620
aaaaacatta tgaagaatta attttaatcg ttgataagcc cgttttaagc aaaaaaaata 145680
ttttagatat aatcgtcgag cagcgcgctg caaatcccac gattgtaata aacatatatc 145740
cctaccacct gttctgcatt aacattccca aggtgagtgc cattcctaaa cataaactaa 145800
ttactcagga ggaggcgcag gagtttttag gtcgcgaata tctgcaaccg caggacctca 145860
tgcaaattag cgcgtcagac cccccggtgg tctggctggg aggaagaccg ggagactttg 145920
tgcaaattga gcggccctca gagacagcta tgcacgctgt tgttatccgc tttatcacca 145980
agtccaaaat ttgagtcccg tgtttaaaga tgacagacag ctaagtaagc atatctgtaa 146040
aattgtcgat gtcctctgtg gatagagcgc tttcctctga gcagcaaatt ttttcataca 146100
tctccatggg ggatggcgag gctttaatag tatgtaggtc acgtaagaac tgttgtatga 146160
tgggatattt gtcttttaaa aactggggat gtttcataac tggaattatt tgaaagataa 146220
agaccttcca tccaaagtag ccaaccacat ttggcatttc gggacacgcg gtttcataag 146280
gcatagaata gtgaatagtg tactgatctt tttgatacag cgtttcaagt agttggcgaa 146340
atgtttccgc gtcgagcgtg ccaaaatctt gaggagcctc ggtgtgctcc tgtgtagagc 146400
agatcgtgat gattccccag gcaagcggga gcatggactc tggagggtgg atatccgtat 146460
tggtctcatt attcgatccc agctgatgaa tgccgcacac gcgaaacatg gcctcgacgt 146520
agatgcccat agagataggc ggcgaaaggg caagaccgga ttgtatttgc ggcatatagt 146580
aggagggcac cgagtttttt atttttcggt tgaatgggga ctttatttct accagcacgg 146640
ggatgcgttt cgtggcctca tagcgtacgt tgttaaaaat tgttttgatt tcccaggact 146700
gttgagtgta tcccagcgtt aggtgacaaa acccatcggg gctattacta tgtccggggt 146760
atcccaaata ggtcccatca atatgaatat tgtcacctat gacggtggtt tggcagaaca 146820
actcaagcag atctttacta acacgctcaa aaagggttcc ccagctacaa gcagcgcggt 146880
tcaaattctt cttaaaaaga tttgcttttt ccgccaaggt tatataatag cttttgtaag 146940
ggtttaaacc taaaacgctg gcaaggtcag agccacccac ctgagtgcga cgaatagcat 147000
gccaggcatc ggagcgctgc tgaggagagt ctttaaacag gcgtacaaag gtttccatta 147060
tacttgtttt aacaggaatt caatataaaa agtcaacaca gtttgcaatt tttccaatct 147120
caagatatag ccatacattt ttttttccaa ttggcgaata tgtttaagct catgtgtttc 147180
aatattagca tccggaaatt taaatgcata aagatgttca aaggcctgat ttatacacgt 147240
atcaaaggat ctgtggtatg ttattagctt cagcatgtgt gccagatctt caagatggtc 147300
taaatttata cggttttcca cgtggtggat catgtctgcc acatcttgag cccccatcca 147360
ggggatcaca aggtactccc ccttaaagat gattcgtcgt ttttttaaaa aatcatgaaa 147420
acgttttaaa gcttcaagaa aggggcagtt gggctttgac cccaaaatgc tgacgacgat 147480
atcctcgggc atgatgtatt cgcagtgagg atagtagttt acggactcta attcagcggc 147540
ccgccgtttt atttcgtatc ttgcccagtt attcagagag tactccacgc ctccgaccac 147600
aacagacatc ctatctatta aaaaataaca ataaaaacct tatgaaatct atgtatagtg 147660
gccgctaaaa tgtctatatt agaaaaaatt acgtcaagtc cctctgaatg cgcagagcat 147720
cttacaaaca aagatagctg tttaagtaaa aaaatacaaa aagagctcac ctcttttttg 147780
gaaaaaaaag agacactcgg ttgcgattcg gagtcctgcg taattaccca ccccgccgtg 147840
aaggcctatg cgcaacaaaa gggactggac ctctccaaag aactggagac tcggtttaaa 147900
gcgccaggac ccagaaacaa cacgggtctt cttacaaact tcaatattga tgaaacgctg 147960
cagaggtggg ccataaaata caccaagttt ttcaactgtc ctttttccat gatggacttt 148020
gagagggtcc attataaatt taatcaagtg gatatggtaa aggtatataa gggagaagag 148080
ctacaatatg tagaaggcaa agtggtcaag cgtccttgta acaccttcgg atgcgtttta 148140
aacacggact tttcaacggg cactggaaaa cactgggtag ccatctttgt ggatatgcgg 148200
ggcgactgct ggagcatcga atattttaat tcgacgggaa attctcctcc aggtcccgtt 148260
attcgttgga tggaacgggt caaacagcag ctattaaaaa tacaccacac cgtgaaaacg 148320
cttgcagtta ccaacattcg tcaccaacgg tcgcagaccg agtgcggccc ctacagcctg 148380
ttttacatca gggcacgcct cgacaacgtg tcatacgccc attttatatc cgctaggatt 148440
accgacgaag acatgtataa gtttagaacc catctgtttc gcatcgcata aactaataaa 148500
gtttgaattc tttataggaa taaaaatgga agcgtttgaa atcagcgatt tcaaagagca 148560
tgcgaagaaa aaaagcatgt gggctggcgc cctcaacaaa gtcactattt cgggtcttat 148620
gggggtcttt accgaagatg aggaccttat ggcgttaccc attcacagag accactgccc 148680
cgctttgtta aaaatttttg acgagatcat cgtaaatgcc acggatcatg aaagagcttg 148740
ccataacaaa acaaaaaagg taacttacat taaaatttcg tttgataaag gtgtgttttc 148800
ttgcgaaaac gatggcccgg gaatccccat tgcaaagcat gagcaagcca gtcttatcgc 148860

-continued caagcgcgat gtgtatgttc ccgaggtggc ttcatgtcac tttttagccg gaacgaacat 148920
caataaggcc aaggactgta tcaagggggg aaccaacggc gtcgggctga agctcgccat 148980
ggtgcattcg cagtgggcca ttcttaccac cgccgacggc gcgcaaaagt atgttcaaca 149040
tatcaaccaa cgcctagata tcattgagcc tcctaccatt acaccctcca gggaaatgtt 149100
tacacgtatc gagctcatgc ccgtatacca ggaactaggg tacgcggagc ctctgtctga 149160
aacagagcag gcggatcttt ccgcctggat ttaccttcgc gcctgccaat gcgcggccta 149220
cgtgggaaaa ggcaccacca tttattacaa tgataagcct tgccgcacgg gctctgtgat 149280
ggcgctagcc aaaatgtaca ccctgttgag cgcgcctaat agcacgatac atacggcgac 149340
cattaaggcc gacgcaaagc cctatagcct gcacccccctg caggttgcgg cggtcgtgtc 149400
ccccaagttt aaaaaatttg aacacgtgtc cgttatcaac ggggtaaatt gcgtaaaagg 149460
agaacatgtc acctttttga aaaagactat taatgaaatg gtcgttaaaa aatttcaaca 149520
aacgattaaa gataaaaacc gcaaaacaac attacgagac agctgttcaa acatctttat 149580
cgttatagtg ggttccattc caggaataga atggaccggc cagcggaagg atgaacttag 149640
catcgcggaa aatgttttta aaacgcatta ctccattcct tctagttttt taacaagtat 149700
gacaaagtct atcgtggata ttcttctgca atccatttct aaaaaagata accataaaca 149760
ggtcgacgta gacaaatata cgcgtgcccg caatgcggga ggaaaaaggg cgcaggactg 149820
catgctactc gcggcggaag gggatagcgc actttccctg ctgcgcacgg gactaaccct 149880
gggaaagtcc aacccaagcg ggccctcctt tgacttctgc ggcatgatct ccctgggagg 149940
agtcatcatg aatgcctgca aaaaggtgac aaacattaca acggactctg gagaaaccat 150000
tatggtgcgc aacgaacagc ttaccaataa taaagtgttg cagggaatcg tgcaggtatt 150060
gggtctagac ttcaactgcc attacaaaac acaggaagag cgagcaaagc tgagatacgg 150120
ctgcattgtt gcgtgcgttg atcaagatct ggatgggtgt ggaaaaatcc ttggactgct 150180
gctggcctac tttcacctgt tttggcctca gcttattatc catggtttcg taaaacgact 150240
gcttaccccg ctgatacgtg tgtatgaaaa gggtaagacc atgcccgtgg aattttacta 150300
tgaacaagag tttgatgcct gggcaaaaaa gcagaccagc ttagccaacc ataccgtaaa 150360
atattacaag ggattggcgg cgcatgacac ccatgaagta aaaagcatgt tcaaacattt 150420
tgacaacatg gtgtacacgt ttaccctgga tgactcagca aaggagttgt ttcatattta 150480
ttttggcggg gagtcggagt tgcgaaaaag agagctttgc accggcgtgg tgccgctcac 150540
cgaaacccag acgcagtcca ttcatagtgt ccgacgaatt ccttgcagcc tgcatctgca 150600
agtagatacc aaggcttaca agctggatgc catcgagcgg cagattccca acttcttaga 150660
cgggatgacg cgggcgcggc gcaaaatttt agccgggggg gtgaaatgct tcgcctccaa 150720
caaccgtgaa cgaaaggttt ttcagttcgg gggctacgtt gcagatcaca tgttttatca 150780
ccatggcgac atgtcgttaa acacaagtat tataaaagcc gcccagtatt acccaggctc 150840
ctcccacctc tatccggtat tcataggcat aggaagtttt ggctccaggc acctgggagg 150900
aaaggatgca ggatccccaa gatacatcag tgtgcagctt gcgtctgaat ttattaaaac 150960
aatgttcccc gcggaggact catggcttct cccctacgtc tttgaggacg gccagcgggc 151020
ggaaccagag tactacgtgc ctgtgttgcc gcttgctatt atggagtacg gcgccaaccc 151080
atcggagggc tggaagtaca ccacttgggc ccggcaactg gaagacattt tggccttggt 151140
gagggcctac gtcgacaaag acaacccaaa acacgagcta ctgcactatg caataaaaca 151200
taagattact atactcccgc tgcggccctc caattacaat ttcaagggcc atttgaagcg 151260
gtttggccaa tactactaca gctacggcac gtacgtcatc tcagagcagc gaaatataat 151320
tactattacg gagcttcctc tgcgtgttcc tacggttgca tacatcgaaa gtataaaaaa 151380
atcgagtaac cgcatgacat ttattgaaga aatcatcgac tacagtagtt cagaaactat 151440
tgaaattctg gtgaaattaa agccaaatag tcttaaccgt atcgtggaag aatttaagga 151500
gactgaagag caagattcca tagaaaattt tctgcgcctg cgcaattgtt tacattcaca 151560
tctaaacttt gtaaaaccta aaggtggcat tatcgagttt aacacgtatt atgaaatttt 151620
gtatgcgtgg ctaccttaca ggcgtgagct ttaccaaaag cgtcttatgc gtgagcacgc 151680
ggtgcttaag ctgcgcatta tcatggaaac tgctattgta cgctacatca atgagtctgc 151740
agagctaaat ctttcccatt atgaggatga aaaggaggca agccgcattc taagcgagca 151800
tggatttccc ccgctgaacc acacgctgat catttcccct gagtttgcct ctatagagga 151860
actcaatcaa aaagcactgc agggctgtta tacctatata ctatctttgc aggctcgaga 151920
attgcttatc gcagccaaaa ctcgtcgggt ggaaaaaaata aaaaaaatgc aagctcgtct 151980
tgataaggtt gagcagcttt tgcaagagtc tccctttccc ggcgccagcg tatggctgga 152040
ggaaattgat gcggtggaaa aggctattat aaaaggaaga aatactcagt ggaaatttca 152100
ttaaacgcta ccggttttat gatgtccaat aggtgttaag caatcagttc atcaacattt 152160
ttttcaagaa tttgaaaagt ttggataatg ttctgaatac ttttttctaa aagagttatc 152220
aaatcttctt gtgaggcctt atgaataatt gttaatacca tttcttgctt atggggaaca 152280
cactgatacc ccacaaagct aatatcagga atcatttcat aaatatatgt ttttagcaga 152340
tttccgatgg tatgggtttc atcttttatc gtgataatgg cctttgtttt ttcctcatcc 152400
atggaaaaca gcacaagttc cggctgcggc tcttcaaagt tttcataaat tttttgaatg 152460
ctttggattc ggccaataat gatccggcag gcgtttttta aatacgtgcg aacggcctgg 152520
ttgatatgtg gcagcggcac cgctggaaag caaagcccca ggcggtggtg acgcgggtct 152580
gaggtcatag agctttgctt gtaaccgcta agcgccatat attctttttt atccgttggg 152640
tactgttcaa tgtcaaggtg ggaaaaaatgt gttttaacgg caagattaaa ggcggcatgc 152700
tttcgtccta tgcccttttt aatatagata tcctctataa tcaacgattt tccgggttgt 152760
aggaagccaa tctcaaaggt aggattaaaa atcgggtatt taagcttagg gcctgccacc 152820
tggatgagat cgcggctata gatggtttta acctcacagc tattgtttaa actccgcaga 152880
gcaaatacca gtgtctcgtt tttcgcataa atcggaatga aattaatgcg gtttctaata 152940
aattgttccg tcataaacag gtccgtggaa tcctcgatct tatacccacc gggcttaata 153000
tctagcatat aattgggaat ttcatcttgc aagacccgcg acaggccgtg gaccgcggct 153060
ctgctaatgc ccttaaagtc cataacaaca ttgaccggga cgaggggcaa ctgctcctcg 153120
agctgaaata gttttttggc cgcattttta ataaagaggt tggaaaagtc tatcaaaaac 153180
ggtttgattt ccacgttttg gaaaattttt tccatttgta ttataaatat atctatatat 153240
attcaaatta tggtagttta tgacttgctc gtttctttaa gtaaggaatc catagatgtg 153300
ctacggtttg tagaggcaaa ccttgcggcg tttaaccagc agtatatttt tttcaatatc 153360
caaagaaaaa actcgatcac gacacccctt ctcattacgc cgcagcagga aaaaatttcg 153420
caaattgttg agtttttaat ggatgaatat aataagaaca atagaaggcc ctccgggccg 153480
ccgcgtgagc agcccatgca cccattattg ccgtatcaac aatcctcgga cgaacagccc 153540
atgatgccgt atcaacagcc cccggggaat gatgatcagc catatgagca aatataccat 153600
aaaaaacacg cgtcgcagca agtaaatact gaactgaacg attattatca acatattctt 153660
gcattaggcg atgaagacaa aggtatggac agcatgttaa aacttccaga aaaggcaaaa 153720
agggatagcg atgatgagga cgacatgttt tctataaaaa actaacgacg taacaattaa 153780
acaaaaaata aaaatcatta taaaatgaat cttgaatacg tccaagttgt tcaaaaattt 153840
aatcaagtac tcctagaact taccaaaaaa gtatgtaccg ttgtgggcgg gagcaaaccc 153900
acctattggt atcaccacat tagaagggtt tgctcagaat gtccatccat gccgatgagt 153960
atgataggtc cgtatctgaa tgtctataaa gcccaaattc taacaaggga caagaatttt 154020
tttatgaatt tcgatcccgc gcataatgag tacaccttta tcattcaaaa actaaaagaa 154080
gcagcccgaa atatgccgga agacgaatta gaacagtact gggtaaaact tttatttta 154140
cttaaaagct acataaaatg taagcccttt attaattaaa gaattgatgc ataactaata 154200
aatggccggt cgtgttaaaa taaaacagaa agagctcata gactctactg taaaaaacaa 154260
aaatgtgatg aatctgttcc atgaaattat aggctcaaaa ggcaatatta attttagcgt 154320
tgtctggccc aagtttaaaa aaatcaaaca gagcgtttat gactacattt ccactctttc 154380
tgtgctggaa aaagcaaacg ttatgcaaaa ctttgaagct gataagaaac tgttggaact 154440
ttttgtacaa aagctgtggg ctgcctatga aggctatttc aaatatcccg agattgaaaa 154500
atatgaggtg gaaggccagg taaatttcaa tctcgtacct cagtgcgtcc tcgaaaagtt 154560
tagccagttg tataggataa gaatcaattc agagcttgtc acactcatcc taaacagctg 154620
tgcctttatg agtaaatata acgattatat tctcaaaaaa gatccctaca tactaaccat 154680
aacccccggc ctatgctttt cccccattcc caacttcgag gacctaaatt ttaaacatct 154740
ttacaacagt gataaaaatt ctcagcatga caaagagttt atcatgttta tattatataa 154800
gctttatacg gctgccctag gagtgtacaa tgccatctcg attccagaca tcgacgtaga 154860
agaccttgaa aatatcatcc tatcctcggt gagccagatt aaaaaacaaa ttccgcgctg 154920
caaagacgcc ttcaacaaaa ttgaatcttc ggtacacctg ttgcgcaaaa attttaacac 154980
atattacagt gactatgtgg gctcaggcta caacccaacc atcattatgg aacagtacat 155040
taaagacata tcacaggatt ccaagaacat atcaccacgc atttcctacc agtttagaac 155100
catcatcaag tattaccgcg acatgattgc caccaggcat caaacgatgg acccccaggt 155160
attaaacctc gtaaagcacg tcgaaaagaa attagatatg cttgatagag aaaaaaatta 155220
gtatatatag ttatggtgaa tctttttcct gtttttacct taattgtgat tattacaatt 155280
ttaattacga ctcgagaact atccaccacg atgcttattg tttctcttgt aacagattat 155340
attattatta atacacagta tacggaacag cagcatgaaa acaatacatt tttcatgccg 155400
caaaaaaatt cttttaacga atcttataat aaagacaaaa aatctaatat acatattccc 155460
taccagtggc tggcgcctga actgaaggaa gctgagagca agtactggtg gggcaattat 155520
gatcctcata gcgagcccgt tctcgctggc gcatcttgaa tatcttcata cgtggcacgt 155580
caccatcaaa aacattgccc aacagcacgg gcttgatata aaggtggcca ttgtggtctc 155640
aacatcgcat ttaaataatt ttttgccaat ttccggggcg cttaacatcg aatgtataac 155700
cttccccagt tgcggcatca aggagataga cctcctatgg gcgcgcatta aactatttca 155760
acattactgc gccatcggtg cccgtctttt atggctggta agtgctgaca tcaggccccc 155820
tgtttcagcg tggccagcca tcgccgacag tctaaaaaag ggagcagatg cggtcgttat 155880
tccctacccc tcccgatgga acaatcttat acctaccgtc atcaaagaaa tagttgtcca 155940
ccaaaaaaaa tgccttgtgg cggtggatgc acgccacctt gatacagata cccagattgt 156000
aggggccggg atgggctgca tcgtcctaac cctaaaggcc cttatggtgc gcctaagtat 156060
tggcaaacag cccgttaaga tactgtggcc cgaccttcac ggcactgccg agggcattcc 156120
tctggagggg gtggaggttg gctggttttt aaacgcttat gcgcataaat taaatatacg 156180
ctgcctaggg gctgatcata ttgcgcagca cttaacttaa ttctttattt aaaaagtcca 156240
cgcatccagt ggcggcctac attaagggcc tacgcacata aatatacact ggctagaagt 156300
acgccttcat ttaaaccatt gaattattta tataatggct gcaaacatta ttgcaacaag 156360
agccgtgcca aagatggcca gcaaaaaaga gcatcaatac tgtctgctag actcccagga 156420
aaagcgtcat gggcattatc ccttttcatt tgaattaaag ccttatgggc aaacaggcgc 156480
aaatatcata ggagtacagg gctcacttac ccatgttatc aaaatgacag tatttccatt 156540
tatgattcct tttcctttac aaaaaactca tatagatgat tttattggtg gacgcattta 156600
tttattttt aaggaactgg acatgcaagc agtttctgat gtaaatggaa tgcaatacca 156660
cttcgagttc aaggttgttc ctgtaagccc caaccaagta gagcttcttc ctgtgaataa 156720
taaatataaa tttacatatg ctataccggt agtgcaatac cttaccccaa tcttttatga 156780
tctttcggga ccgctagatt tcccattaga tactctttcg gtccatgtgg atatcctctc 156840
caatcatata cagcttccta tccaaaacca taacctaaca acgggtgatc gtgtttttat 156900
ttctggatat aaacacctgc aaacgattga attatgtaaa aataacaaga tttttatcaa 156960
aaatataccg ccgctttcat ccgaaaaaat aaaactatat atactaaaaa atcgaatcag 157020
aattccgcta tactttaaat ctttaaaaac gtctaagtaa taacattttt atagtctact 157080
cctagttccg aaataggctg aatttctttt ttaagtcctt taaaccaagg atgtgataca 157140
agactcttaa aggaaagccg cttattttca ttaattgtta aacattccgt gataaactgt 157200
tttcccgtct ctgaaatgtt ctcgggaata taattttccc gtttcaggat atcatttaaa 157260
taaaaatttt ctgcacgaaa tctaaaaaga ttaaccgcga ccatacctat cgtccacacg 157320
gttaaaggaa gctggtagta ataaccataa taataaaatt ctggacacac gtattcccat 157380
gttccaaaca tattatattg gggacgggtt tcgtctaatc taacagcgct tccaaagtca 157440
atgaccttaa tgatcttttg atttatgtct ataataaggt tctcatcctt aatatcccca 157500
tggataaagc ccttctcata aatgttttgt ataataagaa taagctggaa tattattttt 157560
ttggcttcgg tttcctcaag ttttttaaag taatgataat gaagtagatc aacactattt 157620
ggaatatatt ctatgattag tatatgatac atagcatttt cggtatattc gataagctta 157680
ataacaccgg gagtatcttg cagggctttc aacacgatga cttcatttcc tggaatttct 157740
tttttagaaa cgtacttaaa tataatgggt tgccctactt gatgacccaa aaagacgtta 157800
tttctgccac cctcaaacat gggtctcgtc gcaatgaaat acatgtgctg cgttgtggag 157860
atcctttcca cctttgctgt aggataaaac gcatattgtg cctggggatt ttttaacatt 157920
tttttaagct gttgttccgg cctggacatg ttttattagc tttatatata aagggttaga 157980
aggtttaatt tcaatatatg ccttaatgat gggattatat tcgtaaaagg tatagcctaa 158040
tcctacgtct ttgttttttt ggtaaaaaaa ctgtttgccc tcgtaggata tgctataggc 158100
ttttacttcg gcttttacaa gcggttggca gggattgggc aaacgtaaat cgcgttcaaa 158160
gttttcatga aaaagcaaag catttgtggg ctgacacatc agacagccgc tttcgccatt 158220
gaaggcacat tcaatggccg cccttttttag taaatcgcgg aaagcagaat taagatggct 158280
cttttcaagc cccctttcgt gaaaacgctc atcaatcgtt ttttgttcct gactgccttc 158340
gggaatacta taaaacattt tttgattagc caccgcgatg tacaaaaaag gctgtacggt 158400
tttctcctcg ggcggtagcg catcgtggct accaatgcgt ataatgcgcg ccttcacttg 158460
atcctctcgg gccttatccc agtacggctc taggatatga acctgccgcc cgtatttgag 158520
atccaatccc tcagctcctg ttttagagac gagtaaaatt ttaataacct ctccgtgtat 158580
attcagcggc gaattccaaa gctgctggat catgtcgcgc tctttagata aaattttccc 158640
tgtaataagc gtaaatcgtg ttattttgga ggacaggact aacgtatggg tcggcccatc 158700
ttccgcaaag tttttcacca taagatcttt cccatcctta tgaaggagga tggtgttgtg 158760
cccttcttcc aatactttta ggggctgaag gcactggtag ccctctattt ctaaaaagcg 158820
ggccacgacg tgaaggccca attccacaaa ctgtgagtaa atgagcacag ggcccggaga 158880
cgttttaata ttttttagca tgcgtactat tttgggacta gaattttctg tgaaggcctc 158940
tttgggcagc tgctgaacag cctctgataa tttttcatcc tcctttactg ttagcatttc 159000
ggacgcgaag atgctgatca tacgggaacg cacatagtag gaggagcctg actcttgctc 159060
cgatcctggc aggcagaggg cggcggcatt tattttttca tacattcctg agctggcgtg 159120
cttttccgcg ttttcaacgt ctcgggccag cagatattgc ctatactgct cgggtgacat 159180
ttcaaccttt tctataataa gaggaagctc tgtggggaat agcttgttga gctcattctg 159240
gtttccagcg tagcttatca tacccactag gcggtttagt agtttgtccg cgtttaaagg 159300
gctattcgtt gttttattga cataagcggt gtagaatctt tcatagtgaa gaggtaataa 159360
gattcgcccg cttagcatat taaaacaggg caccatttca aaggggtcct tcgaacacgg 159420
ggtgcctgtt aaaaacagaa tacgaatatt tttagcttgc ataatattat tgtacagctg 159480
gcgggcattt gttttatcat tggcgctatt gataattcct ctaaagaggt tgtgtgcctc 159540
gtcaacgatg agcaggcatc catttaggga ccctcccgcc tttatgatct gctgccccat 159600
gttgtaagcg tctagggaca caaacctgaa gcgccgcgag attttttgta gctctttgga 159660
gtgatccgtc gtttccggat ataaaagttt aataagcttt aacaaagact gttggaagtt 159720
tgagtgcaac gacttgggtg cgatcagaat cgggttgtaa atatgtgaaa gtgagatggc 159780
aagcgacagg ctcaaaatgg ttttccccat gcccatctgg tgatagatga ggaggccccg 159840
tgtgttttcc ccctggccta tcccaaattt aggatccgaa aaggcggtgt aaattaaaaa 159900
ctggtagtat ttcagggctc gtgcaaagcg ggcagtgagt gaggtgtctt tgctttcctg 159960
aagctcttta tatttttcat atacctcttt taggtatgct tctatttgga cggggaagga 160020
ggtgttgttg tgcacgcaag acatgactcg ttataaggat cccatattaa aacttcatta 160080
gaagaatagg gctgctgata gctagcgctg cacttaaaaa tggggtagcc ctttttcttg 160140
taaatccggt gcctgtcgta gacctggcta gaaagcgggc ttagtgtatc tttaatgtcc 160200
acaacgatgc gtaccttttt ttcatccgat ccctgccggg taatacgtcc caagatttgc 160260
tccatgttgt ttctgcgggg cgttgccatg atgatcgatg tcatatgctt gaaggaaatg 160320
cctctacgcc cgtagccata ggtcagcaag ataatggaag cgctgtgtgc ctgagaaaga 160380
gcggtatttg aaaccccgcc gcataggagc gccacctccg gaacgataat ttgaacatct 160440
ttgaattctt tggaaagcgc ctgataaaaa atttctaaaa gtttgcgaaa ttccacgaaa 160500
atgatgatgc catacggctc atcggtcccc catttgtgag gctcagcggt atgcagggag 160560
taaagccgct ttgcctcatt tacgacaagt tgtatacgcg aaggatcttg aagtagttta 160620
tcaatggtgg caatggccga taccttttca ttaatataca cagggctaac gaagtcagga 160680
tgtccctgat attcgatttc cctcacgtac ccggaaaagg ttgtggtggg acttacagtc 160740
ctctggggct gtcctagatg gtgaataata atcttgtcca taccatcggg ccggtccagg 160800
ggtgtagcgg acagtcctaa tatccgacta agttgtattt tccaaaaaat tttgtaattc 160860
tccggcgagt gtaattcatg tgcctcatct aacacgacta gaccaaaggg ctcaaagaac 160920
tgctcaggct tcttgcgcag ggtattaatg attcccacga tgacgtcgta ctctttgctc 160980
gtcatgtcct ttttcttgca cgctgcatta ttgtaagcag ctacacgtag gtggggcagg 161040
agcaatgtta gctcgtcgat ccactgtatt tgaatcgcct tggtgggcac gatgaccagg 161100
gtagggtaca aaagtttttg aataatgctg atcgcaatac gcgttttccc caaaccggta 161160
tttagatgta ggtaaaagcg cccatagggg gacaggagct ttttatgaat cttatcgacc 161220
atttcttgct ggtagttaaa tagtggaaat tctgtttcaa cgcatgggag ggcccgcagc 161280
gacacggggc gcgtcgtgta aaccatgtta aacatttcaa actgcttttg cagcaatatg 161340
ggaaaataaa tgtattcccc ctgcagcgtg aaggcagttt cctgtcttat ggctatgtgc 161400
tttggctgcc cgggtaatgc ccgcgccgta acggtgagcg ccttaagaac gcgcccgaaa 161460
tcatgttgta atttactttg tagcttctta taatttattc ctattccagc aaaggatata 161520
atggcctcca ttctcacgct ggacgggtta tatgcagagg ttccaaaatt cttaccagag 161580
gcgttacgag agggctgtgc tggcaagaat cctctaagct tttatattca acaaatttta 161640
aatttaatgg gatgtgacgg taacgagtac catgttcttt ttaccagcag ctccgaggaa 161700
gcaaatactc atatgatcat ggccgccgtg cgtcgccatt tgctgcggac gcagcaaagg 161760
cctcatgtca ttatcggagc agccgagccc cctagcgtca ccgaatgtgt gaaggcattg 161820
gcgcaggaaa aacgctgcgt atacaccatc atccccctaa aaaattttga aatagatcct 161880
gttgcggtat acgatgccat acaaagcaat acctgcttag cgtgcatttc aggcactaat 161940
gctgttgtca aaacgttcaa caaactccag gacatcagca acgtgttaaa aggtattccc 162000
ctgcactcag aagtgagtga tcttgtttat caaggatgta ttcaacaaaa tccgcccgct 162060
gatagttttt caataaatag tctctacggc ttcctgggag tcggtgtttt gggaatgaag 162120
aaaaaggtca tgcaaggatt ggggccgctc atttttggag gagggctgag aggcggaagc 162180
cctaatatac ccggaattca tgccatgtat aaaacgctaa cccagcaaag gccttctatg 162240
aaaaaaataa atacaataca tacgctgttc atgaaaactt taaaaaaaca tcagcatgta 162300
tatctaccca tagggggcgt gtctgcagag gacacgtctg cagaaaacat atctacaaaa 162360
gacatgcctg ttgaaggccc gaagggactc ccgggctata ttttatttag cgttggccgt 162420
cgcgccgagg agctacaaaa aaaaattttc actaaattta atataaaggt tggccgtgtt 162480
gttgacttac aagagatact gtttcgtatc aaaatacccc aaaaatactg ggagacatta 162540
ttgttcatcc aattaagaga taatttgacc aaagaggaca taaaaagagt tatggttgtt 162600
ttgatgcatt tagataccat cactcctcgt ggctctcttc ctcctccgag ccactcttct 162660
tctttttctt aatcgttttt gtttgttcta taataaggga aaagaactcc gtgggatctt 162720
gttccccgta caggttatct gcgaccataa ggatgcttag aatggtaaac aggtgagaat 162780
acataagggt ttgcgtttta agaaaaccct gacgttgaat cataattgaa aacaccttgc 162840
aaagccgact catcagttgt tctgtaatgg cgttaagcat tttctggaat ttttcttggt 162900
tttcgggtgt gattttatat tcatgtagaa agtgtttcac acctgaggag aagaatcttt 162960
cctccttcga gagcccatct ttgatgatgg gaagttcctt gatcagggca aaccattcct 163020
cctcttgggc ttgcggattc tgaagatact gatggcagat atggtttaga atggtgcaca 163080
cgtagctaat aagctctgag ctgattcttt ggttggtttt caaatgttgg cgaaagtagt 163140
ttttcaccga agtgcatgta ataaacgtct tcattttctt ataatataca acagtatgtt 163200
gagtctttaa tttaaaatta caaggagttt tctaggtctt tatgcgtata ggtgtttctt 163260
tgtcgtaaat tttcaatagc cgacattgtt tgtgaagcag tgttctgagt agtgactgtc 163320
gtgtaaggct cagccggatg agcaggagca ctcgcggccg caggtgcggc cgccggcccg 163380
ccagttgcca tgactagtct gtccgtaact gggttgtccg taactggttt gtttgttgct 163440
ggtctgtttg ttgccggtct gcccgtgact ggcttgccta cacttgctgt agtcgctcca 163500
gctggtttag aggtacctgg ttgtggagtg acttctaccc actgctgatc ttgataagga 163560
tttataaact gtatatcttc ctcctcaata gcagcagctt ttttctttct tgaagagaat 163620
agatagatta gaacgatgat aatgatgact aagaccacga tagcaatgag aatagtatac 163680
atatgtgtgg agaagaagct tggtgtagtg actggtgaca aacactcacc ataatgccgc 163740
ggataaaccg gttgaaaaaa ttcagaatcc atttaagata ctattataaa taatatataa 163800
aaatgttgtg gcgcaatgaa attacagaat ttatggacca actttccaag tattctcaag 163860
aaatcttaaa aacgtttaag caattgcgtc ctagtgaata taaacaatac aatgaatttt 163920
taacacaagt tacaccgttg ctgcaaaaaa cccctgaaaa aattccagag ttggttgacc 163980
atatattcaa ttacctagac aacgttgaaa aaatttgtga gctcctcgtg aatgctagct 164040
caattattat tagttcaaaa atacgagaac aagtaaaaca cggaatgagc ttcagctata 164100
aagccgacct cgactccttg gcggacattc tctctcaaaa acagtacgtg cttatgcatc 164160
tttcaaaaaa tattgcggcc gagtatttta atacgtgttt aaaccaaggg aaatccaagt 164220
tagatctcaa agctgcctct gtattttata gtagtcgttc ccgaacggca agctcagcag 164280
aactctatag aaaaatgcta tacgcctatg gttcaccgca ggaaattaat tattatactg 164340
aaaaagcccg aaataagacg ttggatgtgg aggagagcga cagcatggcc atcatcgaac 164400
gaacggcccg acacaacctt tcccttatgc acccgctaga agccatgggg cttacctttg 164460
gggcaaccaa cacggacgcc gacccggagg atctgaagga caaaacggtg ataaatttaa 164520
cgctcccgca ggcaacagaa agcatcacct accatcttaa atccctaatg cagctaaaaa 164580
aagtaagtac ggcttcagga ctaaatacaa acattttgaa agcatttgat aatattattt 164640
ccacccctgt gaaaaaaaat aaaatggcct ccaagttggc gcccgggatg gatgtcgtgt 164700
tcactagcga taacggaaaa acatttttta ctaaaaacat tttaagcaaa aacatgctag 164760
cggggcccaa agagcgggtg tttgcatata ataatctcat tagtaattta aataactcct 164820
gtttcataca aaatcacaac gatttttttaa gacagcagga ctcttggccc ttctatgacg 164880
cgcacaattt taccaacaag tttttaatgc agcctatttt ttcggggcag acccgtcctc 164940
ggcttcaggg agccatggag gcggcgcatg tggaaacgca tctcacggca tttttacaaa 165000
gtattcagcc ctctaggcca caagatccct ctgttttggc ttcccccaag ttatctgctc 165060
taatcttgaa ctaaaaacag cctttcttgg acttaaatga tggtctacca gtttttgaaa 165120
taacttagag aactatgaag attttcatga aatttaaatt agagatttgc aaaggttact 165180
tgcggtcatt ttctgttgaa ttaaataatt attcgaatag tataatgtct gaagatattc 165240
gtcgtggtcc tggcagaccg ccaaagaaaa gggttgttcc caactttgag cgcaagggca 165300
ttctggaaaa accagttcgg ccacaaagcc gtctcgagtt ttcctatgat aacccgctga 165360
tatttaaaaa tctttttatt tactttaaaa accttaaaag taaaaatatt ttggtgcgat 165420
gtacccccac cgagattacc tttttttcac gtgaccagtc gcaggcaagc tttgttattg 165480
ccaccatcga cggaaaaaac gtgaaccatt attacgccag tgatgtcttt tggctaggca 165540
tcaacagaga gctcgttgaa aaaatgttta acagcattga tcgctctttt ttaaaaatta 165600
ccatcgttca ccgctatgac aagcctgaaa ccctgttttt tatctttacg gattttgaca 165660
ttgacaagga gtgcacgtat cagattacgg tctcggagcc cgagctcgat atggacctta 165720
tcgaaatgga aaaaagcatc agtgaagaaa gactcaagaa ctatcctctg cgctgggagt 165780
ttacctccaa gcagctcaag aaaacattta gcgacttatc aaactacacc gagctcgtga 165840
ccattgaaaa actcggcggc gatacgccgc tgcacctgta tttccaaaag tttaactcca 165900
tctcatacca cgagatgtat aaatcttcca acaagatcaa cctgacctcg accattccta 165960
agtcgcaggt gttccagata aatgttaaaa ttgctcacat caagtcgctg gcctcggcta 166020
tggtcaccga caagatccgc attctgtgcg aagaaaatgg gaacctaatc tttcaatcgg 166080
aaatggatgc ccttatgtta aatacgatta ccttgaacac cacgatatag ttcggtaaca 166140
ttagatgttc taatatttag catctaaata atacgctgta gtccggtcag ggttgcgtca 166200
cagttttccc attttttgc ctcgtcggcg gtggccaccg ttgccctatc atttacgccc 166260
ggtaagacaa agctaaaggc gttcagcggg gcttggcaat gcccgcccag cgtgaaggag 166320
ctcggaggat tttgcgcatc ccgaaatccc ttagccatgt tgtttaacac ttcggttacg 166380
tcaatcgagt gaagggatcc cttgggatcc gtgaatgtaa agacgcagtt tctaaagcgc 166440
atgtatgcga tggacgattc atcgggggtt ttgaaggtaa cagtgttccc cttgctgtac 166500
ttaaaggggg accatccggt aaaattatac caaatgaaag caataataat taaaataacc 166560
aacacaatag ttatagacaa cacaaagtct gtagtgccgc ccattattaa ataaaaatat 166620
tttagaccgc cggcttaaaa tttacttatt gctcatagct taagtctatt ttattcatag 166680
cttaagttta ttgctcatgg cttaagtcta ttgcttatag cttaagtcta ttttattcat 166740
agcttaagtc tattgttcat ggcttaagtt tgttgctcat agcttaactc cattactgat 166800
agcttactga tcatgactta aataaaaata ttttgcccgc ttaaaaattg tttaggtttg 166860
aaaaaataag agatggaggg ggcaacttat cgtcattgtg tttacccccca ctggaagaca 166920
tcaaacggta aataattata agaatcaaaa tgattaatat aagggttaaa aaaggatgat 166980
tcatcacatt aattaaaaac gtatttataa cgctgttgca gttgaaattt tggtataggt 167040
cggaaatatt gcccgagcct ccgtattctg caatgttctg acatatggtg agtccggagg 167100
ggcactgctt gttggtcaaa atatttcttt gctccgttgt tttataggca tttttatttc 167160
cattacacgg agcaaacgca cattcagccc atagggtgcc ggagttcaca caggcacaat 167220
actggctata cgcatactca tcctttgagc acaatccctg tttatcgcat atgctcccaa 167280
taatattgtc atcctccgcc gtttgttgat ttgtatgcga gcgtaaaata gcggcccagg 167340
ccttgggctc cttttttgc agctcggaaa tcgaagggcc tgtacagcta aagtcgaccc 167400
aaatatcatt gcatttcgtg gaaactggca tgcaagacat aattgaaata attaataagt 167460
atatatcatg gcaacaaatt tttttattca acctatcacc gaagaagctg aagcatacta 167520
cccaccttcc gtgataacga ataaacggaa ggacctgggg gtagacgtat actgttgctc 167580
cgacctagtg cttcaacctg gactaaatat tgttcgcctg catattaaag tagcatgcga 167640
acacatgggc aaaaaatgcg gttttaaaat catggcgaga agcagtatgt gcacccatga 167700
acggctgctc atccttgcaa acggaattgg tttaatagac ccgggttatg tgggcgagct 167760
catgctcaag atcattaatc ttggcgacac cccggtccaa atatgggcca aagaatgttt 167820

-continued ggtgcagttg gtggcccaag gtgaccatgt gcctgaccat atcaacatcc taaaaagaaa 167880
ccaaatattt ccgctgtttg cgcctacccc aagaggcgag ggtagatttg ggagcacggg 167940
cgaggccggg attatgagaa cttaatttta tttttttct taacataatg ggaggctcta 168000
caagcaaaaa ttcctttaaa aatacgacca acattatcag caattccatt ttcaatcaga 168060
tgcaaagttg tatttccatg ttggatggca aaaattacat aggcgtattc ggtgatggaa 168120
atattttaaa ccacgttttc caggatttaa acttatcatt aaacacaagt tgcgtgcaaa 168180
agcacgtaaa cgaggaaaat ttcattacaa atctttcgaa ccaaattact caaaatttaa 168240
aagaccaaga agttgcgtta acccaatgga tggacgcagg aactcacgat cagaaaacgg 168300
atatagaaga aaatataaag gtaaacttaa caaccacact tattcaaaac tgcgtttcat 168360
ccctgtcggg tatgaacgtg ctggtggtga aggggaatgg caacattgtt gaaaacgcaa 168420
ctcagaagca gtcgcagcaa atcatctcta actgcttgca ggggagcaag caggccatag 168480
acaccacaac cggcatcact aacacggtaa atcagtactc acactacacc tcaaaaaact 168540
tttttgactt cattgcagac gcaatttcgg ctgtttttaa aaacatcatg gtcgcggctg 168600
tagttatcgt tctaatcatc gtagggttta tagccgtctt ttactttttg cattcacggc 168660
accgccatga ggaggaagaa gaagctgaac cactcataag caacaaggta ttaaaaaatg 168720
ctgccgtttc gtaataattt aattaaaagt aaaaaaaaaa ggtattgtta tagtgatggc 168780
agattttaat tctccaatcc agtatttgaa agaagattcg agggaccgga cctctatagg 168840
ttctctagaa tacgatgaaa atgccgacac gatgataccg agcttcgcag caggcttgga 168900
agagtttgaa cccattcccg actatgaccc taccacatca acttccctgt attcacaatt 168960
gacccacaac atggaaaaaa tcgcagagga agaggatagt aattttctac acgatactag 169020
ggagtttact tcactggtcc ccgatgaggc agacaataaa ccggaagatg acgaagaaag 169080
cggtgcaaaa cctaaaaaga aaaaacattt gtttccaaaa ttaagctcgc ataaatcgaa 169140
gtaaaaattg aagcgaaaaa aagtagaaaa aaaatgtttg gagcttttgt aagccaccgt 169200
ttgtggtcag atagtggttg tacgaccacc tgcatcacaa acagcattgc taattatgta 169260
gccttcggcg aacaaattgg atttcccttt aaatcagctc aggtatttat tgccggccct 169320
agaaaggctg tgataaatat tcaggaagat gataaagttg agcttttaaa gatgattgtt 169380
aagcacaatc tttgggttgt tgctcatgga acctacttag atgtgccctg gtcccgtaag 169440
agtgcgtttg ttacacattt tatacaacaa gaactactta tatgcaagga agtcggtatt 169500
aaagggttag ttttacacct aggcgctgtg gagcctgaac ttattatgga aggactaaaa 169560
aaaattaagc cggttgaggg ggttgtcatt tacctggaaa ccccgcataa caaacatcat 169620
acatataaat acagtacaat tgagcagatc aaagaattgt ttttacggat acgaaatacc 169680
aggttgaaac agattggttt atgcattgat acggctcaca tctggtcttc cggtgtcaac 169740
atctccagct ataatgacgc ggggcaatgg ctgcgctcgc tggaaaacat tcattccgtg 169800
atcccaccaa gccacattat gttccaccta aatgatgccg ccacagaatg cggaagcggt 169860
atagaccgac atgcaagtct tttgaagga atgatttgga aatcatatag ccataaaata 169920
aagcaaagcg gtttatattg ttttgttgaa tacgttacgc gacaccagtg tccggctata 169980
ttggagagaa acctcgggtc ttccatgcaa ttacaaaccg ctttaaccgc agaatttact 170040
acattaaaat cgttattaaa ataaggatga gttttagcga atgtccctta gttattagtg 170100
catgcaaaaa atttctacaa aagcgtatta caatagagaa tgaagcactt ataaatgcct 170160
taataaccgc tttagcgcag accagcacgt tgaatgatct ttgtttatta cctattcaaa 170220

```
cctatttgct tagttataaa aatgcttttg agtggataca cttcgtatgt attgcaatca 170280
ccactatttt ggataataag tataactgga aggactgtac ggtagatatt aattatattt 170340
ttctccatgt aacctatatt tacaatatta aaaccaagga atacctagac tactgttctt 170400
aaactttatt ttttctatat ttacgccaaa gagaatattt aaagtttttt ttgaaaaaaa 170460
ataatatatg tagataaaat tcagttacat gatatatgtg taaacatgtg tggtaaacaa 170520
catatggtta tgctttataa gataaatgcg cataatatat gtaaacaaaa tatggttatg 170580
tgttaaatgc atataaatgt attttaacgt atatcttgtg ataatggata tatgcattta 170640
ttaaaagagg ctgtatttat tataaatctt gctaaggatg ccattgtcaa catatatccc 170700
atgttggaca aattgcgttg cgatccagtt cttttttttt tgattttgtt taatgctatc 170760
ctttttgaag ggatggttgt ccaccatatt tattcgatgt tcaatgaata ggtctgcttt 170820
ttcgtaaggc agtgaaggtc gttccaagac tccttgaacg atggacgtgt tttcttggat 170880
ccacttaaaa agcacgtggc attcaaaaac aggacagtga ttggatcctt ggatatgctt 170940
tggacagcca atgcttgaag agatgtagtc ccttttcttt aggacaagct tctccacgct 171000
ggggcaacag agatcgttca agttctggac ggtcgcattt ggaatgttga aacttcgtat 171060
ccattcaccc tcgggtcctc ccttatgaag aaggagtatt tgctcatggt ccttagtaat 171120
cttaaccaaa tgttggaaga tcattttttt acctgcttta aaggcctgaa gggtgtcagt 171180
tggcaaagct attgaattcg ggagtgggct ttcatcaagc gtgaaatggt gaatgtgacg 171240
cgactggaaa gaaaacgacc gttgatttat tttttcaaag attgggtcga ttccgccatg 171300
aaagaacagc tgcaagattt tagaaggcgt atttttttcc caataaaaaa tgaccacttc 171360
tcgtgggatt aaaatcgtct gtgtcccatt ttcattatat aattggccca taaagccatc 171420
aacgtcaatc aacaccaaaa gcatggtata gagagctttt agaaccggag ttcgttaaaa 171480
aaatacaaag ttcgtttaaa acgtgtaatg ttactaaaaa aatgtaatgt ttaaatgata 171540
atgataccac atgcattaat gaaaaaaact tttaaatttt tgttttaata tttgcatgaa 171600
aatggaaaca tttttagtct gtttatttca caatgcagat ggtttacatc aacagattca 171660
ggaaattttg tatttattgc ggatgcatat ttacgaaaca aatctttact taaagcagga 171720
actatcacgg cttatatatc caaataggca actttctttt gtgttactta tgccccttc 171780
ccttctaaga aactgggatg acattgaata tttaacggac gttgtagatg ataagcagac 171840
tctacattac gcggcaaatt tgctgacaaa ctacgttcta catctatcca tgtttcaaaa 171900
gctgacaaaa ccatacttcc ttttagcggt caagcgggtc agcgaaaaac tcaacaaaaa 171960
gcagcgacat tcattttacg aggtattggt aacctccgaa accttgaata attatgaaaa 172020
cctatctaaa aacattttaa atacgttgat gtttgccgtg cgctacgtat ttaaacctac 172080
gccgaactat tcagaaattc tcgcagagtt ggaaaaaaaa aataaaattc accatattat 172140
ttttaatatg gtaattacgg attttgcgca aatccgtgaa caacaaatgg ataaacatct 172200
gtgtgaaaca aataatgagc ttcgtcagga atgtaaagaa actatttttg atttaaaggt 172260
ggtaggaaat gtttagccaa taaactcatg cccgcatttt ttacaggtac aaaatatcgt 172320
ggatggctca tcgagggcgc gtgtttgtac ttctctgtag gtacacatac gctgcttgca 172380
gttgggacac ttataaagtt gtgacgtctt ttcggcgacc ttttgctgcg aacgtagagt 172440
aatttctgtc ttctccttta aggcggcaga ggggcaaagc tcggcgaacg tcatgctacc 172500
aattgcctcc ggttttagct cgccagaaat tagcttatta agggcatcgt tatcctgttg 172560
```

-continued ttggtgactt ttttttcgc agttaataat atgattgatc gtcccacaac gggttgaata 172620
ttcttctaaa aaggtttttt cttgttgctg gtacgtataa tgataacacg aggcctcgat 172680
tttttgcgcg tattcggtgc ataaatcagt atgttcctta aaaaacatat gtttttgaag 172740
cgttctaaaa aacatcattt ggatgatatc acgcatttcc aaaataatat agggttctag 172800
tcttttggaa tctttcataa ctagatcggt ggtaatattc ttagtcatac aatttattaa 172860
aaatggttta atatattgta aatatttttt aggcgtgtca gcctgtaaaa aacattcttg 172920
ttcaatctta tttgtaagga tagtattttg caaatactta tttagcaaaa atacgataga 172980
atcgcgggct atatgcattt tcatataatt ttttttttaa aatttaatac aaaaaaaaga 173040
agtatagact cttcttctag tccggttagt tcgttggttg cctcaacatg gagactcaga 173100
agttgatttc catggttaag gaagccttag aaaaatatca ataccctctt actgctaaaa 173160
atattaaagt agtgatacaa aaagagcaca atgtcgtctt acctacagga tctataaata 173220
gcatactgta cagtaactca gaactttttg agaagattga taagacaaat accatttatc 173280
ccccgctttg gatacggaaa aactaattgt aaccagtagt acatttaagg atagtttaag 173340
cagtaaatgt agaataacac agttaagcaa taaataacaa gtatatagga atatatagga 173400
atatatagaa atatatagaa atagctaagc ttaatactaa ttcagctttt tttttaacta 173460
aaacctgaat agatgcgaag tagcggacat atacatacta aaataagcca tacatttact 173520
ttcttcttga acatgaaacc tttttttctt ctgttgttgg tatataaaca ataggactgt 173580
ttgctgaggt tgtatgatct tctacaactg ctgtctcagg atgacgatgt ttttttaaac 173640
taaaagtgta ggatggaatg agtggaatat agttatggct cgacttatcc tgtttcgtac 173700
aggaatattt tttacaaata gaacgcaaca agcatatgaa taaaaacaga aatgatatac 173760
aggagcataa aatagatatg aacactaagg ggtagcagct tttataacgt tccgtatttt 173820
tcttagctat caattgattt accgtaatat ttatctcggg aaactttgtt ctacaatatt 173880
ttgtttggta ttccagaaac tcatgtcctg gcttattccc gcagcttaaa aaatgataca 173940
aaaatgtgtt attgttacta aaattaattc ttcttaagaa aaactgcgga agacgcttta 174000
ggtacgtctg ttcctgtttt agtaggaagt agtataaggg acaatttctt tttccacaca 174060
ttagattatt gtaatatagg taggttgggg tgttggagcg aataagtttt ctgagtatgt 174120
tataatctat gacttgtaaa tcgttatacc ttaggtccaa aaacttgagt tctttaccaa 174180
agccacctgc aatttcagaa atatttttca tcccgcagcg gataatacgg atgtcctgaa 174240
acgtctttaa aatacttgta ttgtagtgaa tacttatgtt atttttttgt aaataatcta 174300
tgtcatgaca agtgcatgaa atgccagcag cattgcttgg tatagtatta tatgcaggaa 174360
gaactatact actattgaga atagtcacat tgtacttata ccatgtatta ttttctgata 174420
taaagtattt gcaggtgacc tgtggtttaa tcctacctgt taagccactt cctaaaaaaa 174480
caaaaaatat gaaaaccctt agcatcctgt atatactatt aaaaatttat aaaattttct 174540
gtttaaattt catttagaca aaaaaaataa tatatataca tcagcaagaa attatataca 174600
gattatataa ttttctgatt tttttttgcc acaataagca tcattatatg cattaaaatc 174660
tcaatactaa acactaaaat ctaaattcta agcattaaat tctaagcatt aaattctatg 174720
cactaaactg taagcactaa aatctaagta actaaaatca acactaaatg tatgcaacct 174780
aaaatgtaaa gcattactca tcatcctcct cttcttcatc ctcatcatca taggttaaga 174840
tatatgtgtc atcctccatt tcttcacatt catcttcata agcatcactg ggtattggtg 174900
gaacattgga tgcagcattt ttaaaatatt ctatgtcttc tggtgaacac tcatctaatg 174960 atttttttgac agtcctttta acttccatgg gatatgattc caaatcctct ttatataaga 175020
gtttacggta gcttttagct gcatccacat ttgctggaga atctggattt ggctcattga 175080
gcagtgaaat tacactaaga agaatggtat caatcttttg agccggagac caagtcattc 175140
cctgttcttc agcattgtct ccgtgtaaga tagagataca tagttttcca tcagagtaaa 175200
tattaggatg ccacatttca gaggtgaatg ttaatctggg tggtgcatat gggtattctg 175260
gaggaaaggc gatttttgcc ttgaataagc ctccctcata aaaagtgtca ggtgggcccc 175320
ttaagatcac atcccattca gtcatatcct tctcattcac cgaaattttg aaattctcag 175380
agggattctc tatcaggtgt ctgtactctg ctattaaaaa cctggaaacc atggttattt 175440
aatattaatt aaattccctg gtttattcct ccttaaaagt agatgaacct cttttgtttt 175500
ttattgggtt catttttact aaatttatga actggaaaaa actttaacgg cataattatc 175560
aaatgcgaag gggggatccgt ataaaatcct agcttgccgg taatggctat taagttaaat 175620
ttggtaccag taacactaat atttaaaaag ccctgatcat taactttcca cattaaaaga 175680
ttattatatt cgaatgtttg tccaatatgg acaactttgt caccagatgt tacatttgat 175740
ttggttgtta gtggctgaag cttggcacaa tcaaaaataa gcccattaac actaagatat 175800
agaggagtgg gttgatctat tttctcatag tttaatattc catctttcca cgtaatagct 175860
tgataattat ccgcagcaat gagttgaaat tttataaata gtacaggggt tttagttgtc 175920
gttatacatt taaagggtgt tttataaaaa taaaaaataa taattgttaa aagtatgata 175980
ataatcgcca aaataatttc atacattttt tataagaatt atacatagta tggtatttaa 176040
aatattagct aaatttaaaa aaacttcatg atttttaaaa cagggaaaaa ggggattagg 176100
ttgaataaaa aaggtaagca cttgtctata tatttttttt acaatgttgc cttgagtcgc 176160
atttttaact ggctggggag tatcagagtg gaatatcact gtagtaggtc tataaggtct 176220
tgttaaaata tgatcggtca ttgttttcgt actagtgtca tttagggtcg acctgatagc 176280
tcgatataaa gttatagggg ataacctatc aaatacagtc ttatctgtgc tgaaatgtat 176340
atcgtcttct ttatcactaa taatattagg aatggctgtc attaaataat tactacttgt 176400
tgttgtgggt gaaatagttg tactggtatt attggaaatg gctgtcatta aataattact 176460
acttgttgtt gtgggtgaaa tagttgtact agtattatta gaaatggctg tcgttaaata 176520
attactacct attacaagta aactaatgct aactacattt ttaacctcaa taaacctaaa 176580
aagccatact aaatacctaa acaacatcct gttataatat gagcagaaaa aaaaaataag 176640
tataattagg gaattattct tattcgctta ctattaagaa taattcagaa tcttatttag 176700
ttagaaacta tcataaagtg aataggactc atcgtcggat gaagattccg tttcagagat 176760
agtttctttt tcttcctcag aataatctgt tcctacaata gaatcggtgt catcctcaga 176820
aagagaagta tttaaatatg gactatctat agcaatatcc tcttctatct cgcaatcctc 176880
ctcctccatt tccatagtgt gtaggagaat atttttatca tcatgctcac ttcttttttt 176940
gttgaaagat gaaccgtcct caatacggtt catgttaagt tccttcatct tatgtataat 177000
ttccgtaatc cgtgatgttt ttgacatgta agatggtttt aaggttatat ccacaataac 177060
aggagaatct ctatcatttt catttgataa actttgatct ttgatttctt cgtctaaaat 177120
tcttgtcttt ttttgggtac tagatgaaat agaggaattc atattctgaa acgatatatc 177180
aaggggagct ggacgctttt ttccaattaa accgtttttc gagatactat gattagatga 177240
atgatcttta gccaagctgt ccttggatat actatagtta gatattttac ctttaaataa 177300
tattcttcta tacaagttat tcttaggtaa agaattagta tggattccta tatttttatc 177360
tgaaggagtg tccatatcgg agaacgtcct cttacgaata ttttgaccac gagccatttc 177420
atccactata ggcagtattt tggctggcta tggttctttg ttgtgacaat tctatgagat 177480
ttgattgcaa atcaattttt agttttaaat atattggtac ctaggacaaa gaaagtatat 177540
atagccaata attattccac taaattgatt tccagactga tgggtatgga gccatgttgt 177600
ctctgcagac gatcgcaaaa atggccgtag caacaaacac ctactccaag tatcactatc 177660
caatactgaa ggtctttggg ctgtggtgga aaaacaatac gctaaatggc cctattaaaa 177720
tatgtaacca ttgcaacaac ataatggtag gagaatatcc tatgtgttac aatcatggaa 177780
tgagtctgga tatagctttg attcgggcag taaaggagcg taatatatcc ttagtccagc 177840
ttttcaccga atgggggggga aatattgact atggggcact ttgtgctaac actccatcta 177900
tgcaaagatt atgtaaaagt ttgggagcca aaccaccaaa gggccgaatg tatatggatg 177960
ctcttataca tctttcagat accttgaatg ataatgatct gattaggggg tatgagattt 178020
ttgatgataa tagcgtgttg gattgtgtca atctcatacg actcaaaata atgcttacct 178080
tgaaggcccg tatacctctc atggaacaac tagaccaaat tgccttaaaa caacttctgc 178140
agcgatactg gtatgccatg gctgtacaac acaacttaac aatcgctatc cactattttg 178200
ataatcatat tcctaatata aagccattta gtctgcgctg tgctttgtat tttaatgatc 178260
cctttaaaat ccatgatgct tgcagaactg taaatatgga tcctaatgag atgatgaaca 178320
ttgcttgtca acaggattta aactttcaaa gcatttacta ttgttatctt ttaggggctg 178380
atattaatca ggctatgcta atgtctttaa agtatggtca tctttctaat atgtggtttt 178440
gcatagattt gggggcggat gcctttaaag aggcaggggc gcttgctgag aaaaaaaata 178500
aaagagtgtt acaacacata ttaggtctta atatctttaa gcgagagttg attccccccct 178560 gtaaagatcc tgatccttat caaatccaaa ttctgttaaa aaactacatt ctaaaaaatg 178620
tctcaactgt ttttacatat tattgccagt agccattgtt tatatcagaa aataacccat 178680
ttgtttatct ttttttgtgg ggcaaccatt aagacccgac gcaaaaaaag attaatcttt 178740
tatcagatac ctaaaacgtt ctataaggga gtctatgaga tggatcatat tttgatggtc 178800
atagtaagaa gcaagctttt tggcgaaaac aacggagtta aagaatttaa cccgctcatg 178860
tttggatagg acttttaaca gcgagccaaa acagtattta aaaatttggc aatagttttt 178920
ttgggatgca ataaacaaac acttgatcag tgcccgcttc actttctgat cagacatgtt 178980
tgccgcataa caggcctttt taaacttagt aatataatta tgttccgcaa gcaccattaa 179040
caagggaacg atgggaagct gcttttcttg gtgaaattta cgtaaatatt cgatggccac 179100
cgcttggacg actgtgtaat ttactaagtt agaaatgata gctttcatgg ttgtaaaaat 179160
atacatagga ttttcttttt ctgtatacag tttgaaaagc ttatgattac gtgaaatgat 179220
ggccattttt aatacaagat ggtatagtgt atctttaggt aaaaatgcct tgcaagccgc 179280
gatgatgtcg atgttgtctc catgaacagc gatagaaact aatgtttcca atctaaatgt 179340
ttttatctgc attaatagaa gaatgcagtc aatgttatta tacttaataa tactgtaata 179400
caccgaatca atgaccgtca tctgagaatc aagctgactt attagtaaat ttaacgtttt 179460
tttggaggca tgacctttga tcgcggcact aagtgcacac agtatagcaa aattgttaaa 179520
tacattttga tttaggagaa ggagtaatat tttccttcgg ttatagtacg cagcatctgt 179580
gatgattatt ggccgataaa tgttaaaatg tgttaacagc tttttaaaaa aacggaagta 179640 attttttttgg atcgctgttt gcatcatcga aataatgaga taatcagggt atataatggg 179700
taggtcacat gctacctcta acaaagaata gtcgcccaat ctaaaggctg tgttgaaaag 179760
cgtactatca tcatacgtat cgagtacccc tgctgttaca aaccaagcga taagatgaat 179820
gtgccgttcc ttgcaagcta tcgcaaatag ggagtttcct atggaatgtc gaataatgta 179880
ctccctattt ttttccaaaa tgtttggaaa attgtatagc gttgcggcat acagtagaca 179940
ctccattctg gcgttataat ttttactttt acatatgaat aggtggaaga actcgaataa 180000
ttcttgagaa cttgttaaat gcataaatatg gtgatatttt ggtgtcgtta aatggtatga 180060
gaaaatgcat tctaatacat cttttcggtt atgctttagc gcctgagcta aggcatattc 180120
aggctcgacc cataggacta gtgtttctat aattgagata ttcgcctgct ttgccagggc 180180
atactttaag acgctccggt tagaaaaaat gttgttatga agatggataa ccgtatccat 180240
ttttacgatg ggaccattcc agtatagtcc taaatgctgt agcagatctt ttgttagttg 180300
tgaagcgttc tcgggtgtca tataaatatg ttgcagggct tttttctgta aggagaacat 180360
ttcgtcgtaa tcgtacaaaa aaaaattaaa atttgggcat ggatgattca aacataacaa 180420
aatcaagatt ttataacagt ttgcattaac ctatacatat atgcaagtaa atgagatatt 180480
atctatcata acgaatcaag ggatatttgt atatatcagg agtttctgaa ataaagatat 180540
gaagattatc atagtagtat ccatcaatca caatgcaact tcctttaagg cataatttag 180600
taaactcagc actcccatct tctggatgct ttacaactaa cattaaaaac tcctcagtca 180660
tattatctgt aataaaataa gatcctcctg gagccatttg tagcatgtct cttattccta 180720
caaaatcttt tttgggatgg taaaaactca gcagtttcaa actctttttt agtttttttt 180780
cctggtattt aagccatttg ttataaaaca gttttcttat gaaaatgcat ttgaaaatat 180840
tgggaatgtt taaccatgct tcttccgagc acatctccag atacttactt tctttgtttc 180900
ccatgtctaa tttattgctc actaagttag taatgaatct attttaataa tctactttac 180960
taatctatct taataaccta tcttataatc tatcttaata acctaattat aacctattta 181020
taattggcta atgctgccgg catttcatgc ctatctaaac aactcctact aagcaatcta 181080
ctattacata tatagattca ctttttatat ttgtaaatca tgagaattat aaaatcatta 181140
ctcattttta ttgtaaatta gtgggtattt gtaaaaatct tcaaacgttt taagatagtt 181200
ttctagagag aagtaatctt tgccatcaat atataatgct tttcctttaa actccagttt 181260
tgctatgttt agtgagccgt ttctagatct ttttgggcaa taaatagatt ttcattggtt 181320
gcatcgtccg taagcagaaa ggtaccacta ggcacgttaa aaaacatacg ttctatttca 181380
tggtcggatt tttgagaata gaaaaaatct aattttttaa tccgcgttaa ctcttttttta 181440
tcaatctttc cagactgttt tatatatact ttattgcaaa tcttacaatc ctctatggct 181500
tcattatact tattttgctt atcctctatt gacatgtccg tatttgatag gtaacttccg 181560
ttaaggcggt tccccatggt tttagataga tttttaattc agttgtatac ttttattatg 181620
aggctaaaat atagaagttt gatcctaaaa aaataaaaag attttgtaca tttatttatg 181680
gtttatagcg gtatagaggc cgataaaagg tatccgggta gtctcctatg atatcgtcaa 181740
ttttggtata ataacagttg ttatggtagt attgtccaaa ccgagtatgt atgcgccggt 181800
gaagcgtccg cccgctaatg gtacagttcc aggttaagac aatcatatca cacccaaaaa 181860
gagaggaaac agcataggtg cccaaaggtt cattatataa catacgccgc atatatttta 181920
gttttttttc tccatggtaa taatcacagg ttttcatgtc ctgcttaata ggatgattcc 181980
ccatgtatga taatatataa taaatttagt ttttagcttt ttcaaaaaat tgggcgctcg 182040
aaactaaatt ttccttatca cagcgtttgg agaaagcgta tttaaagata tatcttcttc 182100
taacaagact gcaaaaaaaa tcttacccct tatttttata atgttcatca tagcgtttga 182160
agatatcaga aggtgccagg ttttataaaa atatccttta ggatttataa cgatacaagg 182220
gtctataaaa tatatgcggg tataatctta taaaatcatc gattttttca taatattctc 182280
cgtttataca ataaagatca taacagatat tgatgcgtag atgcattatt cgcgtgttcg 182340
ttgggcagct aaaggatatc acaacgtagt ttttttaag aaaagacgaa actacataag 182400
tccctaaggg ttcattgaat agtaaacgcc atatttgttt taaattttgt tgttcaccat 182460
agtagtattc gcactttttc aagtcttttt taataagcct attccccatg tatgcttata 182520
aataaaaatt tagaaatgtg ctatattatt tgttgatgaa tcatgaacac gtcttatatg 182580
ttgatatgtt actttaaaaa catttgtatt ttcaacagac gcgttctatt cttattaaga 182640
atgatgccgt ctttatttta aaccttggtt taaaatttaa agaagtattt ataaactata 182700
atcatgggaa ctttttcagt aactgcctct gcaaaaagtg acgatgctgt ttgtaagtat 182760
ttagaagaac caatagatga aaattacaga aacatattaa gaaatgagca tgttaaaaaa 182820
aatttaaatg aggctctgaa tcgacatatt actacctata atccagtagt tgattggtgt 182880
aataactatt caacattttc atctcaggat ttcgatgaat ataaaattta tatacatagc 182940
gatcttatgg atggacgacc tcgtccaaaa aaaacatggt gtgtcatcat gtaatgtttg 183000
ttagttttat ataaacgcaa aaatattctt ctaggagatg ttgatatact acctattgaa 183060
ttcaatatat taaagtacat ttctggctat tcccattacg gtattattat tactattttt 183120
aagagctaga tgtggattta agtaataata acattctccc gttcctccta gagacacctc 183180
atcaaattcc catcctatgc aacctttatg ttgtaaacat aatgattgac agcattcatc 183240
ttcttttgac caagtcgtcc aaatcctacc aagatctata cgtgtttttc caaatggaga 183300
ttgaagatca gcagtagtgg cattaaacct ataaaaacca ggtgcataat cacatgaacg 183360
gatcgtagga tctaatttaa tatcttttat atcttgtttt actgcttcta gacaactttt 183420
atcagtacat gttccacgta cacagtggtg tcctttatcc ttacaatccg tatctgtctt 183480
acattttttt ttcggcggtt tatgtttcag atggtaaaaa cccagtatta aaataatcac 183540
aagaataatt cctataagta cttgaacaac aggataaaac attttaatat taaatatatt 183600
ttttaattaa atgaatagat ttaatccaag tagtattaaa attttttaga aatagtgttc 183660
tacaaataat gaaatgaatg gtccaaaaaa aataaggtgt acaataatgt aatatattgt 183720
taggctaagt aaatttaata ttttaaagta tttggaaaaa tattttttaa catatgatgt 183780
ctaggaatat tttttagaca tttaaaacca tatagttact ttatttatta cactgaactt 183840
gaaaagactt attacctaaa atattaatag atgaagtaat attgtgtaat tgagtccata 183900
acatgggtgg gaaacaaaaa tctcgtaata tgaaaaataa acatcctaaa aagagtgcaa 183960
ttgttataag tttatgtaac tttattttaa agtaagaata taaaaatatg agtacaagag 184020
gaataggggc cattactaac attggctcca acatcctgtt gtctacaaaa aaaaatattt 184080
tttttagcaa aaaaaaatcc atggaaggat attaatacac ataattattt gacatcacat 184140
tagtgtactt accaaatagt aatatacaac catcctaata ttcaccttta tgaaatgatc 184200
ccaacctata cggtaaaata gtataggttt taataaagaa aaaagatatt ctgtggtttt 184260
tatttttgta tagtgtgtga atacaaaata aaatcccaaa ttttaacctt ttcttttttt 184320
ttctatacag gatgttagaa atagtattgg caacgctgct aggcgacctg cagcggctcc 184380
gggttcttac ccctcagcag cgggcagttg ccttctttcg agccaatact aaggagctag 184440
aggacttctt atgctcagat gggcagtctg aggaggtact gtctggcccc cttcttaacc 184500
gtctactaga accctcaggc cctcttgata ttttaaccgg atatcaccta tttcgtcaga 184560
atcccaaggc aggtcagttg cgcggccttg aggtcaagat gcttgaacgg ttatacgatg 184620
ctaatattta caatatactg tctcggctgc ggcctgaaaa agttcgcaac aaggctattg 184680
agctatactg ggttttccga gctatccata tttgtcatgc tcctttagtt ttagatattg 184740
tacgatatga ggaaccggac tttgctgaac tggcctttat ttgtgctgct tactttggtg 184800
aacctcaggt aatgtatttg ctctacaaat atatgcctct gacccgcgca gttcttacgg 184860
atgccatccg gataagtctt gagagcaaca accaggtagg gatttgctat gcttacttga 184920
tgggaggcag cctcaaggga ctagtctccg ccccactgcg taaacgtctg cgcgccaaac 184980
tacgctcgca gcgcaaaaag aaggacgttc tttcacccca cgacttctta ctgctgctcc 185040
agtagctttt tttgccgcag gagcaccgcg gataggagct cctccacgct cgcgatccgg 185100
cgctggaagc ggaaccgatc gaccgccacc tgctcccagg gacccttgcg ctcgatgtcg 185160
tcggcttccc acacctcgac ggctgtggca aaatggacat gcttcgcgtc gttcgtccgt 185220
tttttgcgcc gcctccccat tattcttcct gtaagattag tgtttaatac ctataataac 185280
ataattttaa gatttaatat accaaaactt aaactatttt tgtatagtaa ctattagcat 185340
gtctacacat gattgttctc taaaagagaa accggttgat atgaacgata tatctgagaa 185400
atcagttgtc gtggataatg cacccgagaa accagctgga gcgaatcata tacctgagaa 185460
gtcggcccgc gaaatgacat catcagaatg gattgctgaa tattggaaag gtataaaacg 185520
tggaaatgac gtgccatgtt gttgtccaag aaaaatgacc agtgcagaca aaaagttttc 185580
agtatttggt aagggatccc taatgcgctc catccagaag aataattaaa aaaaatattt 185640
tttttagcaa gtttttaaac tatttaaata aatgtggtaa aaaaattcac ataataatta 185700
aagtgaacgt gttagaatta atattttttt ataatcggat ataatatcca ttaaatcaat 185760
aaatgatagt gttgctacca cactaaacaa taacaaacag aaacgcacga tacctttcct 185820
catgatttat aatagcgtgt tatctaaaga ttttttttgaa aaaaatatta aattttagtt 185880
gattattttt ttcagttaca acattgcttt agaaaaaata cctaattact acatagcaaa 185940
taaagcgagc gcattgttac aaacaacatt tttttgcgcc tggatactcc tatatatgag 186000
aactataata cggtatatta atcctattac caacattgtc aataatagta tgtaggcaat 186060
gacatacttt aaataccaaa tatccatggt tatttctaaa aatcttgaaa aaacgttaaa 186120
ttttagatcg gtcacctacg acagtaatac taattttaat aattgatgac tgaaatcata 186180
atataatgcc gtgcgaaaaa taattatttt tcggttaaag ataccattac ataaaaaata 186240
tgccatctac tctacaagtg cttgctaaaa aggtattggc cttaggggag cataaagaaa 186300
atgaacatat atctagagaa tattattatc atatattaaa gtgttgcggt ttatggtggc 186360
atgaagctcc gattatactt tgttatgatg ggagtgagca aatgatgata aagactccaa 186420
tctttgaaga aggcatatta cttaatactg cattaatgaa agctgtacag gagaataatt 186480
atgaattaat aaagttgttt actgaatggg gagcaaacat caattatgga ttaatttcca 186540
ttaataccga gcatgcccgg gatctatgtc gaaaattagg agctaaagaa atgcttgaag 186600
gaaatgaatt tatacaaatt atattcaaaa cattagatga taccaccagt agtaatataa 186660
ttttatgtca tgaattattc accaacaatc ctcttttaga gaatgtaaat atgggggaaa 186720
tgaggatgat aatttattgg aggatgaaaa atttaacgaa cctattatta aataatgact 186780
ctattagtga aatattaact aaattctggt atggtatagc agtaaaatat aatcttaagg 186840
atgcgatcca atatttttac cagagattca tggacttcaa cgagtggcga gtaacatgtg 186900
ctctttcttt taataatgtg aatgatcttc ataagatgta tataacagag aaggttcata 186960
tgaataatga cgaaatgatg aatctagcct gcagcattca agacagaaat ttatcaacca 187020
tttactattg ttttctattg gggggctaac atcaatcaag caatgttaac ctcagtatta 187080
aattataata tttttaactt attcttttgt atagacttag gggctgatgc ctttgaagag 187140
ggtaagaccc tggcgaaaca aaaggggtat aatgaaatag tggaaatctt atcattagat 187200
atcatttata gtccaaatac tgacttctca tcaaaaatag aacctgaaca tattagttct 187260
ttgttaaaaa acttttatcc aaaaaatctg ttcgcttttg atcgttgcaa ccccggttta 187320
tattattctt agaggaccgc tacaaaaatt attttttttt cttgatcaaa gctccaaaat 187380
aattattaga ttaaagtcgc ctatagcagc agcccactcc aaaaaaagta ttttatagta 187440
caaaaaacac gaaaaatagt ttgcggccgg cggcaaacta tttgttgttg tctaaaactt 187500
aatgtttttt taatattttt aaatgcaacc atggattgtt ggactatcag ggagaagaac 187560
tatagctaca tcatattgtc aatactggta atactattaa tatggtatct tatacttaac 187620
tattgtcgat cgaaaaaaaa tgcagttaca aacaacatgc cgccaccata cacggtgtca 187680
agtagctgtt ctcaataata gggttgattg acgctcttcg taataaatatg ttgattgacg 187740 catcataaaa tgctgtggtt gattaatatg ttgattgtcg cctactttat tatataagta 187800
atgatttttg tataaaatac gggtttgtga gggctttatt ttttcttatt agaacaaagc 187860
atgcaattta aggcctacag caagagtaat ttaacaccta caacagtaat tttaaggtca 187920
gtaataatgt ttaattaagg cctgaccact aaaacttaaa cgatttttgta aaaaaaaatg 187980 tctactccac tttctctaca gactcttgtt aaaaaagtgc tggccacaca gcacatatct 188040
aaagaacact actttatttt gaaatattgt ggtttatggt ggcatgaagc gccgattacg 188100
atttgcattg atgaggatag ccaaatattg ataaaatcgg caagcttcaa agaaggctta 188160
tctttagata tcgcattaat gaaagtcgtg caagaaaata accatgattt aatagagttg 188220
tttaccaagt ggggtgcaga tatcaactct agcttagtta ctgttaatac ggagtatacc 188280
cggaaccttt gtcagaaatt aggcgcaaag gaagctttga atgaaaggga tattttacaa 188340
atattttata aaacacgtca tcttaaaact agcagtaata ttattttata taatgaattg 188400
ttttctaata atctcctttt ccaaaatata gagagattga gtttaatagt ttataggggc 188460
ttgaaaaact tatcaatcaa ctttatattg gatgatattt catttagcga aatgttaact 188520
agatactggt atagtatggc gatattatat aaccttactg aagccatcca atatttttat 188580
caacgatata ggcattttaa agattggcgg cttatatgtg ggctttcttt taacaatttg 188640
tctgaccttc atgaagtata taacttagag aagacggata tagacattga tgaaatgatg 188700
aagttgacct gtagtacgta tgatggtaat tattcgacta tttattattg ttttatgttg 188760
ggggctgaca tcaatcgggc aatgttaacc tcggtaataa actttcatat tggtaacttg 188820
ttcctttgta tagatttagg agctgatgct ttcgaagaca gcatggaact agcaaaacaa 188880
aagaataata atatattagt agaaatatta tcatttaaaa attattatag ttcaaatacc 188940
tctcttttat caataaaaac gacagatccg gaaaaaatta atgccttatt agatgaagaa 189000
aagtatgagt caaaaaatat gttaatgtat gaagaattat ctcattgata caaaattatt 189060
ttttataaca gaactctctg atggtgacaa atctccgata ggaatatatg acgtaacata 189120
attatttttt tcgcccagaa aaaaattata aatgttatta ttgccagcac ttttatcaac 189180
tatacgtaca aaaaggtgtt gaccaaaaaa ataatttttt ttcttgatca aagtatgtaa 189240
acgcccgctt acagcaagga tcttaagtga gagccattaa attttattga tagctgcttg 189300
ccaccagtag aatacggcca aaccacctaa caggaaatac aaggcggccc ttcggccaat 189360
aaggtggata aaaatcacgc ataagacggt tgtaacatag cactttagtg cgaatatcag 189420
gaatgccaat agcatgtaga taaggcacca aacatcgcag ctatacatgg ctaaagatca 189480
accagaaaag gtttaaattt taacgccggc ccaaaactta aacttttttt gatattttta 189540
agtgcagcca tggattggtc cggccatagg atgacctatg cctacgtggc attctcattg 189600
atggcaatag caataatatg gtatattcta cttatctatt gccgatcgaa aaaaaatgtt 189660
gttacaagcg gtaatacgct cgctttagcg ccaatatcgc atatgtgaaa aatgttcgcc 189720
gaaaaaaaca ttaaaattta gaaccgccgc ggcatctcag gggcggcaac attttttttt 189780
atatggatat tgtcacacac cacctcatct atgacgcaat atattactgc taatatcagg 189840
ttccccaata gtatgtagag aaaccacaca agatagatat tcatggcgat ttttgacgaa 189900
aaaacattaa gttttagctt ctttgacgcc tgtgtactaa taatgtttaa cgcctgtagt 189960
ataataattg atacctacag cagtaattga tacctacggc gataatgtct ctctggccgc 190020
cccaaaaaaa agtatttacg gtagggttta ttaccggcgg cgtaacacca gttatggtca 190080
attttgtctg gcccgccgcc cagccgcaaa aaaaaatcaa ttacaaccgc aaaaaaaaat 190140
atttccggcc gcggcgtttc aaaaaataat ctttgcgaaa taattccgca tcttgtgaaa 190200
tgaacgccta cagtaataat tttaatcttt gacacctaca gcagtagtaa taattttaat 190260
ctttaacgcc tgcagcagta ctaatatttt taatctttaa cgcctacagc agtagtaata 190320
attttaatgt ttaacgccta cagcagtagt aataatttta atctttgacg cctacagcag 190380
tagtaataat tttaatgttt aacgcctaca gcagtacaat aattttaatg tttaacgcct 190440
gcagcagtac taatattttt aatctttaac gcctgcagca gtactaatat ttttaatctt 190500
taacgcctac agcagtagta ataattttaa tgtttaacgc ctacagcagt agtaataatt 190560
ttaatctttg acgcctacag cagt 190584

<210> SEQ ID NO 2
<211> LENGTH: 191558
<212> TYPE: DNA
<213> ORGANISM: Artificial Sequence
<220> FEATURE:
<223> OTHER INFORMATION: Chemically Synthesized

<400> SEQUENCE: 2
actgctgtag gcgtcaaaga ttaaaattat tactactgct gtaggcgtta aacattaaaa 60
ttattactac tgctgtaggc gttaaagatt aaaaatatta gtactgctgc aggcgttaaa 120
gattaaaaat attagtactg ctgcaggcgt taaacattaa aattattgta ctgctgtagg 180
cgttaaacat taaaattatt actactgctg taggcgtcaa agattaaaat tattactact 240
gctgtaggcg ttaaacatta aaattattac tactgctgta ggcgttaaag attaaaaata 300
ttagtactgc tgcaggcgtt aaagattaaa attattacta ctgctgtagg tgtcaaagat 360
taaaattatt actgtaggcg ttcatttcac aagatgcgga attatttcgc aaagattatt 420
ttttgaaacg ccgcggccgg aaatattttt ttttgcggtt gtaattgatt ttttttttgcg 480 gctgggcggc gggccagaca aaattgacca taactggtgt tacgccgccg gtaataaacc 540
ctaccgtaaa tacttttttt tggggcggcc agagagacat tatcgccgta ggtatcaatt 600

```
actgctgtag gtatcaatta ttatactaca ggcgttaaac attattagta cacaggcgtc    660
aaagaagcta aaacttaatg tttttcgtc aaaaatcgcc atgaatatct atcttgtgtg    720
gtttctctac atactattgg ggaacctgat attagcagta atatattgcg tcatagatga    780
ggtggtgtgt gacaatatcc atataaaaaa aaatgttgcc gcccctgaga tgccgcggcg    840
gttctaaatt ttaatgtttt tttcggcgaa catttttcac atatgcgata ttggcgctaa    900
agcgagcgta ttaccgcttg taacaacatt ttttttcgat cggcaataga taagtagaat    960
ataccatatt attgctattg ccatcaatga gaatgccacg taggcatagg tcatcctatg   1020
gccggaccaa tccatggctg cacttaaaaa tatcaaaaaa agtttaagtt ttgggccggc   1080
gttaaaattt aaacctttc tggttgatct ttagccatgt atagctgcga tgtttggtgc   1140
cttatctaca tgctattggc attcctgata ttcgcactaa agtgctatgt tacaaccgtc   1200
ttatgcgtga tttttatcca ccttattggc cgaagggccg ccttgtattt cctgttaggt   1260
ggtttggccg tattctactg gtggcaagca gctatcaata aaatttaatg gctctcactt   1320
aagatccttg ctgtaagcgg gcgtttacat actttgatca agaaaaaaaa attatttttg   1380
gaccccccccc catgttttat acaaaaatca tataataaag tggcgacaat caacatatta   1440
atcaaccaca gcattttatg atgtgttaat caacatatac catattaatc aaccacagca   1500
ttttatgatg cgtcaatcaa catattatta cggagagcgt caatcaatat aatattgaga   1560
acagcgactt gataccgtgt atggtggtgg cggcggcatg ttgtttgtaa cagcattttt   1620
catcattcga agcttacaaa agatatgtat aagatagcat attaatgtta ttaacagtaa   1680
tatcaataag gcgtagctat agatcttcac tttggtagac caataatcca tggttgcgct   1740
taaaaatacc aaaaaaaaca ttaagttttg gagggtaaga ttggtttttc accattggta   1800
aagattatta ttctaaatgt ttaccccata gatgtgaaac aatgattctt catatattaa   1860
catatttttt gacttatact tttcttcatc tagtaaggcg ttaatttttt ccggatctgt   1920
cgtttttatt gataaaagag aagagtctgg actgtaattt ttaaataata agatatttat   1980
taatatccaa ttattcgttt ggctcgctat ttccatgctc tcttcgaaag catcagctcc   2040
taaatctata caaaggaata agttaccttc acaaaaattc attaccgagg taatcattgc   2100
ccgattaatg tcagccccca acataaaaca ataatatata gttgtataat tacaatcata   2160
catacaggcc aactgcatca tttcatcaat gtctatattt gtcttctctt tgttataaat   2220
ttcatgaagg tcaaagacgt tgttataagc aaccccacat attaaccgcc aatctttaaa   2280
atgactatat cgttgataaa aatattggat ggcttcagta agcttatata gtatcgccat   2340
actataccaa tacctagtta gcatttcgtt gaatgaaata ttatccaatg taaagttaat   2400
tgataatgta tctagttcac caaaaattct taatttcagt tgagcattat ttaggaaaag   2460
gggattatca gataataatt catggcatag aataatatta ctgctagttt taacatactg   2520
tacattataa aatatttcta aaattttatt ttcactcaaa gctttcctcg cacctaactt   2580
ttggcatagg tcctggtgca ctccatattg acagtaacca acccaaagct gatgtctgca   2640
ccccattcgg taaacagctc tattaaacca tgattgtttt cctgtacagc cttcattaat   2700
gcaacattta atgttaaacc atgtttaaaa cttgctgttt ttattaatat ttgttcatct   2760
atacaagtat gataaatcgt aattggggct tcatgccacc acaaaccaca acgctctaaa   2820
atacaataat catcttttaa cacaggctgt gtagctagta cttttttagt aagtgcttgt   2880
aaagtagatg gcatcttcta tctgcaaaat aattatttcc gaaaaaaaaa tcaaattaaa   2940
atactaaatt ctattttttt ttttaataaa gcctgtaaat tatataataa atctcgccca   3000
```

```
ccgtattatt tccggacaca actttttata cctcattata tttttagatc tatagttttt   3060
taacaaggca ttaatttttt ctggatctgt cgtttttaaa gataaaagag agacgtttga   3120
actataataa tctttaaatg ataatatttc tactaatata tcatgattct tttgttttgc   3180
taattctaag ctctcttcga aagcattagc tcctaaatct atacaaaaga acaagttatt   3240
catataaaag ttttttaccg aggtaaccat tgcccgattg atgtcagccc ccaatacaaa   3300
acaatagtaa atggttaaaa aattgctatc tctcatacag gccagatata tcatttcatc   3360
aatattcata tcaacctttt ttatatgata catttcatga agatcagaca cgttattaaa   3420
agaaagccca catattagcc gccaatcttt aaaatgacta tatcgttgat aaaaatattg   3480
gatggcttca gtaagcttac atagtatcgc tatactatac caatatctag ttagcatttc   3540
gttgaatgtt atttcattca atataaagtt gatcgatatc ttctctagaa aacaacaaat   3600
tattactttt aattcctcta tattctggaa aaggggatta ttagataaca atttatggca   3660
taaaataata ttactactag ttttaatacg atgtatttta taaaatattt gtacaatatc   3720
catttcattc aaaattttttg cgcctaactc ccggcagaaa ttccaagtat gctccgtatt   3780
gacagtgact aagctagagt tgatgtctgc accccattca gtaaacaact ctattagatc   3840
atagttgttt tcctgcacag ttttcattaa tgcgagattt aactctaaac catctttaaa   3900
aattgctgat tttatcatca attgattatc ctcattagta gaaagcataa ttggagctcc   3960
atgccaccac aaaccacaat atttcaaaat aaagtagtgt tctttagata tgtgctgtgt   4020
ggccagtatt tttttagcaa gagcctgcag agaaattgga gtagacatat tttttttgc   4080
aaaatggttt aagtttttca agaatacaga ttggataaat taggttgttg acttagttac   4140
aggaggtatt aaatattatg tagacataaa aatgagatcc tccaaaaaaa taaacaacaa   4200
aaaaaaatat gtttaatatt aaaatgacaa tttctacatt gcttattgct cttattatac   4260
tacttattat tattttagta gtgtttttat actataagaa acaacaacca ccgaaaaagg   4320
tctgtaaagt agataaagat tgtggtagtg gagagcattg tgttcgtgga tcatgtagct   4380
cattgagctg cttagatgcc gtaaaaaatgg acaaacgaaa tattaagata gattctaaga   4440
tttcctcatg cgaattcact cccaattttt accgttttac ggatactgct gctgatgagc   4500
agcaagaatt tggaaaaaca cggcatccta taaaaataac tccatctcca agtgaatccc   4560
atagcccccca agaggtgtgt gaaaaatatt gttcatgggg aaccgatgac tgtacaggtt   4620
gggaatatgt tggtgatgaa aaggagggaa catgttatgt atataataat ccacatcacc   4680
cggttcttaa atatggtaag gatcacatca tagccttacc tagaaatcat aaacatgcat   4740
aaataaatac attaggctca tcgtatcttt ttaaaatcca taaatattcg tttgatatat   4800
gctgaaattt ttataaaaaa aaataactat ttcctataaa tcatctagaa atagtcctcg   4860
ttttgatcgg tttatatctt ataatattgt gcatcgatgc acaactgctt tttttggtcc   4920
ttctggaaca tcattatatt ttctttcatt aatataccat tcagatgtaa acgttgaata   4980
atttttatgg caacaatcta ccattgaatt atatttagta acatctaata catcgtttgt   5040
tttatcaggc tcagctctat aatcttgata atttttgtta tcagcttcta aagctccatc   5100
attatttttc aaagaagtat ccataattat gtttggtaaa aatactttaa gttttaatgt   5160
gatatttaaa atggttgtta tataaattta ccgcttacag gtaatcttta ttcagtgtca   5220
taaactatac ttttgatgat tcagtatttt gtgaatcagt acatttatta tcattaatat   5280
ttttaggctg tttttccaat gttttattgt tgcaatgagc ctgctcctcc tttgacgagg   5340
```

```
aagtgtctgt tggagtcatc tgtttaggaa gagtatcatc catatctatt atgaagaaaa   5400
tatataaata ttgatataca atcaaaaata tttttgatca cgtctttgtt atctatcgat   5460
attgttgata acgtcttgaa taacctacat cattttttta cataaaaaaa tagatataat   5520
ttttattata tctcaattat tttaaagata attatcaata cagcaaatat cataagctaa   5580
catatttttc gaataatagt tttttagtaa agtattaatc ttttcaggat tggtttcttt   5640
tgataataag ataggattcg ctttataaat ttttaaagat aatatattca caatgataga   5700
ataaccgtat atatctgcta atgtcttact gtgttcaata acattagccc ctaaatccat   5760
acaaaagaac atattttcaa tacaaaagtt ttttaccgag attaacattg ctcgattagc   5820
gttggctccc aatgcaaaac agtagtaaat ggtcaaaaaa ttattatcgc gcatacaggc   5880
cagctccatc attttattaa tactcatatg aattttcgtt gtgttacata tttcatgaag   5940
gtcaaacaca ttgttgaaag aaagtgcaca aattaatcgc cattcatcaa aatgcctgta   6000
ttcttgacaa aaatattgaa tagcttcttt aagattatat tttaccgcta tgccatacca   6060
atatttggtt agcatctcac taaatgagat ctcatttaac atagaatttg ttgttaaatc   6120
cttcaactcc caataaatga tcatccttaa atccaccatg tttacatttt gtaaaaaagg   6180
gttattagaa aataattcat gacacaaaat gacattacta cttgttattt tacactttgt   6240
ttcaaagaaa aatcgtaaaa tttcacttgt ctcaagctct tctttagctc ccaattttcg   6300
gcataggttt cgagtatgct cgttattaat aaaaagtaac ccataattaa tatttgcacc   6360
ccattcagta aacaacatga ttagatcatc attgttttcc ttaactgcca ataccaatgc   6420
agtattaagc cttataccct ctttaaagca taatgtcctt atcattattt gattatcatc   6480
atctatatac attgagatag gagcttcatg ccaccataaa ccataacgct ctaaaatata   6540
ataatcatct ttagatacgt gttgcgtggc caatgccctt ttagcaagtg cttgtaaagt   6600
cgatggctgc atgtttattc tgttaaaaaa aaatcaaatt atcgggtaaa cataaggatc   6660
aacccgtagt taatatttgc agtagtattt tttaacaatg aattataata aaaaaataat   6720
tcattactat ctattataaa acccatcttt aactttaaag aagaactaga tcatcttttt   6780
ttttgttgtg tcagaacttc ttcaatttat tacccacatt ttatctaaaa aaaataaaaa   6840
ctacatcata tcttgtttct tcatcaaatt atcataccat ttatagggtg taggttggga   6900
acattccatc atgtggtaat cagggtattt atatattttt tgatagtaac atctatttgg   6960
cagatgtatt gtccaacaat catgtctaat aaaatcattt tcacctatgg gggaatcatc   7020
ttaaaaacct tattcctaca gattccattt tgacagtccc agcaaaagtc acaatatttt   7080
ccatgagtac accaatgttc aagctctctt tcgggaggaa tgctgccaat tttatgtttt   7140
ttagcttcta actctctgta caacatcagt tgggaaagca gaaagaagat taccaggaga   7200
accattaaat atataatagt ctgcaaacta cgtttgcgaa tgtaatttgc aactaaaaca   7260
caacccacaa ggtaaaatcc ataagttaat aacttttgcc attttcgtat gacagcctcg   7320
tgccattcat ggttgtgttg tgggcattct gttcggtaaa cttcatgagg ctttatagaa   7380
gttacatagt aggtacagaa ttcattgtga cgaaaaacac tgcagttagc tatgtagtca   7440
ttttcaagaa tgggagaatg gttttcaaag accttattct tacagatgcc atcttgacag   7500
tcccaacaga acctacaatg atttgcatag gtgcaccagt attcaagctc cttttcagga   7560
ggggttcttg ttagatccag gagctctagc tcatatgtat aaagaagagt tggaatggat   7620
agtaaagtaa atatttgcag accaagcatg gctacttgtg aacaagtggc tgctcgtcaa   7680
caaatagctg tttatcagca aatagctgtt tatcagcaac aactaattat cagcaaatgc   7740
```

```
tgcttgtggg taagccaata aataggccat acccttgaaa ggagaattca gtttgataaa   7800
aaaaataacg agttttctaa taacccggtc aagcatttaa taaatgaata gcatcacacg   7860
tctgcatcgt gcattctgcc tggaaaatgg gcccatctct aatatattta cactgacggt   7920
gaatcataca gtgttccatg ggatagctat gctcctgtac aggaggcata tcttttagaa   7980
ctttattctt acaaagacca tcttgacaag cccagcaaaa ccgacaattt ttcacatatt   8040
gacaccagta tctaagctcc tcttccaggg gattgtcggt cgaaaacccc tgtagactag   8100
ctaggccagc tagcagcaag ccgaggtaac taaagaacct cattgtagtg ttatattacg   8160
aaaaaacatg ttaaaatttg gaaaaaaaag cccttttat agatctggaa aaaaattttc   8220
acaaatctaa ttaaaagcct tacagatcat ccttttcata aattttcatt aacaattggt   8280
gggggcggtt gtgaggtact ggatcagaac aatccataac atggtaatgt ccatttcctt   8340
caccatatgt acactggtta taccagcgag aaacctcaca agatgtcaaa taactgttct   8400
caacaatcaa tggcatgctc ttattcacct tgttcttgca aattccatgt gcacattccc   8460
agcaaaactt gcagttttcc atgtaagtac accagtatcc aagttcttct tgtggaggat   8520
tatccgttga acgaagatgc cctcctgcct gagtaggtag tcctaagacc tgattggcca   8580
gcaggccaag aatttccaag aagatcacca acattgctac ggctggctga acagctggca   8640
gatagctagc taattagcaa accaagtgac tcgccctctc tactcttaat atgagaattt   8700
aagattcggt ccggcttttt tcccatgttt tacagggaaa aggtattttt agcctatgaa   8760
tgtacatggt tccgcacatt aaaaaaaaat aaaagaaatt atttaatatt ggctgttatt   8820
ttctttcaac tagcaacaag ccaggtaact aaagaacttc attgtagttt tatattacgg   8880
aaaaggttaa attttggaca aaaaaaatca tatctaatta aaaatcctca cagatctttc   8940
ttttcataaa ttttcattaa caattggtag gggcggttgt gaggtactgg atcagaacaa   9000
tccataacat ggtaatgccc atttccttca ccatatgtac actggttata ccagcgagaa   9060
acctcacatg ttgtcaagta gctgttttca ataatcaatg gcatgctatt attcaccttg   9120
ttcttgcaaa ttccatgtgc acattcccag caaaacttgc acctttccat gtaagtgcac   9180
cagtatccaa gttcttcttg tggaggatta tccgttgaac gaagatgccc tcctgcctga   9240
gtaggtagtc ctacgacctg attggccagc aggccaagaa ttcccaagaa gactaccaac   9300
attgctacgg ctggctgaac agctggcaga tagctagcta attagcaaac caagtgactc   9360
accctctcta ctcttaatat gagaatttaa gatccggtcc gacatttttc cgatatttta   9420
caagaaaaag atatttttag ctacaaatac acttcatata tccctaaaaa aaacaaaaat   9480
ttatttaatt ttaactatta ttttctttcc actctctctt taagattttg taaggattcc   9540
agggctttgg ttcagaacag gccattacat ggtgaatccc ctgtcctaga tcatacatac   9600
atttatttag ccagcgggaa actatacatg attgcacata ctcattttca agaattgttg   9660
tattctccaa tttgccctca caaaggccat tttgacaatt ccagcaaaac ttgcagtttt   9720
ctgtataagt gcaccagtat tcaagttctt cttgtggagg attatccgtt ggatgaagtt   9780
gtccagctgg ttgattaggt agccctaaga cctggttgca attcatggta tggtagatac   9840
ccttatctaa atcatacata catttatcca gccaacggga aaccagacat gatttcacat   9900
actcattctt gtaaattact gacccatcta ttttgtttat acaagtgccg tcttggcagt   9960
cccagcaaaa ttggcaactt tccatgtagg cacaccagta ttcgagttct tcctctggag  10020
gctcctctgt tggacgaagt tgtccaacga gctgacttga aacctggctg gccagaaggc  10080
```

```
caagaattcc caagaagatc accaacattg ctacggctgg ctgaacagct gactgaatag  10140
ctagccaatt agcaatccac tgtacttttc ataagatcat ttaagattcg gtcggcattt  10200
tttcaatagt ttgctaggaa aaaattttta attttataga ttcacactac ttcattctca  10260
tgcttaggaa aaaaacaaac taaatcttac aatgtatctg gatctaatga gaagctagaa  10320
ttcatctttt ttcaaatcct ttctgggatg ttcattcttt ttccactcct tccttgcaat  10380
tttataagga ttccagggct ttgggtcaga acagttcatg ctatggtaaa tgtgctcctc  10440
cacatcatat ctacataggt caccccagcg ggaaacctca caatatttta catagtcatt  10500
ctcaataata cttgtggagt tgtttcccca aaccctgctg gtacaaatcc catcttcaca  10560
atcccagcag aaccgacagc tttccacata agtgcaccag tatccaagtt cattctctgg  10620
gggttcaaat gttagaggaa gatgtccacc tacccgagta gaagtggagg atgaaaccag  10680
gttgctactg gccagcaggc caataattcc caggataatc accagcattg tgctcaacca  10740
gcaacggcta gcaacgacta gcaactgact agcaatagct agaaatggct agcaatcagt  10800
agtagctaac gctctactct ttataagaaa atttaaaatt cgatcagatt tttttagaat  10860
tgagaatgag taaaacgctt atattctttt tctagctaga aaaaataagc tagtttaaga  10920
taggatttcc cttactaacg gtttaatttt tagcaaaggt ataggtaaaa tacacttgta  10980
cttagctgca aaaaaataag cttatggcgt ataagccgcc ataagtttat ttaattaaaa  11040
tgttaaactc tgtgataaga ctggaatctt aggcaggttt gatgtggaga acagcatgaa  11100
atacaagagt gcctgttaca cgaataagtt ctctcaaacc ggggatggtc atactcacat  11160
ctatgaaatc ctggtctagg agattcattt gatgcatgat ggccgcaccc acacttatga  11220
gacactgaag aactaaaggg tttaattttg atctgaatgg tactatatag gatgatggca  11280
atccatatca agattagagc aatcaaaatc acctcctcaa gaagcatgat gtagccttaa  11340
atcttagact gctttaaacc ttaggccctc actatcttta atgaaggagt ttaaattttg  11400
atccctttt caagacccat ttagaagaaa aaaataaagt ttatatcaat ctaattcata  11460
agtcatctct ttcataaatc ttcatgtatt ctctatgtgg ataagtatgg gatgttggat  11520
ttgcgcagtc catttgatga tctgtatggt ttttgggtcc ttcataataa ctacatatac  11580
cattccagcg ggaaaccgtg caatttataa tccagtcatt ttgatgaata actggccaat  11640
ctgtttgaat cctgtttcgg cagataccgt ggacgcattc ccagcaaaag tcacattggt  11700
ttgcgtaagt gcaccaataa actagctcat gttcaggagg ataacgggtt ggtagtaaat  11760
cttctaattt acgtatagga gcggcttgaa ggacaaccac ccccagtagt actagaatca  11820
gtacctttat agtggccacc ctacactaga cctctaagtt gaagacaaag aactaaaatt  11880
tagagccgtt taattactac taataattat atttttatt gtctacaata ggattctatt  11940
aaaaaataat gatttttacc aagaaatatt tttataaaaa attaatatat tttgtaataa  12000
actttatttc caatgactgt taaaataagg aaactatcct tagttagtcg aggaagatgg  12060
ttaggttatt tcgcaatccg ataaaatgtt tattttatcg taggtctcgt aaaatccagg  12120
aaaaaaaatt acggaagagt ttaaaaaagc taaattttta ccaccctcca gaagattgtt  12180
gtcaaatata tcgtttgcta gaaaatgttc ctggaggaac ttactttatt acagaaaata  12240
tgacgaatga tttaattatg gtcgtaaagg attcggtgga taaaaaaatt aaaagcatta  12300
aattatatct tcatggaagt tatattaaga ttcatcagca ctattatatt aatatttata  12360
tgtatcttat gagatatacc caaatttata aatatccctt aatttgtttt aacaaatatt  12420
ataacatcta agtaaatatt cttggaatgg attttcttat agaatggtta caggatatgt  12480
```

```
cagcgacagg cttaataaca aatttgttaa tatttttttg ttaaataaat gaacaggcca  12540
ccatttaata ttacccgttg caaaataaga aaaaaaaaac aaacttatag ttacaaatca  12600
tcttgattaa tcacatgtcg ttttaactca atgaaccatt ctaaatcttt gggttgtgaa  12660
caattcatgt tatgttgata gtgtatccta aagtgagctt catacataca ccggtcatgc  12720
caccgggaaa ctgtacaatt aacaatataa tcattttgcg taataatagg gtggtcacta  12780
aacactttat ttttacacat tccatcttta caggtccagc agaagtcaca gtgttttgca  12840
taggtgcacc agaacttgag atccctttca ggaggcctac gcatttgcat cggattatct  12900
gtggaaagag gtaggttcat tattatgttc gtcatcaaaa ttcctaaaag aacatagaag  12960
ccaagaaaga taagcagtct tgtagcggct tgcattcgca ttcgtgagta ttgtttgcga  13020
acatagctta tgagagcaat ggtagctatc atacaaagac aagtatgttt gatattctca  13080
gtgtcaatga ccctatcctc ctttatttgc attaactcat caaaccaatc ataatatgtg  13140
ggatttgtac agctcatgat gtgaaagcgg cgtatcctag agtctgtaaa gtagctacat  13200
ctttcattat agcgagaaac cctacatatt tgtatgtaat catttttttt gatgagaggg  13260
tgtttttcaa aaaccttatt tttacaaacc ccgtgtcgac aattccagca gaagtcacac  13320
gattttgcat aggtgcacca atactcaagc tctctctttg gaggtctccg ggtcattggt  13380
aactctcctg ttcctggaaa agattggctt tgaatgaccg gctgcatgac cgccagtacc  13440
aaaaggaaca caatcacctt catggctgca acttataagt tgcaacttat gggttgcaat  13500
actgcaacgt ataggttgca ccttatagat cgcgactcaa aaggtatgaa aaccttaccc  13560
tcaatacaga atttaagttt taatcctgat aatgtatctg tttatgaaaa aaaatttttt  13620
ttactcatgt atgaattctt atacgaatca taatatgtag gctgagaata ataattcata  13680
tacggtgttg cgggctcaat aaaaattttg ttaccacaaa aaataaatgc tggattttta  13740
agatatatat ctattaatga ctaaaccctt tatacgctgt aggctgaaaa caatccatat  13800
aatgaatata cggtgatttg ggtttaataa aatacataca acggtcaaaa tagcgggcaa  13860
tactacattg actaatataa tcattttgtt taataagagg catatcatcc cacactttat  13920
ttttacaaat accgttccta cattcccagc agaaatcaca gtgttttcca tacgtgcacc  13980
agtattcaag ctctcttata ggaggcgtat aagtccttgg taaattttgt ttcatataaa  14040
agatggaaag gggtcgattt aaacccggct gagatagcca aatcaaaata cataaaagag  14100
caagtagttt catagtggta tttagatgta aatttttata gtatgcaaat acaatgtaac  14160
ctacaaatac aatactaaat acaaggtaaa aacaacaatg tcttataatg attggccaat  14220
aatcaccccc cccccccat ttttccatga atatttcatt tcctgtatag ggtctaggat  14280
gtgaacactc catgttatga tgattaggca ttttaactga tatttcataa aaacaccccc  14340
aggaattgcg attaactata cagtttacaa tcgaattcat cgaattagac tcatttgtta  14400
tcttattttt acaaatgcca ttttgacaat cccagcagaa gtcacaattc tttacatacg  14460
tacaccaata tggaagctcc tccttaggag gatgctgggt tcttggtaat tctggtaatt  14520
catgtgcaag aatgaggact gagtagccca acaaaagtcc tagaaccttc atgttgtgtc  14580
caaatggcac ctgtcatttt aaaaaagatt taaattttgc taccgcaaaa aaaaatccag  14640
tatgtatttt tttaatacat ataattattg aagtcttata agataaagcc gagaacacta  14700
tattttgtat agatgatgta tccggtattc aaactctctt ataagtacat gtaggaaatg  14760
gtcaattatt caagattggc tgagataaca acaaaaccaa aatactcaaa agcataagta  14820
```

-continued

```
atttcatggt tgtactcagt cgtagatttt tgcagatcgc aaatgcaacg caaccagcaa  14880
atacaaagct aaatacaagg taaaaacaat aataccttat aatgattggc caattcttat  14940
ccctccattt ttccatgaac atttcatgtt cataaagtct aggatacgaa caacatttca  15000
tgctatgatg attaggtatt ttaagtgata tttcataaaa acaccacggg gttgttggtg  15060
attgataggt aagaataagg atggttgaat aacctagtaa aagtcctaga aaaaccttca  15120
tattgcgttc ataccacaga tgttatttaa aaaaaatata aattttacag tatgtgatat  15180
acacatacca caaaaatgtt cttatattaa ctaaaatatg tgggcagaga gcaattcata  15240
taatgaatat atggtatttt aggctcaata aagtacatac aacgatcaat aaaacgggta  15300
atactacatt tactgatgta atcattttga acaataagag gcatatcatc caaaacctta  15360
tttttacaaa taccattctt acaatcccag cagaaatcac agtgttttcc atacgtacac  15420
caatattcaa gttctctcat aggaggcgta taggtccttg gtaaaatttg tttcgtataa  15480
aagatggaaa ggggtcgatt taaaactggc tgtgctaacc aaaccaaaat actcaaaaga  15540
acgaaaagtt tcatggttgt actcagacgc agattcttac aaagcgcaca tacaaagcag  15600
cctgtatatg caataccaat gatgaaatag agacagtatt gctttataga taattgttga  15660
tggtcacccc cccccccccc cccatgtttg catgaatatt tcatttcctg tatagggtct  15720
aggatgtaaa cattccatgc taaagtgatt aggcatttta gatgaaattt catataaaca  15780
ggattgagtc ttggaatcac ggaaaactct acagtttaca atagaatgat tggagtcaat  15840
gaaacgagat tccgttatct tatttttgca aatgccatct tgacagtccc aacagaaatc  15900
gcattgtggt acatacgtac accaatatga aagctcactc ttgggaggat gctgggttct  15960
tggtaagtct ggtaattcat gtgcgagaat gaggactgag tagcccaaca aaagtcccag  16020
aagaaccttc atgttgcgtc taaatgacac ctgcacttac aaaaaaaaat ttaaattttg  16080
aatataacac aaaaaaacca ccttaaaatt tcttatatta tttcttggat ctgccccgac  16140
gtcatacaat gtattaaaat tatagaccaa tcatcttttt gtatataggc taatcatctt  16200
tatatataga ttttagatgt ttgcttgttg tatcaactta actgctagcg aagaaaatgg  16260
ataaaaactt tctgtatttt tataggttga aatcatttta tgcacatcgc taggatctaa  16320
tattttattt tgaagaaccg aatgtgggct taaaattttt ttcttagaaa aaagtagaat  16380
cataatattg ctatgttttt gtttaatgat ttcttgtatc ttttttgtat acgggttggc  16440
acccaaacct atacaaaaat atacattact caaataacta ccttctatac ataatctttt  16500
ttccccacgt attttcctat ttatttccct atttatggaa ttaaaggata tcaatctctc  16560
taaggcacgg tcaaggtctg cgcctaaggc aaaacaataa tatataccta atttattccc  16620
agggcgtgca caggcaagaa acatcatgac gtttagccct aaacgtatat tttcctgaaa  16680
atacgcatga tgaacttcat caatattacc taagtatatg gccgtttgta aacgccaaag  16740
atctaaatga ggaaattttt tactaagata atgaataggt tttgtgagat taaaatctat  16800
ggcgaactta taccaaaatt ttaatacaag tgtatttctc gtcatttctt cttctttttc  16860
atctaaatat aagataaaac gattgtaaac aaagtctatc aataggtgaa aatcattgct  16920
attaaagctg tcgagaatca aaatattgtc ataataaatt tcgatcgcca gtaaaacctt  16980
ttttcgtttg acgagataaa caaacatatt atacaaccct acatctaaaa attctggatt  17040
ggctcctagt tggatacaca ggtctttagt ctgcttcgtt ttggcacaca tgatgccaaa  17100
attaatatca gcaccccata aaacaaataa cttgattaga tcagtctggt tttccttcac  17160
agcttttact aaggctctgt caagctcata gctgtcgaca tcagagcatg acatagagcc  17220
```

-continued

```
accggttacc attttacatt gcttacaaaa acctatgggt ccgttttccc accatagtcc  17280
aagctgttgt agaataaaaa tatcatcctc atgataattt gaaaaagcct tggtttctat  17340
caagactttt tttgtaagaa cctgtaaaga gttcatcgta ttattatgaa taacaggagt  17400
aaacgtaatc aattataaaa gtgatttttt cgaaaaaaac tttagatggt tgaaaatgat  17460
aatgtacatg ttcatacaaa aaatagatgc agtgatgtct aaaatcaaaa tttaattttc  17520
tatgtaaaaa gtacagactt acttatttgg gttaaattgt ttattttaaa ctttaattaa  17580
ccgtttgagt tagcgatgtt tgatttatct tccatactca tccggggggg gggtccttat  17640
agctctgaca ttattgtgga ttattgaata taatgaatac ttcatagatg ctaaacattt  17700
taatagtagt tctgaggctt aattgtactc tataaattta taaaaacttt ttgatcaaaa  17760
tttaatttct tataaaaaga gtacagacgt cgcttgttta agcttcatca tgtttcattc  17820
attactttct acaattacgg ggggggagt ccccctcatag ctttagtatt gctatggttt  17880
actaattatt atgtagaatt tatagaagca tatgtacctg aaagtatacc tactctataa  17940
aattaaataa tttcagtata ttttttttat gaatagaacg gaaatgatat aaaaataatt  18000
taatattgca aaaaaaattc ataatgttgg tatgtattat aaacataata gcatgtgtaa  18060
tttataaact gactcctcta tataattatt agatgaggta ccaacctact tatgatatgc  18120
cgatgataga tattgtatac tataaaacaa aattatttta aatgtattca tggatacatt  18180
ataacatttt taccgcaaat tgtctctcag cgaagaaaat gaatgaaacg tttctgtata  18240
ttcataggtt gaaattattt tacgcacttc actaggttct aatattttct tatgaagtat  18300
tgaatggggg cttaaaagtc ctttcttaaa aagaagtttc atcataacat tcttttcttg  18360
tctaagaaga gtttcttgta ttttttttgt ataaggattg gcacccaaac ttatacaaaa  18420
atgtacatta ctccaaatac cataatttga aaagaaagtt atttccctat ttacttcatg  18480
attaatgaaa cctatcaacg tctctaaggc cgtattgata tttgcgccta aggcaaaaca  18540
atagtatata cccaatttat tttgagggta catacaagca agcgacatca tgtcatttgg  18600
atctaaacgt atattttcct gaaaatatgc atgatggatt tcatcaacat tacctaagta  18660
tacagccgtt tttaaacgcc aataatctag gtgaggaaat ttcttactaa gaaaacgaat  18720
aggttttata agattaaact ctatggcgat cttaaaccaa aattttaata catatgtatt  18780
ttttatcatt ttttcttttt catctaaatt taagataaaa cgattgtaaa taaagtctat  18840
caacacgtaa aaatcatggc tatcaaaact gtcgagaatc gaaatattgt cataataaat  18900
atctatagct aataagacct tttgttgttt aattagatca acaaacatat tatacaaccc  18960
tacatctaaa aattttggat cagctcctag ttgaatacac agaactttcg tcctttccgt  19020
cttggcacat atgatgccat aattaatgtt ggcaccccat aaaacaaata acttgattag  19080
atcagtctgg tttttcttca cagccctcac caaggctctg tcaagctcat agctgtcaac  19140
atcagaacat gacatagagc cactggttac cattttacat tgtttacaaa aacctatggg  19200
tccgttttcc caccataatc caagctgctg taaaataaaa atatcatcct catgataatt  19260
tgaaaaagcc ttgttttcta tcaagacttt ttttgtaaga acctgtaaag aattcatcgt  19320
attatcatga atgaaagcag taaatgtaat caattataaa attgacttat tgaagagaaa  19380
tgttaaatga gtgaaatcgg tgtttatgat gatgtacatg atcatacgaa gaaacacgtt  19440
cactggtgtc catgatcaaa atttaatgtt ttacgtaaaa agtacagatg ttaactgttt  19500
agtttaaaca taaatttaac ctttagttta aaccctagtt aatgatgttt aatatttctt  19560
```

```
ctatactcat tcagggaagt gtaatgattc taatactgtt gttatggatt attaatgaaa  19620
actttacaga tgctggaggg aataatttta atcatactgt tttaatgtag ctatataagc  19680
tttcatcaaa atttaatttt tttttataaa aatacacgaa ttaaactaaa gtctaaactt  19740
tagtttgact atttgagtta atgatgctta acttatcttc catgcttatc aagggggggt  19800
cctaatagtt ttgatactat tgttgtggat tgttgaatat aataaatact ttatagatgc  19860
tgaaatgttt gaaaataata gtacatcaat gttgtaagtt tgatcaaaat ttaatttctc  19920
ataaaaaagg tacacatcaa cattgctcat ttaagtttca tgatgtttga ttcattactt  19980
cctacaatta ctgggggggg gggggggctt taatagcttt agcattgtta tggtttgctg  20040
actattatgt agaattcata gaagcacgtt tagatagtaa tatcactgca gtgtagatta  20100
tgaaatacat actaaactaa tttcagtata tttttttgt tcatataagt taaggtacaa  20160
aaatgattaa acattgcaaa aaaagaaaat cacaatgcta ttatacatag tgatcatagt  20220
ggcttgtatc atttctaaac tagttccaaa tgaatattgg gcaatacatc tatttttat  20280
cattatgatt tttatggtat atatgtatga aaagttagat atacatcaaa aatctcagtt  20340
ctggaattat accatgtcag gcttatctgg acataacgta caggtaacat gtaagtgtta  20400
ctaaatacta tgaagtatct attttttttt gttgtaaaaa aaagaacttg atagtatttt  20460
ttaaaaaata aaataattaa ttgtacgtca acttccttat tttattcttt aaaaataact  20520
cgtaagtatt atttatctat tttttgaaaa aatagatgta atcggtttca tcatttaggt  20580
gtgtatttct ttttagcatc tatcaagaat tcattgttta gtgatatgaa aacaatgaat  20640
gatcattatc ttctatttaa caaccaccta aataaatgaa cgtctttttc atcttaactg  20700
attaccaaaa gttattttgc gaaaaggcat acatatgatc aatatcagac ctacaatgaa  20760
tatttccata atatcccttt attgtaataa ttctattttt gcattccgat atctcatcat  20820
ctgtgctatt atatgtttcc ataactgttt catcatcaaa cataaatcct gttaaatagg  20880
caaaagactt taatcccgga tagattttta ccattttcct gagagccgtg tatagcttgt  20940
aataaatggc caaaaatatg caataaagcg tagaaagaga gtaatttttg gcataaaaga  21000
ttttgaaggt ttgatgaatg gctaaatcgc atataatata agatacgatt ttaaagcgca  21060
cctgttcacg cagatttgtt gaaaaattcg tggaaagatt taacaaataa aaggttatta  21120
atagttgctc atcattcccc ttatacgaca tcgtcagacg ctctaatatt ttactactag  21180
gcacatctgc cacatgttga acatttaaag cctgttcttc ttctgtgtta cggcaaaaga  21240
gccgtgcgta ttcaggtgaa gctccccagg ataacaacgt ccttgctacg gctaaatttt  21300
ttttgacgat gacttttatc agaaataagt ctttattttt gcattgatca ctatgcgaat  21360
ttgtatagtt gacgccgttg cattgagtac attgatataa tgttttacaa ttccagcgta  21420
gccctaaatg gtataaaaga actgtatttt cgacataagc atgctgatta acgatgtttt  21480
tgagacaaca cgtcgttaag gacaccatat tgtctccaat ttgttagata aaagtcttta  21540
ctaaaaaaat agatttttag ttttaacaat cgagatttta ttatttggat gcatcatcaa  21600
aaagatttat aagtataaga ggttgtataa gaaaaaaaat gatgttatac tatttatgtt  21660
aaaatttaat ttatcatata aaaagtacag atttaatcag ttggttaaac tatttagtta  21720
attaaactaa atagtttaac catttagtca gactacttgg ttagcaatgt ttgagctttc  21780
ttccattctt atccgggggg ggtcctaatc gttctaatac tattgtggat agttgaatat  21840
aatgaagact ttatagatgc tataatgatg aattctagta tgcctgtata aaataattaa  21900
cctttttgat caaaatttaa ttttttata aaaagctaca gagtagtgtt ttattaaacg  21960
```

```
tggcttattt aaaagttaca caatgttaaa atctctactt actttaattc tttgtggggt  22020
tttattaact ttatccatat tatggcttac tacttaccat gtagaactta tagaggcaat  22080
agatgatttc tacgactgaa atatagaata gtccattttc tatttgtaaa ataatgattt  22140
atattctttc ctaaaaatga tactttatat ggtttgaaaa caaatattaa caacttgatt  22200
tttttttcta taaataaact ataaatgaaa atagtaaaac tcatagagtc ttataagtga  22260
acatcttcat aatgttactc aaacgttgga ctattaaaaa atattccgtg tgcattattg  22320
cttttaatca gtatgattac tttatacgaa gccgctatta aaacgcttat cacacaccga  22380
aaacaaattt taaaacaccc cgatagccgt gaaattttac tagctttggg gttgtactgg  22440
gataaaactc atattcttgt taaatgtcgt gaatgtggga atatgagtct taccggaaaa  22500
cacagtacaa aatgtattaa cattaattgt ctacttattc ttgccataaa aaaaaagaat  22560
aagcgtattg ttgatacctt gataggaatg ggcgcggatg taacatatat acatctttta  22620
aagaataaga taaaactgtc atacaaccag ctgtctatgc ttaaaagcaa ctcgcagatt  22680
tcattgaagg agcttcatgc tatatgctat cttttatatg gtcggcttcc caaaaaaatt  22740
aaacaaggga tgcgactgtg taaaacaatg gcgggactat gtggtgaact tttatgtgca  22800
tttttagctc cgtaaatgat aatatgtatt taaaacaaac agatattacc aaaatatatt  22860
ctatgtacat aatatctggg aaattatttt tttttctcat acccttaaat ataaaaatat  22920
tgggtttctt cactaaactt tagaggtaaa aatttttctt tgttttgcac catcatgtat  22980
gggtttaggc tgtcccaggg attgtttatt tgaatatttc ctaaatagga acacaacgcc  23040
atgatcatat atctttcatt ctggtaagct tttgatacat tcttcaaaga tgccgtacct  23100
ccgagtgtgt aacagcaaac aaacgtccgt acttttccat gggtcgcagc ccattccatt  23160
ccgtagctca gcatcttttg ctgtattttt ttattcgctt tataaaaaaa gtttttcatc  23220
cattccacgt tctcataaaa acaggcactt aaaaagagca ctaggggtag tgtagtctta  23280
ttatagaatg taggaatgta tgttttagtt attttttca acgcgtgttc catactatgt  23340
tttaccgcca taaaaataca aaaccaatac caactttttc tataaaaggt tttgctgtac  23400
acatataaac gagcaaaata tatttcaaac tctatattct ttttataaaa aaactcgaga  23460
cagtcgttta tgttacgact ttttctaaat acctcaaaaa cagtaattaa ttcactgtcg  23520
ctgtggaaat gttcgtaagc taactgttta atgtctttag gggtcaattc tttttttggg  23580
agcagtggtt tgagattcgg caaaggtcgt ctaaagtagt gagcgaactt ttcattcgct  23640
ccccaacaca aaagccgata agccagcatg tagttatcac gttttaccgc gtaaataagc  23700
aaatagttta tattgataca tgtaccatgt tgctgcccgt ttggacatat gttgccgcat  23760
tctgaacact tatgaatgag atcatagttc ttacaacata accccaaacg ggttagtact  23820
tctttgtcac gttttaaaaa ctcgacatga ttctttaatg ttaatgcttt gagcgcaatg  23880
ttaaataaac tctgcatttt attaaaatga ggttagtatc atgttttagt ataaaattta  23940
gcggctgttt acataatgct aaataaactt aacgttccta ctaaaccaaa aaaaaatcaa  24000
attgactaag tcatagagaa tttgacgatg ttggtaggta attttttaac atggtatata  24060
tttttttagg gtcggttata ttaggtaata aaagaggacg tgccgttaaa gtattttgct  24120
taagatcctt tagatcctta caaaaatata gattgttcgt ctgatgatgc cactgtgttg  24180
cagtgatggc ttgatcaata tcacctccca agacaaaaca gtagtatatc gttaaaaagt  24240
tgtaatcttt catacaagcc aactgcatca ttttatcgat gtccatatga acgatctttt  24300
```

```
gctcgtatat ttcatgaagg tcaaatacat tgttgaagta aatggcgcac atgagtcgcc  24360
acatactaag gtgcccatat gtttgataga aaaaggagat agctctttta agcttatatt  24420
ttactgctat ggcatagcag tatttaacga atacgttcat gggtacatta tctaagatat  24480
aaaatatgaa aactttaac tctcgatgaa tctcttcccc catttcctgt acatttagag  24540
cttccaacat aggattttta tcaaatattt catgacataa aataatgtta ttgctcgttt  24600
tatgacgcat taaaccggtg aaaatttcct tattatttaa actatcttta gctcctaact  24660
ttcgacacag ctcctgagtt tgttccgtcc tagcacaggt cagcccataa taaatgtttg  24720
ctccccactc ggtgaacagc cttattacgt catagttatt ttcttttatg gccatgatta  24780
atgccacatc aagatgaaga agttccccct taaagggggt tgagcttaaa ataacgtaat  24840
tacagtagtg acataagcta atgggcttgt tttgccacca taagccacaa tattttaaaa  24900
tataatgata ctcctcaggc acgctctgtt tggccacagc ctttttggcc agggtttgca  24960
aggagagcat gataacttct tgaaaaaaaa actcaaatta agttcctact tttttaaaat  25020
attagtatgg acagatctac catcatatga aggaattctt tcatcgttaa acactgaaga  25080
gataatactt tcatcgtata gagaatatca tgtcaatcca tatattgaat gttatatatc  25140
attaaaccca tcattaatat agtgtttatg tgctatggac aggttttttg aatgataatc  25200
ttttaacata cgttttataa cttcgggatc agtttctttt aaagataaag aatcattcat  25260
gttataacaa tttaatgata acatgctggc aatgaacgag ttgtcttttt gatgcgctag  25320
agtctttccc tcctcaaagg cattggcgcc taagtctata caaaagaata tgtttccgat  25380
attatagaac tgaatagaat gaaacatggc ctgattgata tcagccccta agacgacgca  25440
acagtaataa atcgttaaat agttatagtt cttgcgacag gcccacttta gcatttcatt  25500
catgtctatg cgaatcctct ccttttcgta cacttcgtga agttcaaaca cattattgta  25560
aaaaagggcg cacataagcc gccaccgatg tagatgagca tatctctgat aaaaatagca  25620
aatcgcctcc ttaaggttac attctattgc catcgcgtac caatatttag taaacatctc  25680
gcttaatata tcggtttcta ccattaatcc ctccagttgt tcataaatca ttccctttac  25740
ttcaaaacga tttatggtat ctaaaatggg attattagaa aatacctcat ggcagaaaat  25800
gatgttactg ctagttagat cacgtttcaa tgtgtaaaaa aatcgtaaaa tttcctggtc  25860
atttaactgt tctttggcac ctagctgcct gcacaggtct cgggtgtgct ccgtgttgac  25920
agaaagcaaa ccgtagttga tgtttgcacc ccactcggtg aacaattcta ttagatcgtg  25980
attgttttcc tccacagctt tcaccaaggc cgcgttaaga tttgtgccgt tcttaaaata  26040
cggcgtccat attttctttt gatgatacat gatagggcca ttatgccacc atagaccgca  26100
gcacttcaaa aaatgaggat ggcatttggc cggatactgg ctggccagca cctttttggt  26160
gagagtctgc agagagagga ccatatttct tttttttgaa aaaatcaaat taaaaaaatc  26220
atgcttgttt agcatacatg taatattgtt ataattacgt tataattacg ttataattac  26280
gttataacta tattataaca atggtataac aatggtataa caatgttata acaatgttat  26340
aacgatgtat cattgatgtc atcattcaac taggccaaca tactttttaa tttatagttt  26400
tttaatagat gatatatttt gttaggatct gcttctttta acgttaatag cgaggagtct  26460
gcactataaa tgtctaatga taaatgatga gatatcaaat agtaattccg ttgctctgct  26520
agggcctttg cctcttcaaa ggcgtcggct cccagatcta tacaaaagaa caagttatcc  26580
atattataaa atcgtacgca ggcaagcata gctgaattaa tattagctcc taagagaaaa  26640
caataaatata tggttaaaaa attgttatct tttgtgcagg ccatccgcat catttcatcc  26700
```

-continued acgtccatgc ggatcttttc cttttcatac aaattatgta ggtcaaacag cttattaaaa 26760
caaagagcac agattaacca ccacgtattt agatacttaa aatgttggta aacataagaa 26820
atggcctccc taagattatc ctgcaatgcc actataaaac agtatatcgt taacatatca 26880
ccatccgaca tattacttaa tatgtcggtg tcttctacta accttttcaa cttccaatat 26940
atggatgacc ttatttccct tataatgaca taggctggaa agggattatc attaaaaagt 27000
ttaagacata agataatatt actgctagta gtgccagggt gtattaattt aaagaacatg 27060
tgcataatct tctttttatc cacgcggtac ttggctccta attcccagca aaattctcga 27120
acaggcggcg tattggcgca aattaaccca tagttgatgt ctgcgcccca ttctgtaaac 27180
agttttatta actgatagtt gttttccttt gtagccaaca ttagtgccgt attaaggtcc 27240
aagccgtctg caaagcttgg cagctttatc agcatatgtt tgcaatcaag ggaaattggg 27300
gccttatacc accatagtcc gcagcgttct aagataacat ggtactcaat agatacttgc 27360
tgtctggcta gtaccttttt ggcgaaggat tgtaaggaag gaaacatcct gtttcttttt 27420
tttttaaaaa tcaattatct ttgttcataa tcaagaaaaa tccccatatt tattgagtga 27480
taatttttta acatgcaatt tatttttttca gggtccgtaa cgatcgacaa cagagaaata 27540
accggattgt aatgctttaa tgataaggca tgggctatca gataattttc cttttgttct 27600
gccaaagctt tgccctcctc aaaggcatcg gcacccaggt ctatacaaaa gaacaggttt 27660
ccaagattat agttttgtat ggaaacaagc atggcttgat tgatgttggc tcccatgata 27720
aaacagtagt aaatggccga atagctataa tcttggatgc aggctatgtg catcatttca 27780
tcaatatcca tgcggaccct ttctatttcg tacagctcgt gaaggtcgaa cacgttgttg 27840
taaaaaaggg cgcacatgag ccgccaccta tgtagacgcg ggtatttctg gtaaaagtag 27900
cggatagcat ctttgaggtc atagtccacc gctatcgcgt accagtattt ggttaaaaca 27960
gtgctaaagc tatcatcatg gtccagcatg aaggttatct ccatgagccc tcttaactcc 28020
cacatgattt ccccccctcag atccagatta tctataatcc ttaaattggg gttattggaa 28080
aacacctcgt ggcaaaagat aatattgcta ctggttttat cgcgcgttgt atcaaagaaa 28140
atttttaaaa tatactctct ttctaaatat tctttggctc ccagctcttt gcacagatca 28200
cgggtatttt ccgtgagagc acaaatcatt ccatagttaa tatctgcacc ccattcagta 28260
aacagcttta tcaagtcatg attattctcc ttcacggctt tcatcagtcc tatgtttaac 28320
tcgatacctt gactaaaaca ggttgacctt ataaataatt tattgcgtcg aatatgaagc 28380
ataatggggc cattatgcca ccacaggcca caacacttca ggacatgata ttgatctacc 28440
ggtatacact gcccggccag tactttcttc gtgagggatt gcagggaagg caacatgcct 28500
ttccatcctt tgacggaaat caaattatct actaataact atcagtgttt atattaagta 28560
tttagatatt atcccgggct ggatacgtag tatcgctatt cacatgtact tccaactcta 28620
gccggagcct gcagggtcat ttatttttaa tattgattct tttttgtatt taatcattta 28680
gagaaggtca tcataggagc cagatgttct ctctccagaa cttatgtcga aaaacattac 28740
ctaaccgtaa acttcctgaa ttttttgacg aatatatatt acaactgctg ggattatact 28800
gggaaaacca tggaactatt caacgagcag gaaacaactg tgtgcttata cagcaacata 28860
ccctcattcc cgtaaatgaa gccctgagaa cagcagcatc tgaagaaaat tatgagatcg 28920
tgagcctttt attagcgtgg gaggggaacc tttactatgc tattataggg gctctagagg 28980
gcaaccgcca cgacttaatt cgtaaatatg atgaccaaat caaggaccat catgaaattc 29040

-continued tgccattcat tgacgatcca gtcatatttc acaaatgcca tatcatgcgg caatgctttt 29100
ttgattgtat tttatatcaa gctgtaaaat atagtaagtt tcgcgttctt ctttacttta 29160
aacatagatt agaggatgat ttgcccttca ctcatttact tattgaaaag gcatgtaaag 29220
atcataatta tgaagttatt aaatggatat atgaaaacct acatatctac aatatgatag 29280 ataccttga atgtgctatt gcccataagg atctacatct atattgtttg gggtatagat 29340
ttatatataa cagaatcgta cccgataagt atcatcattt agatattcgc atgctttcaa 29400
gcctacaact cctacataag gtggcagcca aaggatactt agattttatc ctagaaacct 29460
taaagtatga tcataataaa gataatataa atattattct aacacaagct gcaacctata 29520
accatagaaa aattttaatc tatttcattc ctcaatcaac ccacgcacag atagaacaat 29580
gtttactagt ggcgataaaa gcaaaatctt ccaggaaaac cttgaactta ctactgtctc 29640
acctaaacct ttccatcaac ctcatcaaaa aaataagcca ttatgttgcc acttacaatt 29700
caacaaatat aataggcatt ctgagtatgc ggcggaaaaa gaagatatat ttagatatca 29760
tattgacaaa atttgtaaaa aaagctattt ttaataagtt tgtcgttcga tgtatggata 29820
cattttctat aaacccggaa agaatcctta aaatagccgc gcgaataaat aggatgatgt 29880
tagtgaaaaa aatatctgaa catgtttgga aaaatcatgc ggttagactt aaataccta 29940 aacatgcggt acacacgatg aagcataaag atgggaaaaa tagactcatg aactttatct 30000
atgatcgctg ttattaccat atgcaagggg aagaaatctt tagcctcgca agattttatg 30060
caatccatca tgcaccaaag ttgtttgacg tttttatga ttgttgtatc ctagatacga 30120
tacgattcaa aagccttctt ttagattgtt cacatatcat aggtaaaaac gctcatgatg 30180
ctaccaatat caacatcgtg aacaagtata tcggcaacct gtttgttatg ggagttctta 30240
gcaaaaaaga aatcttacag gactatccat ccatttattc taaacaatac atgccttagt 30300
ttattttttt tgcggccgaa acattattct taccctagaa aacgcttata gtcatcttaa 30360
atcataggta aggaagatca tcatattttt tgaaacgtaa ttttttaacg catgatctat 30420
gatttcaggg tccgtgcttt taggcaacgg ggtggtggcc ggactataaa tctttaggga 30480
taaaatgttc tttataagct catacccttc ccctaaagct gtagtaccct cttcgaaaac 30540
atcagccccc agatctatac aaaagaacat gttttctata ttatagtact gtattgagct 30600
aagcatggct tgattgatgt tggcgcccag gacatagcag tagtacatgg ttgaaaggtt 30660
gtggtctttg atgcaggcga tccgcatcat ctcttctatg tccatatgga tcttgtcctt 30720
ttcatacgcc tcatgaaggt caaacacatt attaaaacaa agagcacatg ttaaccgcca 30780
cgtattcagg tgtgtatatt tttggtaaaa atactgtatg gcctctttca ggttatagcg 30840
tatggctata gcgtaccagt atttgagtag taatgtactg agcgaaaact cattatttag 30900
cagatcggtt tttactatta actcccttaa ctcccagaaa atttctatcc tcatttttat 30960
attatttact ttttgtaata tcggattgtt ggaaaacacc tcatggcata aaataatgtt 31020
actactagtt ttatgaaact ttagatctat aaaaatttgt aaaatttctt cttcattcaa 31080
ggtttccttg gcacctagct ctcgacagag gtcccaggtg tgctccgtgt tgacagatac 31140
cagcccgtag ttgatgtccg ccccccactc tgcaaacagt tttataaggt tgtagttgtt 31200
ttcccttaca gccttcacta acgccgtatt taggtttaag ccctctttaa tacctgctga 31260
ttttatgagc cttaggttat gatcaaacgt gatcggagca tcatgccacc ataggtcata 31320
acactttaaa agataatgtt ggttcgtggg cacgcattgt ccagccaaca ccttttttggt 31380 cagagattgc agggaaggca acatgtctct tcatctttta aaaaaaaatc aaattaatta 31440

```
gccgaataaa tttttctttc gagggctttt taaaagagct ctttaagagc tctttaagag  31500
ctttttaaga gattaaaaaa ttattcttgc tggcattctg ccaagtatgc ggcattccta  31560
tcatctatag tatattatga gaatattccc aaatgatgga taagtttttt gatttataat  31620
cttttaataa actgcttatt tcttcggggt cctttaagtt tagtggcaag gaagcatctg  31680
agctgtaaat atccaaagcc aaactatggc tcagaaaatt ataacctttt tgttccgcta  31740
tggcacgacc ctcttcaaag gcattaccac ccaaatctat acagaaaaat atattaccga  31800
tgttataata ttgtactgaa gtaagcatag cttggttgat gttgcccccc agcgcgtaac  31860
agtaatatat tgttaatgga ttgttatcct tggtagaagc cagacatatc atgtcatgga  31920
cgtctatttg gatgttttcc ttgtggtaca tctcatgaag ctcatatatt ttgttataat  31980
acaggagaca ttttaatcgc cattcattaa gatccgtata tttctcatct agaaaacaaa  32040
tggcgtcctt acaatcgtat tgtactgctt tggcgtacca atacttcact agtaaaccat  32100
ttaactcgtc cgtttctttt atttctatga gcccccatag tcttttataa attaagcccc  32160
ttaattgtat aacaaatttg ttttctaaaa taggattatt cataaaaatt tcatggcaca  32220
aaataatact gccgctggtt ttattgtgca ttatcctggt aaaaatacgg aaaatatcgt  32280
tgtcctctag agtttctttg gcgcctagct gtctacacaa ctctcggatg tgcttcgtat  32340
tgatagaaag caaaccatag ttgatatttg cgccccactc tgtaaagagc tttatcagac  32400
tatagttgtt ttccttaaca gctattatta atgccacacg aaggtctata tcttctccta  32460
aaaatcctga ttttatttgt attcggccac gatccataca aagcttgaga ggagcatcat  32520
gccaccatag gccacaatat ttcaaaatgc agtgttcatc tattgacaaa cactggctgg  32580
ctatcgtctt tttgacgagg gtctgcagag agagcggcaa cgacatgttt ctttttcacc  32640
aaaaaaaaat caaatgttct cgtctttaaa ggttaattca tgttcttaaa atgttcattt  32700
catgatagtg attaataata tggtttaata acgctagaag gcttgtttat aagacagtca  32760
taagcagtct ataagacagt ctataagcag tctataagac agtctatgac ttagtctata  32820
actataattt ctggatgggc tgtaagatac tcttcggctc gtttcagatt ttttgaagta  32880
tatgtcttta gcatatcata tatttcctgg ggttcggtta catctaatac caaggtcaca  32940
tcacggctga aaagctgctt tactaagaaa atgttgctca agttatacat ataagctttg  33000
tgcgcaatga gttgtgccct atcaaaatcg gcagcccccca aatcaataca gaaaaacatg  33060
tttaaagtat tattgttata gatagaaaga ttcatgccat aatcgagact agcccccaac  33120
ctatgacagt aataaatggc cgcgtaattt ttttcccgca agcaagcaaa tttcatcatc  33180
agattagggc tgatgcaaat ctctttttca cgacacaact cgtgtatgtc aaaaatgtta  33240
ttaaaataaa ggctacaagc tacccgccaa tagaggtgat ttttatgcct tttatagaaa  33300
tagtgaatag cctttgtaaa attatgtcgt aatgccaggg caaaccaaaa ctttgttaat  33360
aggtggtgcg ccgtatcccc cgtcaacgga atgtttgaac aggtgtacgt aactgtgtct  33420
aaagtggttc tagttacggt ttccaagagt ggattatgac aaaacatgtc ataacccagc  33480
agaactcctg cacaggattt tagcctggcc acttctttta aaatttccag aagacggggt  33540
tcggatacag gcgttaagcc tcccagttcc gcacacagcc gctttagata cacggcagga  33600
acacgtataa gcccatattc aggatttgcg ccccaatcca caaataaacg tataagttca  33660
agattatcgc tcttcacggc ctttactagc gccgcttcga gacaaagatc atcctcagaa  33720
aaacactgta aatgtttata cgaaaaaact tgcttacaat tgttacatag gtgaatagga  33780
```

-continued

```
cctaaatccc accacaaacc aaaacgctgc aacgtataat catagtcact tgaaagataa  33840
ttgcatgcca caactttttt ggccaacgtt tgtaaagaca acatactaag tttaaaacat  33900
cttaaatcta agctagctaa ctttcaagaa aaccctctat ccctaagaat atatcttata  33960
actagactta tagcagtaaa aatcaacttt ggttattctt tttaatataa aacgtctaat  34020
tacttgcaaa ggactataaa gcccattttc ctcagctaga atttttattt tttaatgaag  34080
tagggggata tgtttttccct tcaagacctt tgccgaaagc atctttttat tcttcccgat  34140
gtttttggcg agcatgtact acaacgatta ggactgtatt ggagatgtca cggctccctt  34200
caacgcatag gagacgacca catactcata cgacgggatc tcatcctttc caccaacgag  34260
gccttaagaa tggcgggaga ggaaggaaac aatgaagtag taaagctctt gttactgtgg  34320
aagggaaatc ttcattacgc cgtcatagga gccttgcagg gtgatcaata tgacctgatc  34380
cataagtatg aaaaccaaat cggcgacttt cattttatct taccattgat tcaagacgcg  34440
aatacgtttg aaaaatgcca cgctttagaa cgtttttgtg gtgtttcatg tctgctaaaa  34500
catgctacaa aatacaacat gctccctatt ctccaaaaat accaagaaga gctgtctatg  34560
agagcgtatc ttcacgaaac cctatttgaa ctagcatgcc tatggcagag gtatgatgtc  34620
cttaaatgga tagagcaaac catacatgtt tacgacctaa agattatgtt taatattgcc  34680
atctccaaga gggatctgac tatgtactcc ttaggatata ttttcctttt tgatagaggg  34740
aacaccgaag ctacgttgct aacgcaacat ctcaagaaga cagcggccaa agggctcctc  34800
cactttgtgc tagaaacgtt aaaatacggc ggcaacatag ataccgtcct gacccaagcc  34860
gtaaagtaca atcatagaaa acttttagat tattttctgc gtcaactacc tcgtaaacat  34920
attgaaaaac ttttgttgct ggccgtgcag gaaaaggctt ctaaaaaaac attgaactta  34980
ctgttgtcac atttaaacta ctccgtgaaa cgcatcaaaa aactaccgcg ctatgtgata  35040
gagtacgagt ccaccttggt gataaagatt ttattaaaaa aaagagtgaa cctgatagat  35100
gccatgttgg aaaagatggt aagatatttt tctgcgacga aagtgaggac gatcatggat  35160
gagctttcga ttagtccgga aagagtcatt aagatggcta tacagaaaat gagaacggat  35220
atcgtaatcc atacttctta tgtttgggag gatgatctag aacgtcttac tcgtcttaaa  35280
aatatggtat acaccataaa gtacgaacat gggaaaaaaa tgttaattaa agtcatgcac  35340
ggcatataca aaaacttatt atacggcgaa agggaaaaag tcatgtttta tttagccaag  35400
ctctatgttg ctcaaaacgc ggccacccaa ttcagagaca tttgtaagga ctgttacaaa  35460
ctggatgtgg cacggtttaa accgcggttt aagcaactaa tattagactg tttagaaatt  35520
attactaaaa aatcttgcta tagtatcctg gaaatcttag aaaaacatat tatttccctg  35580
tttactatga aagttatgac tgaagaagaa aaaaacctat gtttagaaat attatataaa  35640
gtaattcatt ataaaacaat acaatgttaa aattcaatag atatccatca ttaatattga  35700
ttatattttc gaatattatc ttctatggtg caagataatc atctagcgcg tgaaacatgt  35760
cctcttctct tcaggaactt tgtcgaaaaa agctgcctga ctgcatactt ccagagtttt  35820
ttgacgacta tgtattgcaa ctgttaggac tgcactggca agatcatggt tcccttcagc  35880
gtatcgagaa gaaccagata cttgttcaac aggaacccat ccatatcaat gaagcactca  35940
aagtagcagc atcggaaggg aactatgaaa tcgtagagct gttgttgtca tgggaggcag  36000
atccccgcta cgccgtcgta ggagccctag aaagcaaata ctatgacctg gtttacaaat  36060
actatgacca agttaaagac tgccatgata tcttgccgct gattcaaaat ccggaaacat  36120
tcgaaagatg tcatgagtta aacagcacct gttcactgaa atgcttattc aagcatgctg  36180
```

```
tgataaatga catgctgccg attcttcaaa aatatacaga ctatctggat aggtgggagt  36240
attgcagcca gatgctgttc gaactggcat gtagtaaaaa aaaatatgag atggttgtgt  36300
ggatagaggg agttctaggc gtcggcaaag ttacatctct tttcaccatt gcgattagca  36360
acagagacct acagctgtat tctctgggct actcaattat ccttgagaat ttgtactcct  36420
gtggacagga ccccaagttt ttactaaatc atttcctgcg agacgtttca ataaaagggc  36480
ttctaccctt tgtaatcaaa accatagaat atggtggaag caaggagata gccataactc  36540
tggctaaaaa atatcagcat aaacatattt tgaaatactt cgaaacctgg gaaagctagg  36600
ttcagtatgg tgtactcact attgtagtga atcgtatcct gtaaattttg taaaaaagct  36660
taaacttttg accacatcat attgttttag aaatctcaaa ccagtgaaca acagtcttat  36720
catacattaa aattccagta aaatttatat tttttttggt aaacaaatgt tttctcttca  36780
agacatctgt cggaaacatc tttttcaact tcctgacgct tttgatgaat atatattaca  36840
agcgctagga ctatactggg aaaaacacgg atctcttcaa cgaataagaa aggacgctgt  36900
gtttgtacag cgaaacatcg tcctttctac caatgaggcc ctgagaatcg cagcctcaga  36960
gggaaacgaa agggtaataa aacttctgtt atcatgggag ggaaattttc attatgtgat  37020
cataggagct ctagagggtg accaatatga cctaattcat aagtatgata gtcaaattaa  37080
agactaccac atgattttat cattgatcca aaatgcaaat acctttgaaa agtgtcatca  37140
gttatccaat agtaatatgt ggtgtcttat acagaatgct ataaaatata atatgctccc  37200
tattctccaa aaacacagaa atattctgac acatgaggga gagaatcagg aattgtttga  37260
gatggcatgt gaggaacaga aatatgacat agttttatgg ataggacaaa ccctaatgtt  37320
aaatgagccg gagtttattt ttgatatcgc cttcgaacgg atagattttt ctttattaac  37380
aatgggttat agccttcttt ttgataacaa gatgagtagt atagacattc atgatgaaga  37440
agatcttact tcattaccaa cagaacacct cgaaaaagca gccactaagg gatgtttctt  37500
ctttatgcta gaaactttaa aacatggtgg aaatgtaaat atggcagtct tatctaaagc  37560
tgttgagtat aatcatagaa aaattttaga ccattttatt cggcggcaaa aatgtttatc  37620
acgtgaagag attgaaaacc tattattaac cgccataacc aattgtgcat ccataaaaac  37680
gttaaactta ctcttgtctt acctaaacta ttccgtaaaa aatatcattg gaaaaatagt  37740
acaacatgtc ataaaagatg gtgattatac catcatatta cttttaaaaa aaaagaaaat  37800
aaacctagtg gaacctgttt taacaggttt tatagattat tactatagct attgttttat  37860
aaaacatttt atccaagagt ttgctattcg tccggaaaaa ctgattaaaa tggccgcgcg  37920
aaaaggtaaa ctaaatatga ttatcgaatt ccttaacgaa aaatatgttc ataaagatga  37980
tcttggaact atatttaaat atctcaaaac cctagtatgt accatgaaac ataaaaaagg  38040
aaaagagaca ttaattgttc ttattcataa aatatatcaa gatattcatc tggagactaa  38100
agaaaaattt aaattattaa gattttatgt catgcatgat gcaactatcc aatttctatc  38160
tatgtgcaaa gactgtttta atttagccgg ttttaaacca tttgttttag aatgtttgga  38220
tattgctatt aaaaaaaatt accctgatat gatacaatat atagaaattc tatcgaaatc  38280
tgagtaaaat ttattttttt gatcagagta agaaaatgtt ctccctccag gagatctgtc  38340
gaaagaacat ctactttcta cctgactggc tcggtgagca tgtgattcag cgactaggtc  38400
tgtactggga aaaacatggt tctcttcagc gaatcggaga caactatgta cttatacaac  38460
aggacctcat catccccatc aatgaagccc taagaatggc aggggaggag gggaatgatg  38520
```

-continued

```
aggtggtaca actcctatta ctatgggagg gaaacattca ttatgccatc ataggagctt  38580
tggagagtga ccattatagc ctaatacgta agctctatga ccaaatcgaa gactgtcacg  38640
acatccttcc cttgattcaa gacccaaaac tctttgaaaa atgccatgaa ttagataaat  38700
cttgtaacat tttatgtctc gtattacacg ccgtaaaaaa cgatatgctt tgcattcttc  38760
aagagtataa aatgcatcta agtggagagg atattcaagt ggtgtttgaa acagcatgcc  38820
gttcacaaaa aaacgatatt gtgtcatgga tgggacaaaa tattgcaata tacaaccccg  38880
aagttatttt tgatattgcc tttgataaga tgaatgtgtc cttattatct atagggtata  38940
cgcttctttt caatcatcat ataaataata cgaacgaaaa tattaattct ttattgacac  39000
aacatcttga atgggctgcc ggcatgggcc ttcttcattt tatgctggaa actttaaagt  39060
atggcgggga tgtaacgata atagtcttgt ctgaggccgt aaaatatgac cacagaaaga  39120
ttttagatta ttttctccgt cgaaaaaact tgtaccaaga agatcttgaa gaactattat  39180
tgttggcgat acgtgcagat tgttctaaaa agaccttaaa cttgttatta tcttacttaa  39240
actattccat aaacaatatc cgtaaaaaaa tattacaatg tgtaaaagaa tatgaaacga  39300
ccgttattat aaaaatttta cggaaaagaa agataaatct gatagagccc attttggcag  39360
actttatagg atatcatagc tatacctata tggtagattt tatgcgtgag ttttccatcc  39420
atccggaaaa aatgatcaaa atggctgcac gagaatcgag ggaggacttg atcataaaat  39480
tttccaaaaa agtttgcaaa gagcctaaag atagacttca ctatctcaaa agcttagtgt  39540
atactatgcg acataaagaa ggcaaacaac tgttaattta tacaatccat aacttataca  39600
aagcttgtca tctagagagt aaagaaatgt ttaatttggc acgattttat gcacggcata  39660
atgcagtgat ccagttcaaa tcgatttgcc acgatctctc caagctcaat attaatatca  39720
aaaacttgtt gttagaatgt ttaggtattg ctattaaaaa aaattacttt caacttatca  39780
aaacaataga aacggatatg cgttatgagt aacattttta gatgagggaa gattctacca  39840
aactaactaa gacctttcgc tagaatgtat cttattgtta atatagatga gatatgtcat  39900
tgtgaaaaaa tagattaggt aggttgtgaa aaacagatta aacttaaaat tatgtgtatt  39960
atgtaaaatt ttagaaataa aaatttattt tttttattg agggtacgga aaatgttctc  40020
cctacaggac ctctgtcgga agaacatttt cttccttcca aatgatttta gcaagcatac  40080
cctacaatgg ctgggattat attggaaaga gcatggatcc gtccatcgag cagaaaaaga  40140
cagcataatg atacagaatg aattggttct ttctatcaat gatgctttac agcttgcagg  40200
agaggagggg gacacagatg tagtacagct cttgttatta tgggagggaa atctgcatta  40260
tgccatcata ggagccttga agactgaaaa atataaccta atatgtgagt atcatagcca  40320
aattcaggac tggcatattc tcctacccat gattcaagat ccagaaacat tcgaaaaatg  40380
tcatgattta agccttggat gtgactttat ttgccttctc caacatgctg taaaatacaa  40440
catgctttct attcttgtca aatataagga ggatctacta aatgcaagga ttaggcatcg  40500
tatccaatcc ctgtttgttt tggcatgcga aaatcggaga attgaaatta ttgattggat  40560
aggccaaaat ctgccaattc ctgaacctga tgccattttt agcattgctg ttgctacaag  40620
agatttagaa ctgttttcct tagggtacaa gattattttt gattacatgc aaagacaggg  40680
aatcattcaa ttaaccaatg gagttcgcat ggttgtgcta aatcgtcaca ttagcatggc  40740
aatagataat ggtcttttac cttttgttct ggaaacttta aaacatggtg ggaatataca  40800
tagagcctta tcttatgcag taacacacaa tagaagaaaa attctggatt atcttattcg  40860
ccagaaaaat atagccccta atacaattga aagactttta tatctggccg tgaaaaatca  40920
```

-continued atcttccagg aaaactttga acttgttgct atcttacata aattacaagg tgaaaaatgt 40980
taaaaagctg gtagagcatg tagtaaatga gaaatccact cttgtgttaa aaattttatt 41040
agaaaaaaag gaaaatctag tggatgctgt tttaacaaga cttgtaaaac attctacata 41100
tttccaggtg agagaattta tccaggagtt ttccatcagc ccagaaaaat tcattaaaat 41160
agctgtgcgg gaaaagaaaa atgtgttaat cgaggctatt tctgaagata tttgggaaaa 41220
tcccacagaa agaattactt atctcaaaca gatagtgcac accataaaat atgaaagtgg 41280
aaggcgattt ttggtagaca tcattcacag catttaccaa agttactcac taaaacacga 41340
agatattctt aaactggcaa cattttatgt caaacacaat gcaatcaccc attttaaaga 41400
cctctgcaaa tatctttggc tgaacagagg aacagaaagt aagaaactgt ttttagagtg 41460
tttagaaatt gctgatgaga aggagtttcc tgatattaaa agtattgtga gtgaatatat 41520
taactacttg tttactgcag gagctattac caaggaagaa atcatgcaag cctatgatgc 41580
tttagagtag ccatgtatta acattctgaa agtagaataa aatatactat atactaaaaa 41640
ccaaattagc catttttaac tatcttcttc ttaaaaactc tggataaaaa tttatttttt 41700
tttaatttgg gtagggaaaa tgttctccct tcaggacctc tgtcggaaga acaccttctt 41760
ccttccaagt gattttagca agcataccct gcatttgctg gggttatact ggaaggggca 41820
tggatctatc caaaggataa agaatgatgg tgtgcttata gagcatgatc ttactctttc 41880
catcaatgaa gccttaattc ttgcaggaga agagggaaac aatgaagtag taaagctctt 41940
gttactatgg gaaggaaatc ttcattatgc catcatagga gctttgagga ctgagaacta 42000
taacctagta tgtgagtacc atagtcaaat tcaggactgg catgttctcc tccctttgat 42060
tcaagatcca gaaacattcg aaaaatgtca tgatttaagc cttgaatgtg atctttcatg 42120
ccttctccaa catgctgtaa aatataacat gctttcgatt cttgttaaat ataaagagga 42180
tctactaaat gtactattta ggcaacaaat tcaaggacta tttattttag catgtgaaaa 42240
tcggaagctt gagattctta cgtggatggg tcaaaatctg ccaattcctg atcctgagcc 42300
tatttttagc attgctgttg tcacaaaaga tttagaaatg ttttccttag ggtacaagat 42360
tgtttttgaa tacatggaaa accaaggact tcatttaacc caggtagttc gtatggttat 42420
gctaaatcat cactttggca tggtaataaa taaaggactt ttaccctttg tgctggaaat 42480
tttaaattat ggtgggaatg taaatagagc cttatcttat gctgtcacac aaaataaaag 42540
aaagatttta gaccatgttg ttcgccaaaa gaatataccc cataaaacca ttgaaagaat 42600
gttgcatctg gctgtaaaaa agcatgctcc caggaaaact ctgaacttgt tactatctta 42660
cataaattac aaggtgaaaa atgttaaaaa gttgttagaa catgtagtga aatacaactc 42720
tactcttgtg ataagactct tgttagaaaa aaagaaaaac ctgctggatg ctactttgac 42780
aagatatgtc aaagattcta catactttca ggtgaaagaa tttatgcaag acttctccat 42840
cagcccagaa aaattcatta aaatagctgt gcgggaaaag agaaatgtgt tgatcaaggg 42900
tatttctgaa gatatttggg aaaatcccgc ggaaagaatc aggaatctta agcagatagt 42960
gtgtaccata aaatatgaaa gtggaagaca attcctgata aatatcattc acaccattta 43020
ccagagttat tctttgaaac ctgaagaaat tcttaaattg gcaacatttt atgtcaaaca 43080
caatgcaacc acccatttta aagatctctg caaatatctt tggctgaaca gaagaacaga 43140
aagtaagaaa ctgtttttag agtgcttgga aattgctgat aagaaggagt ttcctgatat 43200
taaaagtatt gtgagtgaat acattaacta tttgtttact gcaggagcta ttaccaagga 43260

-continued agaaatcatg caagcctatg ctttggagta tgccatgtat taaatttctg aatcagtaag 43320
caatagatag attttagaat atgctgtatt aagttagttt ctgaataagt aattaataga 43380
tagattttag tttatgtaaa aatgttaaca tttgttcata agttttagat accattttag 43440
agttactttt ttagatatta ctattttagc cattattatc ttaaataatc actattttag 43500
ataggtcccc gtattaaaaa ccaaattaac cattatctat gtttttaata atacttttta 43560
aaaaccctcc ataaaaattt attttttttt cataaaagta gagaaaatgt tctccctaca 43620
ggatctctgt cggaagaacc tttttcttcc acttgagccc ttaggcaagc atgtggttca 43680
acggctggga ttatactggg aaggccatgg ttcagttaaa cgagtgggtg attgctttat 43740
atgtgtagac cagatttgga tgctatcaat ccataaggct atacaaattg cagcctcgga 43800
aggaaatgag aacattgtca agcttttctt actatggaag gggagtctac aatatgccat 43860
cataggagcc ttagagggca ggcaatatga tctgattcaa aaatattaca accaaattgg 43920
ggactgccat cagattctac cactgattca agatccagaa atttacgaaa gatgtcatga 43980
attaaatgtt acatgtacct ttcaatgctt atttcaacat gctataagag ataacatgct 44040
gcccattttc caaaaatatg gagaagatct gaatggaaac aggagaatgg ttcaacttct 44100
gtatgagatg gcatgccgat tacaaaatta tgatatcatc aaatggatag gatctaacct 44160
gcatgtttat aacttggaag ccatttttag cattgctttt gttagaaagg atttaacttt 44220
gtattcttta ggctacatgc ttcttctggg tagaatgagt actgaagata gaaactttat 44280
ctcaatcata acacgccatc ttgaatacgc atcaaaaaag ggactttttg actttgtact 44340
agaatctttg aaatatggag gtcaagtgga tacagtgttg tttcaggctg taaaatacaa 44400
ccataggaaa attttggccc attttattca tgaaattccc cgtgaaacgg ttgaaaagct 44460
gatactccat gctgtggagt cacgggcctc cagaaaaaca ttcaacctgc ttttatcttc 44520
cataaactac tgtgtgaacc cttttgtcaa aaaactactg cacgctgtgg tgaaacacaa 44580
gtacatgctt atcataaagc ttttgctcga gcggcccaaa aagaagataa acctggtaga 44640
tgctgctcta ttcaaacttg taaaatactc tacttataca gaaatagtaa aatacatggg 44700
tgagttttct gtggacccaa aaagggtggt caaaatggca gcacgactca tgagagtgga 44760
cctgattaaa aagatttcta atgatgcatg ggaagataaa ctagagagaa tcaagcacct 44820
taaacagatg gtaaatacca tgaaccacag aaatggaaaa aatctattga tgtacaatat 44880
tcacaatatt actggatata cctatctgaa caccaaagaa gcatttaact taacaagatt 44940
ttatgctgtc cacaatgcaa catgtttgtt taaagaaatg tgtaaaagct gttttgtaca 45000
tgataaaata cagctcagag aattgcttga agattgttta catattgcta ataggcatga 45060
ttatatccag attgcagaaa ccgcagatga atgtatcaaa tatatagatc ttattacatt 45120
taagtaaacc atgtatatat caagtaaatc cagattaaat caggctaatt gtaaatagtt 45180
gtagatacca tataatgaat gttttattag gatagtagtt cagttaagat agtagtttag 45240
ttaagatagt agtttagtta agatagtagt tatgttaaga tagtagttct gttaagataa 45300
tagtttagtt aaaactagtt catgttaagt taatagtttt gttaagacaa tagttcattt 45360
aagtcaatag ttcagttaag tcaatagttt tgttaagtca atagtttagt taagtcaata 45420
gtttagttaa gtcaatagtt tagttaagtc aatagttata ttaagacatt agttctgcta 45480
atacattagt tttgttaaga taataaaaat ttattttttt ttcatcaggg tagagaaaat 45540
gttctcccta caggagctct gccggaagaa catttacatt cttccttacc ccttggctaa 45600
gcatgtactt caacaactag ggctgtactg gaagggacat ggatctcttc aacgaatcgg 45660
agatgaccat gtactcttac agcaggacct gatcttttcc atcaacgagg ccttaagaat 45720
ggcaggagag gaaggaaaca atgaagtagt aaagctcttg ttactatggg agggaaacct 45780
tcattatgcc atcataggag ctttagaggg cgaccgatat gaccttatcc ataaatatta 45840
tgatcaaatt ggggactgcc acaagattct tcctttaatc caagacccgc aaatctttga 45900
aaaatgccat gaattgagta actcctgtaa tattcgatgc cttttagaac atgcagtaaa 45960
acacgacatg ctttctattc ttcaaaaaca caaggagcaa ataagattac acatggcatt 46020
aacccaaata ctatttgaat tggcgtgtca tgaacgtaaa aatgacatca ttagatggat 46080
cggttattcc ctgcacatac accatctaga gactattttt gatgttgcat tcgcccataa 46140
aaatttatcc ttatacgttt tagggtatga acttctcatg cacaaagtaa atacagaggc 46200
tgcatatata gaattaccca atttgctatc atatcacctt cgaactgcgg cggcaggagg 46260
tcttcttaac tttatgttag aaacaataaa gcatggtgga tatctggata aaacggtttt 46320
atccgcggct atcaggtaca agcataggaa aattgtggct cattttattc atcaggttcc 46380
ccgtaaaacc gttaaaaaac tgttactcta tgctgtgcag gctcgggccc ccaaaaaaac 46440
actgaaccta cttttatctt ccttaaacta ctccgtgcac accatcacca aacaactcgt 46500
acacaatgtc gtcatctaca gttccacgct tatcgtaaag cttttactca tgcggcgaaa 46560
aaacaagtta aacctagtag atgccgtttt agccagactt gtaaaatatt ccacctatac 46620
agacattgta caattcatgg gtgagttttc tgtgagccca gaaagggtga tcaaaatggc 46680
tgcacgggaa tccaggacct ttctgattga aatgatctcc aaagctgctt ggggaaatca 46740
cccacagacg ttgattcatc atctcaaaca actaaccaat accatgaagc ctcaatctgg 46800
aaaagaccac atcatatata ccatccacta tatttatcta aactctaata tgctggtagc 46860
ggaggaggaa aaaaatattt ttaaattagc aaaattttat gcgaatcata atgcggtaaa 46920
caggtttaaa caaatttgtg aagactatta tatattagat gcacgattta aaacacttat 46980
tttagaatgt tttgaaattg ccgtccagaa aaactatcct agaattgcaa atattgtgga 47040
tgactatatt cgattccttt tttacagggg aaatataacc gaggaagaaa ttcgtgaagc 47100
ctattcttta aaagatgctg aggtttatgt agatttaaaa tggttacaac aaggagaaat 47160
ggtttaaacc aaatccggtt taaactaaat ccaatttaaa ctacatttgg tttatcatta 47220
gtcattgaaa ccatcgaaaa aaaagctatt tgtttatccc cataaactca tctttttttt 47280
gtctcaaagt ttgacactaa aattcagtgt tttatagtgt ttataattaa gtgttttgca 47340
tgcattgcag aaattttcat cttttttaat tggttcaata ccacatgtca tacaatatgt 47400
tgtttgatta tcaagattaa ctttatgaaa ggaaagtaag tgagccgcaa atttaaaagt 47460
aaaatatctt tcatttaaaa tgatcttatg aatgtatttt cgataaggag gaatgaaagc 47520
atttgccaaa ataaatcgca taaaaggctt ggaaaaaccc atatcttcta atcttttgtg 47580
ggtataaacc ctattttggt gttttacaaa aacttcattg ttataatagt cgttatagct 47640
atcaatcatt tttttaagtc ctataatgcc caaggttgca cgcataaagc cacagtttct 47700
gctccaaaaa gcatgcacct gtaaagggtg cttttcatat aaccaattac aaaatttcat 47760
tccgcaacag tagcatgtta tttcagtggg ggatgtatag aataatccgg cattcgaaaa 47820
tttttcataa ttttttatgt catggattgc gaagctttga tttcgtgcat ctatggagct 47880
atagcctaca tatttaggtt ttacttcaaa taatcgcaaa gagatgtatg gatctatcgt 47940
atttatttta ggaaacattt cataatttta aattcttata tataatataa aaaaaattac 48000

-continued

```
aaacatttgt aatgatcatc ctcaattgaa ggctgagttg taggctttat ttttctaatt  48060
atacgaagaa ggtaggttct cataaagcct tcaagatgac tattgatgtt tccaatacat  48120
tttctcaatg agttcataaa cccagacatt ttgctaatgg cttggcaaag tgccaacaag  48180
ttgtccacaa agtactggta gattgccact agctatagct agctatagtg agccaacctc  48240
tctgtatgta ttttatatat ttcatttttt aatagattta atatttttat aaaaaaaatat  48300
ttagtttttt atacaagaat gtcgacaaaa aaaaagccca caattaccaa gcaagagctt  48360
tactccttag tagcggcaga tacccagtta aataaagcat tgattgaaag aatctttaca  48420
agtcagcaaa aaataataca aaatgcttta aagcacaatc aagaagttat tataccaccc  48480
ggaatcaagt tcaccgtcgt tacggtgaaa gctaaacctg ctcgccaggg ccataatccc  48540
gccacaggag agcctattca aattaaagct aaacctgaac ataaagccgt aaagatacga  48600
gcattgaaac ctgtccatga tatgttaaac taaactataa agtcatattc ttctttatcg  48660
ttattatctt caatatattt ttgccaatcg aaatcgaata aattcagatc ctggacattt  48720
aaatacttat catcgtacat tttaatataa tttaaacatg agttgttgtc aaaaactttt  48780
agcgtttttg ttaaaattat catatgaata atttccttat taagagttgc cggaataata  48840
caaaacctat ttttaggtac atcatccatg ataatagtaa aattagtaaa aattgtttct  48900
tgtttttctt ttgtttcaaa taaacgttgt aaggttaaag gtttctcgtt caatggtttc  48960
tttgaagata aaaagaatgt ataatctggt ttaaaggtat ttttggtttc aatcgtgatt  49020
ccatctgctt gagcatatac taaaccagac caaatataac ggtccactat tacaatataa  49080
tttagcttaa gtagcactgc aatttctgcg ataaattcac tacgatgttt tgtaaataat  49140
ttatgtaatt gttccgatga catttctatg gttttattta acacctgcaa tataagatca  49200
ccggtggtcg tgtctggatt aggaaaatgt atacatatag cattataatc catgcattcc  49260
aatgtttctt ttaatttcat tgcctgtgtg ctttttccca caccattgat tccctcgatg  49320
gcaatgagta ttccacgcat gattaataaa aggaaaaaaa gaattcagtt tttaacattt  49380
cttacaaatc ttttttata caacattgta caacactgca ttagcggtat atgatgttat  49440
agcttcatta aatatttgct tttatataat ctttaccaac ctatatttgg tagatcactg  49500
cagatggtca taaataggcc ataactaaga taaaaattat ttcagacgct actacggtag  49560
tattattaaa atcatgtgtg gcaatgtatg acgtcttaat agataaaaca tttaaggaaa  49620
acaaatttga ataaaaaaaa taattgttat gatggcgttg ttacacaaag aaaagcttat  49680
agagtgcatc tatcatgagc tagaaaatgg cgggacaata ttgcttctaa caaaaaaatat  49740
tgttgtgtca gaaatttcat acattggcaa tacttataaa tattttacct ttaatgacaa  49800
tcatgatctg ataagcaaag aagatcttaa aggagcaaca tccaaaaaca ttgctaaaat  49860
gatttataat tggattataa aaaatcctca aaataataag atttggagtg gtgagccgcg  49920
tactcaaatt tattttgaaa atgatttata tcatacaaat tacaatcata aatgtataaa  49980
agatttttgg aatgtttcaa cttcagtcgg tcctcatatc tttaatgatc gtagcatttg  50040
gtgtactaaa tgcacatcct tttacccatt taccaacatt atgtcgccca atatattcca  50100
ataaattaga tatctttgct attaaaatag ttaaaaacct tataggataa ttaggtactt  50160
tattacgata aattatgata ttttataatt agttacttta ttataattaa tctctttatt  50220
aatgaattat cataagataa ctaattattt ttttccatat atcagataat aaatctgata  50280
tgggctaaaa gtatgtttca aactatttac aatagaattt ctgttaagaa aacatacata  50340
atttgaataa aattttttta aatatcaccg aaacaatcaa catggtgtta atagagtttt  50400
```

taacaggttt cttctattta tatggaaaga gactgttttc cattagtaaa gtcatggaca 50460
tgatatgtct agactattat accattattc ctgctcctct ggcgatgatg ttagcggcaa 50520
gactaaaaaa ctatgacctc atgaaacgac tgcacgaatg ggaaatctct attgactacg 50580
ctctacttgt agtagatgat gtgccgtcta ttgactattg cttaagtctt ggcgctagat 50640
ccccgactag agcacaaaaa agagaactgc tgagggacaa cacgtttaat cccgtgtata 50700
agtatcttat gaactgttcc ggcttcccaa caaagagaga aaaaaacatt ccttgtgatg 50760
ttcaatgcga aagactgcaa aaaaacatta taaaagaact ggtatttaac tgctctgtac 50820
tgcttgaaat ggtactgcac acagaaagag aatatgcata cgccctacac tgtgctgcaa 50880
aacataacca attgcccatc ctcatgtatt gttggcaaca atccacagac gcggaatcta 50940
ttttgttgaa aacctgctgt tctgataaga acatcaattg ttttaactat tgtattctat 51000
atggcggcgc ccaaaatttg gatgctgcaa tggtggaagc ggcaaagcac gatgcccgga 51060
tgctgataaa ctactgtgtc atgcttggtg gaagatcctt aaacgaagca aaagaaacgg 51120
ctgccatgtt tggacacatt gaatgcgcac aacactgttt taaactgcag tcttacgtcg 51180
tggacacatc gaatacagac gacactgatt aaagcgacaa tcttacgtca tgaacgactg 51240
tcttttgagt atctatactt acattatatt tttttatgaa aaaaatataa aggttgtata 51300
caaacctttg tatacaagaa atttggatca ttaaacaata attaatttgg acacaggaaa 51360
cgatctagat cgatcaaaaa gctatttttt ttgcacacag aacatttaga taattgagag 51420
attactttcc atacttgtta agcttttta cacacaggaa ctttggattc tgttcaggaa 51480
gtttttcata gacattatgt ttacagccag taataataat tttgggcttt ttcttaaacc 51540
accggtggaa aacatccagc ttgtaaagag ggaaatgcat gtagagaggt tttggtagtc 51600
atggttaaga gatttgacta actccatgtt tcctgtaaag actgcccagt cccaagcagt 51660
aaaacctcta tgatagtctt tttgagtcgg atctgctcca aattttatga gagaaagcat 51720
atttaaagaa cggccccgta ttgcggcctt catcacagga gtcatcccat taaaattcgg 51780
taaacaaatt ctggtcccat tttttccgaa atagcccaac accccttcca ggattaaatg 51840
attttttttc tcagctaaat aatgtaaagc agagtttcca tctttatccc tcctatgagg 51900
gttaattatt tctccaggat aagattcttg ttcaaaaaga aattttaaaa agtctatacg 51960
tccgtagatg catatccaca tgaataccga ggatccattt ttatcgcatc tattgacaat 52020
ccacggatct gttttaaaaa attcctcaaa tagtgtaaga ttcccatttc taatatgttt 52080
tttaatccat ttaacaaaca agttttctat ctccctttct ggaaacatgt gttccatttt 52140
gaatgtcgcc cctactccac tatatgattt tactccttta atttttaatg tcctttttt 52200
tcggacttct ttggataagc tgtttattac catctttaaa tgccttatag cggggaggag 52260
ccaggccctt ttcccatatg tgcggtaatt cttggtgttt atgcttgcct ttggcataac 52320
caggccagta tttttcgata tattcagggt ttgtttttac gtattcttta aaggtccgat 52380
aggcttcttg aatacaggta ggctcaccgg tataatttcc atgttcatct tcctttaaaa 52440
agccattaac cctgtccttt ctccacttaa gattgtgctt tccaaaaatg cgatcaagat 52500
cttgcgcctg ctggggtgga atcataaatc cctttttagg tcgaagcttt ttattttttc 52560
catagcttcg gccatcgcgt tgcgaaacag tggttaggac gcctgatagt ctttccatgg 52620
gcgtcgcatc taatcctatc catccaccct gatgaatatc aatggcaaca agctctcctt 52680
tattttgggc aagccaagtt tccaagaatg ccatgctttc ttcccaggga taaggcccgc 52740
caacaccacg ggttgtccaa tcttgcaagg actccaggtc cgacacctgg taaggctcta 52800
aagaagacgg ttccttgttt ttgtactgca aataagattt aatgacccat ttataccatg 52860
tgtcgaaccg cagcgtggcg cctccaaagt gaaagccgtc gttgatttta ggatatctgc 52920
aacatatttc aaccgtacgt ttgagttctg caaaagcggc cttccaagga agtctttcgc 52980
tgcgggtaag acggtctatt ttgccctgcg tgccatagcg tatggcatgt cgtgccaatt 53040
gcaacaattc tgacaccgat ccgtgggccc cgatccagtt tatcggatag gcaacctccg 53100
aagggtttaa aagatgctcg taaaagcgtg gatcttcaga tgccaaggcg tctgcaaagg 53160
ggataatgct agaaaacctg tctagacata cgttttctgt gtttacttct aaaggtagaa 53220
aaatggttgc gtgaggcttt tgaacctgct tgttcagcgg tctgcatatg ctttgaataa 53280
tgtctctagg actatgtcgc ggcgctgcaa aaaataccgc gtttagttct ggaacctcta 53340
cgccctcttg aaagagtcga cagtttaata aaataacggg ttcctttgag gaacaaaatt 53400
ctgtaaatgt tttgaggata acctgtcgcg gcagggttga gtgagctatc agggcataga 53460
ccccttggtc taccaacgcc gcgtatagct ccttggcctg tttaatatca cgggtaaata 53520
ccagcatttt aggagccggt atattggttt ttaaataggc taaggccatt ataatttgct 53580
ttactatgat ctgtttcgtg gtctcctctt tggtactcgg ttggtgggcc aatttaggcg 53640
cggctaccat ctgcaattca aaatcattta catagccggc ctctatgcct tctcgcagat 53700
agtagcgaaa ggcaacgccg ccaaaaagtt cacgattttt catggaaagc ggggtgtcgt 53760
acctgggcgt tgccgttaaa aaaagtcggt gcccttttt aaagttgagc aacacgtggg 53820
taaagggccg tgtctcccat tcgccgcaaa tccggtgaca ttcatcgcta ataataagat 53880
cgaaatcatc caccagtagc gtggaggatt ggtaggtggc aatcacaaga agagaagggg 53940
cctcccgtat ccgttttgca ataaagacag gattggtggt catttctata ttgtcgtgat 54000
ttagcacaat gcgggtctgg tcagacccca caagcaaaac gttcttcaaa gaaattccat 54060
actgatagag tttttccaga gtctgccgta gtagggacag gcccggcacc aggtacaaaa 54120
cttttccttg aagataattg gagaggataa gataggcgac gcgagttttg ccgcatcggc 54180
aggccatctg cagaatggcc ctcccacttc gccgcagctc ctgatagccc atattggccg 54240
cctccttctg ataaagtcga tcctcgattg cagtccgtgt ctcatctgta gaaaaaaata 54300
atacgtcatc tgcgaaatgt tcatcttcca caggagttat caccaggtgt ctcagtttct 54360
ccttgcttat cagcggatca gagggcaaag atggctcaac cactatcgtg gaatcattca 54420
tctcataggc gggagaatca cacaaagtat agcttatgtc cagacagttt gcaacatcct 54480
cagccaattg ttttattttt tcgggtaaaa gacatacgag ttctttgttt ttgacgcgaa 54540
aaaactgtgc acaatataac accccctgctt caatttttg cgcatccttc tttgtagatg 54600
tttccaatgt gaaacaatac ttccattcat ccgtaaaaca ggttgtataa gatccatcat 54660
gaagcctagc ggccaagttt cctgtgtgcc caactttatg taaggattgg gcctccagcc 54720
agggatgaac cgccacgtaa aatcctgcgc acatgctata tcaaattgca gtttcttaat 54780
aactgtacac aggatctgaa aaacatgtga ttacaaaatt tagataagaa atatttaata 54840
ttaaaaatca cagaatacat gtcactgtgt agagagaaag ccaaaaactc ctcttgaccg 54900
ccgtgggaaa tcatccaggg tagtaggttg tgtttcataa agttgtatgc cgtagtgatc 54960
accgtggact ccagatggtt attggcatct ttgcaatact ttgccatctt ggcagaaaag 55020
acgataaatc cacaaattct accccagttg ataagatcct taaacagctc agtcacaacc 55080
ccagtaaact gggttttaat ttcttgaaca ctcgtaagag aaaaggtaat tgtaacctgt 55140

-continued

```
ttgttcaaac actcatcata ataggttaaa attttttta tttgttgttg atatgggcta 55200
agctcatgct ctgaaatatc attaatgtaa tatttaatat atcccactag tatttcatta 55260
atgatattat gatatattaa ctcttctccc tccatagcgg caccctatat tttttattt 55320
aggtttcaat gttatcacaa ttgcgataca attgtgatac aattgtgaca caactgtgtt 55380
gtatacaaca aatgttaggc cacgtatagc aacctatatg ttaagaaata tttttatccc 55440
aacattagtt ggaaacgagc agccgcaaag aagtcattta aaataagcca tttaaagatt 55500
tagaatttat atgtatacaa ctgtacagcc ggagaaaagt caaaaggggc aggcaattca 55560
tacaccaaaa agttttttt ttctgctagc aagagcgtgt caataatttt aagctgatcg 55620
ttaattaatt tttggtttaa ctctttgtta ttatcaagat ccttcgcata aaccgccata 55680
tttaataaaa acaataaatt atttttataa cattatatgg tgagcaaggg cgaggaggat 55740
aacatggcca tcatcaagga gttcatgcgc ttcaaggtgc acatggaggg ctccgtgaac 55800
ggccacgagt tcgagatcga gggcgagggc gagggccgcc cctacgaggg cacccagacc 55860
gccaagctga aggtgaccaa gggtggcccc ctgcccttcg cctgggacat cctgtcccct 55920
cagttcatgt acggctccaa ggcctacgtg aagcaccccg ccgacatccc cgactacttg 55980
aagctgtcct tccccgaggg cttcaagtgg gagcgcgtga tgaacttcga ggacggcggc 56040
gtggtgaccg tgacccagga ctcctccctc caggacggcg agttcatcta caaggtgaag 56100
ctgcgcggca ccaacttccc ctccgacggc cccgtaatgc agaagaagac catgggctgg 56160
gaggcctcct ccgagcggat gtaccccgag gacggcgccc tgaagggcga gatcaagcag 56220
aggctgaagc tgaaggacgg cggccactac gacgctgagg tcaagaccac ctacaaggcc 56280
aagaagcccg tgcagctgcc cggcgcctac aacgtcaaca tcaagttgga catcacctcc 56340
cacaacgagg actacaccat cgtggaacag tacgaacgcg ccgagggccg ccactccacc 56400
ggcggcatgg acgagctgta caagtagtaa atcaacaact ctcctggcgc accatcgtcg 56460
gctacagcct cgggaattgc taccgagctc gaatttcccc gatcgttcaa acatttggca 56520
ataaagtttc ttaagattga atcctgttgc cggtcttgcg atgattatca tataatttct 56580
gttgaattac gttaagcatg taataattaa catgtaatgc atgacgttat ttatgagatg 56640
ggtttttatg attagagtcc cgcaattata catttaatac gcgatagaaa acaaaatata 56700
gcgcgcaaac taggataaat tatcgcgcgc ggtgtcatct atgttactag atcggacatc 56760
gagtggtatt aaaaggccct acatttgttt ttacaaaaga gatcaagaat ctgggcattc 56820
ctagtaccat caatgttgac tttcaggcca acattgaaaa tatggatgat ctacagaagg 56880
gaaatctcat cggcaagatg aatatcaaag aaggctaaat aaaacaacta acatcaaaaa 56940
acattaaagg ctatgttgtg gacgatgcct ttgtctcaat agtttcgagg tcatccaata 57000
actcatgtaa cgtaaaaaag ttggtccatt tttttgaaaa cattaaaaga cgttcgtctt 57060
cataaataaa aaagtcattc gaaggaaaaa tgatatactc aataccatag tcttgtaata 57120
ttttttttag gtctctcagg gtccagggat ttaccaggct tctacgcgaa gtgagcatca 57180
taaaaatatc taatattttt tgcgccataa gccagcgcgg attctcattg gcccacaaat 57240
caacaataat tctcttatca accgtgagca ttcctacttg attcgaagaa atgattagat 57300
gcccagcagt ccaccccatg agtagataac gcagcgttgt agaaatgtca catatggaag 57360
gcattcctcc acaacatgaa cccaaattag gatgcgtgtg aaacacaaac atagcaggct 57420
tgttggccac cctgctataa atatcagcag gcatcatagc ctcgctgcca aaataaatgt 57480
```

tctctcctgc cctatagggg cttggaatga tttccactat ctcgggtaca ccgtttatca 57540
tattaatgcg gccgcaccat tcacggtcat cgtccaaaaa tttttgatg gcaccccgaa 57600 cattgtccca gttaagcaac agagtattca caatctcatt acgctccgcc cagtattcct 57660
taaaacttct tttagacttg ctgagctgtt cccaggattc gaactcagtc caatgttttt 57720
tttcttttgg ggaagacttc ccttttgaaa cattttttgc ggctccacca tctacactat 57780
gattttccaa aataatctcc ttcatcgttt gagttatatg ggcattgcta agcaccttag 57840
tggtaacctg tttacctatg tgatttagca gaaaaccaag tttgtccatt tgtgtctcaa 57900
ccatttattc ttaacaaaac aaaaaaaaat taaaaatcat cgtcgtttaa aaagagtttg 57960
aaggcaaacg catcatcctt aacacagttc tgatactgcg taggtcttaa ctcgaaaaag 58020
ttggtttttt ctacttcatt aagaaagaat ttagtcatct gaggaaaagg gtttcccacc 58080
ttataaatgc ttttgcactg catcatgaag cacaaattat ctgtaaagta gcgtatatat 58140
tgaaatagca tttcttttga aaaaccggga actcttcctc ttgccttgtc aaaggcatag 58200
ttaataaact catccaccaa ctccacagcc tccttcaaaa ttttgtgaat gatcttttcc 58260
tcgggaatgt tatacacgta atttgagata agaaaacacg caaaactaca gtgcatccct 58320
tcatcacgtg agataaactc attatagctt acaagccccg gcataatatt ctgttcctta 58380
agaaactgga tcgccacaaa gtggttttga aataaaatgc cttctacggc ggcgaagccc 58440
accagccgct cacctagagt gttcctgtcg gggtccatcc actgccgcac ccactgcgcc 58500 attttttta tgatagggtg tttttcaatg ccgctaaaga tgcgctgttg ttccttctca 58560
tccgggatca gcgtttttac ctgtattgag taggcttcgc tatgaacgca ctcttgggca 58620
gcctgcattg tataaaagta taacacttcc tttactttaa tttcgcgcat aaaattggtt 58680
aaaaggtttt cgataacaat ttcgtcggca acaacaaaga aggctaaaat ttgtttataa 58740
aattcgcgct gtggctttgg catggcttcc caatcatcaa tgtccttaca catgtccacc 58800
tcctgcgccg tccacgtcaa actttctaat tttttatacc agttccaaca ttcggggtgc 58860
tgaataggaa aaatagtgaa acgttgggaa ttttcaatta gtaattcctc catatttgaa 58920
ataaatatta acatcttcaa atttattggc tgccatggag acgtttttta ttgagacgtt 58980
ggcatctgat gtgtatggaa aggcgttaaa tgttgattta gatagactat cgcaggcgca 59040
ggttaaatat acccttcaag agcttatttc ctactgcagc gctctaacca ttttacatta 59100
tgactattca acccttgcgg cgcgtctttc ggtgtaccag ctgcaccagt caacggcctc 59160
ctccttctca aaggcggtga ggctgcaggc cgcacaatcc tgctcacgcc tgtcccccca 59220
gtttgtggac gtcgtttaca agtacaaagc catttttgac agctacattg actatagcag 59280
agattacaag ctgtccctcc tggggataga aaccatgaaa aattcttatt tgttaaaaaa 59340
taaagatggg gtcatcatgg aacgcccgca ggatgcttat atgcgggttg ccatcatgat 59400
ctatgggatg ggaagagtgg tcaatatgaa aatgattctg ctaacctatg acctgctttc 59460
ccagcacgtc atcacacacg cgtcgcccac catgttcaat gcaggcacca aaaagccaca 59520
actctccagc tgtttcctgc taaatgtaaa tgataattta gaaaatttat atgatatggt 59580
caaaacggcc ggcatcattt caggcggcgg cggtggaata gggctgtgct tgtcaggaat 59640
acgggcaaag aatagtttta tttctggtag tggtcttaaa agtaacggca tacagaatta 59700
tattgtgctg caaaatgctt cacaatgcta cgcgaaccag ggaggcctac gtcccggagc 59760
ctacgccgtc tacttagagc tgtggcacca agacatcttt acatttttac aaatgcctcg 59820
cctaaaagga caaatggctg aacaacggct taatgcccct aatctcaagt acggcctatg 59880

```
ggtccccgac ctattcatgg aaatacttga agaccaaata cacaacagag gcgacggcaa  59940
atggtacctc ttttcgccgg atcaggcccc caatctacat aaggtctttg atttggaacg  60000
gtcgcagcac gaaaacgcac accgcgaatt taaaaagctt tactatcagt atgttgctga  60060
aaaaaggtac accggcgtca caacggccaa agagattatc aaagagtggt tcaaaacagt  60120
tgttcaagta gggaatccct atatcgggtt taaagatgcc ataaatcgta aaagtaatct  60180
ttcacatgta ggcactatca cgaactccaa tctttgtatt gaagtcacaa tcccctgctg  60240
ggagggtgat aaggctgaac aaggtgtttg taatctggcc gcagtaaatc tagccgcctt  60300
tatacgtgaa aatggctacg actaccgtgg gctcatagaa gcatcaggca atgtcacaga  60360
aaatttagat aatattatag ataatggcta ctaccccaca gaagccacgc ggagaagcaa  60420
tatgcgtcac cgacctattg gcatcggggt ctttggccta gccgacgtgt ttgcgtcttt  60480
aaaaatgaaa tttggttcac ccgaggccat tgccatggat gaggccatcc atgcggccct  60540
atactacggg gccatgcgac gatccataga acttgcaaaa gaaaaaggaa gtcatcccag  60600
ctttccgggg tctgcggcct caaagggtct actgcagccc gacctatggg ttcgctgtgg  60660
tgatttagtt tcctcctggg aagaacgcgt ggcacagacg acgcagggtg tgttgacgcc  60720
gaaaaggtgg tcgcagctac gcctggcggc tatgcaggga cttcgaaatg gatatgtcac  60780
agctcttatg cccaccgcaa cctcctcaaa ttctacagga aaaaacgaat gttttgagcc  60840
ctttacatcc aatctatata cacgtagaac gttaagcggg gagtttattg ttttaaataa  60900
gtatttaata gacgatttaa aagaaattaa tctttggaca gaagccattc aacagcagct  60960
actaaatgcg ggaggtagca ttcagcacat tttggatata ccggccgaga tccgcgatcg  61020
gtataaaacc tccagggaaa tgaatcaaaa aattttaaca aaacacgcgg ccgcacgaaa  61080
ccccttgta tcccaaagta tgtccttgaa ctattacttt tatgaacctg aactaagcca  61140
ggtacttaca gtgctcgtcc taggctggaa aaaaggttta actaccggtt cctattactg  61200
tcattttagc cctggagcgg gtacccaaaa aaagattata agaaactctg agaaagcgtg  61260
taatgcggac tgcgaggcgt gtcttctgta ggtgtctcgc ggtaaaagag cagcggggac  61320
catatggtaa accccaacaa gaggataatg aataaaaaaa gtaaacaggc atccattagt  61380
tccatattaa attttttttt cttctatata atggaatatt ttgttgcggt agacaatgaa  61440
acctccttgg gggtttttac ttctatagag caatgtgaag aaacgatgaa acaatacccc  61500
ggcctccatt atgtcgtttt taagtatatg tgtccggcgg atgcagaaaa tacagatgtt  61560
gtatatttaa taccctcgtt aaccttgcat acccccatgt ttgtagacca ctgtccaaat  61620
cgtaccaaac aagcacgaca cgtattgaaa aaaataaact tagtgttcga ggaagagtct  61680
attgaaaatt ggaaggtttc agtaaatact gtgttccccc atgttcacaa cagattatct  61740
gcgccgaaac tttccatcga cgaggctaat gaagccgtag aaaagttttt gatacaagca  61800
ggacgactca tgtctctgta aatgtctctt cctttatggg tgacgtctct tcctttgccg  61860
aggaagtctc tgttatgggc aagaggtttg aaacaacgca aggactctgc ttaatctgct  61920
gtctcacaaa gggaatcaaa ctacctgctt tcgtattttt aatgtagtaa ttacccttgt  61980
tgtgatgaat tttaagacca tagcgtagtc ccagtacttt attaatgaat tttaaaattg  62040
tttgagggtc cgttttattg ggctttttaa gcttaaactc aaagctgatc gcgcttaaat  62100
catactgaac aaattcatca acgagtttcg tcattaattg ttcattggtc aatatattag  62160
ggtcctgaac gcatttaaag ccgcacttag ttaatagcat aatagcgtac atatgagatt  62220
```

gaaaactata attaaattgt agatcatgat gctctgcgtg ttgcatggcc cattgatgaa 62280
agtttaattc ctgagtttgt aacatagtga gcgactcgta tactgtcttt ccgcggctta 62340
tttggacacg gccagtatag ttctgttttg tcataaaact attgtattgt tcaacaaatt 62400
tgggagtaat tttatgaccg tgccatgcat aaaattcgag tagtttatac ttttcatacg 62460
caaataggtc ttgctggtct actgtgatgc cttcctttaa gttttgttta atttgtaaag 62520
ctttattggc atcaatggtt tcagccgagg caatgtttac atagtcctgg tgtttaattt 62580
ccattttaat gcttgtatat tgtttgactg tctccagctt ttcacccgtc agtataaaca 62640
ccttagcgcc ggtgtcggcg atctggttaa taaatcgggt tataaagtga ttttttgata 62700
gatgttgtat ccgcattgtt tcgagccata gatggtagta tggagtttta taatatatcg 62760
gcctacctgt ttccttacta tacgtgaagg aaagctggtg attgcttatg gtctgaaaaa 62820
gggtgtcacg tttttgtaac gtaaacattt caatgtcttc gatggtttct ggatagtaat 62880
tttgtttccc ctgtaagcag attttataac acttactttt taattcacgc acgcggccca 62940
acatttggca acatgtttct acgtcacacg acatattgtt aaaaaagccg tataaaacat 63000
caaatctctt atcttcgtat gaaacacccg ctgaaatcgt gggcgtatag ataaggatat 63060
caacgagccc ccaataatac gatacattat taaaatggga ttcccgttca tgagcagtgc 63120
ttttagaact ataaaaccca attttttttt ccggaaactt tttttggata aatgattgca 63180
acagccgggc ctccattaat gaatttgtag ggataacaat ttttttgtct tctagcaaat 63240
cctttaaaag gttatttaac caagtttctc gtgaagaggt aaaataatac gtgtcatgct 63300
gggccctttt atattgattc cagtgaaaga agatagggac atccccgcga aaacgctgta 63360
gaatattata cgttcgattt cctaggtttg cgtccaagca tataacataa tttgccgttt 63420
cgagcatcca catgaaaatg gcaaaagagg gagcaaagta tttgtgcagg ccgctattga 63480
attgattaaa aatcgattct acctcatcca aaataagtag gtctacaggc tcggctgtgg 63540
aggttagccg gaaaagtgat tctacctgaa tgatgactct ttcgtagctg tccaaatctc 63600
cagttacttc gctgtacaat gtgaaattcg gtagccggga ttgtatattt tttgagaaga 63660
tctgtcgaaa cgtcacaaac cgtatggttt gttgttttga aatagaatta ttgccgtagt 63720
atttttgcaa atagttgcgc agttggacgg ttttacctat tttcatttga gcctttacaa 63780
caagcgtagg gactcgttca tattctcgca tactactttc atcatagatg tgtttttgag 63840
tatcaggcag ttcttcaaag agaatggact catgaacctc tatgctcttt gtcatcactt 63900
ggtccacata tgtttccaca aaattatttg tgccggaaag gctgcccatg agaaggctat 63960
gtttattgtc atggcgacag tgttgataca ctttgtttcc cgtgactctt aaaattaggg 64020
tattgtcctt atcatgcata cgcttacata tttcgcagta acttggactt gtacgtttaa 64080
acaatactaa atttttatga acacggagga agcaatgatt tttacatagt gttcctgcaa 64140
attttaatac ctcttcaagt tcactttgtt ggatagtatc gcaggaactc ggtgttgttt 64200
cttttacatt tgtgaagata caaggtaaac acgtcgtttc aaagggggtt gctataaggg 64260
tatcactctt tttcgtggtt gtactggtct caaacacctc tgcaagctcc tcattaaaca 64320
ttttaacacg catgctacct tttttatgag accctatgat gcgaaaattt tgaatacttt 64380
tgttgacctg gggggtcaaca aaaggataaa cgtgtttggg aagattttct aacactttgg 64440
atgtaaagac tttggcctca ttattgttta atactgagta tgtataaagt atgatatgaa 64500
aggagtattt aagttctcgc tttttattta atccgataga atctgttagc aaaatttgtt 64560
cacgcgttag attgatgtta taaggtaaag aatatgtctc gtaaaataca tccatgatga 64620

```
cgttaattat catgtcaagg atgtcataga cattgtcttc gacattatca ttgtcatcaa  64680
cattgtcatc agagtatgac ttatttaccg gaaagtcgat gtcaaatttt aagcgctgag  64740
gcaaaaaccc aaataccact tcgtggaaac acttctgctc aaagggctga gccgcctccc  64800
actcccaaaa gtcatcacga cttgaaaaaa ctctaaaaag attattatat tcatctcgca  64860
ccacgaagtg attctttaag gtttcgagag aatatttatc ctctacggct tctccttggg  64920
agttacagcg aagaaacttg aatgtttctt gcattttgat atttaaaatt aaatcaatta  64980
tgatgcggcc gctaatgcgg cggttgacgc ggccgcgccg ctgacgcagc catcatacat  65040
aaagcggcat ggccgtttta taacgactag tcggccgtta tatgacgaac tatataaaaa  65100
tgaattcttt taattagagt taagtattgt tgattgtata atccatcatg gttgagccac  65160
gcgaacagtt ttttcaagat ctgctttcag cagtggatca acaaatggac actgtaaaaa  65220
atgacataaa agacattatg aaagaaaaaa cgtcttttat ggtatcattc gaaaacttta  65280
tagaacgtta cgataccatg gaaaaaaata ttcaagacct tcagaataag tacgaagaaa  65340
tggcggccaa ccttatgacc gtcatgacgg atacaaaaat tcagcttgga gccattatcg  65400
cccaacttga gattctaatg ataaatggca ctccacttcc ggcaaaaaag acaacaatta  65460
aggaggctat gcccttacct tcatcaaaca cgaataatga acaaacgagt cctcccgcct  65520
caggcaaaac aagtgaaaca cctaaaaaaa atcccacgaa tgcgatgttc ttcacgcgta  65580
gcgaatgggc atcctcgaat acttttcgag aaaagttttt aacaccagaa attcaagcca  65640
tattggatga gcagtttgca aacaagaccg ggatcgaaag attgcatgcc gagggtcttt  65700
acatgtggag aacccaattc tctgacgaac agaagaaaat ggtcaaagag atgatgaaga  65760
agtaatattt ttggtaaaaa tatttttatc aaaatttttt taccaaataa taaaaaatat  65820
tttttacttt tttttcttca taatatacat agaatgccta caaaagctgg cacaaaaagt  65880
accgcaaata aaaaaacaac gaagggctcc tccaaatctg gttcttccag aggccacacc  65940
ggcaaaaccc atgcttcttc gtccatgcat tccgggatgc tctataaaga tatggtaaat  66000
attgctagat ctagaggcat tccgatttac cagaatggat cgcgtcttac taaaagtgaa  66060
ttggagaaaa aaattaaacg gtcaaaatga atataatcag gaaacttaag cctggaacaa  66120
ttagccttgt gctgggaccc atgtttgccg gcaaaactac gtttcttatt cattgcattt  66180
acatgctcga acgtttggaa aaaaaagtag tcttcataaa atctaccaaa aacacccgag  66240
acaaaactat taaaacacac tccggtatac agctacgacc caaacaatgt aaaatcatag  66300
aaagcacaca gttatctgac gtgggttctc tcaccgatat ccatgcagtt gtcgtagatg  66360
aagcgcattt ttttgacgat ttaatcacat gccgcacttg ggcagaggaa gaaaaaatta  66420
ttattcttgc gggactcaat gcttccttcg agcagaaaat gtttccgccc atcgttcgta  66480
tttttcctta ctgcagctgg gttaagtata ttggccgcac ctgtatgaaa tgtaaccaac  66540
ataatgcatg ctttaatgtg cgtaagaacg cagacaagac gcttatcctt gcgggaggaa  66600
gtgaactgta cgtaacatgt tgtaacaact gtctaaaaaa tacatttatt aagcagttgc  66660
aacctattaa atattaaaaa tcttatacaa taatggatca ttatcttaaa aaattacaag  66720
atatttatac gaagctcgag ggtcatccct ttctttttag cccgtcgaaa accaatgaaa  66780
aagagtttat tactctgcta aaccaggcct tggcctcaac gcagctttac cgcagcatac  66840
aacagctgtt tttaacgatg tataagctag atcccattgg gtttattaac tatattaaaa  66900
cgagtaaaca agagtattta tgcctgttaa ttaatcctaa actcgttact aagtttttaa  66960
```

-continued aaataacgag ctttaaaatt tacattaatt tcaggctgaa aactttttat ataagtccta 67020
ataagtataa taatttttac accgctccct ctgaagaaaa gactaaccat cttctaaaag 67080
aagaaaaaac ttgggcaaag attgttgaag aaggaggaga agaatcctaa gtcgcttaca 67140
tttttttttg ctatttttat agaatgtaca cgcatgttga tgttgtcgga atagctgaag 67200
cctcagcggc cctctacgtg caaaaagata gggatcgcta cttagacgtg ctaacaacca 67260
ttgaaaactt tatttaccaa cacaaatgca tcataacagg ggaaagcgcc cacctactct 67320
ttttaaaaaa aaatatttat ctttacgaat tttactccaa caatgtggcg gagcacagca 67380
aggctttggc gaccctgctt tataaacttg atccggaata cctcactcgt tacacagtac 67440
tcattaccaa aattcccaac cattggtatg tgattaacgt agatcagcga gaatttgtgc 67500
gcctatatgc catcccggca gttaaacaac acttaccgat tcccatttta cccttctatt 67560
gcaccagcgc actcacccag caagaattgt tttgtttagg acctgaactg cagttaatac 67620
aaatatattc caagctctgt aaccccaact ttgtcgagga atggcctacg ttgctcgact 67680
acgaaaaaag catgcggatg ttatttttag aacagtttcc gcaaagattg gaaatgacgg 67740
gcgggaagaa ggaggagaag gaaaagcatg aaagtatcat taaaaaaata atactagaaa 67800
tggtctctac ccgtcagcga atcgttgttg gggttacat acaaaaaaac ctgtacaacc 67860
atgtactcaa gaatagaaat cgtttacagc ttattacgag cttaaatatt tatgaagaaa 67920
aagatatcat ccagcaattt tgtgattcaa atggactgaa gatcaaaata cgtatcaaca 67980
atccgctctt gcctacaaat ccggaattac ggcgtttgac tatttatttt aatcataata 68040
atgatgatga tcagtcatat ctaatagtag atatgtacaa cacgggaagc tatgagctag 68100
tgcctacaaa tcagataaac acgcttgatg gcagcttttt aataggaaca cccttcgtgc 68160
aagcgcgatt tttgttggta gagatctggg tgcttatgct tattgcgcag caaactaaaa 68220
aggacaccaa aaaaataata caattttttta taaatcaata tgaaatgctt atgaatagtc 68280
cttggcccag tatggaggcc ctttttccct caagcagtaa aagatattta ggcaactatg 68340
tagaccctaa cgcgctcata aagtgggcac aactcaaatt aaaaagaata ccgccttttt 68400
atcctggaaa gccggatgaa gaatcatgtt aagccgatta aaaaatcatg ttaagctggt 68460
tgaaaaatca tgttaagctg gttgaaaaac tcttggtgaa agcacggatg taatattaac 68520
attggccgct cgcatttcgt gttgaaatac gatggaagag cgacggctat ctaccatgcc 68580
gatatcggcc tggacatcac agttcatgca cttgtagatg ggatgactcg cgttatagat 68640
ggcaggctcg ccacagtttc tacagatgta ggagatgcag ccatccgagt cgtcgtgcga 68700
tttttctatg atggtttgca tggcgccctg cgccgtaagc acccaatgct ccatttctcc 68760
cagacgaaga cctccgtgcg atcgtttgcc gtccaacggc tggcctgtga gggcatccgt 68820
gggcccatag cttgcaacgg cgtatcggtc atccagcaca aatttttgca ggcgctggtg 68880
ataggtcggt cctatgaaga tggccgcatc aaagtactcg ccggtctggc cgttgaacat 68940
tttttggcat ccattgaagc gtagaccttc ttgcgccagt ctttctgaaa gaagctgcac 69000
attaataggc aggaatgcgg tgccgtctgt taccaccccc tgtagggcat ttgctagacc 69060
aaccgtggtt tctatcattt gaccgttggt cattcgggag ggatgtgagt gggggtttac 69120
aatgaggtcg ggctgcaatc cgtcctctgt gaagggcatg tctgaagtgg gcagggccag 69180
cgccgcaatg cccttgttcc cgctgcgaga actcattttg tcgcctatat tgagatttct 69240
ttcatagcgc aggcgcatga ggccaaagat ctcgtcatta ggcccatggg gacgcatcac 69300
agcatccacg acggccggct catcgaagcc gtacatgaca gaccggtcga tgtatttgtt 69360
gagttcgtct ttttcgcccc gtattttggc cacttttcct ataatgatgt cgcccttttt 69420
gaccaccgtt cctacgggca cgaatccatc tacaagcttt tcgtaattag caccaggctt 69480
aagatttttg gtgattaaag ggtcgggctt cccaaacgac tctatatcgc tttctaattc 69540
tactttttct tctcggtaga aggtgccggc aaagccgccc ctgtcaataa aggactgcga 69600
cacgatcaca gagtcctcct gattgtagcc gccgtagatc atataagcca caatggtatt 69660
aagcccgttg ggtatgacat agttatgtgc tatggtcttt acaagcggca tttcattgta 69720
aaactggaag aagcggttca tgtcgacacg atatggccag ctaaagcaat accagccccc 69780
cgtttgccgg ccttggtttg tttcataggt aacacgcgca ggttgggtac agtttgcgta 69840
gggggacact agggcggcaa ggcccaaaat agcttggggc acgtccacgt gtgtgaaacg 69900
acgcgttaca tcatgtttat gtttgcgtag ctcgatgatg gagaaggcaa caagacagtt 69960
ttccgcctcc tcgggggtaa tgaactcaca gatgccctgt gctacgagat cttcaagtgt 70020
aagcgttccg gctaaaatgt cttttgccat ttgaggcgta aatcgcgtat tttgaatgaa 70080
agggatttta tgtttttccc agtctttatc gccttttttt ctggcctctg cggccttgta 70140
gcaggcttga ttgtattttt caatattatt atctacaatg agtagggggc gggtcagcct 70200
accgacgtcc aaccaaaatt ctacttcgtc taccatgcta tcccagtaga tggtggtatg 70260
gggatgcaca accttgccct cacggcgaag cattctatac cgctgagcaa gctcaaaggc 70320
attggtgcag cagccgatcc attctccgtt gataaatacg cgcgctaggc cctttcgtac 70380
aatgtccttg ttggaaacat cggctaactg ttgaatggcc ggatctgata gaaggcgttg 70440
ttttaacgaa agtacttctc cggcggtgca gacattggca gtgatggcta actgtttaga 70500
catgcctact ttttcaccag tatcggctga ctgggctacg cagatgtatc caggatagga 70560
tgcgtgcacg cgacgcatca tgtcagccct ttctgtttgt ttggatgcgt tggtggtgtt 70620
atgagtattt accgtacgca atgctgaaat ggtatttaat aaatttttttc tttccaaact 70680
ttgagtagat actctgttta caatggggcg ctgtcgcacc atgatggttt tatttcctga 70740
aatgatagac tgttccatac tgcgattaag atcggaggcg gtattttttg ataaagcggc 70800
agaaaatgcc tcgataatgt ttcgctgagt aagctcctca aaggctgttt gtttaagaag 70860
ttctttgaac ccattgatga tgggtgctat cacggaagta ttaaaaatag ccttaaaggc 70920
cttggcgagt gagacccctg agccgtgcac ccgcttggtg cggtagctat cacggtccgt 70980
gggtggaaac acattcataa tgacaagaag tattttatga ataagcaggc ctaaaaagcg 71040
cagctttcgt acacgtgtat ctgcggtttg gcccatgtgt ggcagcaata ttttgtctaa 71100
aatagtaagt tgtctttcat ttaagtattg taccgcattt tcatcgcttt tgtaagcaga 71160
tgggtttgag acaaatttgg aaaccttctc ggataaaaac tggataattt tttctcggtt 71220
cagctcgtgt tggaccggtt gaaatatggg gtctaaaaca tgaatggatt tttccagaat 71280
ttctatcatg aaggtattca caagggagtt ggattctaga tcaaatacca cttgctcaat 71340
gatgctgtca tcgcctgtca ttccaaacat gcgaaagatg agataccaag gtatgcgaag 71400
ttttgagaac ttggtgctat tgatttcaat ggtaatggcg ccggtggtca tgtagcgtat 71460
aataatttga gagctatttt cgaaggcacc tcccggttgg gagataaact cgccgcgaat 71520
gatttcatta ttcccttgtt gcatggtatg gtaatggatg tgaagcgtgt taaagcggat 71580
gttttctaag aggtctacga cccattcccc gcctcgggct ataaagtagc cgccgggttc 71640
attagggtct tctcctattt cttttttgc ggtttttgat aggtgatgag tgtggcagcg 71700
gttgctgccc cgcatgatgg gaaatgtaga tacctgaaaa ggaggaatac ttgctcgttt 71760
tacctcctgc cgaccattgc tgtagtgcgc cgttaaaata acctcggcgg ctagattaac 71820
cgggcccgaa taggaaaggc cacacaggcg tgccttattg ggtagtaaat ttatcttgtt 71880
tccctgtgaa tagtttcgat gttgcgggcg ttcaatgttc acatctgtaa agttaaattg 71940
gatctgaact gattcccgaa gcttatctat ttcagtatgg tcgcgttggt ctttataagt 72000
aatatccacg ttaaacattt gttttacaat ttgcggaatt ccattgtcca taagatcgtc 72060
gaagcttttg atgttatacc ctatcaatcc tgtagagttt actgcagcgg agataaagct 72120
cagcatatca gcctctgtaa gctcctcatt atccacggtt tcaatggggc cgtaggttat 72180
ttgcggccgc aagggttcca tgattatgaa gtactacatt aatattcagt tattctttaa 72240
aataaatctt tatttataaa tcttatttat aatataagaa tgccttatgc aagagacatc 72300
acaaagttta ttacggcaac ggaaccagag gtgggtcttc ccctgttggc gctgcagcgc 72360
tccaaatcca tcataggggt tattcttctt gtaataagtt tgttatttat tttcattggc 72420
attattatat tatcagtgag tagtggtcat accacagcag cctctatatt tatcgtattg 72480
agtcttatcc taggtggcgg tggttttttt cttatttata aagataattc ttaacccaca 72540
taaaatttga aaaaatatag agtaagaaaa tgtccaatta ctattattac tatggcgggg 72600
ggagatatga ttggttaaaa acagtagaac ccactaattt tttaaaaatc gggttgcctt 72660
accaggcaca cccattacat cttcaacatc aggcaactac tccccccatct atcttagaaa 72720
aatttaaacg agcagacatt cttcttaatg aggtgaaggc cgaaatggac ccactcatgt 72780
tacaaccaga aaccgaaaaa aaactattcc agatattgag tagtattgat atgttcaaag 72840
gtctgcgaaa aaaagtagaa ttcacgtaca atgctcaaat tgttacgaat gcttggctta 72900
aaatgtatga gctgctaaat accatgaatt ttaataatac atctcaggca ttttgcaatt 72960
gtgagcttcc aggagggttt ataagtgcaa ttaaccattt taattataca atgatgcatt 73020
accctacttt taactgggta gcttcctccc tttaccccag ttcggaaaca gatgccctgg 73080
aagatcacta tggtctttat cagtgcaatc cggataactg gttgatgcaa tctcctttac 73140
tgaaaaaaaa tatagattat aataacgggg acgtaaccat cgctagcaat gtaaaaaacc 73200
tagcgcttag agccacacaa aggctgacgc ccatccatct atatacggct gatgggggta 73260
ttaatgtagg acatgactac aataaacagg aagaattaaa tcttaagctt cactttggtc 73320
aagcccttac gggtttgttg agtcttagca aaggcggaaa catgatactc aaacactata 73380
ccttaaatca tgcatttact ctttctttaa tatgtgtatt ttctcacttt tttgaggaac 73440
tatacattac caaacctacc tcctctcggc ccacaaactc tgaaacctat attgtgggta 73500
aaaacagatt acgcttattt acccccaagg aagaacaagt ccttctaaaa cggctagaat 73560
tttttaatga tacgcccctc gtagacctaa gtctttacca aaatttactt gaaagcgttt 73620
actttgccgt agaaacaata catctaaaac aacaaataga atttctaaac ttcggaatga 73680
aatgttatcg acatttttat aacaagatta aactacttaa cgattattta gctccgaaaa 73740
aaaagatttt tcaggatagg tggcgtgtgc ttaataagct ttatgttctt gaaaaaaagc 73800
ataaacttaa gctttgtgcc tcctagggat ctgttgctta atttaacaga tgcaatctta 73860
acagatgtaa actaaaaagt gtgttcatac aaggattgta tttatgaata tttattaaca 73920
tataaggttg tgatgtaaca ctgtataacc tatataacta cactatgaag cacggcgtat 73980
aataatttat attgaacacg atgttgactc atttatttgc aaacaaatat ttgtttgcaa 74040
gacgtttgca tgcatttact aatatgttgt tgactagttt atttgcaaac tagatgtttg 74100

-continued

```
attgcaaact agatgtttgc acgtatttat ttgaactaat atacactcct tgttttattt  74160
gttatataca cagcatacat aagtgtatat tgtttacact tatgtttata actcgacgta  74220
ataacatttt acacgctttt tttttgcaaa tcttaataat attgtatgat aaatcaaaca  74280
atgtcttata tatgtggttt attattttag gcgccgcaag atgtactcca ttctcattgc  74340
atgcttggtg ttattactct gtctagttat atatgtcggt catcgtgccg atcatgcacg  74400
aaaatattta gaaggaatgt ggcatggaga tccggttttt ctaaaacagt cggggctaca  74460
atccttttat ctctacatac aacctgacca tacatgtttt tttagcattg tgaataaaaa  74520
tggtgaaaag ctgatggaaa ccaaaatacc ttgtacgata acaaataaaa tatatatgtt  74580
ttttaaacct atttttgaat ttcatgttgt gatggaagac atacatagct acttccctaa  74640
gcagtttaac tttctgttag atagtacaga aggtaaactt attttagaaa acaatcacgt  74700
tatttatgct gtattgtata aggataattt cgccaccgca ctaggaaaaa cggttgaaaa  74760
atatataaca caaaattaat catgttttct aacaaaaagt acatcggtct tatcaataag  74820
aaggagggtt tgaaaaaaaa aatagatgat tatagtatat taataattgg aatattaatt  74880
ggaactaaca tcttaagcct tattataaat ataataggag agattaataa accaatatgt  74940
taccaaaatg atgataagat attttattgc cctaaagatt gggttggata taataatgtt  75000
tgttattatt ttggcaatga agaaaaaaat tataataatg caagtaatta ttgtaagcaa  75060
ttaaatagta cgcttactaa taataatact attttagtaa atcttactaa aacattaaat  75120
cttactaaaa catataatca cgaatctaat tattgggtta attattcttt aattaaaaat  75180
gagtcagtac tattacgtga tagtggatat tacaaaaaac aaaaacatgt aagtttatta  75240
tatatttgta gtaaataata tttttaatta cttaaaattt ttatatataa gtttttgata  75300
ctatattata aaacatatgt tcataaaatg ataatactta ttttttttaat attttctaac  75360
atagttttaa gtattgatta ttgggttagt tttaataaaa caataatttt agatagtaat  75420
attactaatg ataataatga tataaatgga gtatcatgga atttttttaa taattctttt  75480
aatacactag ctacatgtgg aaaagcaggt aacttttgtg aatgttctaa ttatagtaca  75540
tcaatatata atataacaaa taattgtagc ttaactattt ttcctcataa tgatgtattt  75600
gatacaacat atcaagtagt atggaatcaa ataattaatt atacaataaa attattaaca  75660
cctgctactc ccccaaatat cacatataat tgtactaatt ttttaataac atgtaaaaaa  75720
aataatggaa caaacactaa tatatattta aatataaatg atacttttgt taaatatact  75780
aatgaaagta tacttgaata taactggaat aatagtaaca ttaacaattt tacagctaca  75840
tgtataatta ataatacaat tagtacatct aatgaaacaa cacttataaa ttgtacttat  75900
ttaacattgt catctaacta tttttatact ttttttaaat tatattatat tccattaagc  75960
atcataattg ggataacaat aagtattctt cttatatcca tcataacttt tttatcttta  76020
cgaaaaagaa aaaaacatgt tgaagaaata gaaagtccac cacctgaatc taatgaagaa  76080
gaacaatgtc agcatgatga caccacttcc atacatgaac catctcccag agaaccatta  76140
cttcctaagc cttacagtcg ttatcagtat aatacaccta tttactacat gcgtccctca  76200
acacaaccac tcaacccatt tcccttacct aaaccgtgtc ctccacccaa accatgtccg  76260
ccacccaaac catgtcctcc acctaaacca tgtccttcag ctgaatccta ttctccaccc  76320
aaaccactac ctagtatccc gctactaccc aatatcccgc cattatctac ccaaaatatt  76380
tcgcttattc acgtagatag aattatttaa tatgtactat atattaatta tttaaccttt  76440
```

-continued

```
caagctggtc ttcatttaaa tttaaaatcc actaataaaa tgtattttct agtagcagat  76500
catcgagaac atcatgtgat tccttttctt aaaaccgatt tccatcacat gcatcaaaat  76560
cctatacaaa aaaatcaagc tctcctagaa atcaaacagc tttttactgg agattatctc  76620
atctgcaaaa gcccttctac cattctggcc tgtattgaac gaaaaaccta caaagacttt  76680
gcggcttctt tgaaagatgg acgttataaa aatcgccaaa aaatgctgtc gctgcgagaa  76740
caaaccaact gtcaacttta tttttttgta gaaggcccgg catttcctaa ccctcaaaaa  76800
aaaattaatc acgttgccta tgcaagcatt attactgcta tgacgcatct tatggttaga  76860
gatcatattt ttgtcattca aacgaaaaat gaggcccaca gttcccaaaa gcttgtgcag  76920
ctttttttatg ccttttctaa ggaaatggtg tgcgtcgttc ccacctccct cacccccacg  76980
gatgaagagc tatgcatcaa gctatggtct tctctttctg gtatttcagg cgtgataggt  77040
aaaatcttgg caaacacttg ttccgtagct catttggttc atggaaagct ttcatcgcag  77100
aatattgatc agttaaaaac tccctccaac cgaccattcc ccaaaaaagt aaaacgtatg  77160
cttataagca ttagcaaagg aaataaggag ttagaaataa aattgctctc ggggggttccc  77220
aatatcggga aaaaattagc tgccgaaatt ttaaaagatc atgcgcttct tttttttcta  77280
aatcagcccg tagaatgctt ggcaaatata caaatcgttc aaaaaacccg tacgattaag  77340
ttgggaatga agcgagccga agcgattcat tattttttaa actggtgtgg ctctgcccat  77400
gtaaccgatg atagccaaaa tatcacagag gcgtcgcggt ccacaatgca ggtcgcgacg  77460
cagtccgccg caatacagcc cgctgcaacg cagccattgc acgaagtatc agatgatgca  77520
tcatcagatg cttcatcacc cgtagggtat caaacattat ctaaagaaat gttattgaac  77580
acagcctgat gttaataatt cactacatct aaagaaatgt taacctcgat actaaaaagt  77640
cattgaacac aactactggg gcgctaagtt gtccaacaca tctaaagaaa tgtcaacatc  77700
ctcgatgcta aaagggtcat cgagccggtc aataatgtct tccccaaaaa gtccgggaga  77760
actgtaggcc gagatgtcgt ccatggagct atcttcccca gagcacacaa agtcctctcc  77820
aaaaatcata aagttaaatg caccgggctt acttaacagc ttttcgcttt gaataatagt  77880
gttgagttct gtcagcgcaa actctctcac aatattcaca acccaggagg gctctttaat  77940
ttcatacagc gttaagaaac ttatacataa aaattctata gagtaaagca aggcgctggc  78000
aggatctgtt acccgtaggt gtttaaatgt agtgtgatat tcattcacaa cgttaggcag  78060
caccttttcc aaatcctcct tttcctcgta cgacaggtgc tttacaagcc tttcaacatg  78120
tataggaggc ttgttaaatg tactaacgtg ccgcaaacag ttataattat ataagaaaat  78180
acgtacggca gagtcgaccg ccatgagcct tggatcatcc attgaggtag gtggtggcgg  78240
ggcaccctgg ccttccctga tgtctgcgta ggagcgcccc tccatggccc ctatggcctc  78300
tatcacagca ggactgatat ccaaaatctt ggccgtcttg attatttttc cgtaatcgaa  78360
agtccatggc tcctgtggag gcttgggttg tgtttcggtg gagggcgtgg tcatatcttt  78420
ctttatttga atagaacgga tcgacatctt ttccttatcg tactggtctt tataattatt  78480
ataatagtca tgaactaatt cgggttgaga aagatgatcg tatataatat aggtaaaaag  78540
tccgcacttg acacattttt tatcctggaa gtcgtgtaat cctcccttgg ggcagcgtga  78600
ctcgtagaag gcataaaagg tgttaaattc taagctcgcc tttagggctg tttggacctt  78660
ttttatgttt aattgcccca cctcatgttg tagcacgtgg catacagaac agcgtagatc  78720
ggcaagtgca taatggttgt caattttttt tatgacgtct ttgcgtgtta cttcaatctc  78780
ggcgggtttc tgcgaactgt ctacggcctt gtaaacgtaa atggtccact tatgaggaag  78840
```

```
ccccctttca tcgtataggg ttgaaatggg aagcctttta tactcaaaca gccgagtccg  78900
ttggtcggct cttcctgtgt taggatcaaa tatgttataa aatccttgct gagcaagcag  78960
ggccttttgc tcgccataag cattttcgta cgttttgaat tctgcaagtt cggagttaaa  79020
attaggtgca ttttgtaaat acttaagaaa taattcatag gctctaaggt aaatgagagt  79080
tgaggttttt tcctcatccc gtcctcccca ccacacccgc aggctttctt cttgaaaata  79140
gatgtcattc agacgcgtca actgcgtaaa atcaggccga tatttagagg tataaatttt  79200
atcataaaat tctttttgcg ataatagctc ggccggggta cgtcctatca cggttttaaa  79260
ctcatattca gcctccttgg gagtccgtgg tttgtgcata gggatgctgc cgtcaatacg  79320
ggccactgtg gcagcataat catacatggg gtccagcaga atctctgtca aaagtacctt  79380
ggtgtcgtcc tgcacgctaa gcccttgtag cccattttgg tggataattt ttttgaaagc  79440
ctcccgaaaa ttattagcaa tccactgatc cgtaatctca gatagctgat ttattatacc  79500
gctatattgc tgcatcattt tctccaaaag aaaggtcacg tatgcattca aagagctatc  79560
cgccttcatt ccatgaatgg taatcgtaag aaattcttta tttttttgcg agctataaat  79620
gagattcaaa atataggcat agatgtagat cacagcatac agctgcgtta aaggatcgta  79680
atcctcttcc tttttaatat tttcgatgct atacacgagc ggcaggcaga catttacggc  79740
tatattggca aactgtttca cgtctacaag ctttccaaag tggataaacg tgcaggcctt  79800
catggtttcc tgccaaataa aaacacggag cttactatta agatcgccga tgatgcccac  79860
atctgccgta cgatcctctt gaataaaatg ggccagctct tcgccacaaa ttttgcaaaa  79920
gtaggagtaa ataagcccct ggttgttttc tttctccttg tttattcctg aaaatttcat  79980
tagcttggtt cgcatggtgt cgtaggacgc ttctgccgct tgaagctgta taagcatgtc  80040
cacatgggga caaagcagct taaacccgca ggctttgcat agattccaat tggtggtatt  80100
gtttttttcc ttgtagagta cacgaatact ttctaatact tttaataact ccgcgtattg  80160
aagacccgaa cgcaactgtt ttaccagctt gagatgagca catgcatttt tttcttggag  80220
ttcccactgt tttttaatgt ttaggtattc tgttgtaata agttctgcct cctgtttccc  80280
acaggcttta atgacttctt gaaggatgct gttagggtca tccactttac cctccattgt  80340
aagaatttca cgtatagcat ccgactgcac cctacctatt ttttcttcca taattttaaa  80400
atactgtctc gcctgggtaa tgacctctgt gagcttcatg tccacctgct gcagaatcat  80460
ttgctccttt tcacgctgtt cagcatgttg taaaaacttt tgttctacag ggttccaaag  80520
cacctccaaa tagcctgctc tatataggtc ataaagcaag ggcatgtatc ccgatgtaaa  80580
aaccggggac accgagtaca tcgtagacaa ctcttttaaa aaaaatatca cgcgcttaat  80640
gttctcctcc ggttcaatct cctcggtttc aacgatatta gatatatgac tgccctgatc  80700
ctcacggtct agctttcggt gtaccatctc ctctgctagc cgattaatga gccagctatg  80760
cccgccgctc cgcaaaaact tataaagttc gatatactgg tgcgtaaact ggatgatgtt  80820
ttccttggtg gttacgacaa ccccttctcc gtttttttc caggtttctt gatccacgca  80880
tttcataaat actcgaataa aattggtcaa attggctcct gaggcgacgt agcccaaggt  80940
ttcaggcgag aaggagccta tctcagccat acgcataaaa cactgcgggg aaaaagtttt  81000
tagccgcaac ttaagtccat agatttcaat gggggcttct gcgggaacgg ccaggtgcgt  81060
cccattaatt aaaaaaattt ctttgcgtgt gctagggcga acacgtaatt cctttttttt  81120
ttcactcacg atggggacca catcggggtc taccagcagt tgacgtatgt aggcctctat  81180
```

-continued gggcatggat agatcgggca gctttgactg ctcggcgcga acatggttca caaaatcttt 81240
tagagtgaaa agaaagtcta ttaaacgtat gttttttata tcattagacc ctttaagggt 81300
agagtagatt tcatccacta gtgcctcgat ttcctcatta ttgagcgata agatatctgt 81360
gccacggtgg actatttgcg cgatcgtaat tacttcctcc attagataga aactgaatat 81420
tatatttaaa ataaatacaa aatgtcaaat gaaagttttc ccgaaacgtt ggaaaactta 81480
ctttcaatgt tacagaccaa acagcaaaac gcaattcagt cagaggtgat tgaatggctg 81540
cacagctttt gtgaaacctt tcacttaaaa atacactgcc ataaacagtt tattcctagc 81600
ggggaaaaaa aacgagctaa aatacccgct caagaaacac agggaaacac gcagccctcc 81660
caccatgtgt accgggttgt tctctccaga gcacagccag tcaaagcaca ggaatctctg 81720
ctaacaacca tgtgcaacgg actggtgcta gatgcaaaca catggacatg cctagccatt 81780
cctccgcctg cgccctttca acaggcgacc cgccaggtcc aacactttta ccgtaacaat 81840
ttctacgaag tggttcccat ccaggatggc acccttctca caatctacca ctgggatgac 81900
cctgaatatg gcccctcctg gtgcctagca agtacccacg gatatgatgt gagtaactac 81960
tgttggatag gcgacaaaac cttcgccgag cttgtatacg aattgctgca gcagcactct 82020
acctgcgacg tcaccctgga aaaaaataaa acgcggggaa cgcgtctttt ctttgataac 82080
ttaaatcccg attactgcta tacgattgga atccggcacc ataatttaca gccgctcatc 82140
tatgaccctc aaaatatttg ggcgattcaa tctacaaacc taaaaacgct taaaacggta 82200
tatccagaat actacggcta tataggcatt ccaggaattc agagtcaagt tcctgagctt 82260
ccccagtatg atttacctta tctaatacga tcttataaaa ctgctatgaa tcaagccaaa 82320
aatgctataa aaaatggcaa aaaagacaag ggatacttta attatggcta tttactcatt 82380
tcgcgagcgc ctgccattac taaaagtact tctaatgttt tgttaaaatc gcctctgctg 82440
gtatttttac aaaaaagtgt gtaccagaaa aaacacaata tctctaacag ccagcgacta 82500
gaatttatta tactgcaaaa ctacttgatg cagcattttc gagatcattt cattgctcta 82560
tttccgcagt acatatccta ttatacgaaa taccaaaaca tgttgaatat gattatccat 82620
agtattgcaa ctaaagataa agatcatccc tttgcaggag ccgtggtaaa aaaagtgttg 82680
gaagatattg aaaacgccga aaacattatt gatcatacaa ccattcaaaa ctatgcccat 82740
caaagcaagt acgccatgct ttacttgtca attatttccc atttttaatc taatacggcc 82800
aaagccgcgg gtttttttaat aaactaacat ttaaaaaaac tgttttatta aaaattataa 82860
tacttttatt atatatggaa catccatcta caaactatac tcccgaacag caacacgaaa 82920
aattaaaaca ttatgtttta atccctaaac acctttggtc ttatattaaa tacggaacgc 82980
atgtccggta ctacaccaca caaaatgttt tccgagtcgg tggctttgtg cttcaaaatc 83040
cctacgaagc cgttataaaa aatgaggtaa aaacagcaat aagactgcaa aatagtttta 83100
acacaaaagc gaaagggcat gtaacgtggg ccgtcccata tgataatatt agcaagctat 83160
atgccaaacc agatgcaatt atgcttacca tacaagaaaa tgttgaaaaa gctcttcatg 83220
ctttaaacca aaacgtactg acgctcgcat caaaaaatacg ttaaatataa tttttgtaga 83280
ggataaaaag ctattttagc taaaaaataa ttcatatacg tttatgcaga ggaagaacgg 83340
tggctttcaa attcagattg catccacgta gaccgtagcg ttttttttgc ttctggttta 83400
tatcgtaaac cgtaataaac atcatcattt gtatccgttg gatctttttc ccactccgga 83460
taaaaaatcg gttttctttt tttttggtcg ttttttgcag taagctgtaa attaagggaa 83520
tatagcttat cgaaaagttg ttcctgatcc atataaatag cagcatatat taaaaaaaaa 83580
taaaaaaaga cgcttcaacg agtcagtacc actgcttgcc aacgatttac gttggttggt 83640
gcattatggt gatatagtaa tgagtgcctg cacaagtgct tgcacaagtg cctgcacaag 83700
tgcttgcaca agtgcttgca caagtgctta cacaagtgct tgcacaagtg cctgtacaca 83760
ttactgcatc gccaaagcac ctgcaatgcc tacttcctca acagagtacg ataactaaat 83820
gcttttaagc accgcttgcg tcgatgtgtc cttcggggca atcgggttca attggatcca 83880
atattattag tcataattac ctaatactta ttcaatttta tctttttttac cttgtaagat 83940
ttaaacagcg ttttagcttg tttaaagcaa cgtttaaaac aagctaaaat gctgtttaaa 84000
acaacgtttt aaacaagtta aaacaaataa gcttataaat ataccatgac aaaattagcc 84060
caatggatgt ttgagcagta tgtcaaagat ttaaacctaa aaaatcgagg gtccccctcg 84120
ttccgcaaat ggctcacatt gcaaccctca ctgctgcgct attcgggtgt gatgcgtgct 84180
aacgcctttg acatcctaaa atatggctat cctatgcagc agtcaggtta tacggttgct 84240
acgcttgaaa tccactttaa aaatattagg tcttcctttg ccaacattta ctggaaccgt 84300
gatagcgagg agcctgagta cgtctgctgt tgtgccacct atcaatcgca cgatggcgaa 84360
taccggtatc gatttgtttg gtaccaaccc ttcatagagg cttataatgc catagaggcg 84420
gccctggatc ccctggaaac cattatcctg aacctcattg cggcacgaga tctagacttc 84480
gttgttcaca tatttcctta taataagggc catgaagact atttggcctc cacgcaactt 84540
attctcaaaa tctttattgc gacgctttta atggacattt taagaattaa agacaacacg 84600
ttggacgttc acttaaattc cgactatatt attgtgatgg agcggctttg gcctcacata 84660
aaggatgcca tagaacactt ttttgaagcc cataaggact tactagggta cttaattgcc 84720
tttcgcaatg gggggaactt tgcaggaagt cttagaccct cctgtgggca aaagattgtt 84780
cccctaacga ttcgagaggt cctacaaatg aatgatatta atttagccgt atggcgggag 84840
gtgtttatta tgcaggaatg ttccgactta gtcatcaatg ggatagcgcc ctgtttcccc 84900
atttttaaca cgtggacgta tttgcaaggt attaaccaga tttttttttga aaacacgtct 84960
ttgcaggaga aatttaaaaa agattttatt gcccgagagc tttccaaaga aattatcaag 85020
ggccaaaaaa cgttgaatga caaggagttt aaaaagttaa gcctacatca aatccagtac 85080
atggaatcct ttctacttat gtcggatgtt gccattatga ttaccacaga gtatgttggc 85140
tatacccttc aatccctgcc gggtattatt tcgcgatcca gctatttatc ccccatcgtg 85200
aaaaacattt tgatggacga agactctttt atgtccctac tatttgacct atgctatggc 85260
gcctacgtgt tgcataaaaa agaaaatgtg attcacgcgg atttgcacct gaataacatg 85320
acctactacc atttcaaccc aaccagtttt acagatcgca acaaaccagg aaaatacacc 85380
ttaaaggtca agaatcctgt gattgccttt ataaccgggc ccaaagtcga aaccgaaacg 85440
tacgtgttca agcacataga tgggttcggc tgcatcattg actttagcag agccattatg 85500
gggccaaacc atgcaatcaa gcttgagcgg cagtacggcc tcgcttttgt aaacaccttt 85560
taccgcaatc aaagtgagca tattttaaag gtattacggt actattttcc tgaaatgcta 85620
accaatcgcg aaaacgaaat acagggggtg attttatcaa actttaattt ctttttcaat 85680
agcattactg ccattgattt ttacgccatt gctagaaacc tacgtagtat gctttctttg 85740
gactatttac acacctctga ggtgaaacga aacgtagaaa tttcgcaaac atttttggat 85800
acatgtcaat tttggagga aaaggccgtg gaatttttgt ttaaaaatct tcatactgtc 85860
ttatctggca agccggtcga aaaaacggcc ggggatgtgc ttttacccat cgtatttaaa 85920
aaatttttat acccaaatat tcctaaaaat atattacggt cttttaccgt aatagatgta 85980
tacaattata ataatataaa gcgttattct gggaaagcta tacaaacgtt tccaccctgg 86040
gctcaaacca aagaaatctt gacgcacgcc gagggtcgta catttgaaga tatttttcct 86100
agaggagaat tagtttttaa aaaggcttac gcagaaaaca accatttgga caaaatttta 86160
cagcgtattc gtgagcagct tgctaatgaa aatttgtaag gcttgcagtt cttgtatggt 86220
cagaacctat gtcgatggaa acattatttt tcgctgcagc tgcggcgaaa gcgttcaagg 86280
ggatagtcag aacttgctcg tctctagcaa ggtgtaccac accggggaaa tggaagataa 86340
gtacaagatt tttattaaaa atgcaccctt tgaccccacg aattgccaaa taaaaaagga 86400
ttgcccaaat tgtcatttag actatttgac acaaatctgt attggaagcc aaaaaatcat 86460
tatattggtg tgccgctgtg gctatatgag caacagagga taaaccatat catcccaccg 86520
aattatgaca ttcctttaaa accgtccgcc taaatagttt tcacaccttt ggtggcagac 86580
tattttataa aaagtaatgt tggttcatga agataaagtg tgccaaagaa acttttataa 86640
acaaatgatt aatgtaggtg ctagtcgtgt gtacttaaac agggtattct atagccaagt 86700
attttctata gccaagtatt ttctatagcc agtattagtc aagtatttag atgtcagggt 86760
atttttatag ccagtatttt tctatatgta caaactattc cagtaaacat atgtgtgttc 86820
tttattgagc agcatcatgg cattaacaag tttattaaac tgctctaatg ggcattaaat 86880
gacaactcgg tgcttagcaa aagtgcctat accttttaac aattagggcc gggaggcatt 86940
cccagctttt ttctataatc agccatacag tacccctgag cctcatacac gggaataagg 87000
tccttccatt ccttgttggg atcggcgggc cagctctcaa atgaggtgtg aatgtaaggg 87060
tcctgttctt tttccttaat gaagcgttta atctccattt gatgttgttt actttttttgt 87120
ttgcggcgga gcgtgttccg caccaatacg taaaaaatac caagaatcac acataaaaga 87180
attattaaaa aaaatatcat catcgcgggg tttaaaaaac gatcccatgc aacaggaatc 87240
gttcttaaaa ccttgtctgg cagggctgta aacatgaagt ctcctcctat aatcggggtg 87300
ggactgtagc ctaacagttc aaggtcctgt cgttctagat acttattggc gaactgccca 87360
ccctttgccc ccgttttttt attaatcaag cagcgctgca ttttccacca ttctaaatct 87420
tcaggagaaa gctcaatgcc atatatcaac tttaacgtta ttgcatcttt ttcaatatcc 87480
ttatcaattt ggctgagctt ttgagcttta agcgggtcta gtgtgtactt ccatttaaac 87540
ttagtgtcct gtagtttggc tacatgaaat acggaacatt tcggcggggc ctttgtgacg 87600
cccttacact gcggaagttt atcattagga caggcgcata gatgagactg cgccacagca 87660
tcgcgaacta catcgcagac ggagtacatt ttcctcctat gttaaacaat aaattttttt 87720
catagctgaa atttgtgggc ctatcttttc ccttgcccgg ataataatta taagggagtg 87780
ttgaaacatc tgggagagaa ttgcttaaaa aatgggtttt tgggaggggt aactgcgact 87840
gttgtacgtc gttggccagg gagattctat atgccgggct aaaggtgcaa cgttcctgtg 87900
aacaacttag tacgcgcgtt gttaatacaa atggactggt attagcaaac ctcgtaaact 87960
cttccggact tgtttgtttt tgtatgatgt ttagcaggga gtctgccttt tcgagaatcc 88020
aaagcgtcgc attgtagtaa aataaaaata gcgacttatc ggcaggcgtt gcaaaagcgc 88080
cgtatagaaa ataaagcagt aagtactggg gagacaccac aataaggtta tcttgaatga 88140
tagatatcgc tagctcttta aacatagtgc taaaaaaatg tatgtcgttc gtcttgaata 88200
tagggggact atagtccatg tagggctcac atatctcagt caggtgaagg cccatttctt 88260
ttatgacttc ttccgggttg tacgtcgcta acaccagcgc gggataggct ttgggcatat 88320
ccacggtaag tgttatgttt ttatcattct tatggtagga gtaagatggt tgtggaaatt 88380
ctgttttcca ctccgggact ttgcaggtaa ttctcagctc atttagagtc tggtacagga 88440
gggcgtatgc cgcaaagccg tgtatggcca cttgtttaaa gggaattgaa aacgttttac 88500
tttcgtatgt cgacttcaca ggaacaacgg gaatggggta atatttttct atgaggttat 88560
accgctgcaa atccttttta aacctgctaa aaacatcttc ccttggtggg ttatcaaaag 88620
gaaagcaaaa tgctaggtgt agcccggccc gctggtaatc ggggtgaatg attttaaggt 88680
ttttatacgt taatgtgggt atggtgttaa agatattggg gggcatatat gaaagatcag 88740
caacccacac aaagtccgtg cgcacccgca tggtctgcac atggatggcg cgcaccgtgc 88800
ccacctgctt gaagcccttt tcatacaaaa tgtcagcaag ttcgtaggcg tcctcaacgt 88860
ggttggggga aaacatatca aagtcgggtc tttctccctc gggataaatt gagctgcctt 88920
taagatgcag ggcataatca atggcaatcc ccccgtacaa aataagcttt ttctttatga 88980
taaattcgcg gaccacctcc aaagccgcct caatctccac ggcatttgcc tcacgttttt 89040
gagcaatgag ccggtactta gaaacattaa aatcagtctt tagtaaagac gtcataaata 89100
gtgtttaata tatattaaag gtttgaataa aatactaaat agtaaaaatg gatgccctat 89160
taaaggaaat agaaaagtta tcgcagccat ccttgcagaa agaaaacaat gatgtatgcg 89220
atctctgttt tatgcaaatg aaaaaaattt ctaactatca gcttttatgc gaagagtgcg 89280
gtcagctgaa ggactggttt gaacctgaat ataatgaaaa attcacggta tattctcgtc 89340
taaagatcgt gggtgccaat agttcctatc accagcgcga tttggacaag gccaactcaa 89400
gtgactatag ctccttgcaa tttcatcaca ttttagagga gctcaaatcc ctaaatgtta 89460
agtatatgga tgcggggcaa aagccctttc ctattcaggt gttaaaagaa actgctcaca 89520
gttataacca agtacaacaa catcgggtca tacgcagcat tacaaagctt cagatcttag 89580
ccagtattct acgtagcatt tgtttaaaat taaacattgc ttgtacggtg gcagacgccg 89640
cgaggtttac tcaacttaat accaaaggga tctcaagggg catggatctt ctgcgctccc 89700
tatttgtaga caataaaatt actttaaacg ttgatttaaa ccctatagac agctttatta 89760
atagtaccta cagtgcctta caaattaaac aaatccacca agaactgcag gaggaaaatg 89820
tttataattt aaaagaaatt gttaagagct ttatattata cgcggatgag aagaacatcg 89880
gcgtcgatct taacaggaga accgttgtga ttgctacgat gtataatgtt ttacgccgtg 89940
cctactaccc catagaaatt gatacggtgg tgtatcaatg taaaatacga aaaaatacaa 90000
ttacacgtgc tcttaaaatg tatgaggatt actactccca ctttaagtct ctttatgagc 90060
agtatcattt aaacgcggca aaaaaattaa tttaaactaa acgtttaaac taaatgttta 90120
aactaaacgt taaaactaaa catttcgact aaagtttaaa acctagtcta acagcgggat 90180
gcccatttcc ctggggttcc atatttcaac aattttttga ccttcgggtg ttaccttgat 90240
gcagcgcatg acgagcagtg gaattttcct attaaagagt tcttgcttag ctatatcaat 90300
aggactgcta tatttttttt taagcattgt agatccatta attgccaatt gttgcgctct 90360
aacggcgacc aaccttgtgg cctcaaaggt ggttaaaacg ttggaggtaa tgcgctcgtt 90420
atcgggtata atgaccaatg tttgcgacga ggcctgcaca aagccctcgc agatggacgg 90480
agactccacg atctcgtcct tgtcctcgga ctcctcctca ctgtcgacga ggttctcctc 90540
ttccgtttcc acatattcct ccacgaggtc atccatgata agatcctcgt tgtcattatc 90600
agccatatta cactgttatc aaatgtactg tttaatacgc aaatggattt actacgtttt 90660

```
aattgtatgt cttcatgtgc aggctctagt ggaaagtaat tttctcacaa tttttggcac  90720
cgttacactt gtgcccacaa aaacccgcga ttttttttatt ttatattact tttggaagta  90780
cgagtttaac cagtcgcttt caaaccttat gcgtctatct cgccaaaaaa cgctcacagc  90840
ggtgttggat attaccttta aaaaaataac attaattttt accacagagg gcgtattgcg  90900
tatggattct acgaataagc caggcgtgcc actcgatata gacccccagt tcattgacct  90960
tgatagtatt ttaatggaac tggatcatta ggacctctcc cgcccattta aatttttagt  91020
ttctacaata ataaaatgcg cgaggaatca tgggaagacc acgataccat tcagctcacc  91080
gctcagcgca aatacctcgc cgaggtgcaa gctctagaga ccctttttgac tcgagagctt  91140
tcagtctttc tcacagagcc aggcagcaaa aaaacaaata ttattaatag aatcacagga  91200
aaaacctacg cacttcccag cacagagcta ctaagactct acgagcatct cgagcaatgt  91260
cgcaagcaag gcgccctcat gtattttttg gaaagacagg ggacctactc gggtctcatg  91320
ttggactatg accttaaact caatacaaat gctgttcccc cgctggaacc ccccgcgcta  91380
tcacggcttt gccatcgaat atttgtgcat ataaaaaaca gcagtgtgct gcctgagggc  91440
agccataaaa tccacttctt ttttacatta aaacctgaag tggttcaggg caaatatggg  91500
ttccatgtgc tcattcctgg tctcaagctg gcggcttcta ccaaaaaaag cattatagga  91560
tccctacagc acgatgccac cgtacaaaaa attctacacg agcagggcgt tacaaatcct  91620
gagtcctgtc tggaccccca ctccgcctcc gttccctcgc tcctctacgg ctcctccaaa  91680
ctaaaccaca agccctacca actgaaaacc ggctttgagt tagtctttga tagctctgat  91740
cccgactaca ttcccattca tcaaataaaa aatttagaat cttataattt agtttctgag  91800
ttgagcctta cgaatgaaca gggaagcctt gtaagacctg tctattgcgc ggcagacatt  91860
gccgctgaga aggaggaaga gatcccgacc gaggatcact cgctctccat attaatgcta  91920
catgatcccg aagcccggta tttacataaa attttaaatc tgcttcctcc ggagtattat  91980
gtagagtacc ccctatggag caacgtcgta ttcgctttgg ccaatacatc cgctaactat  92040
cggcccctcg ccgaatggtt ttcgcaaaaa tgccctgaaa aatggaatac gggaggaaaa  92100
gagaaactag aaaaactttg gaatgatgcc tcgcaccaca ctgaaaagaa aatcaccaag  92160
cggtccatta tgtactgggc ccacaaacat gccccccagc aatacaaaga aattgtagaa  92220
caaggctact tttccattct cgctgaatat gtgtatagct ataacggcat gcttgagcac  92280
tacatgatcg ccaaagtcat ctatgctatg atgggcaaca agtttgtagt ggacgtggat  92340
tcaaacggga agtacgtttg gttcgaattt gtgctaccgg gccagccaat gaatcaggga  92400
gaaatatgga agtggcgcaa ggaggtaaac ccggatgagc tgcacatcta tatttccgaa  92460
aacttttcaa gggtgatgga ccgaatcacg gagcacatca aataccacct cagtcaaccc  92520
catgaaagca atattttaaa ttattataaa aaactattaa aagcctttga acgctctaaa  92580
agtaaaatct ttaatgacag ctttaaaaag ggagttatca ggcaagctga gtttttattt  92640
cgccaaagaa gctttattca aactctggat accaatcccc acctactggg ggttggcaac  92700
ggggttctct ccattgagac catcccggct aagctcatta atcattttca cgagcatccc  92760
attcatcagt acacacacat atgttatgtg ccctttaatc ccgaaaaccc ctggacaaaa  92820
ctattattga atgcactcca agacatcatc ccagaacttg atgctaggct gtggatcatg  92880
ttctacctaa gcacggccat atttcgcggc ctgaaggagg ctctgatgct tttgtggctt  92940
ggaggcggct gcaatggaaa aacttttcta atgcgacttg tggccatggt attgggcgat  93000
cactatgcct ccaagctcaa catcagcctt cttacaagct gcagagaaac cgcggaaaaa  93060
```

cccaacagtg cctttatgcg gcttaagggg cggggatatg ggtactttga ggaaaccaac 93120
aaaagcgagg ttctaaatac gtcgcggctg aaggaaatgg taaatccggg cgatgtcacc 93180
gctcgagagc ttaatcaaaa acaggaaagc tttcagatga cggccaccat ggtcgccgcg 93240
tccaactata acttcatcat tgacacgacg gaccacggca catggagaag actgcggcat 93300
tatcggtcaa aggtgaaatt ctgccataac cccgacccca gtaacccccta cgagaaaaag 93360
gaagatcctc gctttattca cgagtacatc atggatccag actgccaaaa cgcattcttc 93420
agcatactcg tctatttttg ggagaagcta cagaaggaat acaacgggca gattaaaaaa 93480
gtgttttgtc ccaccattga gagcgaaacg gaggcgtaca gaaagtcaca agatacgcta 93540
cataggttta tcacagaaag agtcgtggag tcgccctccg cagaaactgt gtacaaccta 93600
tccgaggtcg tgacggccta cgcggaatgg tacaacacca acattaacgt aaagcgccat 93660
attgccctcg agctatccca ggagttagaa aactctgtgc tagaaaaata ccttcagtgg 93720
tctcccaaca aaacgcgaat tctaaagggt tgccgtattt tgcataaatt tgaaacgctg 93780
cagcccggcg aatcctacat tggggtgtcc acggccggca cactcctaaa cacacccata 93840
tgcgagccaa aaaataaatg gtgggaatgg tcccctaatc cctctgcccc tcctgagaaa 93900
gaagcgtctg caccaactcc ttagggaata tccttagaag catgtctttc ggcagagcca 93960
ttaccggtag caaaaaagca acattgagta tattatatgc cttagcctgc tcataagcgt 94020
cctttttttt catggtattt tatgttttta aatattttta attatttttt aaatacgatg 94080
aacagttcgt gctccgaagg ctgtttacta aaaatcggtg tgaatccgca ttctttaaat 94140
atggtttccc attcggggat ggtatggaaa tccatgtctc tacgaatagt atggtgccca 94200
agtgcgtcct gcaggctgtg aagccagaag gcctcctgac cttgatgaag gtcgtacatg 94260
ataagaaaac catcaggttt caacagatgg taaagcttgt taaaatcgtt tatcgtaaga 94320
tgatgcgccg ccataggtaa ccctatgagc tccacagagt tttcatgctg gacatcgtcc 94380
atatcggtat aaaacgtttc acagtaaatg agacgcttaa acgagtatcg atgacaaaca 94440
tttatttcca agtaggtttg cactacgttt ttaggtatat cgggaatcat gttgattaag 94500
gttgtttcgg gaaacttaat catctgacta ggcttcattt tcaactcttt aaaggatttc 94560
ccggagaagt gaaaatgggt ctttacgtat ttatgtaaaa atacctgaat gggcagaggg 94620
ggctcctcct cttcgttctc gacgcctccc aaaatatttg gaatttcctg acgtggcaaa 94680
agaaagttta tgtccacgtt tacgaatcca tcgaggacgg acacaaagct tggctctaat 94740
ctccattcca tatactgttt agaaacggga gatagcataa tcctaggcgt cacaatgcac 94800
gaagggtttt taatcaccgc atcgtggtaa gaaaagtgta ttccatttct tccagtataa 94860
agaagcctat gttcgtcgta gcagaaacaa ttaaggcggt atgcctcata catacactgt 94920
ttcaaagtac aaacacgttt taaaaaggtt tctgcattgg cggaggccaa gcggttttgc 94980
cattggtgga aggggttcaa tcctacaatg gccagctcgt ttaaaatatc ttcgcggcgc 95040
gctaaaatct gcaccataga agaatacttt agcatttttt tttcgcacca ttcgcgaaga 95100
tgtttagcta cattattaac cttattattg ataaagtata cgatggcatg ttggaagcct 95160
tcaaaaataa agagcccctc caaaagatca tctgccaata gaagatggat gttggtgtaa 95220
gcattgtcaa tattttgtag aaacggcgga atgcctgcca aaaccgcttc agcaagcata 95280
gctccgttcc gttgtttact gtccaataga ttcgtaagtt ttttgtccgc aacagacacg 95340
acggctagga tggttgcaat gtcagaaatg gcggcttgcc agaaataacc cgaaaagcac 95400

```
atgcgcgctt cttctataga taaaaacgaa aagcgagagg caatgtctcc gagctgcgtg  95460
agttgaagac ctttttctcc tctggttaaa aggcctgcca caatggcccg ctcaatggct  95520
gatgccagcg catccgtggg gggaggatcc agcatatcaa tctcctctgc cttaaacacg  95580
ccttccttat ttttttaat cgtttctacg acaatgctaa gaaaaatggc cccagggcct  95640
tccgtaatga tttcaggata ctgctgcact ggtatttgct caaagacgtg ttttgtgtaa  95700
agcgggtaaa agtgcccagg aaatactctc cctacacgcc cctttctttg ctcgatacgg  95760
ctttgagccg cggggcgcgt aataagccct cccgcccatt cgggatagta ggtttcaatg  95820
cttctgttcc acccgggatc tatgacgtac ttcagcgttt caatggtaag gcccgtttcc  95880
gcaacaaccg tggaaacaat gacccttctt aaaggttttt ccactttagc ggttaaggga  95940
tttttcaccc acagattctt aatttccgct ttcaggccaa ggtaggcctc attttcctgc  96000
gcaatcgcct cactatcgat cggcaaaatc aacattaacg gcagcttttc tttggcaagg  96060
tccatatttg cattattcag caacatcgaa aggaagcgta tttcagccat accgggcatg  96120
aaaattaaaa tatctgcttc cgtgggacga tcatgaatgt tttctttatg aatagtgaga  96180
gccgtttcgc aggcggtctt aatgtagttg ttggtgttat acagcggcca gtgggtttcc  96240
acaccgtact gtcgtccttc caccaaaata atgttttctt ttccgatacc aaaataggtt  96300
gagtatttat gggtatcaat ggtggcggag gttaaaatta caaagggaat acgcagcgcc  96360
cctatgcttc ctctttgcaa catgcgctga agcatacttt taatatacat gagcataagg  96420
tcgatgccta gggctcgctc atgggcctca tctataatca taaaggcata gcgggaagct  96480
atctcatcat ccgtcattgt atgtagctgc gccaacagaa cccccgcggt tgcataaata  96540
aggccccgat tgggtttttc cgtcagaggc ttcgtttggt agcccactgt ttggcctaat  96600
atcatgtcgg ggtagtgggt tgaggcgccg atgtctttgg cgagggtcac cgcggttagg  96660
actcttggct gggtacaaat aaccgagcgt cccaagtatt tttggaaaga atgcgtgttt  96720
tcatttctca gaattctgaa cacgtgtacg ggtaaggccg tggattttcc ggaaccagtg  96780
cgtgacttta taatgagcac ccggtctgcg agggaggttg gaatggcccc tccaaactcc  96840
gggagacgtt gttttatcca agtgatgatg taatgaatag gaacatcatt cttgtgctca  96900
gcgggcacgt tatagagatg accaggctcc aataaagtcg gttttcccat attctattgt  96960
tttaaggatt gattgttcat aaatattttt atactctgac caagaaatta ttttttttatt  97020
aagccggtta tttacgttgt tatggaacgc gaaggtccag tactgaaagt cctccgagtt  97080
gtttaatgtc aagggatttt ttgtaagata cgaaaaggcg tggtgctggc acctggtgca  97140
tggcagagac tcgataaagt tcagtatcca ttggatggct tcatattttt ctttccagct  97200
aggagcgtct gaaaaaaaga tagcatatag atgcaaggat cgccagtatt taggtcccca  97260
atgcaacatt tataaccttt tgaaaaatct cattccatat agaggtaaat atttttttc  97320
catggagaat ttttttgcac tcttgaaggg attgcgccac atcgtcaaat gtttttttgtt  97380
ttccatgtat tttggcgtaa ttccagccag tatctgtgtc atggtcctta atgtcatccg  97440
ctaactgaaa ggcatgtcca aaacaatggg cagccctttc aatcatccca atgtcttcaa  97500
cggatccagt tcctaaaacc cagcccataa taaacgcgat cttaaaaaag ggaatggttt  97560
tttctggagt gtctactaac tgaccggaac ccgcgctgtt tagagagtgg cttacaaagg  97620
tacacagcag cgctcccagt tggttgggat ccggaaacct tggacagtgt tccttaatcc  97680
agtcgatttg ccggcaaata ttttgaaatc cttgcatggt tagcgccaga gcgctcatct  97740
gcgccttggc tacgccaaag cgggcccaca ctgtatcttt atttcgccgc ttcacatcgt  97800
```

-continued tgtcaaagga gggcatatca tcgataatca aagaagctac gtgaaagtac tccgctgcta 97860
gggcggcctc tgccggataa ataggcgccc caaaggaatg ttgcaactga caggcccgaa 97920
caatttccat caggataatg ggacggatat acttcccacc tcttagagcg taagagcaag 97980
gctctgttag ttgtccctta aagtccccat cttcaatagc attatttaag atggtctcaa 98040
actcttcact aaaggtttta taatttttag gattcagtgg atgtattcca tgaaaaagcg 98100
cgacactacg cggtgctgtg attctaaaat acttaggttt gcgcgtatag gatattaaaa 98160
taataataag aactacaatg atggagatat agatgagatg caacatgctg agttgtctcc 98220
ccgcagggaa tggtcctttt ccgcgcttgt taacggtacc gaggaggcgt tgaaatcttt 98280
aggaaaggtg ctgtctagtt tggaatctcc aattcctccc gtatatttag gtatataatt 98340
attgtgtcta gaaattgttt gctttgaggt atcaaaatat tcagcctgac cgctatttct 98400
tttagaataa ttcggtatag ggcttgagta gttggcaata ctcttaaacc ggggcaccaa 98460
ggtaacaata ttttccatat aatgggtttg atacgctttg tttaaaaatg ggcttaccgg 98520
ctttatgctt gttagttgtg cattgagtac cggtatgtct tctaggattt gtggctttat 98580
agaatgatta gcaaacacag aatgtagtat attagatact tgtagcatat gtctatttgc 98640
ggaaaattcc tggtattctc tgccgtgttg cgaatctttg ggcggaaggg gaccaagcat 98700
cggcacgtcc gtgtaggtac tggtggattt tatgagttcc tgctctatgt tcggtttgac 98760
atgtggattt cctaaaggaa tacctctacc tgcaatccct ttttctaccg acgcaggtag 98820
attgtgcgct aaacacaaaa tattgtacac gtctttgtgc ggaatatatc cgttatagtg 98880
ctggcccggc atctgatcgc caaggtgctg ctcatgctta atggtaccct ttgttctgag 98940
tttaggaaga tcctcgtacg aaaaaaattt tgtgtgctcg ctgaacctcg tagaaggaac 99000
cgaactattt tttgggtttt ttaaggaagg caatgaggaa ggctgggtca gacaattttt 99060
ctgtgtgccc tttaagctag ccacctgcgg aaatgttttt ttttccgtac gaacaacatt 99120
gcgcctaatt aggttttccg tatgggttga aaaagcagga cgatgatttt taaaatgatt 99180
aaaaagttta tttttggaa tggagctgta cggctccaga tcttgcgcat cgccgtaacc 99240
aatgtttttg tgctgagggt tcagcataaa agaaaagtta cgtagatcac tgagttgcaa 99300
tccctttca gccttttcag gactattagt gtattcattg tatacaggcg cggctccatt 99360
tttgttgccg cagtaccggg aatttagtat attatcagaa taccggttat gacgcggcaa 99420
atcgctttcc caaagaggtg gatctgacct ataatcggct aacagctttg aagcataatc 99480
atgatacatt gtatataaaa gttaattatt atattgagaa ggcataatta cttcttgtag 99540
gggtacaaga ggctttgaat caggcaaact gacgggtttt gaatcggccg gctttggacc 99600
ggcaggtatc tttttaggtt gatcttcttc tagctcatta gacacggatg ggggagaaat 99660
aggaggaata atttcatctc cgcccttata tttgtcatgg atagaagaaa caattacatc 99720
catgtttgat ttattataaa tgtcgtttaa ctggtgattt aaaacataat aatgcaaaaa 99780
taatagggct acaatgcata tatatacgta aatagccgtc ttcgtttttc gtttttttatc 99840
caccggcgga ttacaaattg caaaaaatac aactaatacc accgctgtaa tgattaaggc 99900
cacaatgaaa ggattttgaa aggatgtttt gaacggttcg cacgtataaa ttttttctcc 99960
taaattattg atacccgcaa taaaatctac attcatttta tatatttata aattatgaaa 100020
aatttagagt tacatctccg ccggaccaat cattgctaaa atttgaagat tcttcaaaaa 100080
ggcccgactg gttgaatgtc ttctgctcag gtttccaaaa attttccaag aatggatttt 100140

-continued gaacaatagg ctcatcttga ttttcttctt caaggatatt ttctttgata tcaagaacag 100200
cttctttaaa ctcaggtgta tcttgattaa actcaggttt atcctgatca atcgcaaaaa 100260
tattatcttc ttcagatata tcctgtttaa tcgcaagaat agtttcttcc tcaggtttat 100320
cctgatcaat cgcaagaata ttttcttctt caggtttatc ctgaccaaac tcaacaatat 100380
ctttctcgct aaatccgttt ttagtgtgaa gctcttggtt ttgaagagaa ttatcaaaat 100440
ctattttagt tgttgtccta gaccgtggca cgggatagtt atctaatggt ttacttacta 100500
tagtcctcga atgtggcacg ggataattgt ttggtgactt gctggttagc tcttggcttg 100560
ttaatagttc ttgttttctc aataattcca tctctactac ttctttttga tccgctggtg 100620 tctcttttg gtattcttca ttagaaaaat gttcagaggg taatgtttca ataaactttg 100680
tgagtggata gctgctcttt gatgtagaag agcgttgaat ttgctgataa aggagttgaa 100740
caagtcgccg gtattcactc tgtctttttt catatttttt acgtagcgtg gagagatctg 100800
ctaagagcga cttgttttca gatgttaatt cttcaatttg atgaagaagg ctgcgattgt 100860
atgaactaag tcttgcatac gtttcttcta attctgtctc cggctccaca taggcctgtt 100920
ttcgcagaaa tttattgtat agttccattc ttttttgag cagaaaggta agactataat 100980
cttgcatttc tttcgtaact ttatggtagt tttctttccg gtttttgata ataaagggca 101040
gcattttttc tgttgtgata aaggtgccca gattgctaat gtagtcgcac agtagcaatt 101100
ccaagataga ttctttcttt tcaaggctta tagattggct gtattcttta ggtatgaaag 101160
aatcaacaat cgttgttacg aagtttgaaa agtttaatgt tttgctgtta atttgggtaa 101220
tgttacaaaa atatttgtaa aaactatcta gcatttttc ataaagtttt ttattttgtt 101280
taacccctaa aatatagccc tttacttgat actgatattc cgtaacaatg gaatgttttt 101340
tgtatagtgc atttttgtat aaaaagttat aaaaaatgtt gataaaatac gcaccaaggg 101400
tttcaaaaat acttataacg tgggattctt cctgatccat tatatcatat gtaatattat 101460
tttaataaaa aattactgac gaataacatg caaaaaaaat atgtttaaac ttattttaag 101520
ctagcactta tttaaaagtg ttttaaacac gttttaaatt gtatgttaat acacttaaaa 101580
attaagccga aatttgctcc aataaggatt acttttatca atgaccacct ctttactata 101640
aacggcttta cataatttta ataatgcttt agagccaaag ctgaaggcag tgggaagcgg 101700
cactgtacta tggtaaaaat gttgccgatg ttcatcctcg cggatgtaca caagtttcct 101760
atatccttta aacacaatat ggctaatttc ttccacatac tccttatcct gtttggaata 101820
gcggttgctt tgacgggaaa aattcgacat acaaatagag gcatttgtaa aaatggaaac 101880
aaatgcgttt ttacgaagat tggcgggtaa atcggtatca tcttggcagc aaataatcat 101940
cgaaataaaa cagtgacgat tttggtaaaa aaactttta aaaatttctt ttgtaaataa 102000
tgggtgcagt tcggccgcgc agtcgtctaa tattaaaagt aaacgaggat taagattgat 102060
atagtttaac gtaaactttt catcctctgt aaggcataag tttttataca tatgaatgtt 102120
ctgtataata atttttttta aaagttgctg ataaagcgat gtaatctttt cttcttttt 102180 ttggtccgtt tgttcagcct ttaagcactc cacttttgca atatttttgt tttccttttg 102240
ctgtatatcg atcggaagtt tatgatacaa tgtttttagc atatcgatgt tgtttactcg 102300
actgtagatg gaggacatca tagtttgccg ctgccagatg gcctccaaaa agcgttcagc 102360
gcccttgttg tcattttttt tttgcttatc ggcgagccac aagcggtagt gtattagagt 102420
tggatgtaca aaaccctcat atgaacgatt tgagggttcc gagggggcaa ccactaaaat 102480
ttgttcaata tggggttgca ggattttcat aatatgttta acgtacacgg ttttgcctgt 102540
ttttgagggg ccatatagca cagttgtttt atctataaaa tgatgtgctt tgaactgtag 102600
ttcaggaatt agcttccctg aatgggtcgt tagggccatc tctatattat tacaattctg 102660
cttttgtata taaaatttct ttttcgagtt tattattatt gttgacccac atatctaccc 102720
gtatcgtatc atcaggcaca ttgagcattt caagcgcatt atctaactgt ttttttgttt 102780
ttatcagctc gctttcttca tcgggggtta aattttcttt actaagcagt tgcttaattt 102840
tttcttcgca gtcgtctata aaatcatact ctcgagcttt tttgatattt ccagatgctt 102900
tttctaggtt ttttagctcc ttaaaggaaa gcagtccctt aatcccgcta tccgtgtgaa 102960
aggttgaatt atagatggag agccccggag catccgggcc agtttcttgt atattttttg 103020 ctttttgtg gtaaatagta tttcgtaaaa tctcttttcc tatctttagg tcttcctcat 103080
gacggtccaa aatccgtttt attatttcat tattttgatt aaaataattg tagcgctctc 103140
tgttggcctt aaagcttccc aggagtgtcc agttgcctaa ttgaatggat gaaacctctg 103200
agaaaatctg gtctttatat ttataataaa attcatcaac cttttgttgg ttgctgctat 103260
ccaccacatc ataaataatg aaggcaaact ctaggtcggg tttttctggg tagatgcttt 103320
ccgtagcggc ccgcaactct tcgtaattat cctcaatgta ataattccac ttataaaaag 103380
tatcctgagg tggaatatgc tgcgaaagat atctagtaat ttttgtgtta aagagaatgg 103440
gtttaaacgc cctcggattt tcaagcatat gtttaatgct ttggtgaagt tctatatttt 103500
gtaatatgtg ggctgctgcc ctatagccct gtggggtttg ggtgattgca tcaatatcgg 103560
cctgaagctc attaggcaca tttaatgttt tttgcatgat gtgtaaaggg atgcgctcag 103620
gatctgctaa atcggtgtat tctgtgcttg tacaagtgct tgcacaggta tctacattgg 103680
tatctgcaca catgcttgca caggtgtcta cattggtatc tgcacacatg cttgcacaag 103740
tgtctacatt ggtatctgca caagtatacg cactttgagc atgaagatta ggatcaaaca 103800
caaaatgttc tcgtaaaaag ctatcgatcg ttgttttagc ttccttgctt ttctgcgtct 103860
gggttttgca gctatctgct atagataaaa ttgtatttac taccgattca gagggaacat 103920
cattagtttc ctgtttcaaa gtatcaacta acgttattag ctcactgaga agagttttgg 103980
tcgtgtgggt aggttttgaa taggaaggca tccattcctg cagagctttg aagacatatc 104040
caataaagct agtcattata agacgtcgaa tatactgctc ccgcaaattt gtaaaagagc 104100
aaaaggccac cctgctatca tttttgaact gtttgtaagg gttcgtcctt tggtaaagct 104160
gtttaagcgt ttcttcggat atttcagtag agggatcctc caatacgttt ttgagaagct 104220
catcaatatt aaattctgcc atatcttaga gtttattata tacatattaa agctttaata 104280
taaggggggt ataacaatgg acgaaatcat caataaatac caagctgttg aaaaactttt 104340
taaggaaatt cagcaaggat tggccgcgta tgatcaatac aagaccttaa ttagtgaaat 104400
gatgcactat aataatcata tcaagcagga gtattttaac tttttaatga ttatttcacc 104460
ttatcttatt agggcgcata gcggagaaac gctgcgaaac aaagtaaata atgaaattaa 104520
acgtcttatt ttggttgaaa atatcaatac caaaatatct aaaacgctgg taagtgttaa 104580
ttttttacta cagaaaaaac tttcaacgga cggggtgaaa acgaaaaaca tgtggtgcac 104640
caataatccc atgctgcagg taaaaacagc ccacaacctt tttaagcaac tatgcgacac 104700
acagtccaaa actcaatggg tacaaacttt aaaatataag gaatgcaagt attgtcatac 104760
cgacatggtg tttaacacca cgcagtttgg gctgcaatgt cctaactgcg gttgtattca 104820
agaattgatg ggaaccattt ttgatgaaac acatttttac aaccatgatg ggcagaaagc 104880
aaagtcaggt atctttaacc ctaaccgtca ctatcggttt tggatagaac atattcttgg 104940
tagaaatcca gaacaagagt tggggaccaa acaagatccc tgcggaacca aggtgttgca 105000
acaactaaaa aaaattatta agcgcgataa taaatgcatc gcgcttttga cggtcgaaaa 105060
tattcgaaaa atgttaaaag agataaaccg cacagactta aataattgtg tttctcttat 105120
attgcgtaaa cttaccggag tagggccgcc tcaaatatca gagtcgattt tactacgagg 105180
cgaatacata tttacagagg caattaagat acgggaaaaa gtgtgtaaaa aagggcgtat 105240
taataggaat tattatccgt attatatata taaaattttt gacgccattt tgcctccaaa 105300
tgataccacg aatcgacgca ttttacaata tattcatttg caaggaaatg atacgctagc 105360
taataatgat agtgagtggg aatctatctg tatggagctc cctgaaataa aatggaagcc 105420
cacagatcga acccattgtg ttcatttttt ttaaagatga agattttta gatgattttt 105480
tttagttttt taaaagacga aaaaattttt taaaagatga atattcttaa accccgcaaa 105540
ttactttttt ttaggtactg taacgcagca cagctgaacc gttctgaaga agaagaaagt 105600
taatagcaga tgccgatacc acaagatcag ccgtagtgat agaccccacg taatccgtgt 105660
cccaactaat ataaaattct cttgctctgg atacgttaat atgaccactg ggttggtatt 105720
cctcccgtgg cttcaaagca aaggtaatca tcatcgcacc cggatcatcg gggttttaa 105780
tcgcattgcc tccgtagtgg aagggtatgt aagagctgca gaactttgat ggaaatttat 105840
cgataagatt gataccatga gcagttacgg aaatgttttt aataataggt aatgtgatcg 105900
gatacgtaac ggggctaata tcagatatag atgaacatgc gtctggaaga gctgtatctc 105960
tatcctgaaa gcttatctct gcgtggtgag tgggctgcat aatggcgtta acaacatgtc 106020
cgaacttgtg ccaatctcgg tgttgatgag gattttgatc ggagatgttc caggtaggtt 106080
ttaatcctat aaacatatat tcaatgggcc atttaagagc agacattagt ttttcatcgt 106140
ggtggttatt gttggtgtgg gtcacctgcg ttttatggac acgtatcagc gaaaagcgaa 106200
cgcgttttac aaaaaggttg tgtatttcag gggttacaaa caggttattg atgtaaagtt 106260
cattattcgt gagcgagatt tcattaatga ctcctgggat aaaccatggt ttaaagcgta 106320
tattgcgtct actggggcgt ccagctataa aacgtgactg gcgtacaaaa agtccaggaa 106380
attcattcac caaatccttt tgcgatgcaa gctttatggt gataaagcgc tcgccgaagg 106440
gaatggatac tgagggaata gcaaggttca cgttctcatt aaaccaaaag cgcaacttaa 106500
tccagagcgc aagaggggc tgatagtatt taggggtttg aggtccatta cagctgtaat 106560
gaacattacg tcttatgtcc agatacgttg cgtccgtgat aggagtaata tcttgtttac 106620
ctgctgtttg gatattgtga gagttctcgg gaaaatgctg tgaaagaaat ttcgggttgg 106680
tatggctaca cgttcgctgc gtatcatttt catcggtaag aataggtttg ctttggtgcg 106740
gcttgtgcaa atcatgaatg ttgcatagga gagggccact ggttccctcc accgatacct 106800
cctggccaac caagtgctta tatccagtca ttttatcccc tgggatgcaa aatttgcgca 106860
caagcgttgt gacatccgaa ctatattcgt ctagggaatt tccatttaca tcgaatctta 106920
cgttttcata aagtcgttct ccggggtatt cgcagtagta aaccaagttt cggtacgcat 106980
tctttgtgcc gggtacaatg ggtcttccaa aaggatctac aagcgtgtaa acggcgccct 107040
ctaagggtgt ttggttgtcc cagtcatatc cgttgcgagg aaacgtttga agctgcccat 107100
gggcccccat ctgggacgtg ccctgaatcg gagcatcctg ccaggatgaa tgacatgcac 107160
ccaatatatg atggcccacc atatcatgga aaaagtctcc gtactgggga ataccaaagg 107220
taagcttgtt tcccaaggtg gggtacccg tatgcgggcg tactttattg tattcaaacc 107280
ctactggaac ataaggctta aaatgcgcat taaaatgcac caaatgtgtt tcttcgattt 107340
gactcaaagt gggttcggga tcgggtttcc cataactttt gttcacattt ttaatgttag 107400
agatcctgct attcagcaag tcttgggcca atataatctt gtcggccttc ccatcgttag 107460
caataagaca aaaagctcct cctgatgcca tatataatgt tataaaaata atttattgtt 107520
tttattaaat atggcggttt atgcgaagga tcttgataat aacaaagagt taaaccaaaa 107580
attaattaac gatcagctta aaattattga cacgctcttg ctggcagaaa aaaaaaactt 107640
tttggtgtat gaactacctg cccctttga cttttcctcc ggcgaccctt tggccagtca 107700
gcgcgacata tactatgcca tcataaaaag cctcgaggag cgcgggttta ctgtcaaaat 107760
atgtatgaaa ggggatcgtg ccctcctttt catcacctgg aaaaaaatac aatccattga 107820
gataaacaaa aaagaagaat atctgcgcat gcacttcata caagacgaag agaaagcatt 107880
ttattgtaaa tttttagagt ctagatgagc ttttacgcaa tgttgtacag tgttgtatat 107940
atgtcttgta agcatttgtt gtagagtaat aagtaaaaga taaataaaaa tgactattaa 108000
aataaagccc aaaccattaa aaatattttt atctgttaga tttaatttaa taaatggctc 108060
atggaatgtg tggtgcgccg ctgcatgagg tgtggccgca tgggatgtgg tcgcataaga 108120
tgtagctaca tgggatgtgg catttgcttg catgtaagga tcatgatgtg ttgggtcttc 108180
atcccagcaa taatcgccat ctttatctag ctgaattgta taccccatta tatatcactt 108240
attatttttt tttaatgttt catgaatttc attataggcg gtgaaagggt cctcaggccc 108300
cttctgtaaa agattataga gatcttcgga cgctttatgt ttcgtgcgaa ttaaggcggg 108360
atataacaaa agagagggcc ccagttccaa acaaatttta cttagcgggc tcatattttg 108420
caccaagttt cccactactt gcgatgtttc ataacgcatt ttaaagagct ttatcataaa 108480
agtgttatgc aggccggtgt agtctggcct atagttaagg aaggggattt ctctggtacc 108540
gtcaaacacg atctcaagtc ctctagcaag cccgatcaaa atttcttcag caatggatga 108600
gtatctaatt cctacattac gaagcgtaag catttctata acatcatcta tttcctgcat 108660
agaggaatct attgtaggaa ttttaatatc atctgtgctg atttgttcat tcccaagata 108720
ggtaagcagc atattaattt tttctagctt tactagctta gtcttacgct cataatcatg 108780
atcttttta taaaaagagt tgggatcacc gttggaccgt agatgattaa taaggcggtc 108840
tacttgcttt gtactaggtt taatactttt ttcactatac tcgctttcag catagtggtt 108900
tttacgatct cttttagaaa tagctgtttt ttgagatgcc tcagactctg catattttt 108960
tctatgcgta gaaagagaat aaccgcggtc attacgtgaa ctactgttgc atgcaaggcc 109020
tcggcgcgtc ttaccgctgc gcacactgcc attgcgtata ctgccatcgc gcacactgcc 109080
gctgcgtata ctgccattgc gtatactgcc gctgcgtatg ctgccgctgc gtatgctgcc 109140
gctacataca ctatcactac atatgctgtc agtacatacg ctatcgcggc gtatgccgcc 109200
gtgtacctta tcgccgcccc tacccgaggg ttttttagat ataatactgt gtggggagtc 109260
aagcgaaaat tcagggtcat taaagttaat gcccaatgac tttgccaatc cattaagctc 109320
ttcatcaaaa tgatcggtag gaaaactttg ttgcttgccc atgacctgtt tttcaagttc 109380
ctccaaattg gcttgctcat ttatatggag attattcata agcgtcgtaa ttccagcaag 109440
atttgctcct tctaaaaatg tggtgtcctc catcggatat actatactat ttaaaagctt 109500
ttaaataaaa atgtgtttgg aagaaatgct ctcttcaagc gtgtgtagct cagatataaa 109560
tgcctcctca gaaagctttc caccatactc ctttctcatc gtataggagg gcgccggttt 109620

-continued aatgtaggaa atccactggg aggtaaaaaa ccggtacaac atatttagca gctcgcgggc 109680
ctcccacctt ttgggctccg tatagtgcac atcaacataa gaggcggcgc atgaaaagct 109740
gcaaaagttg ccgagaacgc ccatctcaat ctctcctcgc tcattttcac gcatataggt 109800
gggcacgaat tttgggacag tcttgaaata gagatgacat gtccagcatt taaagctaga 109860
atgggtaacc catttggaaa cagtggtgaa tacggagggt agcttttttt cgacctcggc 109920
ttcatcgtca ttcgtattta acgtatcggt ggcagttttt ttggattgca agcattcttc 109980
aatggtaatc ccggataagt ataaaatatt aggacaatta gtttccataa ttttgatagt 110040
tatttttata caacatggat ttaattaaag ataaatggag gacgaaacgg aactgtgttt 110100
tcggtcaaac aaggtgacga ggcttgaaat gtttgtctgc acatacgggg gaaaaattac 110160
cagccttgca tgttcgcata tggagttaat taaaatgttg caaattgctg agccggtgaa 110220
ggcattgaac tgcaactttg gccaccagtg cctaccgggc tacgaatctt taataaagac 110280
tccgaaaaaa actaaaaaca tgttgcgccg tccgcgcaaa acagaaggcg atgggacttg 110340
cttcaatagt gccattgaag cctccatttt gtttaaggac aagatgtata aattaaaatg 110400
ttttcctagt accggggaaa ttcaggtccc gggcgtcatt tttccggatt ttgaagacgg 110460
aaaaaacatt atacagcagt gggtagactt cttgcaacat caacccattg aaaaaaaaat 110520
ccagattatt gaatttaaaa cgattatgat taattttaag tttcaaataa acccagtgtc 110580
tccccgcgtc atcattcatt taaaaaaatt tgcagctttg ttggaacaca tccctactcc 110640
atatcccata cgtgaaataa agcctccatt agaagactca aaagtatccg caaaatttat 110700
ggtcagtccg ggaaaaaaag tacgcattaa tgtttttctt aaaggtaaga taaatatttt 110760
aggctgcaac acaaaggaat ccgcggagac catttatacg tttttgaaag atcttatcag 110820
cgtacattgg caagaaattt tgtgcgtgtt accggtaccc gattaaagaa tgttttcatt 110880
aataaggtaa tcgactatgc taaaaagaat aacaagaaaa ataccttgaa gaactatacc 110940
aaagtaggta ggttttctgc atgtcacggc atggttaaaa ttgctaataa tgtagtccac 111000
aaaagcattg ctcaatacga ctaaaaatag taaaaaaagg ataagtgctc tttttatatc 111060
catatacttt aaaacttatt ttttacacta ataatttcct gcggccgcaa tataaactgt 111120
aggtcatcta taacgcccag acctgttaaa agtagagtac tatgttttaa gggatttaaa 111180
atatccgccg caagaatgtg aatataattt tcaaagtggt ttacaggaat gcgtaagcgt 111240 tttttttgc actgcggttg gtttagggtc gaatactggc aggaggtata tatattaata 111300
agaccgcggt cgatggtttc aatatcttca tagaattcaa tgcgcggcgt caaaagtttt 111360
ttaagatgtt gacataactc atcatacgtg taggactgga ggggggaaag aagggtgtag 111420
tcaaagttaa aaatgttttt ttgaagaacc tttaaagcat gttccgcgtc cgtggtttcc 111480
aaaatatgtt ttatggtatg aatgtcattt aaatctacaa agtctgacag ctttgtgtag 111540
aactcggtga cggaggttat tttctggaaa tcggtttttt gaaaaagatt ttcaatgtgt 111600
ttgcgggttg agttgctttg cagtccatac aagacatcaa aaaattcaat cagcaaaaac 111660
ttatacaaat ggttaatata aaaagctttg ttggccttat tctgctgagg atatggttcc 111720
tctaggggat atagaatggc ttggtctata tccctaggat caatagtcaa tgttgcgatg 111780
ggaagctttt ccagcgtagc gggaagagtt tgggttggag cgtagtaaaa gtatagcccg 111840
gtttttccct ctgaaagaaa gcccacaaat tcttttttta tattttgcag caccgctgag 111900
ggtacgattt cgtactgttt atactgtttg ttgaaaaggg taataaattt ccaggtttct 111960
tcaaagcttg caatctgggt gggccgcaga tcaaagtcga tgggaatgtc gtcatgaatg 112020
taggatgata gtcttatagg aaaataaata gggcgatcgg tgtctgaatc gataagtaaa 112080
gcataacaaa agttatgcct gttgataagt tttttaccaa ccgtgtagcc gggaatgttt 112140
ttcacgtcat ggatatccca ccagttatcc ttgcacataa actcgctcat agactggatg 112200
acctccatca cagggtcatc ttcggtaaaa atatactggg cctcactgtt tttcagaaat 112260
ctttttttgct gggtgatggc cattgggtag atcccttcgt ccgtgtcaaa gataatggct 112320
atcttcttcg atgggctaag aattttttgt attgtgctgg gggacacctc aaacccgatg 112380
tcgccctgtt tatctttaaa aaagacacag tgaaggtcgt agcatatggc aacaaggtcc 112440
agaaagatgt cctgccatgt ggtgtcccat tgaagcagtt ggtttttttg ttcaacaaag 112500
gtttgtaaga taaggtttgc cagctccgcg ccgctggaaa acatgttgcc ggccccattc 112560
cccaaaatat agtactgcgg tgtgttggcc gcctttgcaa tttcaatggc aagggccttg 112620
ggggcaagat ccaaaattcg agcaagggaa taaaaaagcc cggcattgct aattccaagc 112680
atggtttgct ccaccccccac aatgcaaaaa atgtcgggct cttttatcgt atttaaaaac 112740
agttcatctg ctatctggtg gggtagaaag gcaatccggt tcaccggtat tttttttcca 112800
taggacaagg tatgacgcga tgtttgtgta ttaagatcct ccaggtcttg ttctacaaac 112860
gtgtgcttgg tgaggcaggt attgttaata tagaaccgct ttgtgcccag cagggccttc 112920
gtcttttggc agcacggcag acagtaattt agggggtggc ggccttctag taggcttaga 112980
tgagggtagt caggatgcgg gcagctatag taggcaggta ccccctccgt gaaattccaa 113040
tactttacta gctccttgcg cttggctggc ggcatggact tcacctcggc ctctgagtaa 113100
atgacgggtg gccgtgggtg ctggcatagg acggagtaaa ccgttgcctg cgtgtcgtac 113160
ttgcgcaggt catacaggtc ggggtcctgt tcttgaagcg cacgtagctg agaggctccc 113220
tttccttgtt gtttatcgtg cagttgagag agtttattaa ccaaaatttt gtcaggcccg 113280
gtgatcaagt tatctaaaaa cacaaatagg taaacccaaa gatagttaaa ctcttcctgg 113340
gtaatgttaa acatttctat tttgatatct gtaaccctat ggtagatgcg aatgttgcgg 113400
ccgccgtaga ttgtttccca ccgggccgca acatttgtgt caaagaggta cgcatacgtg 113460
ttttggagca acgcaacatt gatgtccatt ttgcgccccg gaccggagga aataatgatc 113520
atccgttcga tttcgtgggg atcatacgaa taaatcccct ttttaaataa aaaattgtag 113580
accccggttt gctggaggcc ccgcacggaa ataatccctg cttgctcgta ttcccgccaa 113640
cgacttttga gctcggtaaa tcccttgcta gaaagcgtat agggccaaaa ggtggacacc 113700
gacatggagc tgatagaaat ttggatgtcc tcgttggagg gaaggggcag actccctcca 113760
cgaggaaacg cggcaggccc catatcatta attgtatgaa taataggatt tatgaaatta 113820
tttagggtgg acaccacgga gttaaagtcg tggcgctcgt tttctgacca attgctttcg 113880
ataaagtagt gcccattatt ttgtatggta agaataaagg cctttttatt gataaagcgt 113940
attaaaataa tagtgggtac acggaatgtt ttattgctga atttttcagg ctccgtggaa 114000
gttatgtggt gtttggaaac cacggtggga cctgttttac tataaaagaa caccaccagc 114060
tgaggaatat cgggagtagc tggaaatagg tcgaaaacat tgcgcacatt aatttgaata 114120
tttacgaggg gtgaaatttt aatcattgcc gaggtgacgg ccaacgtgcc gcgtgttagt 114180
ctattcccct cgtacttggc aatgacttgt tgtgctctgg catacgtaaa gtttattagt 114240
ttttgctcta ggagaagcct ctttttaaga ctggtcaagg atggagaaag agcaggatac 114300
tgtttttcca tttgtaaggg agattgtacc aatagtttaa aggcatcggg ggaaagaaga 114360
ggccaatact tcataataag gccgtaatag agtaagtcaa attggtaatt atcctctatg 114420
gcaatggaga tttggcgccg catgggggcc actagcgtgt tgaggtctgc tacaaagatg 114480
tgatgaatgt tttttatgag ctggaagctg tcgagcgctt ccacatagag ctcatctttt 114540
tgactttcca tagatgcgtc gatgttcacc ccacccacct gttgaaactc ctttttgtag 114600
tcgcgaatgt ctaacgccac cccgctaccg cttaacaata ggcgatacgt tacctgaagc 114660
gcattgtttt gaaaaaagaa aatgtgttgt ctataagggg ggatccctgt ggcaacgtaa 114720
attttttctc gaatgtcttt aaaagtgtct tcagggaaaa tactatactc gctatacatc 114780
gtctcaattt ctggcatcat cacgtttgtc tcctcgccac gatcctccac aaaaagtttt 114840
tcaaactcat ctaaatcatc gctatctcca cccaccacgt attgggaaag ctttttctcc 114900
caatcctcgc cgtaaaaatt ttgtaaaatt tctttgtcct taggggttcg ctgcaggtct 114960
ttgcggcagg cctgtaacac gtttgcagga acggatccca aaaaaataaa cgtcttcgtg 115020
tactcatttt ccacaggatt ataaagagta actcgtagag gatttgttaa aaagtcattt 115080
tggaaatcca ttatacccgg tatagaaaat aaaatttaaa ataaaaaacg gatgatatct 115140
atcatggacc gttctgagat tgttgcacgg gagaacccgg tgattaccca acgagttaca 115200
aatctcctac aaaccaatgc tcctctacta ttcatgccca ttgatatcca tgaagtacga 115260
tatggagcct acacactttt catgtatggt tccctcgaaa acggttacaa agcagaagta 115320
aggattgaaa acatcccagt tttctttgac gtacagattg agttcaatga tacaaaccag 115380
ctttttttaa agtcgctact gacggctgaa aatattgtgt atgaacggct ggagacgctc 115440
acccagcgtc ctgtaatggg gtaccgcgag aaggaaaaag agtttgcacc atacattcga 115500 atattttta aaagcctgta tgagcgacga aaagccatta cttacttaaa taatatgggc 115560
tacaacacgg ccgcggacga cacaacctgt tattaccgaa tggtttcccg agaattaaaa 115620
ctacctctta caagttggat acagcttcag cactattcct acgagcctcg cggcttggta 115680
cacaggtttt ccgtaacccc cgaggatctt gtttcctatc agaatgatgg ccccacagac 115740
cacagcatcg ttatggccta cgatatagag acctatagcc ctgttaaggg aaccgttccg 115800
gacccaaatc aggcaaacga cgtggtgttc atgatatgca tgcgcatttt ttggattcac 115860
tccacagagc ctctagcgag cacgtgcatc accatggcac cctgcaaaaa gtcctcagag 115920
tggaccacca ttctatgctc ctctgaaaaa aatttgttgt taagctttgc tgaacagttt 115980
agccgctggg ctcctgatat atgcacaggg ttcaatgatt ctcggtacga ctggcccttt 116040
atcgttgaaa aatctatgca gcacggtatt ctagaagaaa tctttaacaa aatgagcctt 116100
ttctggcacc aaaagctgga taccattcta aaatgctatt acgtaaagga aaagagagtc 116160
aaaatctcgg ccgaaaaatc gatcatttcc tcctttttgc atacccctgg atgcctaccc 116220
attgatgtcc gcaacatgtg tatgcagctt taccctaaag ccgaaaaaac aagcttgaaa 116280
gcgtttttag aaaattgtgg gttagattcg aaggtagacc tgccgtacca tctcatgtgg 116340
aagtattatg aaacacgaga cagcgaaaaa atagccgacg tggcctatta ctgcattata 116400
gatgcccagc gctgtcagga ccttctggtg cgccacaatg ttatccccga tcgcagagag 116460
gtaggaattc tgtcatacac ctcgctgtat gactgtatct actacgcggg aggacacaag 116520
gtatgcaata tgctcattgc ctatgccatc catgatgaat acggccgtat tgcttgcagt 116580
accattgccc gaggtaagcg ggaacacgga aaatatcccg gcgcctttgt gatagacccc 116640
gttaaagggc ttgaacagga taaacccacc acaggtctcg actttgcgtc gctgtacccc 116700
tcactcatca tggcctacaa cttttcgcca gaaaaatttg tagcctctcg ggatgaggca 116760
aatagcctca tggccaaggg tgaatctctt cactacgtct cctttcactt taacaatcgt 116820
ctcgtggaag gatggtttgt gcggcataat aacgttcctg ataaaatggg attgtaccca 116880
aaagtactca tcgatctact taacaaacgg accgccctta aacaagagct taaaaaacta 116940
ggtgagaaaa aagaatgtat ccatgaatcc catcctgggt ttaaggaact acagtttcgc 117000
catgccatgg tagacgcgaa gcaaaaggcg ttgaaaattt tcatgaacac gttttacggc 117060
gaggcaggta acaatttgtc gcccttcttt ctgcttcctc tagccggagg agtcaccagt 117120
tcgggtcaat ataatcttaa acttgtctat aactttgtta tcaataaagg ttacggcatc 117180
aagtacggtg acaccgactc attatacatt acatgcccag atagtcttta tacagaggta 117240
acagacgcat atttaaacag ccaaaaaacg ataaaacatt atgagcaact ctgccacgaa 117300
aaagtgcttc tgtctatgaa agccatgtct acactatgcg ccgaggtgaa tgaatacctg 117360
cgacaagata atggcaccag ttacctacgt atggcctacg aggaagtact ctttcctgtg 117420
tgctttacag gcaagaaaaa gtattatggt attgctcatg taaacacacc caattttaat 117480
acaaaagaat tattcatccg cggaatagat atcattaagc agggtcaaac aaaactcacc 117540
aaaacgatag gaacgcgaat tatggaagaa tccatgaaac tacgccgccc tgaggaccat 117600
cgcccccctc ttattgaaat cgttaaaacg gttttgaagg atgctgtggt taacatgaag 117660
cagtggaatt ttgaagactt catccaaaca gatgcgtgga gaccggacaa agacaacaaa 117720
gcagtccaaa tctttatgtc tcgcatgcac gctcggcgtg agcaactaaa aaaacacggc 117780
gctgcagcat cgcaatttgc tgagcccgag ccgggagaac gcttctccta cgttatcgtg 117840
gaaaaacagg tacagtttga tatccagggc caccgcacag attcctccag aaagggggac 117900
aagatggaat acgtctctga agcaaaggct aaaaatcttc ctattgatat attgttttat 117960
atcaacaact atgttctagg cttgtgcgcg agattcatta atgaaaatga agaatttcaa 118020
ccccctgaca acgtcagcaa taaggatgaa tacgctcagc gccgagctaa atcctaccta 118080
caaaaattcg tgcaatccat tcaccctaaa gacaagtctg tcattaagca aggcaatgtt 118140
catcgacagt gctacaaata cattcaccaa gaaattaaaa aaaaaatagg catctttgcc 118200
gacctttata aggaattttt taacaacacc acaaacccca tcgaaagctt tattcaaagc 118260
actcagttta tgatacaata ctttgatgga gaacaaaaag taaaccattc tatgaaaaaa 118320
atggttgaac agcatgctac ggctagtaat cgagctggta agcccgctgg taatccagcc 118380
ggcaatgcgc tgatgcgggc tatatttacg cagctgatta cggaagaaaa aaaaattgta 118440
caagccttat acaataaggg ggatgcaata cacgatcttc tcacctatat cattaacaat 118500
ataaattaca aaattgccac gtttcagacg aaacagatgt tgacgttcga gttttccagt 118560
actcatgtag aactgctatt aaagctgaat aaaacgtggc ttattttggc tggaattcat 118620
gtggcaaaaa aacatctgca agctttttttg gattcatata acaatgaatc gccgtctaga 118680
acattcattc agcaggctat agaggaagaa tgtggcagta ttaaaccatc ttgctacgac 118740
tttatttcct aatacttctt aagaaactct ttaaacaagg acttcgcatg gtcaaaggtt 118800
ctaaacccat ggcccttatg attcgccaaa aaagcggttt catcaagatt ttctaaccct 118860
ttcacggatg aagaaataag gtgttcggcc tcgtttgccc attttctatg attttttttc 118920
acctcgggtt ctagatctgt tttctccata tactcattgt ggtcatattt ttttttggga 118980
ggaggcgtgg gtggaggaat gggtggagga agtacacccg actttcccgc ttcaaccgtt 119040
ttataaaaaa atagaagcat aatacaaaga ataaggacta tcgcaaatat gataaccagt 119100

-continued gtcccagtcg agggcatttt gttatataag taacgttttt ttttattttt tataattcga 119160
atgaagaacc atgttgaata gtcttctact caaagacatt ttgttatacg gtaaatgaga 119220
atttataaaa tccgaatatc actatcatac tgtttatctg agaaggtctc actgggtcct 119280
gtgatggaga acccatactc tgtaatgctg gggtttataa tgtggtcagg actgacaagc 119340
acatttctga actgcgagag ttctaggttt agacgcagtc gtaatagtcg ctgtatattt 119400
gtaataaata ttagattgcg tatgaggcga gtgtcaaagc gatcctttcc aatttgtact 119460
aaggtgggct tttgtattcc aactcccact tgtttaacga tggaccaggg tccttcttcc 119520
cgattttgtt ccgtgatata ggtcagcaca ctattttctg tatatgaggt atgatgtcgc 119580
atattaatac ctggtgccat tccaactggc ggttgtgcaa ttcgggctgt accgggaccc 119640
aaccatcgtg gagttttata aacatatcgt tctagcgtat ttaaaaattc cttaaggtta 119700
tttacgagta gcatgaaggg tgctattaaa acaggtggat ggtttataac cattgtcata 119760
aaccattgca ttgcttcaat atcattttgt aatgcttgac ggggaggcgg ggcaggtaat 119820
ccacgtatgt tgaataaagc ggttaattgt gcaccggctg tttggggcgt aatattttgt 119880
attaaattta tcatcgaatt ggcttgcccg gcatttccta taagatcgat taaattggtt 119940
atttgacctc gatattgttg tacccagttt tgaatggcag cgatgatctc aggggttgga 120000
ttgttttgaa tttcaggtgt ttgtattaga ttattcactt ctcttcgtgt atcttcaagc 120060
tgagtcctaa atgcatttaa ctcgcctata atttggtttc tatcaataac atttcttaaa 120120
cctcgaactg tttcagccaa tcgtatagta cgcacaattt catgtaaggc ctggtttatg 120180
tatattgaca tgggatggcc ccaccgctca cgtccacgtt gaatacctgc ggccaaacta 120240
ggacctgcct cgtcataatc aaattgtgta ggataaaggc ttccaaatag cactttattg 120300
aaaatttggt cagaaagaaa tttagggcgg cccatattta gcgcgttgtc ccctctaaag 120360
atgcgtgaca tgtatccggc gttgcctttg gatagtaact cattcccata ttgagtaata 120420
gagaccgaga catagggggtt tataagaagt tttagcataa attctcgagt atttatgggg 120480
ggacgattcg gaatgtttaa tacctctgca acatctggtt gaggagccgt ggtgtccaga 120540
gatcgtactt tttcagccga aatgccgtac ataagacaag caatttcttc aaaactatag 120600
tcatagttgt aaatattggc aagtggtata gatcgcatca gcgcatttac attgataggt 120660
ataatattca tatcaaacaa gttaaatatg cgctcgcgct ctctattaga gccaagagtg 120720
cgtgtttgac ctttcggcga cactattttg tgaatatgat tgatttgctc ctcttggtaa 120780
gagctttcca cgaaggaaat tacgtcttgc aatgttttac gaagcgaata cactgcattc 120840
atccctattc ccgctgttat aatgggttta tcgtctctgt tctcgctaat aagattaact 120900
ccaccaaaag tattttcatt gtacatcatc actgttttaa aactacggat atttatgata 120960
aatcggagag cctgaatggc gtgggtataa aagtgttcaa atcgcgtggg agtaatttgt 121020
tcgcgagcaa ctaccgtttc attatagttt ttcatgataa gctgtactcc gggcatatct 121080
gagagctgta ccggatcatt tcccagtaat tttcttgtgc cgtatagtag tttaaactcg 121140
ggggagccgc tttcaaggtt cgggtaaaga agaggatcat atacctcatt attttctatt 121200
cttaggtcat gtaaataata gagcgaaagt gaaaatggca taagaggctc cttattgtac 121260
cgggacatat agttttgaat gaagtgttct tctgtttcaa gatagatggg atgatcggta 121320
agctcgtgca ggacctccat ggcagaatct gccagagtgt gagagcctct aatgatcccg 121380
tcgatcactg cgaccagtcg ctttcgcaca acatcgctcg tattattttg tgcgtctcct 121440
aggggcataa gcgtaacatt gggacgaaat acgccgccaa ttccccgcag ggccgcctga 121500
ccgacggata gtcctgtcgc aggaacattg ttattattat aataaataac ggaatcatta 121560
ttggctccca agagtgccgt cagattaggg cgagctagtt ggacatttgt gtattgtata 121620
aattgtttta gaagctctcc ctggctaata agaatattaa acattttgtt aaatagtgga 121680
agattggctc tataattttc tttaaggtaa atgggaattt ctgttaaagt agaaataaga 121740
tgctgactca ggccctggcg attggtatcc ttaataagcc gctgaagtat aagtcccaaa 121800
gacagaagaa gcaccgactg ctctgtgggg tcgcctctat gaccaaagac gttgttattg 121860
cgtgctaagt cagggtgagc atatcccatc tccatcactg cttggctaaa gttcccatta 121920
gcgaatgcat taataagatt tagatatatt tttccgctgg gagcatcata aaatcgggta 121980
atatatgaag ctatgagctg gttaaacacc atcatcatac tacgattatt ttgaatacca 122040
tagtctgatc cgtataggcg ataacgtcga aggttgtttg cggcatcatt gacattggca 122100
taggttctga gcgctatgtt gtcccagtag ctaagagtat tttcctcctg ggcgttgttg 122160
gtacgaataa gattggagag tctaaagtct cctagtgcca cctgctctac acgaagtcca 122220
gagttattct ccaaagcatc gtaaaatacg agtctactga atactcttcc gtattgttca 122280
aagcgttcag aggattgggg attgttattt atttgaatat tagccgcgtc ccttctttgc 122340
gccccacctc gaagttgcag tacattataa ggctttgtaa gcaaggtgta ggttttatta 122400
atgatttggt taacccccctc caggcccaat tcaccgccag gaagcggcct tcctccggca 122460
tcggtaggtg gtttaataag tttgtcaatt aaatgttctt ccaaccagta aaatgagcca 122520
ggattagatc tattttcata gtattgaata atgtttttat caatatgcgg gcgtagaaga 122580
tcaagaaaat acttcgtgtc ggccatcaaa gaatcaatta aggaaataag acctgtaaaa 122640
tctaaatgca cttgagcggt gctggtttca gggaagcgaa cttgaaccat tttgttaaaa 122700
ctggaggtca tttcgaagat attggtcaac aggagctgca tgattcgctg attatctact 122760
aaataccttg cggccaactc ttgctccgga cgaactcctc caccagcagg aatacccaca 122820
tatggtacaa tccaagcaaa aagagtttct gtggttaaat ttcggtcttg ggctgctgca 122880
gccgcttcgg tagtgggatc agggtacacc atagaaagcc gcatattgat ttctttaatg 122940
actaatcctg gatttctaat ctcagagatg gccccgtgtt ttcttccgag ccagtcaata 123000
agattggcgc ggttcacgtt ggcagcttgt gtctctcgta accattcgat aatgcttttt 123060
tgaatcgtat ctaggtctaa acctttaatg ttattacgaa agttattaag aagtacgtaa 123120
atagcactca ataagttaag acctgtaata acggtttcat gaaacagaaa tattttgtta 123180
acatctgtat ctgccagtga ctcagagcct tgaataagtt ttgaaacgat ttgaatttta 123240
tcggtatgct cctttttgag ttcattgata gcctggcgaa tgagttcttg gtaggaaatt 123300
ttgcccaatt cttgttgcag actgggatct tcaaacatct cactaagctg tttcctaaat 123360
ttttgtacca aatcccactg ggagttgggc tgcagcattc ctgtttggac atccacagag 123420
tctatattgt atagtgccgg gcgccacttg ggggtaggct gggttgaagg actaataaac 123480
ctatcggagg gaagtaattg tgaggattgt gtatagccat cctcatcagg aagaatggag 123540
tagttggttt gattcatcat tccaaaatca ttcatagttc gcgcttcctg aacaatgcgt 123600
tgaaattttt cccattcggt gcgtgtaatg acaccgaatc tgcggtttat ttcatttaca 123660
aaatggataa gcgctttttt ggttgcttct tgttcaccat actctaagtt aaagtgttgg 123720
taaatgacgt ttatttcttt gataagctga cgaatttcgg tttctgagta gtcaccaatg 123780
ttaataagct caataggacg cataaagata atgcgaataa gtcctgagaa gattccttcc 123840

-continued agctcaggaa gcatcgagat ctgtacattt tcatctctaa aggaaaacaa cttttgataa 123900
aattcggcga ggcggggaag gcggaagtaa agctctgctg cctcgggaat tacctcgggc 123960
tctagctcat cggcaccccc caatatcata cgcgtgggta taagtttgta cacgggctca 124020
ggccgttcaa acatgtcgta aatccctaat acaataaaaa tcttggcggc catacttttc 124080
agcatgaagg tgaagaagac gtcctcggtt tcccagcggg ttgatagggc gtcgttaact 124140
ctcacagtag agaggtagac ccgctgagcc gcttcctcgg cagtctgtgc aagcgccatc 124200
ctttgtcctc caatttctga ttgatttaga tttttaagtc ccacggaaag cgcagaatgt 124260
tgaagatatt caagcaaggt tttatagatt tgcaggggcg acatgggcac catttgccgc 124320
agctcctctc ccccaagcat gtccccaatc cgggcaaagg cattgatgat atttttaagc 124380
gcctgaaagt tagaaagaga gcgcccgata aggtcgcgaa tgtttttagc ctggcttgct 124440
ctgacgggac ggagggtacc aacgcttcgg ccttgttgga tttcagccgc aactttttcg 124500
tagtagtggc ccgcaggagc attatccgta aagacgttgg agtcgttgcc tgtggaggtg 124560
ggaaaacttt caaagacttg tgcaagcgtg tcccctgttg tctcggtgaa ccatcgtcct 124620
ataatgcgca cgccatccag catctgttgg actgtttgaa tagaatctat gttgtttaca 124680
aacgttttgg taatgttttt aagataaaga tctagccctt ccagagctcg atagaatcgg 124740
cgttttacat catactccag ctcgatggcg cttacggttg ccttccagtc tacttcctgg 124800
gcacctccag gatttgggcc cacgtgtcct ctggcaagat ctacagccgg agaattaatg 124860
cgcgcatttt tttccgtatc caactgcatg aggcgtcccg caatagcatc tccgagaata 124920
gtggcatagt tttcctcgta ggattgaaac tcctgtttgt tatgcgttaa attggagtaa 124980
atctgggcca cataatagta atacataaag gtgttaattg cctggttgag gtcaacctgc 125040
gatcgcgcgg ccttgctgag cccaagctct tcaactgtta gggcagcacc gcctacccctt 125100 gtacactcgc agtcctcctc gcctccatac tttttttgca caatatcggt ataaaaatca 125160
ataatctgta gcaagcgaga gcaggagtca taaagatttt taaaattagg gtcggtttta 125220
gatatctcct ccaaaacatt tttaacaagc gtaagctgtg ttaagaaggt ttcgcgttct 125280
tctcgtgcgg ccgcattggt gtaaaagccg ataagactta gatcaagtgc gatggtgccc 125340
atatcattaa tgcgcgaaag agcatctcga agcctcgtta tgttcggcgt caaggcaatt 125400
tctttaacaa gtttgatgcc tattttttttc acattttcca aaaagtcgtt ataggcttgt 125460
gtgcttttat tcaaaaattc catgaggatg tgctttctat ccagtctttg cgcttcaatc 125520
ctcctatcta gtggcgtttt ctcctcatcg ccccccttttt tggcacaact gttctcaagg 125580
attttgtggc gttcattaaa ggtctgtcgc aacaggttca cggctttttc aaactcagca 125640
atgttttctg cggagacaag accactaaac cttttgaggt caagctcctt gtcaaactcc 125700
gcccagtttt tgctttgaag gtactgttca accttgagtc ctactttctg gagagcctta 125760
ttaattttat tcgcaacaga cgcagcaata cctagattac aaagtgtgta cgaaagtact 125820
tttccaaaat ttttggttcc caagacacta tttgtatcat ttaaaagttt aataatatcc 125880
acctcatccg tctgcagttt atcaagttcc ttttgggtgg gagttaaaat attgtcaata 125940
aaattcgtta aaatgttgat ttgcaggttt tgttcattta aaagtcgacg atatactgct 126000
tcaatcatgg tgactgcatt aatgacttcc tcattggggg ctgctttggt tacctccgtc 126060
accatgcgct cgtgaagttg cttaatggcg tcgtttaaca gcttgatatt ttcaagtgta 126120
ttttctatac tgccgtgtac atcaagatac tctgcgcgca gtccatgagt tagggagtta 126180
atgtacagaa ctatttgtcg acatatactg gcggcccctt cggtggtatc tataagctta 126240
tcctgaccta aatcaataaa ttcctggtta atggcgtctg caatcatttt acagacggtc 126300
tcctgttttt ccgcattttt tacaaaggtg gaaccggctc gaggatcggg cagttgtttt 126360
ttgatatctt taagaatatc ttcgatgggc tgctttgtgt ctactttgaa ccctattttg 126420
gcaatcgccc tgataattcc ttctataatc cgcagctttg ctttactcga tacggagtct 126480
atgtgataat ctttaatgtg ttgtacagga tttttgtccc ccccgccatt aaaatatcct 126540
ccccctgaaa aaggacgagt ttgtctttgt atatgatcct gtaacttcgc atatatattt 126600
gcttctgatg aaggcagtgg tctactagag gttgaagatc cacggttacc cattataata 126660
aaaaaaaata aagatttaaa actacaaata ttttgctgtt tataaaccca atcatataag 126720
actaactaaa acattaaatg taggtgagat aaaagcttat ttttttttta aaagtttaat 126780
aaccatgagt cttaccacct ctttttcttc ttcctttaga ggggttccat aaatggtttg 126840
aataaaatta tgtgctctaa taaccttgtt aaaatcaggt gcctttccat attgttcaat 126900
atgttgcaca gtcttttgtg caagcatata cagcttggag tctttaggta cctccgatga 126960
gggctcttgc tcaaacaacg tttcaaagga ggatgtgcat tcattggttt cattatcatt 127020
tttttcatga atgttctccg aagatgctga ggattccgtc tcctcttcaa acagcacatg 127080
cagaatcata ttccattctt cttgagcctg atgttcagta tacccttgcc ctgcatatat 127140
acgagcagat ttcacaatat catacttaac agtactaagc aatgttttta tagcggtcgt 127200
aacaattcta ccgctattga taatctcaac agaaaaccaa ttatacaggc tacccgcatg 127260
aaacacaact tgtgaagatg atcttaaatc cgttttgaag atgacctcca ttttcatgga 127320
tatatttaaa ataaaatcca ttcaatttta aaattataaa ataataagaa gatgccctct 127380
aatatgaaac agttttgcaa gatttctgta tggctacagc agcacgatcc agatttatta 127440
gaaattatca acaacttatg tatgcttggc aatttatccg cggcaaagta caaacacgga 127500
gttaccttca tttaccccaa acaggcaaag atccgcgatg aaataaaaaa acatgcctac 127560
tccaatgacc cttcacaagc cataaagacc ttagaatcac tcatccttcc attttacatt 127620
cccactccag cggagttcac cggggaaatc ggctcctaca ccggagtgaa attagaggtt 127680
gaaaaaacgg aggcgaataa agttatttta aaaaatggag aagcggtcct agtaccggcg 127740
gccgatttta agccctttcc tgatcgccga ctagcggtct ggatcatgga gtcaggctct 127800
atgcccctgg agggtccccc ctataagcgg aaaaaggagg gtggggggaa tgacccgccg 127860
gttcctaagc atatctcgcc gtatactccg cgcacgcgta ttgccattga ggtggaaaag 127920
gcctttgatg actgtatgcg tcaaaactgg tgtagtgtca ataatcccta tcttgccaag 127980
tcggtctcct tgctgtcttt cttgtcgctc aaccatccca ccgagtttat taaggtactg 128040
ccgcttatag actttgaccc cttggtgacc ttttatctac ttcttgagcc ctataaaacg 128100
catggggatg actttttaat tccggaaacc attttattcg gccctaccgg atggaatggt 128160
acagatctgt atcaaagtgc catgctggag tttaaaaagt tttttaccca gattactcgc 128220
caaaccttta tggacatagc cgattcggct actaaggagg tagatgttcc catatgttac 128280
tcggatcccg aaaccgtaca ttcctatgcc aatcacgtgc gtactgaaat tttgcatcac 128340
aatgccgtca ataaggttac aacacctaac ctcgtcgtgc aggcctataa tgagctcgag 128400
caaaccaata ccatacgaca ttacggccct attttcccgg aaagtaccat caacgcactg 128460
cgtttttgga aaaagctgtg gcaggatgaa cagcgatttg ttatccacgg cctgcaccgc 128520
acgttgatgg atcaacccac ctatgaaacc tctgagtttg cagagatcgt tagaaattta 128580
cggttttcgc gtcccggcaa taactatata aacgagctta atattacaag tcccgctatg 128640
tacggcgaca agcataccac cggagatatt gcgcccaatg atagatttgc catgttggtg 128700
gcctttatca acagtactga ctttttatac accgcgattc ccgaggaaaa ggtagggggg 128760
aatgaaaccc aaaccagtag ccttacagac ctagttccaa cacggctaca ctctttttta 128820
aatcataatc taagcaaact taaaatctta aaccgcgcgc agcaaacggt tagaaatatt 128880
ctttcaaatg attgtcttaa tcaactgaaa cattatgtta aacacacggg aaaaaatgaa 128940
atactaaagt tacttcaaga ataagtatgt tgatacctgt ggtgtgtttt acctgtgggt 129000
ttcctattgg aacctacgcg gcaatttttg acaaggctcg taccgagtat attaaaacca 129060
aaatgggcgg aacattgccg caaaatatcc cattagatgc ttctctccag attgagttaa 129120
aagacctcat tacagctctg ggaatcccaa tgcgggtgtg ttgtcgcact catttaatta 129180
ctacgttgga ttatcgtaaa tattattaat atctaaaatt gaaaaaatat ttttaatgtt 129240
actagtaaaa atgactacac acatctttca cgcagatgat ctcctacaag cattgcaaca 129300
agcaaaagca gaaaaaaatt tttcatctgt attttcttta gattgggata aattacgcac 129360
agcgaagcgt aatacaacgg ttaaatatgt tacggtcaat gtcatagtaa aaggcaaaaa 129420
agctccgcta atgtttaact ttcaaaatga aaaacatgta ggaaccattc ctcccagtac 129480
cgatgaagag gttatacgga tgaatgctga aaatccaaag tttttggtga aaaaacgtga 129540
cagggatccc tgtttgcagt tcaacaaata caaaatctcg ccgccattgg aagatgatgg 129600
tctcactgtt aaaaagaatg agcagggtga agaaatatac cccggcgacg aagaaaaatc 129660
taagttgttt caaattattg aactgttaga agaagccttt gaagacgctg tgcaaaaagg 129720
tcctgaagcc atgaaaacga aacatgttat aaaattaatt caaagaaaaa tttctaatag 129780
cgcggttaaa aacgcagaca aacctttgcc gaatcctatc gcacgcattc gtattaaaat 129840
caatcccgct acaagtatac taacaccaat attgcttgat aaaaataagc ccattacttt 129900
acagaatggt aaaacaagct ttgaagagtt aaaagatgaa gacggcgtta aggccaatcc 129960
ggataatatt cataagctta tagaatcgca ttctatacat gatggcatca ttaatgctag 130020
atctatttgc atcagcaata tgggcatttc atttccgctt tgcttggaaa tgggagttgt 130080
aaaagttttt gaaaaaaata atgggattga tgtgaactcc atttatggct cagacgatat 130140
ttcaactctt gttaatcaga ttgctattgc ttaaacaatt tgctcaaaac aagcttataa 130200
acgtttctta ggtatgcgat acgtaaatcc taattcttta ataagttctt tttcagtagt 130260
gatttttaga ggtactaaag tttgattttt aaataatcca tactgattta gcttataatt 130320
cttttttttt aacgcagctc gaattcttat taaataagaa acgggacccg taaaatgaag 130380
tactgcgtat ggcttttcct cggctaaggc cgtaaaaaga tcaagttgat atgtgttttt 130440
tttccattca ataaaaagta cacactttcg ttctccgcag acttttacag aaaaagaaag 130500
atcctttatg cgaatgttgg gcaggacgtg ttttaaaagt ttttttctg gaacaataat 130560 aagaagatcc acgtcattaa gcattttctc ttcgcgtctt aagctaccaa cagcaacgat 130620 gtttttgat aaaattttta taagttgtcc attatattca aacgcaagtc gggagcgtaa 130680
gtcatttaca attttttttc cttgaataag cgttaacatt ttatatttaa tattaaaatc 130740
ttttcatttt atatattata tacgcaaaat ggcacttgat ggttcaagtg gtggaggctc 130800
taatgtagaa acattactta tagtagcaat cattgtggtt attatggcaa tcatgcttta 130860
ctatttttgg tggatgcccc gccagcaaaa aaaatgtagc aaggctgaag aatgcacatg 130920
taataacgga agctgttccc taaaaacaag ttaaaacatg caattatatg catgcatata 130980
aacgcatgca tataaacgca tacatataaa atgcgtaaat actatataaa aaactataac 131040
atatcaatca aggaatcaac acttttataa ttttccgtaa tatatttttc atccataatg 131100
atgtcagagt acatggtccc tatgcgagga acagagccca taagggtagg cgcggcaata 131160
ccgtaaatgg gattcacggc ggagtcaacc gcagcatctg tcaagacctg gactggagac 131220
gacaaggcca ttcgcaacaa cacgttggaa ggctctcttg cattaagccc tgccttttct 131280
agagaggtaa cctgtcccgt tcttgtcatg agatctgcgt acatgagtaa atgacgatgg 131340
ttgggaccct tgtcccccat aaccgttcta atttcactaa taattttttg ccgtgccgct 131400
tctatgccgt aaagctccat ggtgtctcct atagaggacg atacgatggt gtatgggtcg 131460
atgttatcat caagcattgc gccaaaaata ttagtcccgt ttgttttgat ggcgtagata 131520
ttgtctagtc ttaccagttt cccctgggca tccacacggt ggcgcataag cttaacaaca 131580
ttcgcatttt tgatgcctgg tattcctcta atcgtgctat ttaatagttt atccaccaca 131640
tttacggcaa ttttttcatc cgtagccatt cgggtattgg tactgcgtct aaaggcgctt 131700
tcccgtaggt atatgcgaat aatgatggga atccctgagg ccgtgttttc cacagaatgc 131760
atgatgtagg tgttggggtg tttagctctt agactattaa taatactttc tagactaatg 131820
ctttttaata tcatggttgt tttgtttaat tccaagcgga tacaccagtt tgcaatatcc 131880
tctgggggct gtagtagagg atggttttcc agaaaatccg tcatccattc cacatcactt 131940
gcaaaatcgg ggtacatcac attttttttt gtgcttgaat acgtttcgta caataggtgc 132000
cactgcaata tcaaccgttc gaacgttata agctctatgc tgttagcaat ttcttgcgca 132060
tatgttttat ttgtttccac ttccgggttc tttagacgta aaagcatttc agaggattgt 132120
tcagcctcta cgggcttcgc gctaaagatc tcctggggcc gcacaattcc cgacttgttg 132180
gttcccccgg ccacggaccg gtggtgggag tccagcatat attgtgtcaa gggctctgat 132240
acggactgcg ccgccaggat tcccactgcc tcaccgtagt taataagact ttgagtatat 132300
tgtagcctta tgaggtccag gatggcactc atctgctcgc aggtaatgtt taatgtttta 132360
acggttgcca gttcgatgcg aataagcatg cgcatcagag aggcagcccg tttaagataa 132420
acgggtatgg gcgtttgtag tcgttcctga atgttgttaa taaacacgta tggaagattt 132480
ttgcaaaacg ttttgaccat cgcgtatttt tgtagaatac ttttttcgtc gaagggaagc 132540
acgccactgg tggagctcag tagaatgttt tttacgatgc tggccacgtt taccggcacc 132600
tgtctaacat ctgtaagcag ctgactgaaa ttaaaatttt cgacgtttag gaagatctgt 132660
cgatatttat ctctatcctt tttaaggcgt gaaaattctt cttcaaacaa gggcgattgt 132720
atcccggtgt acttgaattt gtcttcaagt tcctggtccg acagcatgat ggtttcaaac 132780
cgtacggttt caagctggcg cgcatcaagg ccgtcctctc cgtacaactg ctgcacaaga 132840
cgcgtatcga tggaaacccg tcggtaataa tccacaatac aggattgaag gccaaagatg 132900
gctttacggt tggcatagcc tgtggatgat gtcgataatg ctttgttgat caagtcgaat 132960
cttccattca tttccccaaa gataaattca ggggaggtaa ggcccgcaat atagctgttg 133020
cagatgaacc cgtaggcctg cgcctccagg gcaaacctgg ggtagtacac cagggtccta 133080
ccgaaggaaa actggggttg aatgcgttgt gtattaattt caatttggcc gatgcccgcc 133140
atgatgtgaa tcatattggg gtttgagccc ttggcgccag tggccaccat ctgaaaaagc 133200
ccattggttt ccggattaat ggaattcata atcggcttta aaattctatc gggaaattta 133260
agcgcattca gctgcaattt ttcgtagaag tcatgcgttg tcaggcctat aggcggcatg 133320
atgtctccat gaagcagccg gttgtttatt tcctccgact caagcagcag ttcattgata 133380
atttcttgga cctcctgatg tgcctccggg gttaggagca tgtcggccgt ggacactgtg 133440
aatccggcgt tgcgcacgta gtttagggcg agctgctggg tcgcaaatat cattttcaag 133500
gcctgctgcg gcccatacct acgcgaaata aggtgataga ttccaccgga ggaacccgct 133560
ccgacggcct ttttgtcaag gacgccttca atgagttcgc cgttgcgtat ttgtgtagag 133620
atgtcctgct tgttataatg catgtagggt gcatacactt ctgagtacca tgtgggggct 133680
cgttgataat tgatgggggt ctgcctcagt agcatagata caaccgattt gccatccagc 133740
aggtcagttg gggagtagtt ggcaaaacaa ggtgggtcgg tttgggttgt ttgaaacaac 133800
cccatggcgt gcagcttgtt catcacattt ttccccatgg gggtgttcgt gcgtgtaagc 133860
aaaaagcttc ccaccgtgga gtcctgcacc tgcccattaa cgggacccga gctctttgtg 133920
gaaatgaacc agtttcgcac agaacaaagt agttcggcct caacgcggct catgacgctc 133980
cagggaaccc agagattcat ctgatccccg tcaaagtccg cattatacca ggcacatgcg 134040
ctgacattca tttgaaacgt agaaattttt gggttttcaa gaacgacaat ccggtgaacc 134100
cctatgctgc ttcgttcgag agaaggctgg cgattaaaaa acgcgacgtc gccagtgacg 134160
acgtcacggt aaaggatgtc tcctacctcc agcctaaagt cttgtttgag accctcaatg 134220
tcgtgaacgg attgtgttat ttgcttatac actcttgaac aaccagggta ctggcgcttt 134280
ccatttaaaa aatagggcat taatctatta atattataat gttgcactgt ttccgcaact 134340
tgcagcgttc gtgcaaagga aatgggatag ccaacctcgt ccaggtgaag gtctgagttc 134400
ccgcagatgg tggaccggct gatcgaccat acctggctgc ccagtaggga tttacgaatt 134460
cttccctcct tgcgaggaag tcttcgcatg atggagggag cagggcgtgc ccccatgacg 134520
atcccacgct ttcccgtgcc tccctgggtt gcggtggtgg aaacggaatc caacaaaaag 134580
ttatagtaaa gttgctgtat ggtttgcaaa ttgcggtcaa tatttaaagg tattttttgg 134640
ccgcgcacga tttgtaggtc cttcgggatc agcagattct ttcgaaccag atactgaatc 134700
acgttgttaa tgtcgtgaaa gctttggggg cctgacccga ttcccaatct gatgccaggt 134760
cgtatgctga tggggggat ctgaatggcc ttaagcacaa gtttttcggg atgggagttt 134820
ttacttcgcc ccagttttac aacggtgtcg taggttacgc gcgaaaaaat ctctctgatg 134880
atctgcgggt acagtttgtc aatcttgccc tgctgatccg cccaaaaggt aaaataatct 134940
tccgagtcct taacaatttt ggggtgtact gccttacaga cgtagcactg ctttccttcg 135000
gtttggcttg aagccgcttc aataagacgc ttaggcctaa taaggtgctc gtacctcttt 135060
aggtcaacga tgggagcccc gcagttgaga catataaccc ttaaccatcg tcgtatttcg 135120
gcgatgaaga gcggctgaag caccggagca tgcatctgca gtatcccagg gtgtcccata 135180
cattgcttgc gctggtgtga gcaagtgatg catttataat ggtgatcggt ggttcccatt 135240
cgcgcatcat agataccccc ttcggcggga agggtgccct caaataaatt agaaatggta 135300
acctccataa cgccttgcct cttatgatca ttgtcaccgg caatattgaa ctgaacggcg 135360
gctatttcgg catatccagc ctccatattt ttgctaaata cataataaaa cttcaaatgt 135420
taaaaaaaaa taacatcggt tggcatattt ttttgttaaa accaagtgtt aaatgatttc 135480
taaaacattt atcggttcac gaaaacctac cgcacgggcc tgaagaggaa tgccagtttt 135540
gggggaaagc tcggcatatt ccacggtaag ctcttttcca taaagatgtt ttttaaataa 135600
ggcgggcgtg agtttttgaa aaagagcata acgatccgcg tacgtcaaat gcttaggagt 135660
gactacaaac cgctttttgt ttggcaattc gcaaacccat aaaatggcgc ctaagtcctt 135720 tcccttttttt ccctgagtat agtccactaa aataaattca gcgtctagca gcggtttcag 135780
cttggcaaga tgcgctgagt ggtagttgtt gtatcccggc tcatagggcc cattggcatt 135840
gcgtacgatg gctccctcgt agccctcctt aataaactgc gccttaagcc taagggcctc 135900
atccacattc ttcacgctaa aattttcaac ttggtggata aaggtaagat cttccttctg 135960
tttaaaaata tttgttaata gctgttgtct cttgttggaa ggcatttgaa gctgatcact 136020
ccaaaaacag tcaaacacgt aaaagtgcag ctcggaggaa tctgtcttcg cattcgcctg 136080
ccccgcgatc cattgcagag gtttgcggtg taaataaagc tcaccatcca aatatactct 136140
cacgtctata aataaataaa gctgtttgag ctctttttta atattgtcaa gacctaaaaa 136200
ttccttttttc gtgcgcgaat acaagagaat gctaccatcg ccctgctggc aggccacagc 136260
tcgaacgcca ttacgcttgc gctgcacgat gggatctgtt tcttcttcaa aaaatgtctt 136320
aggaattata ttaaaatatt ttaccagcat agggggggata attcctctat ttgtgtgggc 136380
tccccgcttt tgtctggcat ggcgattata tttactaagg gcgtccttga atgcctgatg 136440
gactaccgtt gtggcatttt ttttacccaa gtttttttccc tcggtaacac gtgtcatttt 136500
tgatatccgc accgcccctt cttccacaaa aaattttgtg aaaatttcag caacggcgtc 136560
ttttacatct gtggaaaaca tctcatctgt gatgggaatg atcgtgttgt gctgcaccac 136620
ttgcacacaa ataatccatg aggccttttt tccgcttttc gtttcagact caatcggagg 136680
aaaacaaaaa atgttgtttg aatattgccc aggaaattga tttagcatgg ttttaacaat 136740
aaaataagcc tatcaatttt tttataattt gaatagttat tccaaattca atatggcttc 136800
tttagataat ttagtggcac gatatcagag gtgctttaat gaccagtctc ttaaaaaatag 136860
tactattgaa cttgaaatac gttttcaaca gataaatttt ttattattca aaaccgtata 136920
tgaggcactt gtggcacaag agatccctag caccatctcc cacagcatcc gctgcatcaa 136980
aaaagttcac catgaaaacc actgccggga aaaaatttttg ccgtcggaaa atctttactt 137040
caaaaaaacag cctctcatgt tttttaagtt ttcagagcct gcatctctgg gctgtaaggt 137100
ctcgctggcc atcgagcagc ccattcgtaa atttatcttg gactcctcca ttctcgttcg 137160
gctcaaaaat cgtacgacct ttcgggtatc tgaactttgg aaaatagagc ttaccattgt 137220
aaagcagctg atgggaagcg aggtctctgc aaaacttgcc gctttcaaaa cgcttctgtt 137280
tgacacccca gagcaacaaa cgacaaaaaa tatgatgacg ttaataaacc cagatgacga 137340
atatctttac gaaatagaaa tagagtatac aggaaagccc gaatccctaa cggcggcaga 137400
tgttataaaa attaaaaaca cggtgttgac acttatttct ccaaaccatt taatgctaac 137460
agcctaccac caggccattg aattcattgc ctcccatata ctgtcctcag aaatccttct 137520
tgctcgtatt aagagcggga agtgggggct taaacgcctc ctcccccagg tgaaatccat 137580
gaccaaagcg gattacatga aattttatcc gcccgttggc tactatgtaa cggacaaagc 137640
agatggaatt agaggcatcg ccgtcattca ggacacgcaa atttatgtgg ttgcagacca 137700
gttatacagc ctaggtacca ccggcattga accccttaaa ccaaccattt tggacggtga 137760
atttatgcct gaaaaaaaag aattttatgg gtttgacgtc atcatgtatg agggcaatct 137820
attgacgcaa caggggtttg aaacaagaat tgagtcttta agcaagggca ttaaagtctt 137880
acaagcgttt aacataaaag cagaaatgaa gccctttatt tcgctaacaa gtgcagatcc 137940
caacgtgctc ctcaaaaact ttgaaagcat ttttaagaaa aaaactcgcc catattctat 138000
tgatggcatc attttagtag aacctggcaa ttcttatcta aatacaaaca cctttaagtg 138060
gaagcccacc tgggataaca cattagactt tttggtgcga aaatgtccgg agagtttaaa 138120
cgtaccagag tacgcgccca aaaaagggtt ttccctgcat ctactatttg taggcatctc 138180
cggagagctt tttaaaaaat tagcgctaaa ttggtgtcca ggatatacga aactattccc 138240
cgttacacag cgcaaccaaa actactttcc agtacagttc cagccatcgg attttccatt 138300
ggcatttctt tattaccacc cagatacctc gtcattttct aatatagatg gaaaggtcct 138360
tgaaatgcgt tgtcttaaga gagaaatcaa tcacgtcagc tgggaaattg taaaaatccg 138420
ggaggatagg cagcaggatc ttaaaaccgg cgggtatttt ggcaatgatt tcaaaacagc 138480
cgaactcaca tggcttaact atatggatcc cttttccttt gaggagctgg caaagggccc 138540
ttctggaatg tacttcgccg gtgccaaaac cggcatatac cgcgctcaaa cagcacttat 138600
ttcctttatt aaacaagaaa tcatccaaaa aataagtcac caatcctggg ttatcgatct 138660
tggaatagga aaagggcagg acctaggacg ttacctggac gcagggataa ggcatcttgt 138720
tgggatcgat aaggatcaaa ccgcgcttgc ggagcttgtt tatcgaaaat tttcgcatgc 138780
tacgacccga cagcacaagc acgctaccaa catttacgtg ttgcatcaag acctcgcaga 138840
gcctgcgaaa gaaatcagcg aaaaggtaca ccaaatttac gggtttccca aggagggagc 138900
ttcttccatt gttagcaacc tgtttattca ctatcttatg aaaaacacgc agcaggtgga 138960
aaacctggcc gttctgtgcc ataagcttct tcagccgggg ggaatggtgt ggtttaccac 139020
catgttggga gaacaggtct tagaattact tcatgaaaat agaatagagc tcaatgaagt 139080
atgggaggct cgtgaaaacg aagtggtcaa atttgctatt aaacgtctct ttaaagagga 139140
tatattacag gaaactgggc aagaaattgg agtcctgtta cccttcagca atggcgactt 139200
ctacaatgaa tatcttgtga acacagcgtt tttaattaaa atatttaaac atcacggctt 139260
ttccctagtt caaaagcagt cctttaagga ctggattcca gaatttcaaa actttagtaa 139320
aagtttgtat aaaattctta cagaagccga taaaacttgg acaagccttt ttgggtttat 139380
ttgtctgcgc aaaaattaaa tattttttca taagaagtac tacccaggtt ttaaagaaat 139440
agctaaaaat atcatatgga tactgccatg cagcttaaaa cgtctattgg tttaattaca 139500
tgtcgtatga acacccaaaa taaccaaata gaaactattc tggttcaaaa acgttacagc 139560
cttgcttttt cagaatttat tcattgtcat tactctataa atgctaatca aggtcatctg 139620
attaaaatgt ttaataacat gacaattaat gaacgactgc ttgtcaaaac actggatttt 139680
gaccgcatgt ggtatcatat ttggattgaa actccagtct acgaactata ccacaaaaaa 139740
taccaaaaat ttaggaaaaa ttggcttctc ccggataatg ggaaaaagct tatttcatta 139800
atcaaccaag caaagggctc aggaacactt ctatgggaaa tccctaaggg taagccgaag 139860
gaagacgagt cggaccttac ctgtgccata cgggagtttg aagaagaaac cgggattacc 139920
cgcgaatatt accagattct cccagagttt aaaaaatcta tgtcatactt tgacggtaaa 139980
acagaatata agcatatcta cttccttgca atgttatgta agtcgttgga ggaacccaat 140040
atgaatcttt ctttacaata cgaaaaccga attgccgaaa tttctaaaat ttcttggcaa 140100
aatatggagg ctgtacgttt tattagcaaa cgccagtcat taaacctgga gcctatcatc 140160
gggcctgcat ttaattttat taaaaactat ttacgataca agcactagga tgccgcatta 140220
aaatgccaca taaggtaata cactaggaat gtcgcacacg cacaagaata caacgtcgcc 140280
ggagatttat tatctagtac acgttttatg tatgtacaat ccgccttcat ttaatatatt 140340
gagcggatgt actatgtatt tattttaaca aaaaacatta ttttttttta atcttcatca 140400
tctgttttta taaactcagt aatatcaaaa gtagcttgtg gggtttcaga gggttcacct 140460
tggttatcct ccgtgaggat aacatgttct tcaggttcgt cgtcactgga gaacccatca 140520
tttaattcct cttcactcaa catctgtaaa aaatcttcca agctttcgct atcgttaaaa 140580
tcctcatcat ccataagaat aatggtacct tcctcatcgt ttcctccttg tttcgtgtct 140640
aaataggcct gcatggcatt tgcaaaagta tcaaaatagg ctgagtcaga ttgctgttcc 140700
aaaatatggc cttgcgtatt aaatgtggtt gcatcgttgt taaatgcttg caaatacagt 140760
aagggattta tatccattat tattaagcaa aaaaaattta aattattttt cgaccgatgt 140820
taggtaaaat taaacaattg ctataggtgt taagcaatgt ttattgattt taagtactca 140880
acaaccatga tgtaaatact atacagcact tttggatttt taatcaaatc cagattaata 140940
ctaacttctt ttgtgataca gttcgtaata atagtatcct gctcatcgtt ttgtaagatt 141000
tcttttaata tatttttttt taccgggata ctaagcaatt gattattttc ttttaaaaac 141060
tccttttgat attcaatcgt cttattcatt gaatatttgt atataactat aattacaaat 141120
gttcaatgaa ttgttattca tgtcgggaga tggctattta aaaatcatgt cctatttttc 141180
tttgctcaat aagcatccaa atattttcat ggcgttttat taattgttca ttattgaacg 141240
tatcacaaag atcatttata aattgcagat agtttattat ttctttcaag agagtaacaa 141300
acattacttc agcagaacat ataataggta attcagtggc gttaaaagaa ttttgatctt 141360
gttgatacgc caatggcgag gacttaagga gatttggggg tcttgcccaa aaccctaggc 141420
tgctgttctt gttttttagg gcgtcataaa gaaatgaaag cacattgcaa ggcttaagcc 141480
gcgacatctc cttccccttg ggccctttcc atatttttag atctaagatc tcatccgagc 141540
ttatagagta ggtatagtaa agtttttcaa aaaagcatat ctgcttgaag tctttttttag 141600
aacgactttc aagaagcatt tctataatgt taacaagttt tgttaggttt aaggcctgtt 141660
cctgtgtaag ctcctcttgc acgtgataga ctgaaaaagt gtgcttagga atgaaaatac 141720
tccccgtggc actggcctgt tgtctgccag gtatatagta cacgctgctg ttagcaagct 141780
gtaccggcac aatttgcccc acttctgcaa cattattttg cgattcggac gagggtatga 141840
caatagttac gggttcagtc aataggcttt cgccgagaat aatattactg tcatttttaa 141900
taattttaac ggccgctatt aaatcaaagg catttaagta agaaacaaca gcagaaaatc 141960
ttacatgcat atatcctctt ccgctattat tcgtacgcat aataaaacaa ggggagcgtt 142020
gtataacgcc agtaatatta agaataaaac tgtttttgaa acacttaccc acataaatgt 142080
tttcaagctc cttcaaaaga tgagcctcca catttgtaca aaaattggta ggatcatcaa 142140
tattcaacgt tgtctcaaaa attttttggt cgatcatatc tataatatat tctgtctatt 142200
tcaatttaaa taatatacga ataaataacg agattatttt attaaataag caatggtgta 142260
tacactttgt atttactttg agatatactt tgtgtatcac aacgtgccct aagatgtgtg 142320
cacaagtgac ggcattttgt cgttaaaaag gtaaaaccag cggattccat cctgcattcc 142380
atttggttga ttacgagcct ccatttcttt ttgcaaaagg ttattgcgaa tgagtaagca 142440
gagcttgatg gcactaatct ttgtaaggtt taaacttatg cccaattggt cagcaatttt 142500
ttgttgctcc tcccgtccgc gtgtttcgca tacggctccc cggtttagca tgcgaatatc 142560
agtaatctca ttcttttttta aaacctggat aggtgggcgg attttaaatt taagggcctt 142620
tcccttgctt tccatatagc ctatgacgat gtcgttttct tttcgtttaa cattaatatt 142680
aagcatataa agcggaattt catgccaggt tttatcttct cgcgaggtaa taagtcgcac 142740
ggagtcctcc gtggcatagc ccactagagt gttgtcatcc ccaggcacgt ggcttataat 142800
tttaaaaatg tccggaaatg gctgaatatc ttttttgaa aaagcgatga aaaacttttt 142860
ataaacctcg acaagggccc ccatacctgc aagattatct ataataagtg cttctagcat 142920
cgtatagtga aatgaagcgg ggtagtggat gagtacctgc tccattggct catcctgaaa 142980
atccttctga aacttttcat acaatacttg aaagggttct ttggtctgcg agtgttcgag 143040
gtatttggta atacggatgc tgtgcatcgc gggaggctga aaatcccgaa tatatgtttc 143100
aatatctaat accggttcct ttttatggtt aagcaccgca gcgacgtaca aatgctcagg 143160
ctttgccggc acatgcataa tggtgcaaag acgattctgt atccataatt ccttgcactg 143220 gtttttgag tagcatagag aaatgagcgc cagcgcgaag ttgtcctctg agaagagttt 143280
attatcgatg gtaattccct gtatgagctt gggagtggaa acagccttcc atagctcgga 143340
gtacgtccac acggggcgtg ccataaacaa agatataata atattagaaa ttgtttttac 143400
ctcttgctcc ccgtatccat aggcctcaaa ggtattgagg acggtggctc cgacgtttgc 143460
cggcgtgatg gatggactaa ggggcagact ttccaacata ggcttatcaa tcttaatctg 143520
gttggtgaac ccatcaatgg cgtgctttcg cagcgcctta tccccctcct gtattaaaat 143580
gtattctttt aatttttgtg cgtacttagc gagctctggc cctccatcgg gtgttgtcga 143640
tacgtacaaa taaattgtca cgttgcgctc actgggggg agctccatgt gtgaattttt 143700
tcgcaccacc ctcccaaata cctgaataag ccggggaata tcaaggggca atgacataat 143760
catctcgtac cgcacggcct gaaagttcaa accctccaca atcaccttgg acccgatgag 143820
aatacgcagc tggtggcctt ccaggttgga cgaggcgtta aaaagagcca ggcttcgttc 143880
gcgtacagcg ggctctattt cgctgtgcag aatggtgaac cgtactggaa taaactgatg 143940
gtcgctatgt gtgtgctcat cgcgaatcgc ggcgcagatg gagcagcggg tcgttcccac 144000
aggggacgaa acttcattta aaatgccatt actttgtaaa atttcttgca agataagaac 144060
ccccgacatg cggacccgat tgtggtaaat taaaattttc ccccggcctt gccgaataat 144120
ggaaagaatg tctttcatca tttgagtgta ttttccgcta taaaaggcca atcccgagat 144180
gtgcgttggt ggctgcagcg acaaaaagct gccactcaca ttaaaggggg ctctacgcga 144240
aggctcaata atctgtaccc cgttttccag aagccagtct gtgcttgcca tagaaagggc 144300
ggtgggggtt tccgtcgagt taaacaggcc gtaagccttg ggttccgttt gttttgaaaa 144360
ttttgggttg ggaaacacca tgtcataaat gctgtacgca ttactcgaga ttttagggtc 144420
agggcccagc tgtttaagcg tttcaagctg atactcagac atggggcatt cgatgaaatg 144480
taagtacggc aatgtttcgt ctttatagga caacatcttt ccggcaaata ttctttcggg 144540
gtaaaaattg gtgttggtat ccaacaaaaa agataccctt ccggtgctca gtctttccac 144600
aagagctagg gcgtcctttt tccatttaac ggaatgccca ctgctgtcaa acagttgctg 144660
gcgctggagg ggctggccgt tgggcagctc atgccgcgga accaaaaggt ttaacaggtc 144720
gacgtattcc atgacactcc cggttacggg cgttgccgac atgaagacgg ccctgggggc 144780
ctggtgaggt ggaaaggcat ccaggacata ctgtaaagcg atgccataat tatttcgttc 144840
ctggatattg tacacgttgt gtatttcatc cgcaatgagc agtcctcccc taagttgctc 144900
catgattttt tgattcaccc ggatgaggcc gtttgtctcg gcctcgctaa tttttgcac 144960 gaactgagat atatcgttct cattcaatgt atcttctgct tcgtcagaac gatgaaacag 145020
agaaagcaca tcaaagtttt tctcttcacc cttactcgta atattgaaaa gcttggatgc 145080
aaattcctta tagccgtaaa actgaaaaaa gcctccgcgg tttctatcgg ttaaacggcg 145140
ctttaacgta ctaacgaacc catttagatg ccgtgattcg accgacgtgg tgctgccaga 145200
ctgctttgca atgtgaagaa gccggtgtag ctcagcgacc tccttgtaag aaacaaatcc 145260
cagctcagga cgtcttagca tttctgtttg aatgatggcg cgtgtaaagc ctaccacaaa 145320
aatccagggc gcattttcaa taaaattcat gtagtggttc ataaattgac gcgcgatggc 145380
aatcgcggca atgctttttc ccgtcccggt ctgccagttt aataaaagac gcgagtaggg 145440
cgtgttggga ttttgaaagt tttggacgaa aagctgggca ttatgcaatt ggagaccctt 145500
gatggaagga aagggcgacg cgtaggggtc acacggaaaa aacgctcgcc ccccccttctc 145560
gcagccaggc ccaccgatct ggacaaaatg agcccgcaga tcacgaatga gctcttttttg 145620
gtcgacagga ggggaaatca acgatttaaa ctcctttctt cgcgccaact gctgcaaaaa 145680
gtctgcggca tccaattcgg gatacgccat attatcataa aaaaaataaa cctttttatg 145740
aaaactttta tgtgattctg tattgcaatt gttttttatg aatactgtaa ataagcgtat 145800
caacttgttt ttctaacgaa gaggcgttat tctttttttc tggatataaa ataataataa 145860
gtataataat taagactaaa cagcaggcaa tcactatcaa actcatatta tacttacttt 145920
tttataaaaa gtattatatc ttatgaatgc gcaagttcag ctaattgttc gtcgcttgga 145980
atgtgggact gcagggaggt ggagtttttc ctttttctaa agaataccgg gaaatggtgg 146040
tgaggctcag gttgttgtac atagtagcta ggaggaggtt taggtatgct cgacttgcag 146100
tcaatagtcc ggttatagta aacgatggca acgatgataa gaataataat gagcaaaatc 146160
aaaatgccca ggagaatcgc agttgttccg ggatatttgg cgattgtatg ggctaaaagg 146220
ccttgggtgc tttgtttaat tccctcgcgg gttgacaggt tatgagaaag cagtggagac 146280
gtttcagtgt ccatttatta caattgaaca gttatattaa tctcaaataa aatataacac 146340
aaaattaatt atggccatgc aaaagttatt tacgtatatt tacgagttta ttgaatatcg 146400
taagatggtg ctgttggaag aaaaggtacc atatgataag tttgttcaaa tggtacttaa 146460
tacaggattt tttcgtatta acgcggagac gctgaatcac ggaatcgtat ccgtgtttat 146520
ctttggagca aatggcaagt acgttcacca cggaggcgac atgagaacgc ttttaacgaa 146580
tacgcttaat gaaaaaaaac attatgaaga attaatttta atcgttgata agcccgtttt 146640
aagcaaaaaa aatattttag atataatcgt cgagcagcgc gctgcaaatc ccacgattgt 146700
aataaacata tatccctacc acctgttctg cattaacatt cccaaggtga gtgccattcc 146760
taaacataaa ctaattactc aggaggaggc gcaggagttt ttaggtcgcg aatatctgca 146820
accgcaggac ctcatgcaaa ttagcgcgtc agaccccccg gtggtctggc tgggaggaag 146880
accgggagac tttgtgcaaa ttgagcggcc ctcagagaca gctatgcacg ctgttgttat 146940
ccgctttatc accaagtcca aaatttgagt cccgtgttta aagatgacag acagctaagt 147000
aagcatatct gtaaaattgt cgatgtcctc tgtggataga gcgctttcct ctgagcagca 147060
aatttttca tacatctcca tgggggatgg cgaggcttta atagtatgta ggtcacgtaa 147120
gaactgttgt atgatgggat atttgtcttt taaaaactgg ggatgtttca taactggaat 147180
tatttgaaag ataaagacct tccatccaaa gtagccaacc acatttggca tttcgggaca 147240
cgcggtttca taaggcatag aatagtgaat agtgtactga tctttttgat acagcgtttc 147300
aagtagttgg cgaaatgttt ccgcgtcgag cgtgccaaaa tcttgaggag cctcggtgtg 147360
ctcctgtgta gagcagatcg tgatgattcc ccaggcaagc gggagcatgg actctggagg 147420
gtggatatcc gtattggtct cattattcga tcccagctga tgaatgccgc acacgcgaaa 147480
catggcctcg acgtagatgc ccatagagat aggcggcgaa agggcaagac cggattgtat 147540

-continued

```
ttgcggcata tagtaggagg gcaccgagtt ttttattttt cggttgaatg gggactttat 147600
ttctaccagc acggggatgc gtttcgtggc ctcatagcgt acgttgttaa aaattgtttt 147660
gatttcccag gactgttgag tgtatcccag cgttaggtga caaaacccat cggggctatt 147720
actatgtccg gggtatccca aataggtccc atcaatatga atattgtcac ctatgacggt 147780
ggtttggcag aacaactcaa gcagatcttt actaacacgc tcaaaaaggg ttccccagct 147840
acaagcagcg cggttcaaat tcttcttaaa aagatttgct ttttccgcca aggttatata 147900
atagcttttg taagggttta aacctaaaac gctggcaagg tcagagccac ccacctgagt 147960
gcgacgaata gcatgccagg catcggagcg ctgctgagga gagtctttaa acaggcgtac 148020
aaaggtttcc attatacttg ttttaacagg aattcaatat aaaaagtcaa cacagtttgc 148080
aatttttcca atctcaagat atagccatac attttttttt ccaattggcg aatatgttta 148140
agctcatgtg tttcaatatt agcatccgga aatttaaatg cataaagatg ttcaaaggcc 148200
tgatttatac acgtatcaaa ggatctgtgg tatgttatta gcttcagcat gtgtgccaga 148260
tcttcaagat ggtctaaatt tatacggttt tccacgtggt ggatcatgtc tgccacatct 148320
tgagcccccca tccaggggat cacaaggtac tccccccttaa agatgattcg tcgttttttt 148380
aaaaaatcat gaaaacgttt taaagcttca agaaaggggc agttgggctt tgaccccaaa 148440
atgctgacga cgatatcctc gggcatgatg tattcgcagt gaggatagta gtttacggac 148500
tctaattcag cggcccgccg ttttatttcg tatcttgccc agttattcag agagtactcc 148560
acgcctccga ccacaacaga catcctatct attaaaaaat aacaataaaa accttatgaa 148620
atctatgtat agtggccgct aaaatgtcta tattagaaaa aattacgtca agtccctctg 148680
aatgcgcaga gcatcttaca aacaaagata gctgtttaag taaaaaaata caaaaagagc 148740
tcacctcttt tttggaaaaa aaagagacac tcggttgcga ttcggagtcc tgcgtaatta 148800
cccaccccgc cgtgaaggcc tatgcgcaac aaaagggact ggacctctcc aaagaactgg 148860
agactcggtt taaagcgcca ggacccagaa acaacacggg tcttcttaca aacttcaata 148920
ttgatgaaac gctgcagagg tgggccataa aatacaccaa gtttttcaac tgtccttttt 148980
ccatgatgga ctttgagagg gtccattata aatttaatca agtggatatg gtaaaggtat 149040
ataagggaga agagctacaa tatgtagaag gcaaagtggt caagcgtcct tgtaacacct 149100
tcggatgcgt tttaaacacg gacttttcaa cgggcactgg aaaacactgg gtagccatct 149160
ttgtggatat gcggggcgac tgctggagca tcgaatattt taattcgacg ggaaattctc 149220
ctccaggtcc cgttattcgt tggatggaac gggtcaaaca gcagctatta aaaatacacc 149280
acaccgtgaa aacgcttgca gttaccaaca ttcgtcacca acggtcgcag accgagtgcg 149340
gcccctacag cctgttttac atcagggcac gcctcgacaa cgtgtcatac gcccatttta 149400
tatccgctag gattaccgac gaagacatgt ataagtttag aacccatctg tttcgcatcg 149460
cataaactaa taaagtttga attctttata ggaataaaaa tggaagcgtt tgaaatcagc 149520
gatttcaaag agcatgcgaa gaaaaaaagc atgtgggctg gcgccctcaa caaagtcact 149580
atttcgggtc ttatgggggt ctttaccgaa gatgaggacc ttatggcgtt acccattcac 149640
agagaccact gccccgcttt gttaaaaatt tttgacgaga tcatcgtaaa tgccacggat 149700
catgaaagag cttgccataa caaaacaaaa aaggtaactt acattaaaat ttcgtttgat 149760
aaaggtgtgt tttcttgcga aaacgatggc ccgggaatcc ccattgcaaa gcatgagcaa 149820
gccagtctta tcgccaagcg cgatgtgtat gttcccgagg tggcttcatg tcacttttta 149880
gccggaacga acatcaataa ggccaaggac tgtatcaagg ggggaaccaa cggcgtcggg 149940
```

ctgaagctcg ccatggtgca ttcgcagtgg gccattctta ccaccgccga cggcgcgcaa 150000
aagtatgttc aacatatcaa ccaacgccta gatatcattg agcctcctac cattacaccc 150060
tccagggaaa tgtttacacg tatcgagctc atgcccgtat accaggaact agggtacgcg 150120
gagcctctgt ctgaaacaga gcaggcggat ctttccgcct ggatttacct tcgcgcctgc 150180
caatgcgcgg cctacgtggg aaaaggcacc accatttatt acaatgataa gccttgccgc 150240
acgggctctg tgatggcgct agccaaaatg tacaccctgt tgagcgcgcc taatagcacg 150300
atacatacgg cgaccattaa ggccgacgca aagccctata gcctgcaccc cctgcaggtt 150360
gcggcggtcg tgtcccccaa gtttaaaaaa tttgaacacg tgtccgttat caacggggta 150420
aattgcgtaa aaggagaaca tgtcaccttt ttgaaaaaga ctattaatga aatggtcgtt 150480
aaaaaatttc aacaaacgat taaagataaa aaccgcaaaa caacattacg agacagctgt 150540
tcaaacatct ttatcgttat agtgggttcc attccaggaa tagaatggac cggccagcgg 150600
aaggatgaac ttagcatcgc ggaaaatgtt tttaaaacgc attactccat tccttctagt 150660
tttttaacaa gtatgacaaa gtctatcgtg gatattcttc tgcaatccat ttctaaaaaa 150720
gataaccata aacaggtcga cgtagacaaa tatacgcgtg cccgcaatgc gggaggaaaa 150780
agggcgcagg actgcatgct actcgcggcg gaaggggata gcgcactttc cctgctgcgc 150840
acgggactaa ccctgggaaa gtccaaccca agcgggccct cctttgactt ctgcggcatg 150900
atctccctgg gaggagtcat catgaatgcc tgcaaaaagg tgacaaacat tacaacggac 150960
tctggagaaa ccattatggt gcgcaacgaa cagcttacca ataataaagt gttgcaggga 151020
atcgtgcagg tattgggtct agacttcaac tgccattaca aaacacagga agagcgagca 151080
aagctgagat acggctgcat tgttgcgtgc gttgatcaag atctggatgg gtgtggaaaa 151140
atccttggac tgctgctggc ctactttcac ctgttttggc ctcagcttat tatccatggt 151200
ttcgtaaaac gactgcttac cccgctgata cgtgtgtatg aaaagggtaa gaccatgccc 151260
gtggaatttt actatgaaca agagtttgat gcctgggcaa aaaagcagac cagcttagcc 151320
aaccataccg taaaatatta caagggattg gcggcgcatg acacccatga agtaaaaagc 151380
atgttcaaac attttgacaa catggtgtac acgtttaccc tggatgactc agcaaaggag 151440
ttgtttcata tttattttgg cggggagtcg gagttgcgaa aaagagagct ttgcaccggc 151500
gtggtgccgc tcaccgaaac ccagacgcag tccattcata gtgtccgacg aattccttgc 151560
agcctgcatc tgcaagtaga taccaaggct tacaagctgg atgccatcga gcggcagatt 151620
cccaacttct tagacgggat gacgcgggcg cggcgcaaaa ttttagccgg gggggtgaaa 151680
tgcttcgcct ccaacaaccg tgaacgaaag gtttttcagt tcgggggcta cgttgcagat 151740
cacatgtttt atcaccatgg cgacatgtcg ttaaacacaa gtattataaa agccgcccag 151800
tattacccag gctcctccca cctctatccg gtattcatag gcataggaag ttttggctcc 151860
aggcacctgg gaggaaagga tgcaggatcc ccaagataca tcagtgtgca gcttgcgtct 151920
gaatttatta aaacaatgtt ccccgcggag gactcatggc ttctccccta cgtctttgag 151980
gacggccagc gggcggaacc agagtactac gtgcctgtgt tgccgcttgc tattatggag 152040
tacggcgcca acccatcgga gggctggaag tacaccactt gggcccggca actggaagac 152100
attttggcct tggtgagggc ctacgtcgac aaagacaacc caaaacacga gctactgcac 152160
tatgcaataa aacataagat tactatactc ccgctgcggc cctccaatta caatttcaag 152220
ggccatttga agcggtttgg ccaatactac tacagctacg gcacgtacgt catctcagag 152280
cagcgaaata taattactat tacggagctt cctctgcgtg ttcctacggt tgcatacatc 152340
gaaagtataa aaaaatcgag taaccgcatg acatttattg aagaaatcat cgactacagt 152400
agttcagaaa ctattgaaat tctggtgaaa ttaaagccaa atagtcttaa ccgtatcgtg 152460
gaagaattta aggagactga agagcaagat tccatagaaa attttctgcg cctgcgcaat 152520
tgtttacatt cacatctaaa ctttgtaaaa cctaaaggtg gcattatcga gtttaacacg 152580
tattatgaaa ttttgtatgc gtggctacct tacaggcgtg agctttacca aaagcgtctt 152640
atgcgtgagc acgcggtgct taagctgcgc attatcatgg aaactgctat tgtacgctac 152700
atcaatgagt ctgcagagct aaatctttcc cattatgagg atgaaaagga ggcaagccgc 152760
attctaagcg agcatggatt tcccccgctg aaccacacgc tgatcatttc ccctgagttt 152820
gcctctatag aggaactcaa tcaaaaagca ctgcagggct gttataccta tatactatct 152880
ttgcaggctc gagaattgct tatcgcagcc aaaactcgtc gggtggaaaa aataaaaaaa 152940
atgcaagctc gtcttgataa ggttgagcag cttttgcaag agtctccctt tcccggcgcc 153000
agcgtatggc tggaggaaat tgatgcggtg gaaaaggcta ttataaaagg aagaaatact 153060
cagtggaaat ttcattaaac gctaccggtt ttatgatgtc caataggtgt taagcaatca 153120
gttcatcaac attttttca agaatttgaa aagtttggat aatgttctga atactttttt 153180
ctaaaagagt tatcaaatct tcttgtgagg ccttatgaat aattgttaat accatttctt 153240
gcttatgggg aacacactga taccccacaa agctaatatc aggaatcatt tcataaatat 153300
atgtttttag cagatttccg atggtatggg tttcatcttt tatcgtgata atggcctttg 153360 tttttcctc atccatggaa aacagcacaa gttccggctg cggctcttca aagttttcat 153420
aaattttttg aatgctttgg attcggccaa taatgatccg gcaggcgttt tttaaatacg 153480
tgcgaacggc ctggttgata tgtggcagcg gcaccgctgg aaagcaaagc cccaggcggt 153540
ggtgacgcgg gtctgaggtc atagagcttt gcttgtaacc gctaagcgcc atatattctt 153600
ttttatccgt tgggtactgt tcaatgtcaa ggtgggaaaa atgtgtttta acggcaagat 153660
taaaggcggc atgctttcgt cctatgccct ttttaatata gatatcctct ataatcaacg 153720
attttccggg ttgtaggaag ccaatctcaa aggtaggatt aaaaatcggg tatttaagct 153780
tagggcctgc cacctggatg agatcgcggc tatagatggt tttaacctca cagctattgt 153840
ttaaactccg cagagcaaat accagtgtct cgtttttcgc ataaatcgga atgaaattaa 153900
tgcggtttct aataaattgt tccgtcataa acaggtccgt ggaatcctcg atcttatacc 153960
caccgggctt aatatctagc atataattgg gaatttcatc ttgcaagacc cgcgacaggc 154020
cgtggaccgc ggctctgcta atgcccttaa agtccataac aacattgacc gggacgaggg 154080
gcaactgctc ctcgagctga aatagttttt tggccgcatt tttaataaag aggttggaaa 154140
agtctatcaa aaacggtttg atttccacgt tttggaaaat tttttccatt tgtattataa 154200
atatatctat atatattcaa attatggtag tttatgactt gctcgtttct ttaagtaagg 154260
aatccataga tgtgctacgg tttgtagagg caaaccttgc ggcgtttaac cagcagtata 154320 ttttttcaa tatccaaaga aaaaactcga tcacgacacc ccttctcatt acgccgcagc 154380
aggaaaaaat ttcgcaaatt gttgagtttt taatggatga atataataag aacaatagaa 154440
ggccctccgg gccgccgcgt gagcagccca tgcacccatt attgccgtat caacaatcct 154500
cggacgaaca gcccatgatg ccgtatcaac agcccccggg gaatgatgat cagccatatg 154560
agcaaatata ccataaaaaa cacgcgtcgc agcaagtaaa tactgaactg aacgattatt 154620
atcaacatat tcttgcatta ggcgatgaag acaaaggtat ggacagcatg ttaaaacttc 154680
cagaaaaggc aaaaagggat agcgatgatg aggacgacat gttttctata aaaaactaac 154740
gacgtaacaa ttaaacaaaa aataaaaatc attataaaat gaatcttgaa tacgtccaag 154800
ttgttcaaaa atttaatcaa gtactcctag aacttaccaa aaaagtatgt accgttgtgg 154860
gcgggagcaa acccacctat tggtatcacc acattagaag ggtttgctca gaatgtccat 154920
ccatgccgat gagtatgata ggtccgtatc tgaatgtcta taaagcccaa attctaacaa 154980
gggacaagaa ttttttatg aatttcgatc ccgcgcataa tgagtacacc tttatcattc 155040
aaaaactaaa agaagcagcc cgaaatatgc cggaagacga attagaacag tactgggtaa 155100
aacttttatt tttacttaaa agctacataa aatgtaagcc ctttattaat taaagaattg 155160
atgcataact aataaatggc cggtcgtgtt aaaataaaac agaaagagct catagactct 155220
actgtaaaaa acaaaaatgt gatgaatctg ttccatgaaa ttataggctc aaaaggcaat 155280
attaatttta gcgttgtctg gcccaagttt aaaaaaatca aacagagcgt ttatgactac 155340
atttccactc tttctgtgct ggaaaaagca aacgttatgc aaaactttga agctgataag 155400
aaactgttgg aactttttgt acaaaagctg tgggctgcct atgaaggcta tttcaaatat 155460
cccgagattg aaaaatatga ggtggaaggc caggtaaatt tcaatctcgt acctcagtgc 155520
gtcctcgaaa agtttagcca gttgtatagg ataagaatca attcagagct tgtcacactc 155580
atcctaaaca gctgtgcctt tatgagtaaa tataacgatt atattctcaa aaaagatccc 155640
tacatactaa ccataacccc cggcctatgc ttttccccca ttcccaactt cgaggaccta 155700
aattttaaac atctttacaa cagtgataaa aattctcagc atgacaaaga gtttatcatg 155760
tttatattat ataagcttta tacggctgcc ctaggagtgt acaatgccat ctcgattcca 155820
gacatcgacg tagaagacct tgaaaatatc atcctatcct cggtgagcca gattaaaaaa 155880
caaattccgc gctgcaaaga cgccttcaac aaaattgaat cttcggtaca cctgttgcgc 155940
aaaaatttta acacatatta cagtgactat gtgggctcag gctacaaccc aaccatcatt 156000
atggaacagt acattaaaga catatcacag gattccaaga acatatcacc acgcatttcc 156060
taccagttta gaaccatcat caagtattac cgcgacatga ttgccaccag gcatcaaacg 156120
atggaccccc aggtattaaa cctcgtaaag cacgtcgaaa agaaattaga tatgcttgat 156180
agagaaaaaa attagtatat atagttatgg tgaatctttt tcctgttttt accttaattg 156240
tgattattac aattttaatt acgactcgag aactatccac cacgatgctt attgtttctc 156300
ttgtaacaga ttatattatt attaatacac agtatacgga acagcagcat gaaaacaata 156360
catttttcat gccgcaaaaa aattctttta acgaatctta taataaagac aaaaaatcta 156420
atatacatat tccctaccag tggctggcgc ctgaactgaa ggaagctgag agcaagtact 156480
ggtggggcaa ttatgatcct catagcgagc ccgttctcgc tggcgcatct tgaatatctt 156540
catacgtggc acgtcaccat caaaaacatt gcccaacagc acgggcttga tataaaggtg 156600
gccattgtgg tctcaacatc gcatttaaat aattttttgc caatttccgg ggcgcttaac 156660
atcgaatgta taaccttccc cagttgcggc atcaaggaga tagacctcct atgggcgcgc 156720
attaaactat ttcaacatta ctgcgccatc ggtgcccgtc ttttatggct ggtaagtgct 156780
gacatcaggc cccctgtttc agcgtggcca gccatcgccg acagtctaaa aaagggagca 156840
gatgcggtcg ttattcccta cccctcccga tggaacaatc ttatacctac cgtcatcaaa 156900
gaaatagttg tccaccaaaa aaaatgcctt gtggcggtgg atgcacgcca ccttgataca 156960
gatacccaga ttgtaggggc cgggatgggc tgcatcgtcc taaccctaaa ggcccttatg 157020
gtgcgcctaa gtattggcaa acagcccgtt aagatactgt ggcccgacct tcacggcact 157080
gccgagggca ttcctctgga gggggtggag gttggctggt ttttaaacgc ttatgcgcat 157140
aaattaaata tacgctgcct aggggctgat catattgcgc agcacttaac ttaattcttt 157200
atttaaaaag tccacgcatc cagtggcggc ctacattaag ggcctacgca cataaatata 157260
cactggctag aagtacgcct tcatttaaac cattgaatta tttatataat ggctgcaaac 157320
attattgcaa caagagccgt gccaaagatg gccagcaaaa aagagcatca atactgtctg 157380
ctagactccc aggaaaagcg tcatgggcat tatccctttt catttgaatt aaagccttat 157440
gggcaaacag gcgcaaatat cataggagta cagggctcac ttacccatgt tatcaaaatg 157500
acagtatttc catttatgat tccttttcct ttacaaaaaa ctcatataga tgattttatt 157560
ggtggacgca tttatttatt ttttaaggaa ctggacatgc aagcagtttc tgatgtaaat 157620
ggaatgcaat accacttcga gttcaaggtt gttcctgtaa gccccaacca agtagagctt 157680
cttcctgtga ataataaata taaatttaca tatgctatac cggtagtgca ataccttacc 157740
ccaatctttt atgatctttc gggaccgcta gatttcccat tagatactct ttcggtccat 157800
gtggatatcc tctccaatca tatacagctt cctatccaaa accataacct aacaacgggt 157860
gatcgtgttt ttatttctgg atataaacac ctgcaaacga ttgaattatg taaaaataac 157920
aagattttta tcaaaaatat accgccgctt tcatccgaaa aaataaaact atatatacta 157980
aaaaatcgaa tcagaattcc gctatacttt aaatctttaa aaacgtctaa gtaataacat 158040
ttttatagtc tactcctagt tccgaaatag gctgaatttc ttttttaagt cctttaaacc 158100
aaggatgtga tacaagactc ttaaaggaaa gccgcttatt ttcattaatt gttaaacatt 158160
ccgtgataaa ctgttttccc gtctctgaaa tgttctcggg aatataattt tcccgtttca 158220
ggatatcatt taaataaaaa ttttctgcac gaaatctaaa aagattaacc gcgaccatac 158280
ctatcgtcca cacggttaaa ggaagctggt agtaataacc ataataataa aattctggac 158340
acacgtattc ccatgttcca aacatattat attggggacg ggtttcgtct aatctaacag 158400
cgcttccaaa gtcaatgacc ttaatgatct tttgatttat gtctataata aggttctcat 158460
ccttaatatc cccatggata aagcccttct cataaatgtt ttgtataata agaataagct 158520
ggaatattat ttttttggct tcggtttcct caagtttttt aaagtaatga taatgaagta 158580
gatcaacact atttggaata tattctatga ttagtatatg atacatagca ttttcggtat 158640
attcgataag cttaataaca ccgggagtat cttgcagggc tttcaacacg atgacttcat 158700
ttcctggaat ttcttttttta gaaacgtact taaatataat gggttgccct acttgatgac 158760
ccaaaaagac gttatttctg ccaccctcaa acatgggtct cgtcgcaatg aaatacatgt 158820
gctgcgttgt ggagatcctt tccacctttg ctgtaggata aaacgcatat tgtgcctggg 158880
gatttttttaa catttttta agctgttgtt ccggcctgga catgttttat tagctttata 158940
tataaagggt tagaaggttt aatttcaata tatgccttaa tgatgggatt atattcgtaa 159000
aaggtatagc ctaatcctac gtctttgttt ttttggtaaa aaaactgttt gccctcgtag 159060
gatatgctat aggcttttac ttcggctttt acaagcggtt ggcagggatt gggcaaacgt 159120
aaatcgcgtt caaagttttc atgaaaaagc aaagcatttg tgggctgaca catcagacag 159180
ccgctttcgc cattgaaggc acattcaatg gccgcccttt ttagtaaatc gcggaaagca 159240
gaattaagat ggctcttttc aagccccctt tcgtgaaaac gctcatcaat cgttttttgt 159300
tcctgactgc cttcgggaat actataaaac attttttgat tagccaccgc gatgtacaaa 159360
aaaggctgta cggttttctc ctcgggcggt agcgcatcgt ggctaccaat gcgtataatg 159420
cgcgccttca cttgatcctc tcgggcctta tcccagtacg gctctaggat atgaacctgc 159480
cgcccgtatt tgagatccaa tccctcagct cctgttttag agacgagtaa aattttaata 159540
acctctccgt gtatattcag cggcgaattc caaagctgct ggatcatgtc gcgctcttta 159600
gataaaattt tccctgtaat aagcgtaaat cgtgttattt tggaggacag gactaacgta 159660
tgggtcggcc catcttccgc aaagtttttc accataagat ctttcccatc cttatgaagg 159720
aggatggtgt tgtgcccttc ttccaatact tttaggggct gaaggcactg gtagccctct 159780
atttctaaaa agcgggccac gacgtgaagg cccaattcca caaactgtga gtaaatgagc 159840
acagggcccg gagacgtttt aatatttttt agcatgcgta ctattttggg actagaattt 159900
tctgtgaagg cctctttggg cagctgctga acagcctctg ataatttttc atcctccttt 159960
actgttagca tttcggacgc gaagatgctg atcatacggg aacgcacata gtaggaggag 160020
cctgactctt gctccgatcc tggcaggcag agggcggcgg catttatttt ttcatacatt 160080
cctgagctgg cgtgcttttc cgcgttttca acgtctcggg ccagcagata ttgcctatac 160140
tgctcgggtg acatttcaac cttttctata ataagaggaa gctctgtggg gaatagcttg 160200
ttgagctcat tctggtttcc agcgtagctt atcataccca ctaggcggtt tagtagtttg 160260
tccgcgttta aagggctatt cgttgtttta ttgacataag cggtgtagaa tctttcatag 160320
tgaagaggta ataagattcg cccgcttagc atattaaaac agggcaccat ttcaaagggg 160380
tccttcgaac acggggtgcc tgttaaaaac agaatacgaa tatttttagc ttgcataata 160440
ttattgtaca gctggcgggc atttgtttta tcattggcgc tattgataat tcctctaaag 160500
aggttgtgtg cctcgtcaac gatgagcagg catccattta gggaccctcc cgcctttatg 160560
atctgctgcc ccatgttgta agcgtctagg gacacaaacc tgaagcgccg cgagattttt 160620
tgtagctctt tggagtgatc cgtcgtttcc ggatataaaa gtttaataag ctttaacaaa 160680
gactgttgga agtttgagtg caacgacttg ggtgcgatca gaatcgggtt gtaaatatgt 160740
gaaagtgaga tggcaagcga caggctcaaa atggttttcc ccatgcccat ctggtgatag 160800
atgaggaggc cccgtgtgtt ttccccctgg cctatcccaa atttaggatc cgaaaaggcg 160860
gtgtaaatta aaaactggta gtatttcagg gctcgtgcaa agcgggcagt gagtgaggtg 160920
tctttgcttt cctgaagctc tttatatttt tcatatacct cttttaggta tgcttctatt 160980
tggacgggga aggaggtgtt gttgtgcacg caagacatga ctcgttataa ggatcccata 161040
ttaaaacttc attagaagaa tagggctgct gatagctagc gctgcactta aaaatggggt 161100
agcccttttt cttgtaaatc cggtgcctgt cgtagacctg gctagaaagc gggcttagtg 161160
tatctttaat gtccacaacg atgcgtacct ttttttcatc cgatccctgc cgggtaatac 161220
gtcccaagat ttgctccatg ttgtttctgc ggggcgttgc catgatgatc gatgtcatat 161280
gcttgaagga aatgcctcta cgcccgtagc cataggtcag caagataatg gaagcgctgt 161340
gtgcctgaga aagagcggta tttgaaaccc cgccgcatag gagcgccacc tccggaacga 161400
taatttgaac atctttgaat tctttggaaa gcgcctgata aaaaatttct aaaagtttgc 161460
gaaattccac gaaaatgatg atgccatacg gctcatcggt cccccatttg tgaggctcag 161520
cggtatgcag ggagtaaagc cgctttgcct catttacgac aagttgtata cgcgaaggat 161580
cttgaagtag tttatcaatg gtggcaatgg ccgatacctt ttcattaata tacacagggc 161640
taacgaagtc aggatgtccc tgatattcga tttccctcac gtacccggaa aaggttgtgg 161700
tgggacttac agtcctctgg ggctgtccta gatggtgaat aataatcttg tccataccat 161760

-continued cgggccggtc caggggtgta gcggacagtc ctaatatccg actaagttgt attttccaaa 161820
aaattttgta attctccggc gagtgtaatt catgtgcctc atctaacacg actagaccaa 161880
agggctcaaa gaactgctca ggcttcttgc gcagggtatt aatgattccc acgatgacgt 161940
cgtactcttt gctcgtcatg tcctttttct tgcacgctgc attattgtaa gcagctacac 162000
gtaggtgggg caggagcaat gttagctcgt cgatccactg tatttgaatc gccttggtgg 162060
gcacgatgac cagggtaggg tacaaaagtt tttgaataat gctgatcgca atacgcgttt 162120
tccccaaacc ggtatttaga tgtaggtaaa agcgcccata gggggacagg agctttttat 162180
gaatcttatc gaccatttct tgctggtagt taaatagtgg aaattctgtt tcaacgcatg 162240
ggagggcccg cagcgacacg gggcgcgtcg tgtaaaccat gttaaacatt tcaaactgct 162300
tttgcagcaa tatgggaaaa taaatgtatt ccccctgcag cgtgaaggca gtttcctgtc 162360
ttatggctat gtgctttggc tgcccgggta atgcccgcgc cgtaacggtg agcgccttaa 162420
gaacgcgccc gaaatcatgt tgtaatttac tttgtagctt cttataattt attcctattc 162480
cagcaaagga tataatggcc tccattctca cgctggacgg gttatatgca gaggttccaa 162540
aattcttacc agaggcgtta cgagagggct gtgctggcaa gaatcctcta agcttttata 162600
ttcaacaaat tttaaattta atgggatgtg acggtaacga gtaccatgtt ctttttacca 162660
gcagctccga ggaagcaaat actcatatga tcatggccgc cgtgcgtcgc catttgctgc 162720
ggacgcagca aaggcctcat gtcattatcg gagcagccga gccccctagc gtcaccgaat 162780
gtgtgaaggc attggcgcag gaaaaacgct gcgtatacac catcatcccc ctaaaaaatt 162840
ttgaaataga tcctgttgcg gtatacgatg ccatacaaag caatacctgc ttagcgtgca 162900
tttcaggcac taatgctgtt gtcaaaacgt tcaacaaact ccaggacatc agcaacgtgt 162960
taaaaggtat tcccctgcac tcagaagtga gtgatcttgt ttatcaagga tgtattcaac 163020
aaaatccgcc cgctgatagt ttttcaataa atagtctcta cggcttcctg ggagtcggtg 163080
ttttgggaat gaagaaaaag gtcatgcaag gattggggcc gctcattttt ggaggagggc 163140
tgagaggcgg aagccctaat atacccggaa ttcatgccat gtataaaacg ctaacccagc 163200
aaaggccttc tatgaaaaaa ataaatacaa tacatacgct gttcatgaaa actttaaaaa 163260
aacatcagca tgtatatcta cccatagggg gcgtgtctgc agaggacacg tctgcagaaa 163320
acatatctac aaaagacatg cctgttgaag gcccgaaggg actcccgggc tatattttat 163380
ttagcgttgg ccgtcgcgcc gaggagctac aaaaaaaaat tttcactaaa tttaatataa 163440
aggttggccg tgttgttgac ttacaagaga tactgtttcg tatcaaaata ccccaaaaat 163500
actgggagac attattgttc atccaattaa gagataattt gaccaaagag gacataaaaa 163560
gagttatggt tgttttgatg catttagata ccatcactcc tcgtggctct cttcctcctc 163620
cgagccactc ttcttctttt tcttaatcgt ttttgtttgt tctataataa gggaaaagaa 163680
ctccgtggga tcttgttccc cgtacaggtt atctgcgacc ataaggatgc ttagaatggt 163740
aaacaggtga gaatacataa gggtttgcgt tttaagaaaa ccctgacgtt gaatcataat 163800
tgaaaacacc ttgcaaagcc gactcatcag ttgttctgta atggcgttaa gcattttctg 163860
gaatttttct tggttttcgg gtgtgatttt atattcatgt agaaagtgtt tcacacctga 163920
ggagaagaat ctttcctcct tcgagagccc atctttgatg atgggaagtt ccttgatcag 163980
ggcaaaccat tcctcctctt gggcttgcgg attctgaaga tactgatggc agatatggtt 164040
tagaatggtg cacacgtagc taataagctc tgagctgatt ctttggttgg ttttcaaatg 164100
ttggcgaaag tagtttttca ccgaagtgca tgtaataaac gtcttcattt tcttataata 164160
tacaacagta tgttgagtct ttaatttaaa attacaagga gttttctagg tctttatgcg 164220
tataggtgtt tctttgtcgt aaattttcaa tagccgacat tgtttgtgaa gcagtgttct 164280
gagtagtgac tgtcgtgtaa ggctcagccg gatgagcagg agcactcgcg gccgcaggtg 164340
cggccgccgg cccgccagtt gccatgacta gtctgtccgt aactgggttg tccgtaactg 164400
gtttgtttgt tgctggtctg tttgttgccg gtctgcccgt gactggcttg cctacacttg 164460
ctgtagtcgc tccagctggt ttagaggtac ctggttgtgg agtgacttct acccactgct 164520
gatcttgata aggatttata aactgtatat cttcctcctc aatagcagca gctttttttct 164580
ttcttgaaga gaatagatag attagaacga tgataatgat gactaagacc acgatagcaa 164640
tgagaatagt atacatatgt gtggagaaga agcttggtgt agtgactggt gacaaacact 164700
caccataatg ccgcggataa accggttgaa aaaattcaga atccatttaa gatactatta 164760
taaataatat ataaaaatgt tgtggcgcaa tgaaattaca gaatttatgg accaactttc 164820
caagtattct caagaaatct taaaaacgtt taagcaattg cgtcctagtg aatataaaca 164880
atacaatgaa tttttaacac aagttacacc gttgctgcaa aaaacccctg aaaaaattcc 164940
agagttggtt gaccatatat tcaattacct agacaacgtt gaaaaaattt gtgagctcct 165000
cgtgaatgct agctcaatta ttattagttc aaaaatacga gaacaagtaa aacacggaat 165060
gagcttcagc tataaagccg acctcgactc cttggcggac attctctctc aaaaacagta 165120
cgtgcttatg catctttcaa aaaatattgc ggccgagtat tttaatacgt gtttaaacca 165180
agggaaatcc aagttagatc tcaaagctgc ctctgtattt tatagtagtc gttcccgaac 165240
ggcaagctca gcagaactct atagaaaaat gctatacgcc tatggttcac cgcaggaaat 165300
taattattat actgaaaaag cccgaaataa gacgttggat gtggaggaga gcgacagcat 165360
ggccatcatc gaacgaacgg cccgacacaa cctttccctt atgcacccgc tagaagccat 165420
ggggcttacc tttggggcaa ccaacacgga cgccgacccg gaggatctga aggacaaaac 165480
ggtgataaat ttaacgctcc cgcaggcaac agaaagcatc acctaccatc ttaaatccct 165540
aatgcagcta aaaaaagtaa gtacggcttc aggactaaat acaaacattt tgaaagcatt 165600
tgataatatt atttccaccc ctgtgaaaaa aaataaaatg gcctccaagt tggcgcccgg 165660
gatggatgtc gtgttcacta gcgataacgg aaaaacattt tttactaaaa acattttaag 165720
caaaaacatg ctagcggggc ccaaagagcg ggtgtttgca tataataatc tcattagtaa 165780
tttaaataac tcctgtttca tacaaaatca caacgatttt ttaagacagc aggactcttg 165840
gcccttctat gacgcgcaca attttaccaa caagttttta atgcagccta ttttttcggg 165900
gcagacccgt cctcggcttc agggagccat ggaggcggcg catgtggaaa cgcatctcac 165960
ggcattttta caaagtattc agccctctag gccacaagat ccctctgttt tggcttcccc 166020
caagttatct gctctaatct tgaactaaaa acagcctttc ttggacttaa atgatggtct 166080
accagttttt gaaataactt agagaactat gaagattttc atgaaattta aattagagat 166140
ttgcaaaggt tacttgcggt cattttctgt tgaattaaat aattattcga atagtataat 166200
gtctgaagat attcgtcgtg gtcctggcag accgccaaag aaaagggttg ttcccaactt 166260
tgagcgcaag ggcattctgg aaaaaccagt tcggccacaa agccgtctcg agttttccta 166320
tgataacccg ctgatattta aaaatctttt tatttacttt aaaaacctta aaagtaaaaa 166380
tattttggtg cgatgtaccc ccaccgagat taccttttttt tcacgtgacc agtcgcaggc 166440
aagctttgtt attgccacca tcgacggaaa aaacgtgaac cattattacg ccagtgatgt 166500
cttttggcta ggcatcaaca gagagctcgt tgaaaaaatg tttaacagca ttgatcgctc 166560
ttttttaaaa attaccatcg ttcaccgcta tgacaagcct gaaaccctgt tttttatctt 166620
tacggatttt gacattgaca aggagtgcac gtatcagatt acggtctcgg agcccgagct 166680
cgatatggac cttatcgaaa tggaaaaaag catcagtgaa gaaagactca agaactatcc 166740
tctgcgctgg gagtttacct ccaagcagct caagaaaaca tttagcgact tatcaaacta 166800
caccgagctc gtgaccattg aaaaactcgg cggcgatacg ccgctgcacc tgtatttcca 166860
aaagtttaac tccatctcat accacgagat gtataaatct tccaacaaga tcaacctgac 166920
ctcgaccatt cctaagtcgc aggtgttcca gataaatgtt aaaattgctc acatcaagtc 166980
gctggcctcg gctatggtca ccgacaagat ccgcattctg tgcgaagaaa atgggaacct 167040
aatctttcaa tcggaaatgg atgcccttat gttaaatacg attaccttga acaccacgat 167100
atagttcggt aacattagat gttctaatat ttagcatcta aataatacgc tgtagtccgg 167160
tcagggttgc gtcacagttt tcccattttt ttgcctcgtc ggcggtggcc accgttgccc 167220
tatcatttac gcccggtaag acaaagctaa aggcgttcag cggggcttgg caatgcccgc 167280
ccagcgtgaa ggagctcgga ggattttgcg catcccgaaa tcccttagcc atgttgttta 167340
acacttcggt tacgtcaatc gagtgaaggg atcccttggg atccgtgaat gtaaagacgc 167400
agtttctaaa gcgcatgtat gcgatggacg attcatcggg ggttttgaag gtaacagtgt 167460
tccccttgct gtacttaaag gggaccatc cggtaaaatt ataccaaatg aaagcaataa 167520
taattaaaat aaccaacaca atagttatag acaacacaaa gtctgtagtg ccgcccatta 167580
ttaaataaaa atattttaga ccgccggctt aaaatttact tattgctcat agcttaagtc 167640
tattttattc atagcttaag tttattgctc atggcttaag tctattgctt atagcttaag 167700
tctattttat tcatagctta agtctattgt tcatggctta agtttgttgc tcatagctta 167760
actccattac tgatagctta ctgatcatga cttaaataaa aatattttgc ccgcttaaaa 167820
attgtttagg tttgaaaaaa taagagatgg agggggcaac ttatcgtcat tgtgtttacc 167880
cccactggaa gacatcaaac ggtaaataat tataagaatc aaaatgatta atataagggt 167940
taaaaaagga tgattcatca cattaattaa aaacgtattt ataacgctgt tgcagttgaa 168000
attttggtat aggtcggaaa tattgcccga gcctccgtat tctgcaatgt tctgacatat 168060
ggtgagtccg gaggggcact gcttgttggt caaaatattt ctttgctccg ttgttttata 168120
ggcattttta tttccattac acggagcaaa cgcacattca ggccataggg tgccggagtt 168180
cacacaggca caatactggc tatacgcata ctcatccttt gagcacaatc cctgtttatc 168240
gcatatgctc ccaataatat tgtcatcctc cgccgtttgt tgatttgtat gcgagcgtaa 168300
aatagcggcc caggccttgg gctccttttt ttgcagctcg gaaatcgaag ggcctgtaca 168360
gctaaagtcg acccaaatat cattgcattt cgtggaaact ggcatgcaag acataattga 168420
aataattaat aagtatatat catggcaaca aattttttta ttcaacctat caccgaagaa 168480
gctgaagcat actacccacc ttccgtgata acgaataaac ggaaggacct gggggtagac 168540
gtatactgtt gctccgacct agtgcttcaa cctggactaa atattgttcg cctgcatatt 168600
aaagtagcat gcgaacacat gggcaaaaaa tgcggtttta aaatcatggc gagaagcagt 168660
atgtgcaccc atgaacggct gctcatcctt gcaaacggaa ttggtttaat agacccgggt 168720
tatgtgggcg agctcatgct caagatcatt aatcttggcg acaccccggt ccaaatatgg 168780
gccaaagaat gtttggtgca gttggtggcc caaggtgacc atgtgcctga ccatatcaac 168840
atcctaaaaa gaaaccaaat atttccgctg tttgcgccta ccccaagagg cgagggtaga 168900
tttgggagca cgggcgaggc cgggattatg agaacttaat tttatttttt ttcttaacat 168960
aatgggaggc tctacaagca aaaattcctt taaaaatacg accaacatta tcagcaattc 169020
cattttcaat cagatgcaaa gttgtatttc catgttggat ggcaaaaatt acataggcgt 169080
attcggtgat ggaaatattt taaaccacgt tttccaggat ttaaacttat cattaaacac 169140
aagttgcgtg caaaagcacg taaacgagga aaatttcatt acaaatcttt cgaaccaaat 169200
tactcaaaat ttaaaagacc aagaagttgc gttaacccaa tggatggacg caggaactca 169260
cgatcagaaa acggatatag aagaaaatat aaaggtaaac ttaacaacca cacttattca 169320
aaactgcgtt tcatccctgt cgggtatgaa cgtgctggtg gtgaagggga atggcaacat 169380
tgttgaaaac gcaactcaga agcagtcgca gcaaatcatc tctaactgct tgcaggggag 169440
caagcaggcc atagacacca caaccggcat cactaacacg gtaaatcagt actcacacta 169500
cacctcaaaa aactttttg acttcattgc agacgcaatt tcggctgttt ttaaaaacat 169560
catggtcgcg gctgtagtta tcgttctaat catcgtaggg tttatagccg tcttttactt 169620
tttgcattca cggcaccgcc atgaggagga agaagaagct gaaccactca taagcaacaa 169680
ggtattaaaa aatgctgccg tttcgtaata atttaattaa aagtaaaaaa aaaaggtatt 169740
gttatagtga tggcagattt taattctcca atccagtatt tgaaagaaga ttcgagggac 169800
cggacctcta taggttctct agaatacgat gaaaatgccg acacgatgat accgagcttc 169860
gcagcaggct tggaagagtt tgaacccatt cccgactatg accctaccac atcaacttcc 169920
ctgtattcac aattgaccca caacatggaa aaaatcgcag aggaagagga tagtaatttt 169980
ctacacgata ctagggagtt tacttcactg gtccccgatg aggcagacaa taaaccggaa 170040
gatgacgaag aaagcggtgc aaaacctaaa aagaaaaaac atttgtttcc aaaattaagc 170100
tcgcataaat cgaagtaaaa attgaagcga aaaaaagtag aaaaaaaatg tttggagctt 170160
ttgtaagcca ccgtttgtgg tcagatagtg gttgtacgac cacctgcatc acaaacagca 170220
ttgctaatta tgtagccttc ggcgaacaaa ttggatttcc ctttaaatca gctcaggtat 170280
ttattgccgg ccctagaaag gctgtgataa atattcagga agatgataaa gttgagcttt 170340
taaagatgat tgttaagcac aatctttggg ttgttgctca tggaacctac ttagatgtgc 170400
cctggtcccg taagagtgcg tttgttacac attttataca acaagaacta cttatatgca 170460
aggaagtcgg tattaaaggg ttagttttac acctaggcgc tgtggagcct gaacttatta 170520
tggaaggact aaaaaaaatt aagccggttg agggggttgt catttacctg gaaaccccgc 170580
ataacaaaca tcatacatat aaatacagta caattgagca gatcaaagaa ttgtttttac 170640
ggatacgaaa taccaggttg aaacagattg gtttatgcat tgatacggct cacatctggt 170700
cttccggtgt caacatctcc agctataatg acgcggggca atggctgcgc tcgctggaaa 170760
acattcattc cgtgatccca ccaagccaca ttatgttcca cctaaatgat gccgccacag 170820
aatgcggaag cggtatagac cgacatgcaa gtctttttga aggaatgatt tggaaatcat 170880
atagccataa aataaagcaa agcggtttat attgttttgt tgaatacgtt acgcgacacc 170940
agtgtccggc tatattggag agaaacctcg ggtcttccat gcaattacaa accgctttaa 171000
ccgcagaatt tactacatta aaatcgttat taaaataagg atgagtttta gcgaatgtcc 171060
cttagttatt agtgcatgca aaaaatttct acaaaagcgt attacaatag agaatgaagc 171120
acttataaat gccttaataa ccgctttagc gcagaccagc acgttgaatg atctttgttt 171180
attacctatt caaacctatt tgcttagtta taaaaatgct tttgagtgga tacacttcgt 171240
atgtattgca atcaccacta ttttggataa taagtataac tggaaggact gtacggtaga 171300
tattaattat atttttctcc atgtaaccta tatttacaat attaaaacca aggaatacct 171360
agactactgt tcttaaactt tattttttct atatttacgc caaagagaat atttaaagtt 171420
ttttttgaaa aaaaataata tatgtagata aaattcagtt acatgatata tgtgtaaaca 171480
tgtgtggtaa acaacatatg gttatgcttt ataagataaa tgcgcataat atatgtaaac 171540
aaaatatggt tatgtgttaa atgcatataa atgtatttta acgtatatct tgtgataatg 171600
gatatatgca tttattaaaa gaggctgtat ttattataaa tcttgctaag gatgccattg 171660
tcaacatata tcccatgttg gacaaattgc gttgcgatcc agttcttttt tttttgattt 171720
tgtttaatgc tatccttttt gaagggatgg ttgtccacca tatttattcg atgttcaatg 171780
aataggtctg ctttttcgta aggcagtgaa ggtcgttcca agactccttg aacgatggac 171840
gtgttttctt ggatccactt aaaaagcacg tggcattcaa aaacaggaca gtgattggat 171900
ccttggatat gctttggaca gccaatgctt gaagagatgt agtccctttt ctttaggaca 171960
agcttctcca cgctggggca acagagatcg ttcaagttct ggacggtcgc atttggaatg 172020
ttgaaacttc gtatccattc accctcgggt cctcccttat gaagaaggag tatttgctca 172080
tggtccttag taatcttaac caaatgttgg aagatcattt ttttacctgc tttaaaggcc 172140
tgaagggtgt cagttggcaa agctattgaa ttcgggagtg ggctttcatc aagcgtgaaa 172200
tggtgaatgt gacgcgactg gaaagaaaac gaccgttgat ttattttttc aaagattggg 172260
tcgattccgc catgaaagaa cagctgcaag attttagaag gcgtattttt ttcccaataa 172320
aaaatgacca cttctcgtgg gattaaaatc gtctgtgtcc cattttcatt atataattgg 172380
cccataaagc catcaacgtc aatcaacacc aaaagcatgg tatagagagc ttttagaacc 172440
ggagttcgtt aaaaaaatac aaagttcgtt taaaacgtgt aatgttacta aaaaaatgta 172500
atgtttaaat gataatgata ccacatgcat taatgaaaaa aacttttaaa tttttgtttt 172560
aatatttgca tgaaaatgga aacattttta gtctgtttat ttcacaatgc agatggttta 172620
catcaacaga ttcaggaaat tttgtattta ttgcggatgc atatttacga aacaaatctt 172680
tacttaaagc aggaactatc acggcttata tatccaaata ggcaactttc ttttgtgtta 172740
cttatgcccc tttcccttct aagaaactgg gatgacattg aatatttaac ggacgttgta 172800
gatgataagc agactctaca ttacgcggca aatttgctga caaactacgt tctacatcta 172860
tccatgtttc aaaagctgac aaaaccatac ttccttttag cggtcaagcg ggtcagcgaa 172920
aaactcaaca aaaagcagcg acattcattt tacgaggtat tggtaacctc cgaaaccttg 172980
aataattatg aaaacctatc taaaaacatt ttaaatacgt tgatgtttgc cgtgcgctac 173040
gtatttaaac ctacgccgaa ctattcagaa attctcgcag agttggaaaa aaaaaataaa 173100
attcaccata ttatttttaa tatggtaatt acggattttg cgcaaatccg tgaacaacaa 173160
atggataaac atctgtgtga aacaaataat gagcttcgtc aggaatgtaa agaaactatt 173220
tttgatttaa aggtggtagg aaatgtttag ccaataaact catgcccgca ttttttacag 173280
gtacaaaata tcgtggatgg ctcatcgagg gcgcgtgttt gtacttctct gtaggtacac 173340
atacgctgct tgcagttggg acacttataa agttgtgacg tcttttcggc gaccttttgc 173400
tgcgaacgta gagtaatttc tgtcttctcc tttaaggcgg cagaggggca aagctcggcg 173460
aacgtcatgc taccaattgc ctccggtttt agctcgccag aaattagctt attaagggca 173520
tcgttatcct gttgttggtg actttttttt tcgcagttaa taatatgatt gatcgtccca 173580
caacgggttg aatattcttc taaaaaggtt ttttcttgtt gctggtacgt ataatgataa 173640
cacgaggcct cgatttttg cgcgtattcg gtgcataaat cagtatgttc cttaaaaaac 173700
atatgttttt gaagcgttct aaaaaacatc atttggatga tatcacgcat ttccaaaata 173760
atatagggtt ctagtctttt ggaatctttc ataactagat cggtggtaat attcttagtc 173820
atacaattta ttaaaaatgg tttaatatat tgtaaatatt ttttaggcgt gtcagcctgt 173880
aaaaaacatt cttgttcaat cttatttgta aggatagtat tttgcaaata cttatttagc 173940
aaaaatacga tagaatcgcg ggctatatgc attttcatat aatttttttt ttaaaattta 174000
atacaaaaaa aagaagtata gactcttctt ctagtccggt tagttcgttg gttgcctcaa 174060
catggagact cagaagttga tttccatggt taaggaagcc ttagaaaaat atcaataccc 174120
tcttactgct aaaaatatta aagtagtgat acaaaaagag cacaatgtcg tcttacctac 174180
aggatctata aatagcatac tgtacagtaa ctcagaactt tttgagaaga ttgataagac 174240
aaataccatt tatcccccgc tttggatacg gaaaaactaa ttgtaaccag tagtacattt 174300
aaggatagtt taagcagtaa atgtagaata acacagttaa gcaataaata acaagtatat 174360
aggaatatat aggaatatat agaaatatat agaaatagct aagcttaata ctaattcagc 174420
ttttttttta actaaaacct gaatagatgc gaagtagcgg acatatacat actaaaataa 174480
gccatacatt tactttcttc ttgaacatga aaccttttt tcttctgttg ttggtatata 174540
aacaatagga ctgtttgctg aggttgtatg atcttctaca actgctgtct caggatgacg 174600
atgtttttt aaactaaaag tgtaggatgg aatgagtgga atatagttat ggctcgactt 174660
atcctgtttc gtacaggaat attttttaca aatagaacgc aacaagcata tgaataaaaa 174720
cagaaatgat atacaggagc ataaaataga tatgaacact aaggggtagc agcttttata 174780
acgttccgta tttttcttag ctatcaattg atttaccgta atatttatct cgggaaactt 174840
tgttctacaa tattttgttt ggtattccag aaactcatgt cctggcttat tcccgcagct 174900
taaaaaatga tacaaaaatg tgttattgtt actaaaatta attcttctta agaaaaactg 174960
cggaagacgc tttaggtacg tctgttcctg ttttagtagg aagtagtata agggacaatt 175020
tctttttcca cacattagat tattgtaata taggtaggtt ggggtgttgg agcgaataag 175080
ttttctgagt atgttataat ctatgacttg taaatcgtta taccttaggt ccaaaaactt 175140
gagttcttta ccaaagccac ctgcaatttc agaaatattt ttcatcccgc agcggataat 175200
acggatgtcc tgaaacgtct ttaaaatact tgtattgtag tgaatactta tgttattttt 175260
ttgtaaataa tctatgtcat gacaagtgca tgaaatgcca gcagcattgc ttggtatagt 175320
attatatgca ggaagaacta tactactatt gagaatagtc acattgtact tataccatgt 175380
attattttct gatataaagt atttgcaggt gacctgtggt ttaatcctac ctgttaagcc 175440
acttcctaaa aaaacaaaaa atatgaaaac ccttagcatc ctgtatatac tattaaaaat 175500
ttataaaatt ttctgtttaa atttcattta gacaaaaaaa ataatatata tacatcagca 175560
agaaattata tacagattat ataattttct gatttttttt tgccacaata agcatcatta 175620
tatgcattaa aatctcaata ctaaacacta aaatctaaat tctaagcatt aaattctaag 175680
cattaaattc tatgcactaa actgtaagca ctaaaatcta agtaactaaa atcaacacta 175740
aatgtatgca acctaaaatg taaagcatta ctcatcatcc tcctcttctt catcctcatc 175800
atcataggtt aagatatatg tgtcatcctc catttcttca cattcatctt cataagcatc 175860
actgggtatt ggtggaacat tggatgcagc atttttaaaa tattctatgt cttctggtga 175920
acactcatct aatgattttt tgacagtcct tttaacttcc atgggatatg attccaaatc 175980

```
ctctttatat aagagtttac ggtagctttt agctgcatcc acatttgctg gagaatctgg 176040
atttggctca ttgagcagtg aaattacact aagaagaatg gtatcaatct tttgagccgg 176100
agaccaagtc attccctgtt cttcagcatt gtctccgtgt aagatagaga tacatagttt 176160
tccatcagag taaatattag gatgccacat ttcagaggtg aatgttaatc tgggtggtgc 176220
atatgggtat tctggaggaa aggcgatttt tgccttgaat aagcctccct cataaaaagt 176280
gtcaggtggg ccccttaaga tcacatccca ttcagtcata tccttctcat tcaccgaaat 176340
tttgaaattc tcagagggat tctctatcag gtgtctgtac tctgctatta aaaacctgga 176400
aaccatggtt atttaatatt aattaaattc cctggtttat tcctccttaa aagtagatga 176460
acctcttttg tttttattg ggttcatttt tactaaattt atgaactgga aaaaacttta 176520
acggcataat tatcaaatgc gaagggggat ccgtataaaa tcctagcttg ccggtaatgg 176580
ctattaagtt aaatttggta ccagtaacac taatatttaa aaagccctga tcattaactt 176640
tccacattaa aagattatta tattcgaatg tttgtccaat atggacaact ttgtcaccag 176700
atgttacatt tgatttggtt gttagtggct gaagcttggc acaatcaaaa ataagcccat 176760
taacactaag atatagagga gtgggttgat ctattttctc atagtttaat attccatctt 176820
tccacgtaat agcttgataa ttatccgcag caatgagttg aaattttata aatagtacag 176880
gggttttagt tgtcgttata catttaaagg gtgttttata aaaataaaaa ataataattg 176940
ttaaaagtat gataataatc gccaaaataa tttcatacat tttttataag aattatacat 177000
agtatggtat ttaaaatatt agctaaattt aaaaaaactt catgattttt aaaacaggga 177060
aaaaggggat taggttgaat aaaaaaggta agcacttgtc tatatatttt ttttacaatg 177120
ttgccttgag tcgcattttt aactggctgg ggagtatcag agtggaatat cactgtagta 177180
ggtctataag gtcttgttaa aatatgatcg gtcattgttt tcgtactagt gtcatttagg 177240
gtcgacctga tagctcgata taaagttata ggggataacc tatcaaatac agtcttatct 177300
gtgctgaaat gtatatcgtc ttctttatca ctaataatat taggaatggc tgtcattaaa 177360
taattactac ttgttgttgt gggtgaaata gttgtactgg tattattgga aatggctgtc 177420
attaaataat tactacttgt tgttgtgggt gaaatagttg tactagtatt attagaaatg 177480
gctgtcgtta aataattact acctattaca agtaaactaa tgctaactac atttttaacc 177540
tcaataaacc taaaaagcca tactaaatac ctaaacaaca tcctgttata atatgagcag 177600
aaaaaaaaaa taagtataat tagggaatta ttcttattcg cttactatta agaataattc 177660
agaatcttat ttagttagaa actatcataa agtgaatagg actcatcgtc ggatgaagat 177720
tccgtttcag agatagtttc tttttcttcc tcagaataat ctgttcctac aatagaatcg 177780
gtgtcatcct cagaaagaga agtatttaaa tatggactat ctatagcaat atcctcttct 177840
atctcgcaat cctcctcctc catttccata gtgtgtagga gaatattttt atcatcatgc 177900
tcacttcttt ttttgttgaa agatgaaccg tcctcaatac ggttcatgtt aagttccttc 177960
atcttatgta taatttccgt aatccgtgat gtttttgaca tgtaagatgg ttttaaggtt 178020
atatccacaa taacaggaga atctctatca ttttcatttg ataaactttg atctttgatt 178080
tcttcgtcta aaattcttgt cttttttttgg gtactagatg aaatagagga attcatattc 178140
tgaaacgata tatcaagggg agctggacgc ttttttccaa ttaaaccgtt tttcgagata 178200
ctatgattag atgaatgatc tttagccaag ctgtccttgg atatactata gttagatatt 178260
ttacctttaa ataatattct tctatacaag ttattcttag gtaaagaatt agtatggatt 178320
cctatatttt tatctgaagg agtgtccata tcggagaacg tcctcttacg aatattttga 178380
```

ccacgagcca tttcatccac tataggcagt attttggctg gctatggttc tttgttgtga 178440
caattctatg agatttgatt gcaaatcaat ttttagtttt aaatatattg gtacctagga 178500
caaagaaagt atatatagcc aataattatt ccactaaatt gatttccaga ctgatgggta 178560
tggagccatg ttgtctctgc agacgatcgc aaaaatggcc gtagcaacaa acacctactc 178620
caagtatcac tatccaatac tgaaggtctt tgggctgtgg tggaaaaaca atacgctaaa 178680
tggccctatt aaaatatgta accattgcaa caacataatg gtaggagaat atcctatgtg 178740
ttacaatcat ggaatgagtc tggatatagc tttgattcgg gcagtaaagg agcgtaatat 178800
atccttagtc cagcttttca ccgaatgggg gggaaatatt gactatgggg cactttgtgc 178860
taacactcca tctatgcaaa gattatgtaa aagtttggga gccaaaccac caaagggccg 178920
aatgtatatg gatgctctta tacatctttc agataccttg aatgataatg atctgattag 178980
ggggtatgag atttttgatg ataatagcgt gttggattgt gtcaatctca tacgactcaa 179040
aataatgctt accttgaagg cccgtatacc tctcatggaa caactagacc aaattgcctt 179100
aaaacaactt ctgcagcgat actggtatgc catggctgta caacacaact taacaatcgc 179160
tatccactat tttgataatc atattcctaa tataaagcca tttagtctgc gctgtgcttt 179220
gtattttaat gatcccttta aaatccatga tgcttgcaga actgtaaata tggatcctaa 179280
tgagatgatg aacattgctt gtcaacagga tttaaacttt caaagcattt actattgtta 179340
tcttttaggg gctgatatta atcaggctat gctaatgtct ttaaagtatg gtcatctttc 179400
taatatgtgg ttttgcatag atttgggggc ggatgccttt aaagaggcag gggcgcttgc 179460
tgagaaaaaa aataaaagag tgttacaaca catattaggt cttaatatct ttaagcgaga 179520
gttgattccc ccctgtaaag atcctgatcc ttatcaaatc caaattctgt taaaaaacta 179580
cattctaaaa aatgtctcaa ctgtttttac atattattgc cagtagccat tgtttatatc 179640
agaaaataac ccatttgttt atcttttttt gtgggggcaac cattaagacc cgacgcaaaa 179700
aaagattaat cttttatcag atacctaaaa cgttctataa gggagtctat gagatggatc 179760
atattttgat ggtcatagta agaagcaagc tttttggcga aaacaacgga gttaaagaat 179820
ttaacccgct catgtttgga taggactttt aacagcgagc caaaacagta tttaaaaatt 179880
tggcaatagt ttttttggga tgcaataaac aaacacttga tcagtgcccg cttcactttc 179940
tgatcagaca tgtttgccgc ataacaggcc tttttaaact tagtaatata attatgttcc 180000
gcaagcacca ttaacaaggg aacgatggga agctgctttt cttggtgaaa tttacgtaaa 180060
tattcgatgg ccaccgcttg gacgactgtg taatttacta agttagaaat gatagctttc 180120
atggttgtaa aaatatacat aggattttct ttttctgtat acagtttgaa aagcttatga 180180
ttacgtgaaa tgatggccat ttttaataca agatggtata gtgtatcttt aggtaaaaat 180240
gccttgcaag ccgcgatgat gtcgatgttg tctccatgaa cagcgataga aactaatgtt 180300
tccaatctaa atgtttttat ctgcattaat agaagaatgc agtcaatgtt attatactta 180360
ataatactgt aatacaccga atcaatgacc gtcatctgag aatcaagctg acttattagt 180420
aaatttaacg tttttttgga ggcatgacct ttgatcgcgg cactaagtgc acacagtata 180480
gcaaaattgt taaatacatt ttgatttagg agaaggagta atattttcct tcggttatag 180540
tacgcagcat ctgtgatgat tattggccga taaatgttaa aatgtgttaa cagcttttta 180600
aaaaaacgga agtaattttt ttggatcgct gtttgcatca tcgaaataat gagataatca 180660
gggtatataa tgggtaggtc acatgctacc tctaacaaag aatagtcgcc caatctaaag 180720
gctgtgttga aaagcgtact atcatcatac gtatcgagta cccctgctgt tacaaaccaa 180780
gcgataagat gaatgtgccg ttccttgcaa gctatcgcaa atagggagtt tcctatggaa 180840
tgtcgaataa tgtactccct attttttttcc aaaatgtttg gaaaattgta tagcgttgcg 180900
gcatacagta gacactccat tctggcgtta taatttttac ttttacatat gaataggtgg 180960
aagaactcga ataattcttg agaacttgtt aaatgcataa tatggtgata ttttggtgtc 181020
gttaaatggt atgagaaaat gcattctaat acatcttttc ggttatgctt tagcgcctga 181080
gctaaggcat attcaggctc gacccatagg actagtgttt ctataattga gatattcgcc 181140
tgctttgcca gggcatactt taagacgctc cggttagaaa aaatgttgtt atgaagatgg 181200
ataaccgtat ccatttttac gatgggacca ttccagtata gtcctaaatg ctgtagcaga 181260
tcttttgtta gttgtgaagc gttctcgggt gtcatataaa tatgttgcag ggcttttttc 181320
tgtaaggaga acatttcgtc gtaatcgtac aaaaaaaaat taaaatttgg gcatggatga 181380
ttcaaacata acaaaatcaa gattttataa cagtttgcat taacctatac atatatgcaa 181440
gtaaatgaga tattatctat cataacgaat caagggatat ttgtatatat caggagtttc 181500
tgaaataaag atatgaagat tatcatagta gtatccatca atcacaatgc aacttccttt 181560
aaggcataat ttagtaaact cagcactccc atcttctgga tgctttacaa ctaacattaa 181620
aaactcctca gtcatattat ctgtaataaa ataagatcct cctggagcca tttgtagcat 181680
gtctcttatt cctacaaaat cttttttggg atggtaaaaa ctcagcagtt tcaaactctt 181740
ttttagtttt ttttcctggt atttaagcca tttgttataa aacagttttc ttatgaaaat 181800
gcatttgaaa atattgggaa tgtttaacca tgcttcttcc gagcacatct ccagatactt 181860
actttctttg tttcccatgt ctaatttatt gctcactaag ttagtaatga atctatttta 181920
ataatctact ttactaatct atcttaataa cctatcttat aatctatctt aataacctaa 181980
ttataaccta tttataattg gctaatgctg ccggcatttc atgcctatct aaacaactcc 182040
tactaagcaa tctactatta catatataga ttcacttttt atatttgtaa atcatgagaa 182100
ttataaaatc attactcatt tttattgtaa attagtgggt atttgtaaaa atcttcaaac 182160
gttttaagat agttttctag agagaagtaa tctttgccat caatatataa tgcttttcct 182220
ttaaactcca gttttgctat gtttagtgag ccgtttctag atctttttgg gcaataaata 182280
gattttcatt ggttgcatcg tccgtaagca gaaaggtacc actaggcacg ttaaaaaaca 182340
tacgttctat ttcatggtcg gatttttgag aatagaaaaa atctaatttt ttaatccgcg 182400
ttaactcttt tttatcaatc tttccagact gttttatata tactttattg caaatcttac 182460
aatcctctat ggcttcatta tacttatttt gcttatcctc tattgacatg tccgtatttg 182520
ataggtaact tccgttaagg cggttcccca tggttttaga tagattttta attcagttgt 182580
atacttttat tatgaggcta aaatatagaa gtttgatcct aaaaaaaataa aaagattttg 182640
tacatttatt tatggtttat agcggtatag aggccgataa aaggtatccg ggtagtctcc 182700
tatgatatcg tcaattttgg tataataaca gttgttatgg tagtattgtc caaaccgagt 182760
atgtatgcgc cggtgaagcg tccgcccgct aatggtacag ttccaggtta agacaatcat 182820
atcacaccca aaaagagagg aaacagcata ggtgcccaaa ggttcattat ataacatacg 182880
ccgcatatat tttagttttt tttctccatg gtaataatca caggttttca tgtcctgctt 182940
aataggatga ttccccatgt atgataatat ataataaatt tagtttttag ctttttcaaa 183000
aaattgggcg ctcgaaacta aattttcctt atcacagcgt ttggagaaag cgtatttaaa 183060
gatatatctt cttctaacaa gactgcaaaa aaaatcttac cccttatttt tataatgttc 183120
atcatagcgt ttgaagatat cagaaggtgc caggttttat aaaaatatcc tttaggattt 183180
ataacgatac aagggtctat aaaatatatg cgggtataat cttataaaat catcgatttt 183240
ttcataatat tctccgttta tacaataaag atcataacag atattgatgc gtagatgcat 183300
tattcgcgtg ttcgttgggc agctaaagga tatcacaacg tagttttttt taagaaaaga 183360
cgaaactaca taagtcccta agggttcatt gaatagtaaa cgccatattt gttttaaatt 183420
ttgttgttca ccatagtagt attcgcactt tttcaagtct tttttaataa gcctattccc 183480
catgtatgct tataaataaa aatttagaaa tgtgctatat tatttgttga tgaatcatga 183540
acacgtctta tatgttgata tgttacttta aaaacatttg tattttcaac agacgcgttc 183600
tattcttatt aagaatgatg ccgtctttat tttaaacctt ggtttaaaat ttaaagaagt 183660
atttataaac tataatcatg ggaacttttt cagtaactgc ctctgcaaaa agtgacgatg 183720
ctgtttgtaa gtatttagaa gaaccaatag atgaaaatta cagaaacata ttaagaaatg 183780
agcatgttaa aaaaaattta aatgaggctc tgaatcgaca tattactacc tataatccag 183840
tagttgattg gtgtaataac tattcaacat tttcatctca ggatttcgat gaatataaaa 183900
tttatataca tagcgatctt atggatggac gacctcgtcc aaaaaaaaca tggtgtgtca 183960
tcatgtaatg tttgttagtt ttatataaac gcaaaaatat tcttctagga gatgttgata 184020
tactacctat tgaattcaat atattaaagt acatttctgg ctattcccat tacggtatta 184080
ttattactat ttttaagagc tagatgtgga tttaagtaat aataacattc tcccgttcct 184140
cctagagaca cctcatcaaa ttcccatcct atgcaacctt tatgttgtaa acataatgat 184200
tgacagcatt catcttcttt tgaccaagtc gtccaaatcc taccaagatc tatacgtgtt 184260
tttccaaatg gagattgaag atcagcagta gtggcattaa acctataaaa accaggtgca 184320
taatcacatg aacggatcgt aggatctaat ttaatatctt ttatatcttg ttttactgct 184380
tctagacaac ttttatcagt acatgttcca cgtacacagt ggtgtccttt atccttacaa 184440
tccgtatctg tcttacattt ttttttcggc ggtttatgtt tcagatggta aaaacccagt 184500
attaaaataa tcacaagaat aattcctata agtacttgaa caacaggata aaacatttta 184560
atattaaata tattttttaa ttaaatgaat agatttaatc caagtagtat taaaattttt 184620
tagaaatagt gttctacaaa taatgaaatg aatggtccaa aaaaaataag gtgtacaata 184680
atgtaatata ttgttaggct aagtaaattt aatattttaa agtatttgga aaaatatttt 184740
ttaacatatg atgtctagga atatttttta gacatttaaa accatatagt tactttattt 184800
attacactga acttgaaaag acttattacc taaaatatta atagatgaag taatattgtg 184860
taattgagtc cataacatgg gtgggaaaca aaaatctcgt aatatgaaaa ataaacatcc 184920
taaaaagagt gcaattgtta taagtttatg taactttatt ttaaagtaag aatataaaaa 184980
tatgagtaca agaggaatag gggccattac taacattggc tccaacatcc tgttgtctac 185040
aaaaaaaaat attttttta gcaaaaaaaa atccatggaa ggatattaat acacataatt 185100
atttgacatc acattagtgt acttaccaaa tagtaatata caaccatcct aatattcacc 185160
tttatgaaat gatcccaacc tatacggtaa aatagtatag gttttaataa agaaaaaaga 185220
tattctgtgg tttttatttt tgtatagtgt gtgaatacaa aataaaatcc caaattttaa 185280
ccttttcttt ttttttctat acaggatgtt agaaatagta ttggcaacgc tgctaggcga 185340
cctgcagcgg ctccgggttc ttacccctca gcagcgggca gttgccttct ttcgagccaa 185400
tactaaggag ctagaggact tcttatgctc agatgggcag tctgaggagg tactgtctgg 185460 ccccccttctt aaccgtctac tagaaccctc aggccctctt gatattttaa ccggatatca 185520
cctatttcgt cagaatccca aggcaggtca gttgcgcggc cttgaggtca agatgcttga 185580
acggttatac gatgctaata tttacaatat actgtctcgg ctgcggcctg aaaaagttcg 185640
caacaaggct attgagctat actgggtttt ccgagctatc catatttgtc atgctccttt 185700
agttttagat attgtacgat atgaggaacc ggactttgct gaactggcct ttatttgtgc 185760
tgcttacttt ggtgaacctc aggtaatgta tttgctctac aaatatatgc ctctgacccg 185820
cgcagttctt acggatgcca tccggataag tcttgagagc aacaaccagg tagggatttg 185880
ctatgcttac ttgatgggag gcagcctcaa gggactagtc tccgccccac tgcgtaaacg 185940
tctgcgcgcc aaactacgct cgcagcgcaa aaagaaggac gttctttcac cccacgactt 186000
cttactgctg ctccagtagc ttttttgcc gcaggagcac cgcggatagg agctcctcca 186060
cgctcgcgat ccggcgctgg aagcggaacc gatcgaccgc cacctgctcc cagggaccct 186120
tgcgctcgat gtcgtcggct tcccacacct cgacggctgt ggcaaaatgg acatgcttcg 186180
cgtcgttcgt ccgtttttg cgccgcctcc ccattattct tcctgtaaga ttagtgttta 186240
atacctataa taacataatt ttaagattta atataccaaa acttaaacta tttttgtata 186300
gtaactatta gcatgtctac acatgattgt tctctaaaag agaaaccggt tgatatgaac 186360
gatatatctg agaaatcagt tgtcgtggat aatgcacccg agaaaccagc tggagcgaat 186420
catataccctg agaagtcggc ccgcgaaatg acatcatcag aatggattgc tgaatattgg 186480
aaaggtataa aacgtggaaa tgacgtgcca tgttgttgtc caagaaaaat gaccagtgca 186540
gacaaaaagt tttcagtatt tggtaaggga tccctaatgc gctccatcca gaagaataat 186600
taaaaaaaat atttttttta gcaagttttt aaactattta aataaatgtg gtaaaaaaat 186660
tcacataata attaaagtga acgtgttaga attaatattt ttttataatc ggatataata 186720
tccattaaat caataaatga tagtgttgct accacactaa acaataacaa acagaaacgc 186780
acgatacctt tcctcatgat ttataatagc gtgttatcta aagatttttt tgaaaaaaat 186840
attaaatttt agttgattat ttttttcagt tacaacattg ctttagaaaa aatacctaat 186900
tactacatag caaataaagc gagcgcattg ttacaaacaa catttttttg cgcctggata 186960
ctcctatata tgagaactat aatacggtat attaatccta ttaccaacat tgtcaataat 187020
agtatgtagg caatgacata ctttaaatac caaatatcca tggttatttc taaaaatctt 187080
gaaaaaacgt taaattttag atcggtcacc tacgacagta atactaattt taataattga 187140
tgactgaaat cataatataa tgccgtgcga aaaataatta tttttcggtt aaagatacca 187200
ttacataaaa aatatgccat ctactctaca agtgcttgct aaaaaggtat tggccttagg 187260
ggagcataaa gaaaatgaac atatatctag agaatattat tatcatatat taaagtgttg 187320
cggtttatgg tggcatgaag ctccgattat actttgttat gatgggagtg agcaaatgat 187380
gataaagact ccaatctttg aagaaggcat attacttaat actgcattaa tgaaagctgt 187440
acaggagaat aattatgaat taataaagtt gtttactgaa tggggagcaa acatcaatta 187500
tggattaatt tccattaata ccgagcatgc ccgggatcta tgtcgaaaat taggagctaa 187560
agaaatgctt gaaggaaatg aatttataca aattatattc aaaacattag atgataccac 187620
cagtagtaat ataattttat gtcatgaatt attcaccaac aatcctcttt tagagaatgt 187680
aaatatgggg gaaatgagga tgataattta ttggaggatg aaaaatttaa cgaacctatt 187740
attaaataat gactctatta gtgaaatatt aactaaattc tggtatggta tagcagtaaa 187800
atataatctt aaggatgcga tccaatattt ttaccagaga ttcatggact tcaacgagtg 187860
gcgagtaaca tgtgctcttt cttttaataa tgtgaatgat cttcataaga tgtatataac 187920
agagaaggtt catatgaata atgacgaaat gatgaatcta gcctgcagca ttcaagacag 187980
aaatttatca accatttact attgttttct attggggggc taacatcaat caagcaatgt 188040
taacctcagt attaaattat aatattttta acttattctt ttgtatagac ttaggggctg 188100
atgcctttga agagggtaag accctggcga aacaaaaggg gtataatgaa atagtggaaa 188160
tcttatcatt agatatcatt tatagtccaa atactgactt ctcatcaaaa atagaacctg 188220
aacatattag ttctttgtta aaaaactttt atccaaaaaa tctgttcgct tttgatcgtt 188280
gcaaccccgg tttatattat tcttagagga ccgctacaaa aattattttt ttttcttgat 188340
caaagctcca aaataattat tagattaaag tcgcctatag cagcagccca ctccaaaaaa 188400
agtattttat agtacaaaaa acacgaaaaa tagtttgcgg ccggcggcaa actatttgtt 188460
gttgtctaaa acttaatgtt tttttaatat ttttaaatgc aaccatggat tgttggacta 188520
tcagggagaa gaactatagc tacatcatat tgtcaatact ggtaatacta ttaatatggt 188580
atcttatact taactattgt cgatcgaaaa aaaatgcagt tacaaacaac atgccgccac 188640
catacacggt gtcaagtagc tgttctcaat aatagggttg attgacgctc ttcgtaataa 188700
tatgttgatt gacgcatcat aaaatgctgt ggttgattaa tatgttgatt gtcgcctact 188760
ttattatata agtaatgatt tttgtataaa atacgggttt gtgagggctt tattttttct 188820
tattagaaca aagcatgcaa tttaaggcct acagcaagag taatttaaca cctacaacag 188880
taattttaag gtcagtaata atgtttaatt aaggcctgac cactaaaact taaacgattt 188940
tgtaaaaaaa aatgtctact ccactttctc tacagactct tgttaaaaaa gtgctggcca 189000
cacagcacat atctaaagaa cactacttta ttttgaaata ttgtggttta tggtggcatg 189060
aagcgccgat tacgatttgc attgatgagg atagccaaat attgataaaa tcggcaagct 189120
tcaaagaagg cttatcttta gatatcgcat taatgaaagt cgtgcaagaa aataaccatg 189180
atttaataga gttgtttacc aagtggggtg cagatatcaa ctctagctta gttactgtta 189240
atacggagta tacccggaac ctttgtcaga aattaggcgc aaaggaagct ttgaatgaaa 189300
gggatatttt acaaatattt tataaaacac gtcatcttaa aactagcagt aatattattt 189360
tatataatga attgttttct aataatctcc ttttccaaaa tatagagaga ttgagtttaa 189420
tagtttatag gggcttgaaa aacttatcaa tcaactttat attggatgat atttcattta 189480
gcgaaatgtt aactagatac tggtatagta tggcgatatt atataacctt actgaagcca 189540
tccaatattt ttatcaacga tataggcatt ttaaagattg gcggcttata tgtgggcttt 189600
cttttaacaa tttgtctgac cttcatgaag tatataactt agagaagacg gatatagaca 189660
ttgatgaaat gatgaagttg acctgtagta cgtatgatgg taattattcg actatttatt 189720
attgttttat gttgggggct gacatcaatc gggcaatgtt aacctcggta ataaactttc 189780
atattggtaa cttgttcctt tgtatagatt taggagctga tgctttcgaa gacagcatgg 189840
aactagcaaa acaaaagaat aataatatat tagtagaaat attatcattt aaaaattatt 189900
atagttcaaa tacctctctt ttatcaataa aaacgacaga tccggaaaaa attaatgcct 189960
tattagatga agaaaagtat gagtcaaaaa atatgttaat gtatgaagaa ttatctcatt 190020
gatacaaaat tattttttat aacagaactc tctgatggtg acaaatctcc gataggaata 190080
tatgacgtaa cataattatt tttttcgccc agaaaaaaat tataaatgtt attattgcca 190140
gcacttttat caactatacg tacaaaaagg tgttgaccaa aaaaataatt ttttttcttg 190200

-continued

```
atcaaagtat gtaaacgccc gcttacagca aggatcttaa gtgagagcca ttaaatttta 190260

ttgatagctg cttgccacca gtagaatacg gccaaaccac ctaacaggaa atacaaggcg 190320

gcccttcggc caataaggtg gataaaaatc acgcataaga cggttgtaac atagcacttt 190380

agtgcgaata tcaggaatgc caatagcatg tagataaggc accaaacatc gcagctatac 190440

atggctaaag atcaaccaga aaaggtttaa attttaacgc cggcccaaaa cttaaacttt 190500

ttttgatatt tttaagtgca gccatggatt ggtccggcca taggatgacc tatgcctacg 190560

tggcattctc attgatggca atagcaataa tatggtatat tctacttatc tattgccgat 190620

cgaaaaaaaa tgttgttaca agcggtaata cgctcgcttt agcgccaata tcgcatatgt 190680

gaaaaatgtt cgccgaaaaa aacattaaaa tttagaaccg ccgcggcatc tcaggggcgg 190740

caacattttt ttttatatgg atattgtcac acaccacctc atctatgacg caatatatta 190800

ctgctaatat caggttcccc aatagtatgt agagaaacca cacaagatag atattcatgg 190860

cgatttttga cgaaaaaaca ttaagtttta gcttctttga cgcctgtgta ctaataatgt 190920

ttaacgcctg tagtataata attgatacct acagcagtaa ttgataccta cggcgataat 190980

gtctctctgg ccgccccaaa aaaaagtatt tacggtaggg tttattaccg gcggcgtaac 191040

accagttatg gtcaattttg tctggcccgc cgcccagccg caaaaaaaaa tcaattacaa 191100

ccgcaaaaaa aaatatttcc ggccgcggcg tttcaaaaaa taatctttgc gaaataattc 191160

cgcatcttgt gaaatgaacg cctacagtaa taattttaat ctttgacacc tacagcagta 191220

gtaataattt taatctttaa cgcctgcagc agtactaata tttttaatct ttaacgccta 191280

cagcagtagt aataatttta atgtttaacg cctacagcag tagtaataat tttaatcttt 191340

gacgcctaca gcagtagtaa taattttaat gtttaacgcc tacagcagta caataatttt 191400

aatgtttaac gcctgcagca gtactaatat ttttaatctt taacgcctgc agcagtacta 191460

atatttttaa tctttaacgc ctacagcagt agtaataatt ttaatgttta acgcctacag 191520

cagtagtaat aattttaatc tttgacgcct acagcagt                         191558
```

<210> SEQ ID NO 3
<211> LENGTH: 414
<212> TYPE: DNA
<213> ORGANISM: African swine fever virus

<400> SEQUENCE: 3

```
atggaagcag ttcttaccaa actcgaccag gaggaaaaaa aggctctcca aaattttcat     60

cgttgtgctt gggaagaaac taaaaatatt ataaacgatt ttcttgaaat ccctgaggaa    120

cgatgcacct ataaattcaa ctcatacaca aaaaaaatgg agcttttatt tacccctgaa    180

ttccacaccg cctggcatga agttcctgag tgcagagagt tcatattaaa ctttttgaga    240

ctcatttcgg gacatcgagt ggtattaaaa ggccctacat ttgtttttac aaaagagatc    300

aagaatctgg gcattcctag taccatcaat gttgactttc aggccaacat tgaaaatatg    360

gatgatctac agaagggaaa tctcatcggc aagatgaata tcaaagaagg ctaa          414
```

<210> SEQ ID NO 4
<211> LENGTH: 137
<212> TYPE: PRT
<213> ORGANISM: African swine fever virus

<400> SEQUENCE: 4

```
Met Glu Ala Val Leu Thr Lys Leu Asp Gln Glu Glu Lys Lys Ala Leu
1               5                   10                  15
```

-continued

Gln Asn Phe His Arg Cys Ala Trp Glu Glu Thr Lys Asn Ile Ile Asn
20 25 30

Asp Phe Leu Glu Ile Pro Glu Glu Arg Cys Thr Tyr Lys Phe Asn Ser
35 40 45

Tyr Thr Lys Lys Met Glu Leu Leu Phe Thr Pro Glu Phe His Thr Ala
50 55 60

Trp His Glu Val Pro Glu Cys Arg Glu Phe Ile Leu Asn Phe Leu Arg
65 70 75 80

Leu Ile Ser Gly His Arg Val Val Leu Lys Gly Pro Thr Phe Val Phe
85 90 95

Thr Lys Glu Ile Lys Asn Leu Gly Ile Pro Ser Thr Ile Asn Val Asp
100 105 110

Phe Gln Ala Asn Ile Glu Asn Met Asp Asp Leu Gln Lys Gly Asn Leu
115 120 125

Ile Gly Lys Met Asn Ile Lys Glu Gly
130 135

<210> SEQ ID NO 5
<211> LENGTH: 165
<212> TYPE: DNA
<213> ORGANISM: Artificial Sequence
<220> FEATURE:
<223> OTHER INFORMATION: Chemically Synthesized

<400> SEQUENCE: 5
ggacatcgag tggtattaaa aggccctaca tttgttttta caaaagagat caagaatctg 60
ggcattccta gtaccatcaa tgttgacttt caggccaaca ttgaaaatat ggatgatcta 120
cagaagggaa atctcatcgg caagatgaat atcaaagaag gctaa 165

<210> SEQ ID NO 6
<211> LENGTH: 53
<212> TYPE: PRT
<213> ORGANISM: Artificial Sequence
<220> FEATURE:
<223> OTHER INFORMATION: Chemically Synthesized

<400> SEQUENCE: 6

His Arg Val Val Leu Lys Gly Pro Thr Phe Val Phe Thr Lys Glu Ile
1 5 10 15

Lys Asn Leu Gly Ile Pro Ser Thr Ile Asn Val Asp Phe Gln Ala Asn
20 25 30

Ile Glu Asn Met Asp Asp Leu Gln Lys Gly Asn Leu Ile Gly Lys Met
35 40 45

Asn Ile Lys Glu Gly
50

DEVELOPMENT OF A NOVEL LIVE ATTENUATED AFRICAN SWINE FEVER VACCINE BASED IN THE DELETION OF GENE A137R

BACKGROUND OF THE INVENTION

Field of Invention

The present disclosure provides details on the construction of a recombinant African Swine Fever Virus (ASFV) live attenuated vaccine for prevention of ASF caused by various strains of ASFV, such as the highly virulent Georgia 2007 isolate ("ASFV-G"). An exemplary vaccine comprises the ASFV-GΔA137R modified virus, a recombinant ASFV-G modified by deleting a portion of the A137R ORF rendering the A137R gene nonfunctional.

Background

African Swine Fever (ASF) is a contagious viral disease of swine. The causative agent, ASF virus (ASFV), is a large enveloped virus containing a double-stranded DNA genome of approximately 190 kilobase pairs. ASFV shares aspects of genome structure and replication strategy with other large double-stranded DNA viruses, including the Poxviridae, Iridoviridae and Phycodnaviridae (Costard et al, Phil. Trans. Royal Soc. B, (2009) 364:2683-96). ASFV infections in domestic pigs are often fatal and are characterized by fever, hemorrhages, ataxia and severe depression. However, the course of infection varies, ranging from highly lethal to sub-clinical, depending on the host characteristics and the particular virus strain (Tulman et al, Curr. Top. Microbial. Immunol. (2009) 328:43-87).

Currently, the disease is endemic in more than twenty sub-Saharan African countries. In Europe, ASF is still endemic on the island of Sardinia (Italy) and new outbreaks have been declared in the Caucasus region since 2007, affecting Georgia, Armenia, Azerbaijan and Russia. Outbreaks have been recently reported in Ukraine, Belarus, Lithuania, Latvia and Poland, affecting both wild boar and swine farms. In 2018-2019 ASF spread into China, causing a rapid spread across South-East Asia including Mongolia, Vietnam, Thailand, Timor Leste, Cambodia, Philippines South and North Korea, in both wild boar and domestic swine farms. In 2020 ASF has also spread to wild boar populations in Germany, where ASF is currently only affecting a small containment area in the country. Recent ASF outbreaks pose the risk of further dissemination into neighboring countries. The parental epidemic virus ASFV Georgia 2007/1, is a highly virulent isolate belonging to the genotype II (Chapman et al, Emerging Infect. Dis. (2011) 17:599-605), and is responsible for all the current outbreaks in Asia and Europe, with outbreak viruses having 90% or greater similarity to the parental strain.

Currently, there is no commercial vaccine available for ASF and disease outbreaks are controlled by animal quarantine and slaughter. Attempts to vaccinate animals using infected cell extracts, supernatants of infected pig peripheral blood leukocytes, purified and inactivated virions, infected glutaraldehyde-fixed macrophages, or detergent-treated infected alveolar macrophages failed to induce protective immunity (Coggins, L., Prag. Med. Viral. (1974) 18:48-63; Forman et al, Arch. Viral., (1982) 74:91-100; Kihm et al, (1987) In: *African Swine Fever*, Becker, Y. (ed), Martinus Nijhoff, Boston, pp 127-44; Mebus, C. A., Adv. Virus Res., (1988) 35:251-69). Homologous protective immunity does develop in pigs surviving viral infection. Pigs surviving acute infection with moderately virulent or attenuated variants of ASFV develop long-term resistance to homologous, but rarely to heterologous, virus challenge (Hamdy and Dardiri, *Am. J. Vet. Res*. (1984) 45:711-14; Ruiz-Gonzalvo et al, (1981) In: *FAO/CEC Expert Consultation in ASF Research*, Wilkinson, P. J. (ed), Rome, pp 206-16). Herein, we report the development of a recombinant vaccine in which a portion of the A137R gene has been deleted from the ASFV-G genome. Vaccination of pigs with this virus protected swine from developing ASF. Because there are not ASFV vaccines currently available, the development of any vaccine that may induce protection against the lethal presentation of the disease is of great interest.

SUMMARY OF THE INVENTION

The present disclosure provides a genetically modified virus, where the virus genome is at least 99% identical to SEQ ID NO: 2. In some instances, the virus genome is at least 99.8% identical to SEQ ID NO:2. In other instances, the viral genome is identical to SEQ ID NO: 2

The present disclosure further provides a vaccine composition against African Swine Fever Virus (ASFV), comprising a genetically modified virus having a virus genome at least 99% identical to SEQ ID NO: 2. In particular embodiments, the ASFV is ASFV-Georgia 2007 isolate (ASFV-G).

Also provided herein is a method for the protection of swine against ASFV, comprising administering to a swine a live attenuated vaccine comprising a genetically modified virus having a virus genome at least 99% identical to SEQ ID NO: 2 in an amount effective to protect said swine from clinical ASFV disease. In particular embodiments, the ASFV is ASFV-Georgia 2007 isolate (ASFV-G). In an additional embodiment the amount effective to protect said swine from clinical ASFV disease is a vaccine comprising $10^2$-$10^6$ $HAD_{50}$ of the genetically modified virus.

The present disclosure further provides a recombinant ASFV mutant virus, comprising a synthetic mutation in the A137R open reading frame or in a regulatory element controlling the expression of the A137R protein, resulting in a non-functional genomic A137R gene. In a particular embodiment, the synthetic mutation is a deletion mutation resulting the deletion of one or more nucleotides between positions 55531 and 55779 of SEQ ID NO:1. In an additional embodiment, the synthetic mutation is a frameshift mutation, insertion mutation, nonsense mutation of one or more nucleotides between positions 55531 and 55779 of SEQ ID NO:1. In some embodiments, the mutant ASFV is an ASFV-Georgia isolate. In some embodiments, the mutant ASFV comprises a genome at least 95% or 99% identical to SEQ ID NO: 2. Further provided herein is a vaccine composition against ASFV-G, comprising a recombinant virus of described in this paragraph.

The present disclosure also provides a method for the protection of swine against ASFV, comprising administering to a swine a live attenuated vaccine comprising the recombinant virus having a synthetic mutation in the A137R open reading frame or in a regulatory element controlling the expression of the A137R protein, resulting in a non-functional genomic A137R gene in an amount effective to protect said swine from clinical ASFV disease. In a particular embodiment, the ASFV is ASFV-G. In still another embodiment, the amount effective to protect said swine from clinical ASFV disease is a vaccine comprising at least $10^2$ $HAD_{50}$ of the genetically modified virus.

INCORPORATION BY REFERENCE

All publications, patents and patent applications mentioned in this specification are herein incorporated by reference to the same extent as if each individual publication, patent or patent application was specifically and individually indicated to be incorporated by reference.

BRIEF DESCRIPTION OF THE DRAWINGS

The novel features of the invention are set forth with particularity in the claims. Features and advantages of the present invention are referred to in the following detailed description, and the accompanying drawings of which:

DETAILED DESCRIPTION OF THE INVENTION

Figure 1:
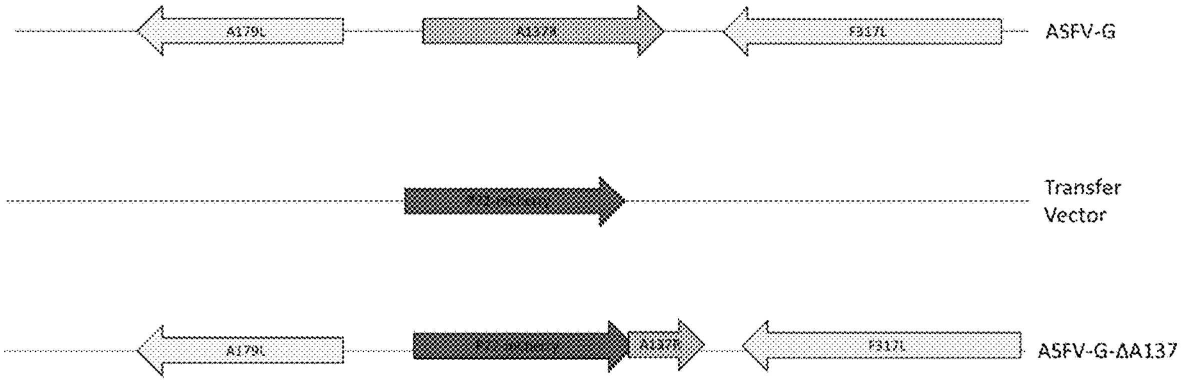
FIG. 1 provides a graphic representation of the cassette used to create the ASFV-G ΔA137R recombinant mutant virus.

African swine fever virus (ASFV) is the etiological agent of a contagious and often lethal viral disease of domestic pigs that has significant economic consequences for the swine industry. The control of African Swine Fever (ASF) has been hampered by the unavailability of vaccines. Experimental vaccines have been previously reported that were derived from naturally occurring, cell culture-adapted, or genetically modified live attenuated ASFV. However, none of these vaccines have been developed for commercial use. Here we report the discovery that deletion of a previously uncharacterized gene, A137R, from the highly virulent ASFV isolate Georgia isolate (ASFV-G) produces its complete attenuation in swine. Animals inoculated with the virus lacking a functional A137R gene—such as the specific ASFV-G-ΔA137R mutant described herein—administered intramuscularly (IM) remain clinically normal during a 28-day observational period. Importantly, ASFV-G-ΔA137R infected animals were protected when challenged with the virulent parental strain ASFV-G.

Preferred embodiments of the present invention are shown and described herein. It will be obvious to those skilled in the art that such embodiments are provided by way of example only. Numerous variations, changes, and substitutions will occur to those skilled in the art without departing from the invention. Various alternatives to the embodiments of the invention described herein may be employed in practicing the invention. It is intended that the included claims define the scope of the invention and that methods and structures within the scope of these claims and their equivalents are covered thereby.

Technical and scientific terms used herein have the meanings commonly understood by one of ordinary skill in the art to which the instant invention pertains, unless otherwise defined. Reference is made herein to various materials and methodologies known to those of skill in the art. Standard reference works setting forth the general principles of recombinant DNA technology include Sambrook et al., "Molecular Cloning: A Laboratory Manual", 2d ed., Cold Spring Harbor Laboratory Press, Plainview, N.Y., 1989; Kaufman et al., eds., "Handbook of Molecular and Cellular Methods in Biology and Medicine", CRC Press, Boca Raton, 1995; and McPherson, ed., "Directed Mutagenesis: A Practical Approach", IRL Press, Oxford, 1991.

Any suitable materials and/or methods known to those of skill can be utilized in carrying out the instant invention. Materials and/or methods for practicing the instant invention are described. Materials, reagents and the like to which reference is made in the following description and examples are obtainable from commercial sources, unless otherwise noted. This invention teaches methods and describes tools for producing genetically altered strains of ASFV.

As used in the specification and claims, use of the singular "a", "an", and "the" include plural references unless the context clearly dictates otherwise.

The terms isolated, purified, or biologically pure as used herein, refer to material that is substantially or essentially free from components that normally accompany the referenced material in its native state.

The term "about" is defined as plus or minus ten percent of a recited value. For example, about 1.0 g means 0.9 g to 1.1 g and all values within that range, whether specifically stated or not.

The term "a nucleic acid consisting essentially of", and grammatical variations thereof, means nucleic acids that differ from a reference nucleic acid sequence by 20 or fewer nucleic acid residues and also perform the function of the reference nucleic acid sequence. Such variants include sequences which are shorter or longer than the reference nucleic acid sequence, have different residues at particular positions, or a combination thereof.

The term "adjuvant" means a substance or vehicle that non-specifically enhances the immune response to an antigen. Adjuvants can include a suspension of minerals (alum, aluminum hydroxide, or phosphate) on which antigen is adsorbed; or water-in-oil emulsion in which antigen solution is emulsified in mineral oil (for example, Freund's incomplete adjuvant), sometimes with the inclusion of killed mycobacteria (Freund's complete adjuvant) to further enhance antigenicity. Immunostimulatory oligonucleotides can also be used as adjuvants (for example, see U.S. Pat. Nos. 6,194,388; 6,207,646; 6,214,806; 6,218,371; 6,239,116; 6,339,068; 6,406,705; and 6,429,199). Adjuvants also include biological molecules, such as costimulatory molecules.

The term "administer"/"administration" means any method of providing a subject with a substance, such as a therapeutic agent by any effective route. Exemplary routes of administration include, but are not limited to, injection (such as subcutaneous, intramuscular, intradermal, intraperitoneal, and intravenous), oral, intraductal, sublingual, rectal, transdermal, intranasal, vaginal and inhalation routes.

The terms "coding sequence" and "coding region" as used herein refer to nucleotide sequences and nucleic acid sequences, including both RNA and DNA, that encode genetic information for the synthesis of an RNA, a protein, or any portion of an RNA or protein.

The term "effective amount" of a composition provided herein refers to the amount of the composition capable of performing the specified function for which an effective amount is expressed. The exact amount required can vary from composition to composition and from function to function, depending on recognized variables such as the compositions and processes involved. An effective amount can be delivered in one or more applications. Thus, it is not possible to specify an exact amount, however, an appropriate "effective amount" can be determined by the skilled artisan via routine experimentation.

The terms "A137R", "ASFV A137R", and "genomic A137R" are synonyms and refer to the gene defined herein as SEQ ID NO: 3, or any version of SEQ ID NO: 3 with base substitutions that result in a protein with a sequence identical to SEQ ID NO: 4). These terms, in the appropriate context, can also refer to modified versions of these SEQ ID NOs, such as those comprising deletions, insertions, and other recombinant modifications. ASFV-G open reading frame A137R encodes a 137 amino acid protein (SEQ ID NO: 4) and is positioned on the reverse strand between nucleotide positions 55531 and 55944 of SEQ ID NO:1 (Wild-type ASFG, sequenced herein; see also Genbank Accession #FR682468.2.

In the context of the present invention, the term "non-functional genomic A137R" refers to a modified A137R gene, located in the genome of an ASFV, wherein such modification of the ASFV A137R gene results in no ASFV A137R gene product at all or a biologically non-functional ASFV A137R gene product as compared to an unmodified functional ASFV A137R gene. Such modifications can include, but are not limited to, full or partial deletion of the coding sequence, disruption of the open reading frame (e.g., by insertion of a shift mutation or insertion of a nonsense codon), modification of upstream or downstream regulatory elements, and/or any other currently known or conceivable method of inactivating or knocking-out functional expression of such ASFV I117L gene.

The term "immunize" means to render a subject protected from an infectious disease, such as by vaccination.

For the purpose of this invention, the "sequence identity" of two related nucleotide or amino acid sequences, expressed as a percentage, refers to the number of positions in the two optimally aligned sequences which have identical residues (×100) divided by the number of positions compared. A gap, i.e., a position in an alignment where a residue is present in one sequence but not in the other is regarded as a position with non-identical residues. The alignment of the two sequences is performed by the Needleman and Wunsch algorithm (Needleman and Wunsch, J Mol Biol, (1970) 48:3, 443-53). A computer-assisted sequence alignment can be conveniently performed using a standard software program such as GAP which is part of the Wisconsin Package Version 10.1 (Genetics Computer Group, Madison, Wisconsin, USA) using the default scoring matrix with a gap creation penalty of 50 and a gap extension penalty of 3.

The phrase "high percent identical" or "high percent identity", and grammatical variations thereof in the context of two polynucleotides or polypeptides, refers to two or more sequences or sub-sequences that have at least about 80%, identity, at least about 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, or 100% nucleotide or amino acid identity, when compared and aligned for maximum correspondence, as measured using a sequence comparison algorithm or by visual inspection. In one exemplary embodiment, the sequences are high percent identical over the entire length of the polynucleotide or polypeptide sequences.

The term "swine" can generally refer to any member of the Suidae family and includes domesticated and wild pigs, hogs and boars.

A "vaccine" is herein defined as a biological agent capable of providing a protective response in an animal to which it has been delivered but not capable of causing a serious disease. Administration of the vaccine results in immunity from the disease. Thus, the vaccine stimulates antibody production or cellular immunity against the disease-causing pathogen (e.g., ASFV). Immunity is herein defined as the induction of significantly higher levels of protection against lethality and clinical symptoms following vaccination in a swine population, as compared to the non-vaccinated group. In particular, the vaccine according to the invention protects most of the vaccinated animals against the development of clinical symptoms and lethality of the disease. The vaccine of the present disclosure is typically a genetically engineered (recombinant) mutant virus vaccine.

In the context of the present disclosure, the term "non-deficient in its replication" refers to a non-naturally occurring recombinant ASFV which is able to replicate in vitro and/or in vivo and/or is capable of producing viral progeny although such replication and/or viral progeny production may also occur at reduced levels compared to the unmodified parent strain. Therefore, it can be the case that such ASFV is non deficient in its replication in vitro, e.g. in a cell culture, although in vivo in a mammal such ASFV is at least partially impaired in its replication, e.g. resulting in a replication and/or viral progeny production below detection limits.

As used herein, the term "minimal dose" or "minimal effective dose" refers to a dose that demonstrates the absence of, or minimal presence of, toxicity to the recipient, but still results in producing a desired result (e.g., protective immunity).

Viruses/Vaccines

Provided herein is a novel mutant ASFV-G ΔA137R virus (SEQ ID NO: 2), resulting from the recombinant deletion of a portion of the A137R gene (SEQ ID NO: 3) of the parental ASFV-G genome (SEQ ID NO: 1). The genomic nucleotide sequence of a specific recombinant mutant ASFV-G ΔA137R (SEQ ID NO: 2) is described herein and differs from the genomic nucleotide sequence encoding the parental ASFV-G (SEQ ID NO: 1). The ASFV-G A137R-encoded protein of 137 amino acids (SEQ ID NO: 4) differs from the predicted mutant A137R protein encoded by the mutant nucleotide sequence of ASFV-G ΔA137R. The A137R protein (SEQ ID NO: 6) from ASFV-GΔA137R is predicted to lack amino acids 1 through 85 of the wild-type A137R protein. Because the p72Mcherry Cassette is inserted in this position (see Examples section), it is not believed that the remaining coding region is transcribed, resulting in no functional A137R protein being produced during viral infection.

The exemplary mutant strain (ASFV-GΔA137R (SEQ ID NO: 2)) is representative of the genus of recombinant vaccines in which the ASFV A137R gene is non-functional, which includes, without limitation, deletion mutants, nonsense mutants, insertional mutants, frameshift mutants and other mutants resulting in non-expression of the A137R protein, or expression of a non-functional A137R protein. Other recombinant viruses envisioned include mutants in regulatory elements resulting in non-expression or non-translation of the A137R protein.

Modifications intended to preclude functional expression of a target protein (e.g., A137R) or reduced expression or reduced activity of a target protein can involve mutations of the DNA or gene encoding the target protein, including deletion of all or a portion of a target gene, including but not limited to the open reading frame of a target locus, transcriptional regulators such as promoters of a target locus, and any other regulatory nucleic acid sequences positioned 5' or 3' from the open reading frame, insertion of premature stop codons in the open reading frame, and insertions or deletions that shift the reading frame leading to premature termination of translation. Such deletional mutations can be achieved using any technique known to those of skill in the art. Reduced levels of the target protein or reduced activity of the target protein may also be achieved with point mutations or insertions in the DNA or gene encoding the target protein. Mutational, insertional, and deletional variants of the disclosed nucleotide sequences and genes can be readily prepared by methods which are well known to those skilled in the art. Techniques used to achieve reduced levels and/or reduced activity of the target protein may include CRISPR/Cas, TALEN, and Zn-finger nuclease. It is well within the skill of a person trained in this art to make mutational, insertional, and deletional mutations which are equivalent in function to the specific ones disclosed herein.

The approaches described herein that were used to create a deletion mutant of A137R in ASFV-G can be used in different isolates of ASFV (such as isolates circulating in Asia, Europe or Africa), where a functional A137R is present. Such approaches can be varied by methodologies known in the art, such as using different selection markers that can select recombinant virus by purification such as, but not limited to, fluorescent proteins, enzymes such as beta-glucuronidase or beta-galactosidase that can be used with chromogenic substrates, and drug selection makers. Such approaches can also be used to create any mutation to the ORF of A137R as well as to regulatory elements controlling the expression and translation of the A137R gene that results in a non-functional A137R protein.

Mutants of A137R (and related strain-specific alleles) in other ASFV strains and genotypes is also encompassed by the present disclosure. Any ASFV known in the art, or later discovered, is contemplated as a potential platform for the construction of such synthetic mutations. ASFV strains comprising synthetic mutations in nucleic acid sequences that exhibit at least 80%, 81%, 82%, 83%, 84%, 85%, 86%, 87%, 88%, 89%, 90%, 91%, 92%, 93%, 94%, 95%, 96%, 97%, 98%, or 99% identity to SEQ ID NO: 3 are encompassed in the instant invention. ASFV strains comprising entire genomes with 95%, 96%, 97%, 98%, 99%, 99.1%, 99.2%, 99.3%, 99.4%, 99.5%, 99.6%, 99.7%, 99.8%, 99.9% or higher identity to SEQ ID NO: 2 are also encompassed in the instant invention.

The present disclosure further contemplates the combination of a non-functional A137R gene with other recombinant mutations. As such, it is not only wild-type viruses that can be modified as disclosed herein, but also strains containing non-naturally occurring mutations in other genes or genomic regions (see, e.g., U.S. Pat. No. 9,814,771).

The present disclosure provides that such rationally-designed, live, attenuated ASFV-G ΔA137R can be incorporated into immunogenic compositions to produce a vaccine effective to protect an animal, such as a pig, from clinical ASF disease when challenged with ASFV-G. Thus, one object of the invention is to provide a method for protecting an animal against ASFV-G by administering an effective amount of rationally designed live attenuated ASFV-GΔA137R vaccine. In another embodiment, the present disclosure provides a method for eliciting a protective immune response in an animal, preferably of the family Suidae (e.g., domestic pigs (*Sus scrofa domesticus*), wild pigs (*Sus scrofa scrofa*), warthogs (*Potamochoerus porcus*), bushpigs (*Potamochoerus larvatus*), giant forest hogs (*Hylochoerus meinertzhageni*) as well as feral pigs), Such methods will typically comprise administering to such animal the one or more ASFV immunogenic compositions and vaccines described herein.

An additional object of the present disclosure is to provide a method for distinguishing animals infected with a wild-type ASFV from animals vaccinated with a recombinant virus described herein. Such methodologies for differentiating infected from vaccinated animals (DIVA) can be accomplished by serological tests that detect the difference between wild-type A137R protein and a mutant A137R protein. Alternately, such methodologies can include genetic screening approaches such as PCR amplification and detection of different products based. Typically, such approaches utilize one or more primer sets that flank the site of a mutation and expand the same region, resulting in products of different lengths or sequences.

The immunogenic composition(s) of the invention herein, regardless of other components included, comprise a recombinant ASFV with a non-functional A137R gene/protein. A137R proteins of the present invention can comprise the entirety of SEQ ID NO: 4 and proteins with 90%, 91%, 92%, 93%, 94%, 95%, 96%, 97%, 98%, 99%, or higher identity to the protein of SEQ ID NO: 4.

The immunogenically effective amounts of immunogenic compositions disclosed herein can vary based upon multiple parameters. In general, however, effective amounts per dosage unit for intramuscular application can be about $10^2$ 50% hemadsorption dose ("$HAD_{50}$") to $10^6$ $HAD_{50}$. One, two, or more dosage units can be utilized in practicing the methodologies of the present invention. A dosage unit can readily be modified to fit a desired volume or mass by one of skill in the art. Regardless of the dosage unit parameters, immunogenic compositions disclosed herein can be administered in an amount effective to produce an immune response.

Dosage levels of active ingredients in vaccines disclosed herein, can be varied by one of skill in the art to achieve a desired result in a subject or per application. As such, a selected dosage level can depend upon a variety of factors including, but not limited to, formulation, combination with other treatments, severity of a pre-existing condition, and the presence or absence of adjuvants. In preferred embodiments, a minimal dose of an immunogenic composition is administered. Determination of a minimal dose is well within the capabilities of one skilled in the art.

Vaccines of the present invention can be prepared by conventional methods used for commercially available live attenuated ASFV vaccines. In a specific embodiment, a susceptible substrate is inoculated with an ASFV-GΔA137R mutant and propagated until the virus has replicated to a desired titer after which ASFV-GΔA137R-containing material is harvested. Following this, the harvested material can be formulated into a vaccine preparation with immunogenic properties. Every substrate which is able to support the replication of the recombinant viruses provided herein can be used in the present invention, including primary cultures of swine peripheral blood macrophages or blood from infected swine.

Formulations and Administration

A vaccine provided herein comprises one of the recombinant viruses as defined above in a live form, and a pharmaceutically acceptable carrier or diluent customarily used for such compositions. Carriers include stabilizers, preservatives and buffers. Suitable stabilizers include, for example, SPGA (sucrose, phosphate, glutamate and albumin), carbohydrates (sorbitol, mannitol, starch, sucrose, dextran, glutamate, and glucose), proteins (dried milk, serum, albumin, casein), or degradation products thereof. Suitable buffers include, for example alkali metal phosphates. Preservatives that can be utilized, include, but are not limited to, thimerosal, merthiolate and gentamicin. Diluents include water, aqueous buffers (e.g., buffered saline), alcohols and polyols (e.g., glycerol).

In some instances, vaccines of the present invention also contain or comprise one or more adjuvants, which includes any material included in the immunogenic composition formulation that enhances an immune response in the recipient that is induced by the immunogenic composition. In some instances, such adjuvants can include proteins other components included with the recombinant virus. Other adjuvants can be included as an extra component of the immunogenic compositions, and include such categories as aluminum salts (alum), oil emulsions, saponins, immune-stimulating complexes (ISCOMs), liposomes, microparticles, nonionic block copolymers, derivatized polysaccharides, cytokines, and a wide variety of bacterial derivatives. Any relevant adjuvant known in the art can be utilized in practicing the inventions disclosed herein. Factors influencing the selection of an adjuvant include animal species, specific pathogen, antigen, route of immunization, and type of immunity needed and can be readily determined by one of skill in the art.

Immunogenic compositions of the present disclosure can also comprise carriers in addition to the recombinant virus. Carriers utilized in practicing the immunogenic compositions provided herein can be any known in the art and can be liquid, solid, semi-solid, or gel. The type of formulation can be modified depending on the route of administration of the antigen. Preferably, carriers are non-toxic to the recipient. One of skill in the art is readily able to choose such carriers for application to recipient animals such as poultry.

The present disclosure provides immunogenic compositions for introducing a recombinant ASFV lacking a functional A137R gene/protein in a composition containing, at a minimum, the recombinant virus, into targets (e.g., swine). Thus, the compositions provided herein can be utilized to induce immunity or resistance to ASFV disease.

Vaccines provided herein may be administered by intramuscular, subcutaneous, intranasal or injection in an amount which is effective to protect the animal against challenge by a virulent strain of ASFV. The vaccine may be administered orally, through direct oral inoculation, dosed in drinking water, or though bait delivery systems. The effective amount of recombinant virus may vary according to parameters considered by those skilled in the art. Effective amounts can be experimentally determined as necessary by those of skill in the art by following any known method or the guidance provided in the Examples herein.

As originally described, the ASFV A137R gene encodes for a 137 amino acid protein A137 (Alcami et al, J. Gen. Virol. (1993), 11:2317-24). The translated product of the ASFV A137R gene is a protein expressed late during the virus replication cycle, with a electrophoretic mobility of 11.5 KD and has been detected in preparations of purified virus (Alejo et al, J. Virol., (2018) 92: e01293-18). The protein is highly conserved and found in all isolates of ASF. Not much is known about A137, other than it is translated at late times of infection and incorporated into the virus particle. To date, no role in pathogenesis has been conducted and no mutant phenotypes have been described.

Having generally described this invention, the same will be better understood by reference to certain specific examples, which are included herein to further illustrate the invention and are not intended to limit the scope of the invention as defined by the claims.

EXAMPLES

Example 1

Cell Culture and Viruses.

Primary swine macrophage cell cultures were prepared from defibrinated swine blood as previously described (Zsak et al, J. Virol., (1998) 72:1028-35). Briefly, heparin-treated swine blood was incubated at 37° C. for 1 hour to allow sedimentation of the erythrocyte fraction. Mononuclear leukocytes were separated by flotation over a Ficoll-Paque (Pharmacia, Piscataway, N.J.) density gradient (specific gravity, 1.079). The monocyte/macrophage cell fraction was cultured in plastic Primaria (Falcon; Becton Dickinson Labware, Franklin Lakes, N.J.) tissue culture flasks containing macrophage media, composed of RPMI 1640 Medium (Life Technologies, Grand Island, NY) with 30% L929 supernatant and 20% fetal bovine serum (HI-FBS, Thermo Scientific, Waltham, MA) for 48 hours at 37° C. under 5% CO2. Adherent cells were detached from the plastic by using 10 mM EDTA in phosphate buffered saline (PBS) and were then reseeded into Primaria T25, 6- or 96-well dishes at a density of $5\times10^6$ cells per ml for use in assays 24 hours later.

Virus titration was performed on primary swine macrophage cell cultures in 96-well plates. Virus dilutions and cultures were performed using macrophage medium. Presence of virus was assessed by hemadsorption (HA) and virus titers were calculated by the Reed and Muench method (Amer. J. Hygiene, (1938) 27:493-497).

ASFV Georgia (ASFV-G) utilized for this study was a field isolate kindly provided by Dr. Nino Vepkhvadze, from the Laboratory of the Ministry of Agriculture (LMA) in Tbilisi, Republic of Georgia.

Example 2

Construction of a Recombinant ASFV-G ΔA137R

Recombinant ASFVs were generated by sequential homologous recombination between the parental ASFV genome and recombination transfer vectors in infection and transfection procedures using swine macrophage cell cultures (Neilan et al, Virol., (2004) 319:337-42; Zsak et al, supra). Recombinant transfer vector (p72mCherryΔA137R) containing flanking genomic regions including portions of A137R mapping to the left (1 kbp) and right (1 kbp) of the gene and a reporter gene cassette containing the mCherry gene with the ASFV p72 late gene promoter, p72mCherry was used. This construction created a 249-nucleotide deletion in the A137R ORF (amino acid residues 1 to 85) (FIG. 1). Recombinant transfer vector p72mCherryΔA137R was obtained by DNA synthesis (Epoch Biosciences, Bothwell, WA, USA). Macrophage cell cultures were infected with ASFV-G and transfected with p72mCherryΔA137R. Recombinant viruses representing independent primary plaques were purified to homogeneity by successive rounds of plaque assay purification. The recombinant virus was obtained after 9 successive plaque purification events on monolayers of primary swine macrophage cell cultures.

Example 3

Full Genome Sequence Analysis of ASFV-G ΔA137R Relative to Parental ASFV-G.

To evaluate the accuracy of the genetic modification and the integrity of the genome of the recombinant virus, full genome sequences of ASFV-G ΔA137R and parental ASFV-G were obtained using Next Generation Sequencing (NGS) and compared. As a first step, a full-length genome comparison between the parental ASFV-G laboratory strain used to construct the ASFV-G ΔA137R mutant virus and the original ASFV Georgia 2007/1 (Chapman et al, Emerg. Infect. Dis., (2001) 17:599-605; GenBank accession FR682468.2) was performed. ASFV DNA was obtained from the cytoplasm of infected cells using the Trizol method (Life Technologies, Grand Island, NY, USA). DNA concentration was determined using the Qubit® dsDNA HS assay kit (Life Technologies) and read on a Qubit® 2 Flourometer (Life Technologies). In Brief, the viral DNA was sheared using enzymatic reactions assessed for the distribution of size fragmentation, then ligation of identifying barcodes using an adapter sequence were added to the DNA fragments. Using a Pippin Prep™ (Sage Science, Beverly, MA) the required size range of the library was collected, and normalized. We then used this DNA library for NGS sequencing using the NextSeq (Illumnia, San Diego, CA) following the manufactures protocol. Sequence analysis was performed using CLC Genomics Workbench software (CLCBio, Waltham, MA).

The following differences were observed between these two viruses (nucleotide positions are provided based on ASFV Georgia 2007/1, GenBank accession FR682408.2 (i) one nucleotide insertions an A at position 1363, (ii) two deletions a G at position 19792, GT at 2008 and a G at 21797. (iii) single nucleotide variants 98378 and 190543 have an A to G change [mark in this case and all following A is in the vaccine described here and G is the reference], an C to G change at position 167188. Position 93878 is in ORF B438L but is a silent mutation that does not affect the amino acid sequence of the protein product. The change at 167188 changes protein E119L from an Alanine to Proline. None of the other changes described here affect any known ORF and are located in non-coding areas of the genome.

To determine if the recombinant virus acquired additional genetic changes from the parent strain, a full-length genome comparison between ASFV-G ΔA137R and the parental ASFV-G was performed. The DNA sequence assemblies of ASFV-G ΔA137R and ASFV-G revealed a deletion of 249 nucleotides in A137R gene corresponding with the introduced modification. The consensus sequence of the ASFV-G ΔA137R genome showed an insertion of 3944 nucleotides in A137R gene corresponding to the p72-mcherry cassette sequence introduced to generate a 249-nucleotide deletion in the targeted gene. Besides the insertion of the cassette, no additional differences were observed between ASFV-G ΔA137R and ASFV-G genomes. In summary, ASFV-G ΔA137R virus did not accumulate any significant mutations during the process of homologous recombination and plaque purification.

Example 4

Assessment of ASFV-G ΔA137R Virulence in Swine.

Animal experiments were performed under biosafety level 3 conditions in the animal facilities at PIADC following a protocol approved by the Institutional Animal Care and Use Committee.

ASFV-G ΔA137R was assessed for its virulence phenotype relative to the virulent parental ASFV-G virus using 80-90-pound commercial breed swine. Five pigs were inoculated intramuscularly (IM) either with $10^2$, of ASFV-G ΔA137R or with $10^2$ $HAD_{50}$ of ASFV-G virus. Clinical signs (anorexia, depression, fever, purple skin discoloration, staggering gait, diarrhea and cough) and changes in body temperature were recorded daily throughout the experiment. In protection experiments animals were IM inoculated with $10^2$ $HAD_{50}$ and 28 days later IM challenged with $10^2$ $HAD_{50}$ of parental virulent ASFV Georgia 2007 strain. Presence of clinical signs associated with the disease was performed as described earlier.

All pigs inoculated via IM with $10^2$ $HAD_{50}$ of ASFV-G exhibited increased body temperature (>104° F.) by 3 to 4 days post-infection. Pigs presented clinical signs associated with the disease including anorexia, depression, purple skin discoloration, staggering gait and diarrhea (Table 1). Signs of the disease aggravated progressively over time and animals either died or were euthanized in extremis by days 7 or 9 post-infection. Conversely, animals inoculated via IM with $10^2$ of ASFV-G ΔA137R did not present any signs of clinical disease during the entire observation period (21 days). Therefore, deletion of A137R gene produced a complete attenuation of the parental virulent ASFV-G. That the ASFV-G ΔA137R mutant was attenuated was surprising as we have deleted many single genes with unknown function, and no observed changes in virulence resulted. All animals in the Mock vaccinated group were euthanized due to humanitarian reasons following the corresponding IACUC protocol.

TABLE 1

Swine survival and fever response following infection with $10^2$ $HAD_{50}$ doses of ASFV-G-ΔA137R or parental ASFV-G.

| | | | Fever | | |
|---|---|---|---|---|---|
| Virus and dose ($HAD_{50}$) | No. of survivors/ total | Mean time to death (days ± SD) | No. of days to onset (days ± SD | Duration No. of days (days ± SD) | Maximum daily temp (° F. ± SD) |
| ASFV-G | 0/5 | 7 (0) [(1)] | 4.6 (0.55) | 2.4 (0.55) | 105.52 (0.79) |
| ASFV-G-ΔA137R | 5/5 | — | — | — | 103.4 (0.46) |

Example 5

Protective Effect of ASFV-G ΔA137R Against Challenge with Parental ASFV-G.

Because pigs inoculated via IM with $10^2$ $HAD_{50}$ of ASFV-G ΔA137R survived the infection without signs of the disease, groups of animals (n=5) inoculated with $10^2$ $HAD_{50}$ of ASFV-G ΔA137R were challenged via IM with $10^2$ $HAD_{50}$ of parental ASFV-G at day 28 post-inoculation (homologous challenge). Five naive animals that were challenged using the same route and dose served as a non-inoculated/challenged control group. All animals were IM vaccinated with $10^2$ $HAD_{50}$ of ASFV-G ΔA137R and challenged IM 28 days later with $10^2$ $HAD_{50}$ of ASFV-G virus. All animals in the Mock vaccinated group were euthanized due to humanitarian reasons following the corresponding IACUC protocol. All animals in the ASFV-G ΔA137R vaccinated group remain clinically normal during the observational period of 21 days after the challenge.

The five ASFV-G ΔA137R-inoculated and challenged animals remained completely asymptomatic during all the observational period (21 days) (Table 2). All the animals in the mock inoculated/challenged control group developed disease with a clinical course similar to that observed in animals inoculated with $10^2$ $HAD_{50}$ of ASFV-G (see above). Therefore, ASFV-G ΔA137R is able to induce protection against the presentation of clinical disease when challenged with the highly virulent parental virus.

TABLE 2

Swine survival and fever response in animals challenged with ASFV-G virus at 28 days post-ASFV-G-ΔA137R infection.

| Virus ($10^2$ $HAD_{50}$) | No. of survivors/ total | Mean time to death (days ± SD) | Fever: No. of days to onset (days ± SD | Fever: Duration No. of days (days ± SD) | Fever: Maximum daily temp (° F. ± SD) |
|---|---|---|---|---|---|
| Mock | 0/5 | 7 (0) [(1)] | 4.2 (0.45) | 2.8 (0.45) | 105.98 (0.94) |
| ASFV-G-ΔA137R | 5/5 | — | — | — | 102.22 (1.06) |

In summary, here we present evidence that deletion of the A137R gene drastically alters virulence of ASFV-G producing a completely attenuated virus named ASFV-G ΔA137R. Animals immunized with ASFV-G ΔA137R were protected against challenge with the virulent parental ASFV-G.

Example 6

The Ability of ASFV-G-A137R to Grow in Swine Macrophages

Figure 2:
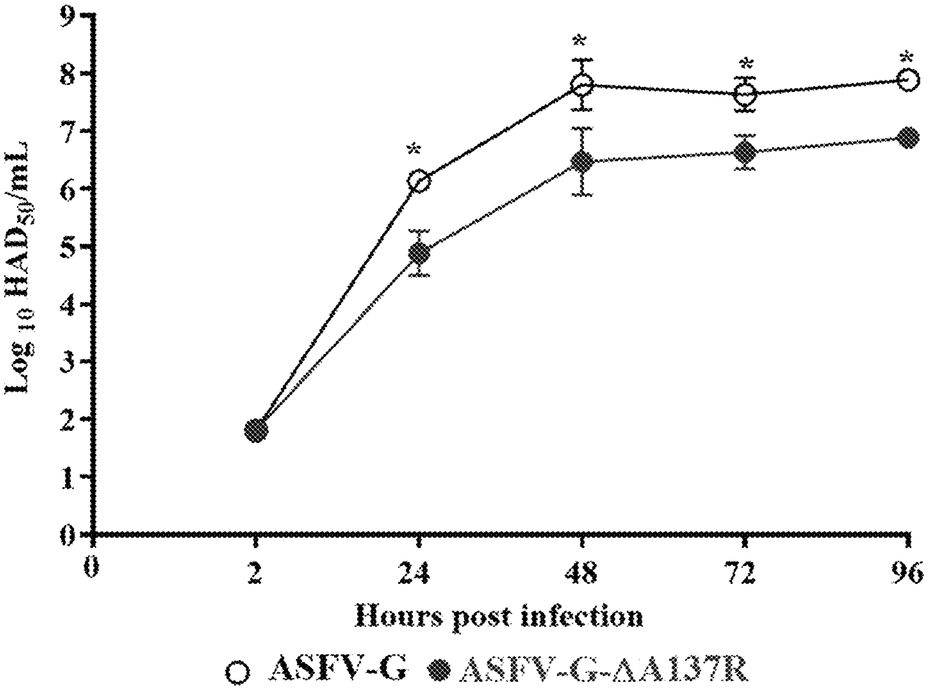
FIG. 2 provides graphic representation of in vitro growth characteristics of ASFV-G-A A137R and parental ASFV-G. Primary swine macrophage cell cultures were infected (MOI=0.01) with each of the viruses and virus yield titrated at the indicated times post-infection. Data represent means from three independent experiments. Sensitivity of virus detection: >1.8 $\log_{10}$ $HAD_{50}$/ml.

In vitro growth characteristics of ASFV-G-ΔA137R were evaluated in primary swine macrophage cell cultures, the primary cell targeted by ASFV during infection in swine and compared relative to parental ASFV-G in multistep growth curves (FIG. 2). Cell cultures were infected at a MOI of 0.01 and samples were collected at 2, 24, 48, 72 and 96-hours post-infection (hpi). Results demonstrated that ASFV-G-ΔA137R displayed a growth kinetic significantly decreased when compared to parental ASFV-G. ASFV-G-ΔA137R yields are approximately 10-100-fold lower than those of ASFV-G depending on the time point considered.

Therefore, deletion of the A137R gene significantly decreased the ability of ASFV-G-ΔA137R, relative to the parental ASFV-G isolate, to replicate in vitro in primary swine macrophage cell cultures.

Example 7

ASFV-G-ΔA137R Infected Animals Shed Vaccine Virus

In the above example where different groups of five pigs were infected IM with $10^2$ $HAD_{50}$ of ASFV-G-ΔA137R, a mock infected animal was cohabitating in each of the groups as sentinel to detect the potential virus shedding from the infected animals. All sentinel animals remained clinically normal, although the presence of ASFV-G-ΔA137R in sentinel animals indicates the presence of virus shedding and explains the late rise of ASFV specific antibodies by day 28 post infection.

Example 8

Host Antibody Response in Animals Infected with ASFV-G-ΔA137R

Figure 3:
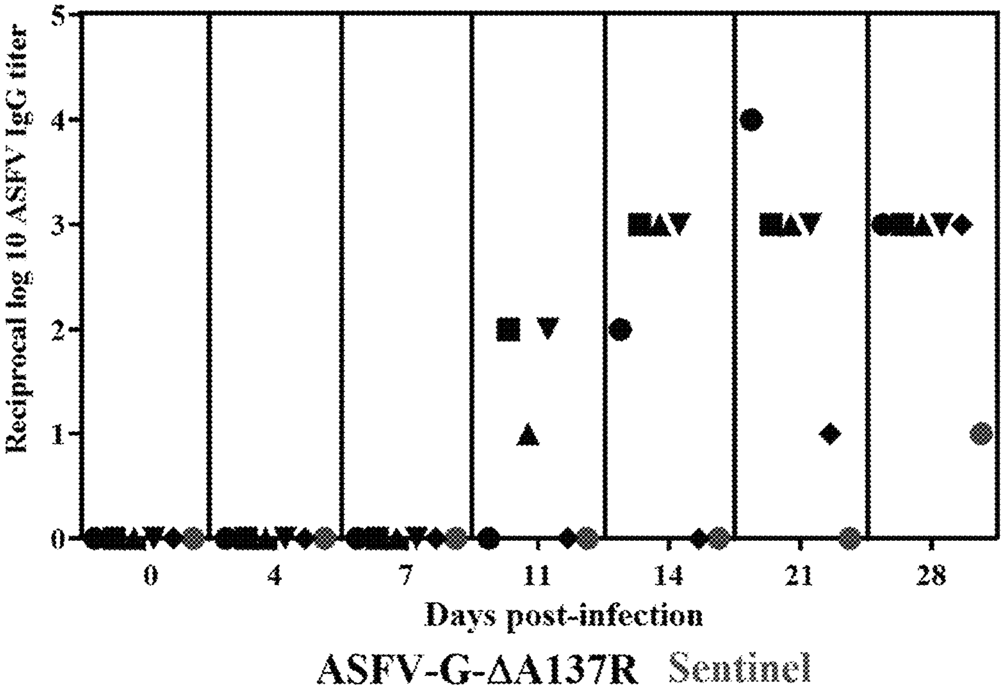
FIG. 3 provides graphic representation of anti-ASFV antibody (IgM mediated shown in panels in the left column, and IgG mediated shown in panels in the right column) titers detected by ELISA in pigs IM inoculated with either $10^2$ of ASFV-G-A137R (black) or Sentinel animals mock vaccinated housed with vaccinated animals (blue).

All animals infected with ASFV-G-ΔA137R, regardless of the dose of virus received possessed similar high titers of circulating anti-ASFV antibodies. Antibody response, mediated by IgG isotypes, starts being detected in three of the animals by day 11 pi and 4 of the animals day 14 pi and in all of the animals by day 21 and was also observed in all five animals day 28 pi reaching maximum levels in all animals inoculated with ASFV-G-ΔA137R. Therefore, there is a close correlation between presence of anti-ASFV antibodies at the moment of the challenge and protection. It should be mentioned that a low level of antibodies was detected in one of the serum samples obtained from one of the sentinel animals (FIG. 3).

Example 9

Induction of Sterile Immunity

Using an A137R specific real time PCR to specifically detect only challenge virus (which allows the detection of approximately 10 $HAD_{50}$) all blood samples tested negative for the presence of challenge virus. Furthermore, tonsils and spleen samples were obtained from all animals at the end of the observational period (21 days post challenge) and tested for the presence of virus by virus isolation in swine macrophage cultures. Most of the animals in each group showed presence of infectious virus either in tonsils or spleen (data not shown). All positive samples were then assessed using the A137R specific real time PCR detecting the presence of the challenge virus in only one spleen belonging to one of the animals initially infected with $10^2$ $HAD_{50}$/ml of ASFV-G-ΔA137R. These results suggest that replication of challenge virus was absent in all infected animals receiving $10^2$ $HAD_{50}$/ml of ASFV-G-ΔA137R.

In summary, sterile immunity (immunity that doesn't allow the replication of challenge virus) was achieved in animals vaccinated with $10^2$ $HAD_{50}$/ml of ASFV-G-ΔA137R.

While the invention has been described with reference to details of the illustrated embodiments, these details are not intended to limit the scope of the invention as defined in the appended claims. The embodiments of the disclosure in which exclusive property or privilege is claimed is defined as follows:

What is claimed is:

1. A genetically modified virus, wherein the virus genome of the genetically modified virus comprises a viral genome at least 99.5% identical to SEQ ID NO: 2.

2. The genetically modified virus of claim 1, wherein the viral genome comprises a viral genome at least 99.8% identical to SEQ ID NO:2.

3. The genetically modified virus of claim 1, wherein the viral genome comprises SEQ ID NO: 2.

4. A vaccine composition against African Swine Fever Virus (ASFV), comprising the genetically modified virus of claim 1.

5. The vaccine composition of claim 4, wherein the ASFV is ASFV-Georgia 2007 isolate (ASFV-G).

6. A method for the protection of swine against ASFV, comprising administering to a swine a live attenuated vaccine comprising the genetically modified virus of claim 1 in an amount effective to protect said swine from clinical ASFV disease.

7. The method of claim 6, wherein the ASFV is ASFV-G.

8. The method of claim 6, wherein the amount effective to protect said swine from clinical ASFV disease is $10^2$-$10^6$ $HAD_{50}$ of the genetically modified virus.

9. A recombinant ASFV virus, comprising a synthetic mutation in the genomic A137R open reading frame or in a regulatory element controlling the expression of the genomic A137R protein, resulting in a non-functional genomic A137R gene.

10. The recombinant ASFV virus of claim 9, wherein the synthetic mutation is a deletion mutation resulting in the deletion of one or more nucleotides between positions 55531 and 55779 of SEQ ID NO:1.

11. The recombinant ASFV virus of claim 9, wherein the synthetic mutation is a frameshift mutation, insertion mutation, or nonsense mutation of one or more nucleotides between positions 55531 and 55779 of SEQ ID NO:1.

12. The recombinant ASFV virus of claim 9, wherein the ASFV recombinant virus is derived from an ASFV-Georgia isolate.

13. The recombinant ASFV virus of claim 9, wherein the ASFV recombinant virus comprises a genome at least 95% identical to SEQ ID NO: 2.

14. The recombinant ASFV virus of claim 9, wherein the ASFV recombinant virus comprises a genome at least 99% identical to SEQ ID NO: 2.

15. A vaccine composition against ASFV-G, comprising the recombinant ASFV virus of claim 9.

16. A method for the protection of swine against ASFV, comprising administering to a swine a live attenuated vaccine comprising the recombinant ASFV virus of claim 9 in an amount effective to protect said swine from clinical ASFV disease.

17. The method of claim 16, wherein the ASFV is ASFV-G.

18. The method of claim 16, wherein the amount effective to protect said swine from clinical ASFV disease is at least $10^2$ $HAD_{50}$ of the recombinant ASFV virus.

* * * * *